United States Patent
Shiraishi et al.

(10) Patent No.: US 6,235,771 B1
(45) Date of Patent: May 22, 2001

(54) ANILIDE DERIVATIVE, PRODUCTION AND USE THEREOF

(75) Inventors: Mitsuru Shiraishi, Hyogo; Masanori Baba, Kagoshima; Masaki Seto; Naoyuki Kanzaki, both of Osaka; Osamu Nishimura, Ibaraki, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/463,924
(22) PCT Filed: Dec. 20, 1999
(86) PCT No.: PCT/JP99/07148
  § 371 Date: Apr. 19, 2000
  § 102(e) Date: Apr. 19, 2000
(87) PCT Pub. No.: WO00/37455
  PCT Pub. Date: Jun. 29, 2000

(30) Foreign Application Priority Data

Dec. 21, 1998 (JP) .................................................. 10-363404
Jun. 16, 1999 (JP) .................................................. 11-170212

(51) Int. Cl.$^7$ .......................... A61K 31/38; C07D 337/00
(52) U.S. Cl. ................................................. 514/431; 549/9
(58) Field of Search ................................. 514/431; 549/9

(56) References Cited

U.S. PATENT DOCUMENTS

| | | | |
|---|---|---|---|
| 4,379,162 | * 4/1983 | Rosen | 549/9 |
| 5,158,943 | * 10/1992 | Sohda et al. | 514/96 |
| 5,705,524 | * 1/1998 | McGee et al. | 514/431 |
| 5,994,391 | * 11/1999 | Lee et al. | 514/431 |
| 6,096,780 | * 8/2000 | Shiraishi et al. | 514/431 |

FOREIGN PATENT DOCUMENTS

| | | |
|---|---|---|
| WO 96/01267 | 1/1996 | (WO) . |
| WO 97/24325 | 7/1997 | (WO) . |
| WO 99/32100 | 7/1999 | (WO) . |
| WO 99/32468 | 7/1999 | (WO) . |
| WO 00/10965 | 3/2000 | (WO) . |

OTHER PUBLICATIONS

M. Baba et al., "A small-molecule, nonpeptide CCR5 antagonists with highly potent and selective anti-HIV-1 activity" Proc. Natl. Acad. Sci. USA, vol. 96, pp. 5698–5703, May 1999.

J. Balzarini et al., "Inhibitory activity of diarylamidine derivatives on murine leukemia L1210 cell growth", Investigational New Drugs, vol. 1, pp. 103–114 (1983).

E. De Clercq et al., "Diaryl Amidine Derivatives as Oncornaviral DNA Polymerase Inhibitors", Journal of Medical Chemistry, vol. 23, pp. 787–795 (1980).

C. Bright et al., "Identification of a non peptidic rantes antagonist", Bioorganic & Medicinal Chemistry Letters, vol. 8, pp. 771–774 (1998).

G. Simmons et al., "Potent Inhibition of HIV–1 Infectivity in Macrophages and Lymphocytes by a Novel CCR5 Antagonist", Science, vol. 276, pp. 276–279 (1997).

T. N. C. Wells et al., "Definition, function and pathophysiological significance of chemokine receptors", Trends in Pharmacological Sciences, vol. 19, pp. 376–380 (1998).

R. Horuk, "Chemokine receptors and HIV–1: the fusion of two major research fields", Immunology Today, vol. 20, No. 2, pp. 89–94 (1999).

\* cited by examiner

*Primary Examiner*—Deborah C. Lambkin
(74) *Attorney, Agent, or Firm*—Philippe Y. Riesen; Mark Chao

(57) ABSTRACT

This invention is to provide a compound of the formula:

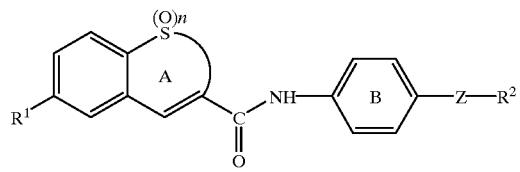

wherein $R^1$ is an optionally substituted 5- to 6-membered ring; the ring A is an optionally substituted 6- to 7-membered ring; the ring B is an optionally substituted benzene ring; n is an integer of 1 or 2; Z is a chemical bond or a divalent group; $R^2$ is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, (3) a group binding through a sulfur atom or (4) a group of the formula:

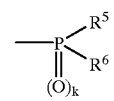

wherein k is 0 or 1, and when k is 0, a phosphorus atom may form a phosphonium; and $R^5$ and $R^6$ are independently an optionally substituted hydrocarbon group, an optionally substituted hydroxy group or an optionally substituted amino group, and $R^5$ and $R^6$ may bind to each other to form a cyclic group together with the adjacent phosphorus atom, or a salt thereof , which is useful for antagonizing CCR5 and also for the prevention and treatment of infectious disease of HIV.

33 Claims, No Drawings

SEQUENCE LISTING

```
<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: primer DNA sequence based on nucleotide
      sequence of CCR5 gene

<400> SEQUENCE: 1
caggatccga tggattatca agtgtcaagt ccaa                                34

<210> SEQ ID NO 2
<211> LENGTH: 34
<212> TYPE: DNA
<213> ORGANISM: Artificial Sequence
<220> FEATURE:
<223> OTHER INFORMATION: primer DNA sequence based on nucleotide
      sequence of CCR5 gene

<400> SEQUENCE: 2
tctagatcac aagcccacag atatttcctg ctcc                                34
```

ANILIDE DERIVATIVE, PRODUCTION AND USE THEREOF

This Application is the National Stage of International Patent Application Ser. No. PCT/JP99/07148, field Dec. 20, 1999.

TECHNICAL FIELD

The present invention relates to a novel anilide derivative, production and use thereof.

BACKGROUND ART

Recently, HIV (human immunodeficiency virus) protease inhibitors have been developed for method of the treatment of AIDS (acquired immunological deficient syndrome) and use of the protease inhibitors in combination with conventional two HIV reverse transcriptase inhibitors provides further progress of the treatment of AIDS. However, these drugs and their combination use are not sufficient for the eradication of AIDS, and development of new anti-AIDS drugs having different activity and mechanism are sought for.

As a receptor from which HIV invades to a target cell, CD4 is so far known, and recently CCR5 as a second receptor of macrophage-tropic HIV and CXCR4 As a second receptor of T cell-tropic HIV, each of which is a G protein-coupled chemokine receptor having seven transmembrane domains, are respectively known. These chemokine receptors are thought to play an essential role in establishment and spread of HIV infection. In fact, it is reported that a person who is resistant to HIV infection in spite of several exposures retains mutation of homo deletion of CCR5 gene. Therefore, a CCR5 antagonist is expected to be a new anti-HIV drug. However, so far, there has been no report that a CCR5 antagonist have been developed as a therapeutic agent of AIDS.

In order to investigate an anti-AIDS drug having CCR5 antagonistic activity, it is necessary to clone CCR5 gene from a human tissue derived cDNA library, to ligate said gene with a vector for expression in animal cell , to introduce said gene into animal cells and to obtain cells expressing CCR5. In addition, with using this transformant, it is necessary to screen a compound which Strongly inhibits binding of CC chemokine RANTES, natural ligand, to CCR5 (which strongly antagonizes CCR5). However, so far there has been no report on a low molecule compound having CCR5 antagonistic activity. The present invention is to provide a novel anilide derivative which is useful for the treatment or prevention of infectious disease of HIV and, in particular, AIDS and also which is suitable for oral administration, production and use thereof

DISCLOSURE OF INVENTION

The present inventors diligently made extensive studies on compounds having CCR5 antagonistic activity and, as a result, they found that an anilide derivative of the following formula (I) or a salt thereof [hereinafter, referred to as Compound (I)] unexpectedly possesses potent CCR5 antagonistic activity and clinically desirable pharmaceutical effect (e.g. remarkable inhibition of HIV infection to human peripheral mononuclear cells, etc.) and also that Compound (I) has superior absorb ability when orally administered. Based on the finding present invention was accomplished.

More specifically, the present invention relates to
(1) A compound of the formula (I):

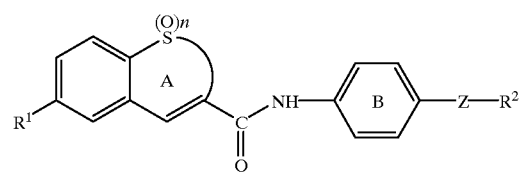

(I)

wherein $R^1$ is an optionally substituted 5- to 6-membered ring; the ring A is an optionally substituted 6- to 7-membered ring; the ring B is an optionally substituted benzene ring; n is an integer of 1 or 2; Z is a chemical bond or a divalent group; $R^2$ is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, (3) a group binding through a sulfur atom or (4) a group of the formula:

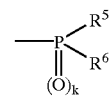

wherein k is 0 or 1, and when k is 0, a phosphorus atom may form a phosphonium; and $R^5$ and $R^6$ are independently an optionally substituted hydrocarbon group, an optionally substituted hydroxy group or an optionally substituted amino group, and $R^5$ and $R^6$ may bind to each other to form a cyclic group together with the adjacent phosphorus atom, or a salt thereof; and a pro-drug of the compound or a salt thereof as described in the above (1);

(2) A compound as described in the above (1), wherein $R^1$ is benzene, furan, thiophene, pyridine, cyclopentane, cyclohexane, pyrrolidine, piperidine, piperazine, morpholine, thiomorpholine or tetrahydropyran, each of which may be substituted;

(3) A compound as described in the above (1), wherein $R^1$ is an optionally substituted benzene;

(4) A compound as described in the above (1), wherein the ring A is a group of the formula:

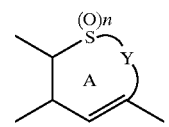

wherein Y is —$(CH_2)_m$— (m is an integer of 1 or 2), —CH=CH— or —N=CH—, which may have a substituent at any possible position;

(5) A compound as described in the above (4), wherein Y is —$(CH_2)_m$— (m is an integer of 1 or 2);

(6) A compound as described in the above (4), wherein Y is —$(CH_2)_2$—;

(7) A compound as described in the above (1), wherein the ring B is a benzene which may be substituted with a substituent selected from the class consisting of a halogen atom, a $C_{1-4}$ alkyl group optionally substituted with a halogen atom and a $C_{1-4}$ alkoxy group optionally substituted with a halogen atom;

(8) A compound as described in the above (1), wherein n is 2;

(9) A compound as described in the above (1), wherein Z is an optionally substituted $C_{1-3}$ alkylene;

(10) A compound as described in the above (1), wherein Z is a divalent group of the formula: —Z'—$(CH_2)n'$— (Z' is —CH(OH)—, —C(O)— or —$CH_2$—, and n' is an integer of 0–2) in which an optional methylene group may be substituted;

(11) A compound as described in the above (1), wherein Z is methylene;

(12) A compound as described in the above (1), wherein $R^2$ is (1) an optionally substituted amino group, (2) an optionally substituted nitrogen-containing heterocyclic ring group which may contain a sulfur atom or an oxygen atom as ring constituting atoms, (3) a group binding through a sulfur atom or (4) a group of the formula:

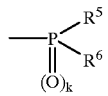

wherein k is 0 or 1; and $R^5$ and $R^6$ are independently an optionally substituted hydrocarbon group or an optionally substituted amino group, and $R^5$ and $R^6$ may bind to each other to form a cyclic group together with the adjacent phosphorus atom;

(13) A compound as described in the above (1), wherein $R^2$ is (1) an optionally substituted amino group, (2) an optionally substituted nitrogen-containing heterocyclic ring group which may contain a sulfur atom or an oxygen atom as ring constituting atoms or (3) a group of the formula:

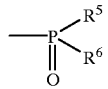

wherein $R^5$ and $R^6$ are independently an optionally substituted hydrocarbon group, and $R^5$ and $R^6$ may bind to each other to form a cyclic group together with the adjacent phosphorus atom;

(14) A compound as described in the above (1), wherein $R^2$ is a group of the formula: —NRR' wherein R and R' are independently an optionally substituted aliphatic hydrocarbon group (aliphatic acyclic hydrocarbon group and aliphatic cyclic hydrocarbon group) or an optionally substituted non-aromatic heterocyclic ring group;

(15) A compound as described in the above (14), wherein R is an optionally substituted acyclic hydrocarbon group and R' is an optionally substituted alicyclic hydrocarbon group (aliphatic cyclic hydrocarbon group) or an optionally substituted non-aromatic heterocyclic ring group;

(16) A compound as described in the above 14), wherein R is an optionally substituted $C_{1-6}$ alkyl group and R' is an optionally substituted $C_{3-8}$ cycloalkyl group or an optionally substituted saturated heterocyclic ring group;

(17) A compound as described in the above (16), wherein R' is an optionally substituted cyclohexyl, an optionally substituted tetrahydropyranyl, an optionally substituted tetrahydrothiopyranyl or an optionally substituted piperidyl;

(18) A compound selected from the class consisting of N-[4-[N-methyl-N-(tetrahydropyran-4-yl)aminomethyl]phenyl]-7-(4-propoxyphenyl-1,1-dioxo-2,3-dihydro-1-benzothiepine-4-carboxamide, 7-(4-butoxyphenyl)-N-[4-[N-methyl-N-(tetrahydropyran-4-yl)aminomethyl]phenyl]-1,1-dioxo-2,3-dihydro-1-benzothiepine-4-carboxamide, 7-[4-[N-methyl-N-(2-propoxyethyl)amino]phenyl]-N-[4-[[N-methyl-N-(tetrahydropyran-4-yl)amino]methyl]phenyl]-1,1-dioxo-2,3-dihydro-1-benzothiepine-4-carboxamide 7-[4-(2-ethoxyethoxy)phenyl]-N-[4-[[N-methyl-N-(tetrahydropyran-4-yl)amino]methyl]phenyl]-1,1-dioxo-2,3-dihydro-1-benzothiepine-4-carboxamide N-[4-[[N-methyl-N-(tetrahydropyran-4-yl)amino]methyl]phenyl]-7-[4-(2-propoxyethoxy)phenyl]-1,1-dioxo-2,3-dihydro-1-benzothiepine-4-carboxamide, 7-[4-(2-butoxyethoxy)phenyl]-N-[4-[[N-methyl-N-(tetrahydropyran-4-yl)amino]methyl]phenyl]-1,1-dioxo-2,3-dihydro-1-benzothiepine-4-carboxamide, 7-[4-(2-ethoxyethoxy)-3,5-dimethylphenyl]-N-[4-[[N[-methyl-N-(tetrahydro-2H-pyran-4-yl)amino]methyl]phenyl]-1,1-dioxo-2,3-dihydro-1-benzothiepine-4-carboxamide, 7-[2-chloro-4-(2-propoxyethyl)phenyl]-N-[4-[[N-methyl-N-(tetrahydropyran-4-yl)amino]methyl]phenyl]-1,1-dioxo-2,3-dihydro-1-benzothiepine-4-carboxamide 7-(3-methyl-4-propoxyphenyl)-N-[4-[[N-methyl-N-(tetrahydropyran-4-yl)amino]methyl]phenyl]-1,1-dioxo-2,3-dihydro-1-benzothiepine-4-carboxamide and 7-(3,4-dipropoxyphenyl)-N-(4-((N-methyl-N-(tetrahydro-2H-pyran-4-yl)amino)methyl)phenyl)-1,1-dioxo-2,3-dihydro-1-benzothiepine-4-carboxamide; or a salt thereof;

(19) A method for producing a compound of the formula:

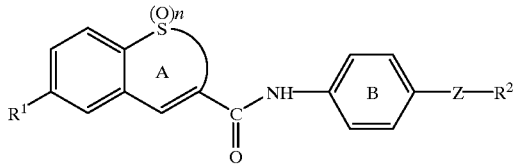

wherein each symbol is as described in the above (1), or a salt thereof, which comprises subjecting a compound of the formula:

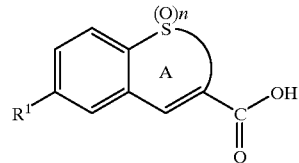

wherein each symbol is as described in the above (1), a salt or a reactive derivative thereof to condensation reaction with a compound of the formula:

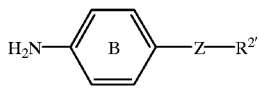

wherein B and Z is as described in the above (1) and R[2'] is (1) an optionally substituted amino group in which a nitrogen atom may form a quaternary ammonium; (2) an optionally substituted nitrogen-containing heterocyclic ring group which may contain a sulfur atom or an oxygen atom as ring constituting atoms and wherein a nitrogen atom may form a quaternary ammonium; (3) a group binding through a sulfur atom; or (4) a group of the formula:

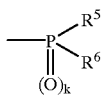

wherein k is 0 or 1, and when k is 0, a phosphorus atom may form a phosphonium; and $R^5$ and $R^6$ are independently an optionally substituted hydrocarbon group, an optionally substituted hydroxy group or an optionally substituted amino group, and $R^5$ and $R^6$ may bind to each other to form a cyclic group together with the adjacent phosphorus atom; each of which may be protected, or a salt thereof, and, if desired, subjecting the obtained product to deprotection, oxidation, reduction and/or ammoniumation:

(20) A compound of the formula:

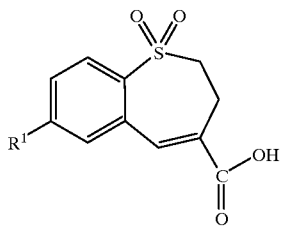

wherein $R^1$ is an optionally substituted 5- to 6-membered ring, or a salt thereof;

(21) A pharmaceutical composition which comprises the compound as described in the above (1) or a salt thereof;

(22) A composition as described in the above (21), which is for antagonizing CCR (preferably, CCR5);

(23) A composition as described in the above (21), which is for the treatment or prevention of infectious disease of HIV;

(24) A composition as described in the above (21), which is for the treatment or prevention of AIDS;

(25) A composition as described in the above (21), which is for the prevention of the progression of AIDS;

(26) A composition as described in the above (23), which is used in combination with a protease inhibitor and/or a reverse transcriptase inhibitor;

(27) A composition as described in the above (26), wherein the reverse transcriptase inhibitor is zidovudine, didanosine, zalcitabine, lamivudine, stavudine, nevirapine, delavirdine, efavirenz or abacavir;

(28) A composition as described in the above (26), wherein the protease inhibitor is saquinavir, ritonavir, indinavir, amprenavir or nelfinavir;

(29) Use of the compound as described in the above (1) or a salt thereof in combination with a protease inhibitor and/or a reverse transcriptase inhibitor for the treatment or prevention of infectious disease of HIV;

(30) A method for antagonizing CCR which comprises administering to a mammal in need thereof an effective amount of the compound as described in the above (1) or a salt thereof;

(31) Use of the compound as described in the above (1) or a salt thereof, for the manufacture of a medicament for antagonizing CCR; etc.

In the above formula (I), examples of the "5- to 6-membered ring" of the "optionally substituted 5- to 6-membered ring" represented by $R^1$ include a 6-membered aromatic hydrocarbon such as benzene, etc.; a 5- to 6-membered aliphatic hydrocarbon (aliphatic cyclic hydrocarbon group) such as cyclopentane, cyclohexane, cyclopentene, cyclohexene, cyclopentanediene, cyclohexanediene, etc.; 5- to 6-membered aromatic heterocyclic ring containing 1 to 4 hetero-atoms consisting of 1 to 2 kinds of hetero-atoms selected from oxygen atom, sulfur atom and nitrogen atom such as furan, thiophene, pyrrole, imidazole, pyrazole, thiazole, oxazole, isothiazole, isoxazole, tetrazole, pyridine, pyrazine, pyrimidine, pyridazine, triazole, etc.; 5- to 6-membered non-aromatic heterocyclic ring containing 1 to 4 hetero-atoms consisting of 1 to 2 kinds of hetero-atoms selected from oxygen atom, sulfur atom and nitrogen atom such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, tetrahydrothiopyran, etc.; etc. Among others, benzene, furan, thiophene, pyridine, cyclopentane, cyclohexane, pyrrolidine, piperidine, piperazine, morpholine, thiomorpholine, tetrahydropyran (preferably, 6-membered ring), etc. are preferable, and in particular, benzene is referable.

Examples of the "substituents", which the "5- to 6-embered ring" in the "optionally substituted 5- to 6-embered ring" represented by $R^1$ may have, include halogen atom, nitro, cyano, an optionally substituted alkyl, an optionally substituted cycloalkyl, an optionally substituted hydroxy group, an optionally substituted thiol group wherein a sulfur atom may be optionally oxidized to form a sulfinyl group or a sulfonyl group, an optionally substituted amino group, an optionally substituted acyl, an optionally esterified or amidated carboxyl group, an optionally substituted aromatic group, etc.

Examples of the halogen as the substituents for $R^1$ include fluorine, chlorine, bromine, iodine, etc. Among others, fluorine and chlorine are preferable.

Examples of the alkyl in the optionally substituted alkyl as the substituents for $R^1$ include a straight or branched $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., and preferably lower ($C_{1-6}$) alkyl.

Examples of the substituents in the optionally substituted alkyl include halogen (e. g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkoxy (e.g. methoxy, ethoxy, propoxy, butoxy, trifluoromethoxy, trifluoroethoxy, etc.), an optionally halogenated $C_{1-4}$ alkoxy-$C_{1-4}$ alkoxy (e.g. methoxymethoxy, methoxyethoxy, ethoxyethoxy, trifluoromethoxyethoxy, trifluoroethoxyethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the cycloalkyl in the optionally substituted cycloalkyl as the substituents for $R^1$ include $C_{3-7}$ cycloalkyl, etc. such as cyclopropyl, cyclobutyl, cyclopentyl, cyclohexyl, cycloheptyl, etc.

Examples of the substituents in the optionally substituted cycloalkyl include halogen (e.g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxycarbonyl, carbamoyl, mono-$C_{1-4}$ alkylcarbamoyl, di-$C_{1-4}$ alkylcarbamoyl, etc.), an optionally halogenated $C_{1-4}$ alkyl (e.g. trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the substituents in the optionally substituted hydroxy group as the substituents for $R^1$ include (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl which may contain a hetero-atom (e.g. $C_{3-7}$ cycloalkyl such as cyclopropyl, cyclobutyl, cyclopentyl, cyclohexyl, cycloheptyl, etc.; a saturated 5- to 6-membered heterocyclic ring group containing 1–2 hetero-atoms (preferably, tetrahydropyranyl, etc.) such as tetrahydrofuranyl, tetrahydrothienyl, pyrrolidinyl, pyrazolidinyl, piperidyl, piperazinyl, morpholinyl, thiomorpholinyl, tetrahydropyranyl, tetrahydrothiopyranyl, etc.; etc.);

(3) an optionally substituted alkenyl (e.g. $C_{2-10}$ alkenyl such as allyl, crotyl, 2-pentenyl, 3-hexenyl, etc., preferably lower ($C_{2-6}$)alkenyl, etc.);

(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(5) an optionally substituted aralkyl (e.g. phenyl-$C_{1-4}$ alkyl (e.g. benzyl, phenethyl, etc.), etc.);

(6) formyl or an optionally substituted acyl (e.g. $C_{2-4}$ alkanoyl (e.g. acetyl, propionyl, butyryl, isobutyryl, etc.), $C_{1-4}$ alkylsulfonyl (e.g. methanesulfonyl, ethanesulfonyl, etc.), etc.);

(7) an optionally substituted aryl (e.g. phenyl, naphthyl, etc.); etc.

Examples of the substituents which the above-mentioned (1) optionally substituted alkyl, (2) optionally substituted cycloalkyl, (3) optionally substituted alkenyl, (4) optionally substituted cycloalkenyl, (5) optionally substituted aralkyl, (6) optionally substituted acyl and (7) optionally substituted aryl may have include halogen (e.g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g. trifluoromethyl, methyl, ethyl, etc.), an optionally halogenated $C_{1-6}$ alkoxy (e.g. methoxy, ethoxy, propoxy, butoxy, trifluoromethoxy, trifluoroethoxy, etc.; preferably an optionally halogenated $C_{1-4}$ alkoxy), formyl, $C_{2-4}$ alkanoyl (e.g. acetyl, propionyl, etc.), $C_{1-4}$ alkylsulfonyl (e.g. methanesulfonyl, ethanesulfonyl, etc.), an optionally substituted 5- to 6-membered aromatic heterocyclic ring [e.g. 5- to 6-membered aromatic heterocyclic ring containing 1 to 4 hetero-atoms consisting of 1 to 2 kinds of hetero-atoms selected from oxygen atom, sulfur atom and nitrogen atom such as furan, thiophene, pyrrole, imidazole, pyrazole, thiazole, oxazole, isothiazole, isoxazole, tetrazole, pyridine, pyrazine, pyrimidine, pyridazine, triazole, etc.; Examples of the substituents which said heterocyclic ring may have include halogen (e.g. fluorine, chlorine, bromine, iodine, etc.), nitro, cyano, hydroxy group, thiol group, amino group, carboxyl group , an optionally halogenated $C_{1-4}$ alkyl (e.g. trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3], etc., and the number of the substituents are preferably 1 to 3.

Examples of the substituents in the optionally substituted thiol group as the substituents for $R^1$ are similar to the above-described substituents in the optionally substituted hydroxy group as the substituents for $R^1$, and among others, (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted aralkyl (e.g. phenyl-$C_{1-4}$ alkyl (e.g. benzyl, phenethyl, etc.), etc.);

(4) an optionally substituted aryl (e.g. phenyl, naphthyl, etc.); etc. are preferable.

Examples of the substituents which the above-mentioned (1) optionally substituted alkyl, (2) optionally substituted cycloalkyl, (3) optionally substituted aralkyl and (4) optionally substituted aryl may have include halogen (e.g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g. trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the substituents in the optionally substituted amino group as the substituents for $R^1$ are similar to the above-described substituents in the optionally substituted hydroxy group as the substituents for $R^1$, and examples of the optionally substituted amino group as the substituents for $R^1$ include an amino group which may have one to two substituents selected from the above-described substituents in the optionally substituted hydroxy group as the substituents for $R^1$, etc. Among others, as the substituents in the optionally substituted amino group as the substituents for $R^1$, (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted alkenyl (e.g. $C_{2-10}$ alkenyl such as allyl, crotyl, 2-pentenyl, 3-hexenyl, etc., preferably lower ($C_{2-6}$) alkenyl, etc.);

(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(5) formyl or an optionally substituted acyl (e.g. $C_{2-4}$ alkanoyl (e.g. acetyl, propionyl, butyryl, isobutyryl, etc.), $C_{1-4}$ alkylsulfonyl (e.g. methanesulfonyl, ethanesulfonyl, etc.), etc.);

(6) an optionally substituted aryl (e.g. phenyl, naphthyl, etc.); etc. are preferable.

Examples of the substituents, which each of the above-described (1) optionally substituted alkyl, (2) optionally substituted cycloalkyl, (3) optionally substituted alkenyl, (4) optionally substituted cycloalkenyl, (5) optionally substituted acyl and (6) optionally substituted aryl may have, include halogen (e.g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g. trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

The substituents in the optionally substituted amino group as the substituents for $R^1$ may bind to each other to form a cyclic amino group (e.g. 5- to 6-membered cyclic amino, etc. such as tetrahydropyrrole, piperazine, piperidine, morpholine, thiomorpholine, pyrrole, imidazole, etc.). Said cyclic amino group may have a substituent, and examples of the substituents include halogen (e.g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g. trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the optionally substituted acyl as the substituents for $R^1$ include a carbonyl group or a sulfonyl group binding to (1) hydrogen;

(2) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(3) an optionally substituted cycloalkyl (e.g. $C_{3-7}$ cycloalkyl, etc. such as cyclopropyl, cyclobutyl, cyclopentyl, cyclohexyl, cycloheptyl, etc.);

(4) an optionally substituted alkenyl (e.g. $C_{2-10}$ alkenyl such as allyl, crotyl, 2-pentenyl,3-hexenyl, etc., preferably lower ($C_{2-6}$) alkenyl, etc.);

(5) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(6) an optionally substituted 5- to 6-membered monocyclic aromatic group (e.g. phenyl, pyridyl, etc.); etc.

Examples of the acyl include acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, methanesulfonyl, ethanesulfonyl, etc.

Examples of the substituents, which the above-mentioned (2) optionally substituted alkyl, (3) optionally substituted cycloalkyl, (4) optionally substituted alkenyl, (5) optionally substituted cycloalkenyl and (6) optionally substituted 5- to 6-membered monocyclic aromatic group may have, include halogen (e.g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g. trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the optionally esterified carboxyl group as the substituents for $R^1$ include a carbonyloxy group binding to (1) hydrogen;

(2) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(3) an optionally substituted cycloalkyl (e.g. $C_{3-7}$ cycloalkyl, etc. such as cyclopropyl, cyclobutyl, cyclopentyl, cyclohexyl, cycloheptyl, etc.);

(4) an optionally substituted alkenyl (e.g. $C_{2-10}$ alkenyl such as allyl, crotyl, 2-pentenyl,3-hexenyl, etc., preferably lower ($C_{2-6}$) alkenyl, etc.);

(5) an. optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(6) an optionally substituted aryl (e.g. phenyl, naphthyl, etc.); etc., and preferably carboxyl, lower ($C_{1-6}$) alkoxycarbonyl, aryloxycarbonyl (e.g. methoxycarbonyl, ethoxycarbonyl, propoxycarbonyl, phenoxycarbonyl, naphthoxycarbonyl, etc.), etc.

Examples of the substituents, which the above-mentioned (2) optionally substituted alkyl, (3) optionally substituted cycloalkyl, (4) optionally substituted alkenyl, (5) optionally substituted cycloalkenyl and (6) optionally substituted aryl may have, include halogen (e.g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g. trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e. g. methanesulfonyl, ethanesulfonyl, etc.), etc., and the number of the substituents are preferably 1 to 3.

Examples of the optionally amidated carboxyl group as the substituents for $R^1$ include an carbonyl group binding to an optionally substituted amino group, etc. which is similar to the above-described "optionally substituted amino group as the substituents for $R^1$", and among others, carbamoyl, mono-$C_{1-6}$ alkylcarbamoyl, di-$C_{1-6}$ alkylcarbamoyl, etc. are preferable.

Examples of the aromatic group in the optionally substituted aromatic group as the substituents for $R^1$ include 5- to 6-membered aromatic homocyclic or heterocyclic ring such as phenyl, pyridyl, furyl, thienyl, pyrrolyl, imidazolyl, pyrazolyl, thiazolyl, oxazolyl, isothiazolyl, isoxazolyl, tetrazolyl, pyrazinyl, pyrimidinyl, pyridazinyl, triazolyl, etc.; fused aromatic heterocyclic ring such as benzofuran, indole, benzothiophene, benzoxazole, benzothiazole, indazole, benzimidazole, quinoline, isoquinoline, quinoxaline, phthalazine, quinazoline, cinnoline, etc.; etc.

Examples of the substituents for these aromatic group include halogen (e.g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g. trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

The number of the above-mentioned substituents for $R^1$ is 1–4 (preferably 1–2) and they may be same or different and present at any possible position on the ring represented by $R^1$. When two or more substituents are present on the 5-to 6-membered ring in the "an optionally substituted 5- to 6-membered ring" represented by $R^1$, two substituents among them may bind to each other to form a lower ($C_{1-6}$) alkylene (e.g. trimethylene, tetramethylene, etc.), a lower ($C_{1-6}$) alkyleneoxy (e.g. —CH$_2$—O—CH$_2$—, —O—CH$_2$—CH$_2$—, —O—CH$_2$—CH$_2$—CH$_2$—, —O—CH$_2$—CH$_2$—CH$_2$—CH$_2$—, —O—CH(CH$_3$)(CH$_3$)—CH$_2$—CH$_2$—, etc.), a lower ($C_{1-6}$) alkylenethio (e.g. —CH$_2$—S—CH$_2$—, —S—CH$_2$—CH$_2$—, —S—CH$_2$—CH$_2$—CH$_2$—, —S—CH$_2$—CH$_2$—CH$_2$—CH$_2$—, —S—CH(CH$_3$)(CH$_3$)—CH$_2$—CH$_2$—, etc.), a lower ($C_{1-6}$) alkylenedioxy (e.g. —O—CH$_2$—O—, —O—CH$_2$—CH$_2$—O—, —O—CH$_2$—CH$_2$—CH$_2$—O—; etc.), a lower ($C_{1-6}$) alkylenedithio (e.g. —S—CH$_2$—S—, —S—CH$_2$—CH$_2$—S—, —S—CH$_2$—CH$_2$—CH$_2$—S—, etc.), an oxy-lower ($C_{1-6}$) alkylene-amino (e.g. —O—CH$_2$—NH—, —O—CH$_2$—CH$_2$—NH—, etc.), an oxy-lower ($C_{1-6}$) alkylene-thio (e.g. —O—CH$_2$—S—, —O—CH$_2$—CH$_2$—S—, etc.), a lower ($C_{1-6}$) alkylene-amino (e.g. —NH—CH$_2$—CH$_2$—, —NH—CH$_2$—CH$_2$—CH$_2$—, etc.), a lower ($C_{1-6}$) alkylene-diamino (e.g. —NH—CH$_2$—NH—, —NH—CH$_2$—CH$_2$—NH—, etc.), a thia-lower ($C_{1-6}$) alkylene-amino (e.g. —S—CH$_2$—NH—, —S—CH$_2$—CH$_2$—NH—, etc.), a lower ($C_{2-6}$) alkenylene (e.g. —CH$_2$—CH=CH—, —CH$_2$—CH$_2$—CH=CH—, —CH$_2$—CH=CH—CH$_2$—, etc.), a lower ($C_{4-6}$) alkadienylene (e.g. —CH=CH—CH=CH—, etc.), etc.

When two substituents of $R^1$ bind to each other to form a divalent group containing a hetero-atom (oxygen atom, sulfur atom, nitrogen atom, etc.), said divalent group may contain a unsaturated bond. Examples of the divalent group containing a hetero-atom and a unsaturated bond include —O—CH=CH—, —O—CH=CH—CH$_2$—, —O—CH$_2$—CH=CH—, —S—CH=CH—, —S—CH=CH—CH$_2$—, —S—CH$_2$—CH=CH—, —O—CH=CH—O—, —O—CH=CH—CH$_2$—O—, —S—CH=CH—S—, —S—CH=CH—CH$_2$—S—, —O—CH=N—, —O—CH$_2$—CH=N—, —O—CH=CH—NH—, —S—CH=N—, —S—CH$_2$—CH=N—, —S—CH=CH—NH—, —O—CH=CH—S—, —N—CH—CH$_2$—, —NH—CH=CH—, —N=CH—CH$_2$—CH$_2$—, —NH—CH=CH—CH$_2$—, —NH—CH$_2$—CH=CH—, —N=CH—NH—, —NH—CH=CH—NH—, —N=CH—CH$_2$—NH—, (preferably, —O—CH=CH—, —S—CH=CH—, —O—CH=N—, —S—CH=N—, etc.), etc.

The divalent group formed by two substituents of $R^1$ binding to each other may have 1–3 substituents similar to the substituents, which the "5- to 6-membered ring" in the "optionally substituted 5- to 6-membered ring" represented by $R^1$ may have, such as halogen atom, nitro, cyano, an optionally substituted alkyl, an optionally substituted cycloalkyl, an optionally substituted hydroxy group, an optionally substituted thiol group wherein a sulfur atom may be optionally oxidized to form a sulfinyl group or a sulfonyl group, an optionally substituted amino group, an optionally substituted acyl, an optionally esterified or amidated carboxyl group, an optionally substituted aromatic group, etc.

Preferred examples of the "substituents", which the "5- to 6-membered ring" in the "an optionally substituted 5- to 6-membered ring" represented by $R^1$ may have, include a lower ($C_{1-4}$) alkyl optionally substituted with a halogen or a lower ($C_{1-4}$) alkoxy (e.g. methyl, ethyl, t-butyl, trifluoromethyl, methoxymethyl, ethoxymethyl, propoxymethyl, butoxymethyl, methoxyethyl, ethoxyethyl, propoxyethyl, butoxyethyl, etc.), a lower ($C_{1-4}$) alkoxy optionally substituted with a halogen or a lower ($C_{1-4}$) alkoxy (e.g. methoxy, ethoxy, propoxy, isopropoxy, butoxy, t-butoxy, trifluoromethoxy, methoxymethoxy, ethoxymethoxy, propoxymethoxy, butoxymethoxy, methoxyethoxy, ethoxyethoxy, propoxyethoxy, butoxyethoxy, methoxypropoxy, ethoxypropoxy, propoxypropoxy, butoxypropoxy, etc.), halogen (e.g. fluorine, chlorine, etc.), nitro, cyano, an amino group optionally substituted with 1–2 lower ($C_{1-4}$) alkyl groups, lower ($C_{1-4}$) alkoxy-lower ($C_{1-4}$) alkyl groups, formyl groups or lower ($C_{2-4}$) alkanoyl groups (e.g. amino, methylamino, dimethylamino, formylamino, acetylamino, etc.), 5- to 6-membered cyclic amino (e.g. 1-pyrrolidinyl, 1-piperazinyl, 1-piperidinyl, 4-morpholino, 4-thiomorpholino, 1-imidazolyl, 4-tetrahydropyranyl, etc.), etc., and when $R^1$ is a benzene, the "substituent" is preferably present at para position.

In the above formula (I), examples of the substituents which the "6- to 7-membered ring" in the "optionally substituted 6- to 7-membered ring" represented by A may have are similar to those which the "5- to 6-membered ring" in the "optionally substituted 5- to 6-membered ring" represented by $R^1$ may have The number of said substituents for the ring A is 1–3 (preferably 1–2), and they may be same or different and present at any possible position on the ring represented by A.

In the group of the formula:

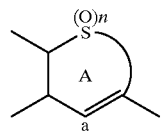

represented by A, a carbon atom at the position a is preferably unsubstituted.

Examples of the "6- to 7-membered ring" in the "optionally substituted 6- to 7-membered ring" represented by A include a 6- to 7-membered ring group of the formula:

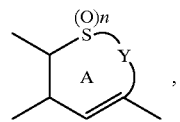

which may have a substituent at any possible position, etc.

In the above formula, the divalent group represented by Y may be any divalent group as far as the ring A forms an optionally substituted 6- to 7-membered ring, and preferred examples of the divalent groups include (1) —$CH_2$—O—;

(2) —$CH_2$—S—;

(3) —$(CH_2)_{d1}$— ($d_1$ is 1 or 2), —CH=CH—;

(4) —$(CH_2)_{e1}$—NH—$(CH_2)_{e2}$— ($e_1$ and $e_2$ are same or different and one of them is 0 and the other one is 0 or 1), —N=CH—, —CH=N—; etc. More preferred examples of the divalent groups include —$CH_2$—O—, —$CH_2$—S—, $CH_2$—, —$(CH_2)_2$—, —CH=CH—, —NH—, —N=CH—, —CH=N—, etc.

The divalent group may have a substituent. Examples of the substituent include those for the "5- to 6-membered ring" in the "optionally substituted 5- to 6-membered ring" represented by $R^1$ and an oxo group, etc. Among others, a lower ($C_{1-3}$) alkyl (e.g. methyl, ethyl, propyl, etc.), a phenyl group, an oxo group, a hydroxy group, etc. are preferable. In addition, the divalent group may be —O—C(O)— etc. The number of the substituents are preferably 1 to 2, and they may be same or different and bind to the divalent group at any possible position.

As the divalent group represented by Y, a group of the formula: —$(CH_2)_m$— (m is an integer of 1 or 2), —CH=CH—, —N=CH—, etc. is preferable. Among others, a group of the formula: —$(CH_2)_m$— (m is an integer of 1 or 2), etc. is preferable. In particular, Y is preferably —$(CH_2)_2$—.

Examples of the "substituents", which the "benzene ring" in the "optionally substituted benzene ring" represented by B may have, include those for the "5- to 6-membered ring" in the "optionally substituted 5- to 6-membered ring" represented by $R^1$, etc. Among others, halogen (e.g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g. trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc. are preferable and in particular, halogen, an optionally halogenated $C_{1-4}$ alkyl, an optionally halogenated $C_{1-4}$ alkoxy, etc. are preferable. The number of the substituents are preferably 1 to 3.

In the above formula (I), n is an integer of 1 or 2 (preferably, 2).

In the above formula (I), examples of the divalent group represented by Z include an optionally substituted divalent group whose straight chain is constituted by 1 to 4 carbon atoms (e.g. $C_{1-4}$ alkylene, $C_{2-4}$ alkenylene, etc., preferably $C_{1-3}$ alkylene, more preferably methylene), etc.

The divalent group represented by Z may be any divalent group whose straight chain is constituted by 1 to 4 atoms and exemplified by an alkylene chain of the formula: $-(CH_2)_{k1}-$ ($k_1$ is an integer of 1–4), an alkenylene chain of the formula: $-(CH_2)_{k2}-(CH=CH)-(CH_2)-$ ($k_2$ and $k_3$ are same or different and 0, 1 or 2, provided that the sum of $k_2$ and $k_3$ is 2 or less), etc.

Examples of the substituent for the divalent group represented by Z include any one which is capable of binding to the straight chain of the divalent group, and preferably $C_{1-6}$ lower alkyl (e.g. methyl, ethyl, propyl, isopropyl, butyl, isobutyl, sec-butyl, tert-butyl, pentyl, isopentyl, neopentyl, hexyl, etc.), lower ($C_{3-7}$) cycloalkyl (e.g. cyclopropyl, cyclobutyl, cyclopentyl, cyclohexyl, cycloheptyl, etc.), formyl, lower ($C_{2-7}$) alkanoyl (e.g. acetyl, propionyl, butyryl, etc.), an optionally esterified phosphono group, an optionally esterified carboxyl group, hydroxy group, oxo, etc., and more preferably $C_{1-6}$ lower alkyl (preferably $C_{1-3}$ alkyl), hydroxy group, oxo, etc.

Examples of the optionally esterified phosphono group include a group of the formula: $P(O)(OR^7)(OR^8)$ wherein $R^7$ and $R^8$ are independently hydrogen, a $C_{1-6}$ alkyl group or a $C_{3-7}$ cycloalkyl group, and $R^7$ and $R^8$ may bind to each other to form a 5- to 7-membered ring.

In the above formula, examples of the $C_{1-6}$ alkyl group represented by $R^7$ and $R^8$ include methyl, ethyl, propyl, isopropyl, butyl, isobutyl, sec-butyl, tert-butyl, pentyl, isopentyl, neopentyl, hexyl, etc., and examples of the $C_{3-7}$ cycloalkyl include cyclopropyl, cyclobutyl, cyclopentyl, cyclohexyl, cycloheptyl, etc. Among other, a straight $C_{1-6}$ lower alkyl is preferable and $C_{1-3}$ lower alkyl is more preferable. The groups $R^7$ and $R^8$ may be same or different, and preferably the groups $R^7$ and $R^8$ are same. When $R^7$ and $R^8$ may bind to each other to form a 5- to 7-membered ring, the groups $R^7$ and $R^8$ bind to each other to represent a straight $C_{2-4}$ alkylene chain of the formula: $-(CH_2)_2-$, $-(CH_2)_3-$, $-(CH_2)_4-$, etc. Said chain may have a substituent, and examples of the substituent include hydroxy group, halogen, etc.

Examples of the optionally esterified carboxyl group include a carboxyl group and an ester group formed by binding a carboxyl group to a $C_{1-6}$ alkyl group or a $C_{3-7}$ cycloalkyl group (e.g. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, etc.).

As the divalent group represented by Z, an optionally substituted $C_{1-3}$ alkylene is preferable, and $C_{1-3}$ alkylene which may be substituted by $C_{1-3}$ alkyl, hydroxy group or oxo is more preferable.

Among others, as the divalent group represented by Z, a group of the formula: $-Z'-(CH_2)n'-$ or $-(CH_2)n'-Z'-$ (Z' is $-CH(OH)-$, $-C(O)-$ or $-CH_2-$, and n' is an integer of 0–2) in which each of the above formulas represent that it binds to the benzene ring through its left chemical bond and each of the methylene groups may be substituted by 1–2 same or different substituents is preferable, a group of the formula: $-Z'-(CH_2)n'-$ (Z' is $-CH(OH)-$, $-C(O)-$ or $-CH_2-$, and n' is an integer of 0–2 (preferably, n is 0)) in which the formula binds to the benzene ring through its left chemical bond and each of the methylene groups may be substituted by 1–2 same or different substituents is more, preferable, and methylene is particularly preferable.

In the above-mentioned formula (I), examples of the "amino group" in the "optionally substituted amino group in which a nitrogen atom may form a quaternary ammonium (preferably, optionally substituted amino group)" represented by $R^2$ include an amino group which may have 1–2 substituents, an amino group having 3 substituents wherein the nitrogen atom forms a quaternary ammonium, etc. When the number of the substituents on the nitrogen atom is 2 or more, these substituents may be same or different. When the total number of the substituents and hydrogen atoms on the nitrogen atom is 3, the "amino group" represented by $R^2$ may be any type of an amino group represented by the formula: $-N^+R_3$, $-N^+RR'$ or $-N^+R_2R'R''$ (R, R' and R'' are independently a hydrogen atom or a substituent). Examples of the counter anion of the amino group wherein the nitrogen atom forms a quaternary ammonium include an anion of a halogen atom (e.g. Cl⁻, Br⁻, I⁻, etc.), etc., and also an anion derived from an inorganic acid such as hydrochloric acid, hydrobromic acid, nitric acid, sulfuric acid, phosphoric acid, etc.; an anion derived from an organic acid such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.; an anion derived from an acidic amino acid such as aspartic acid, glutamic acid, etc.; etc. Among others, Cl⁻, Br⁻, I⁻, etc. are preferable.

Examples of the substituents for said amino group include (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-8}$ cycloalkyl, etc. such as cyclopropyl, cyclobutyl, cyclopentyl, cyclohexyl, cycloheptyl, cyclooctyl, etc.), provided that (2-1) said cycloalkyl may contain one hetero-atom selected from a sulfur atom, an oxygen atom and a nitrogen atom to form oxirane, thiorane, aziridine, tetrahydrofuran, tetrahydrothiophene, pyrrolidine, tetrahydropyran, tetrahydrothiopyran, tetrahydrothiopyran 1-oxide, piperidine, etc. (preferably, 6-membered ring such as tetrahydropyran, tetrahydrothiopyran, piperidine, etc.) and these groups preferably bind to the amino group at their 3- or 4-position (preferably, 4-position), that (2-2) said cycloalkyl may be fused with a benzene ring to form indane, tetrahydronaphthalene, etc. (preferably, indane, etc.), and that (2-3) said cycloalkyl may have a bridging comprising a straight chain constituted by 1–2 carbon atoms to form a bridged hydrocarbon residue such as bicyclo[2.2.1]heptyl, bicyclo[2.2.2]octyl, bicyclo[3.2.1]octyl, bicyclo[3.2.2] nonyl, etc., preferably, a cyclohexyl group, etc. having a bridging comprising a straight chain constituted by 1–2 carbon atoms, and more preferably bicyclo[2.2.1]heptyl, etc.;

(3) an optionally substituted alkenyl (e.g. $C_{2-10}$ alkenyl such as allyl, crotyl, 2-pentenyl, 3-hexenyl, etc., preferably lower ($C_{2-6}$)alkenyl, etc.);

(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(5) an optionally substituted aralkyl (e.g. phenyl-$C_{1-4}$ alkyl (e.g. benzyl, phenethyl, etc.), etc.);

(6) formyl or an optionally substituted acyl (e.g. $C_{2-4}$ alkanoyl (e.g. acetyl, propionyl, butyryl, isobutyryl, etc.), $C_{1-4}$ alkylsulfonyl (e.g. methanesulfonyl, ethanesulfonyl, etc.), etc.);

(7) an optionally substituted aryl (e.g. phenyl, naphthyl, etc.);

(8) an optionally substituted heterocyclic ring group (e.g. 5- to 6-membered aromatic heterocyclic ring containing 1 to 4 hetero-atoms consisting of 1 to 2 kinds of hetero-atoms selected from oxygen atom, sulfur atom and nitrogen atom such as furan, thiophene, pyrrole, imidazole, pyrazole, thiazole, oxazole, isothiazole, isoxazole, tetrazole, pyridine, pyrazine, pyrimidine, pyridazine, triazole, etc.; 5- to 6-membered non-aromatic heterocyclic ring containing 1 to 4 hetero-atoms consisting of 1 to 2 kinds of hetero-atoms selected from oxygen atom, sulfur atom and nitrogen atom such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, etc.; etc.; preferably 5- to 6-membered non-aromatic heterocyclic ring, etc.; more preferably 5-to 6-membered non-aromatic heterocyclic ring; further more preferably 5- to 6-membered non-aromatic heterocyclic ring containing one hetero-atom, etc. such as tetrahydrofuran, piperidine, tetrahydropyran, tetrahydrothiopyran, etc.); etc.

In addition, the substituents for the amino group may bind to each other to form a 5- to 7-membered cyclic amino group such as piperidine, piperazine, morpholine, thiomorpholine, etc.

Examples of the substituents, which the above-mentioned (1) optionally substituted alkyl, (2) optionally substituted cycloalkyl, (3) optionally substituted alkenyl, (4) optionally substituted cycloalkenyl, (5) optionally substituted aralkyl, (6) optionally substituted acyl, (7) optionally substituted aryl and (8) optionally substituted heterocyclic ring group may have, include halogen (e.g. fluorine, chlorine, bromine, iodine, etc.), an optionally halogenated lower ($C_{1-4}$) alkyl, an optionally halogenated $C_{1-4}$ alkoxy (e.g. methoxy, ethoxy, propoxy, butoxy, trifluoromethoxy, trifluoroethoxy, etc.), $C_{1-4}$ alkylenedioxy (e.g. —O—$CH_2$—O—, —O—$CH_2$—$CH_2$—O—, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), phenyl-lower ($C_{1-4}$) alkyl, $C_{3-7}$ cycloalkyl, cyano, nitro, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), lower ($C_{1-4}$) alkoxy-carbonyl, oxo (preferably, halogen, an optionally halogenated lower ($C_{1-4}$) alkyl, an optionally halogenated lower ($C_{1-4}$) alkoxy, phenyl-lower ($C_{1-4}$) alkyl, $C_{3-7}$ cycloalkyl, cyano, hydroxy group, etc.), etc., and the number of the substituents are preferably 1 to 3.

In the above formula (I), preferred examples of the "optionally substituted amino group in which a nitrogen atom may form a quaternary ammonium" represented by $R^2$ include an amino group which may have 1–3 substituents (preferably 1–2 substituents) selected from the class consisting of (1) a straight or branched lower ($C_{1-6}$) alkyl which may have 1 to 3 substituents selected from halogen, cyano, hydroxy group or $C_{3-7}$ cycloalkyl;

(2) a $C_{5-8}$ cycloalkyl which may have 1 to 3 substituents selected from halogen, an optionally halogenated lower ($C_{1-4}$) alkyl or phenyl-lower ($C_{1-4}$) alkyl, which may contain one hetero-atom selected from a sulfur atom, an oxygen atom and a nitrogen atom, which may be fused with a benzene ring, and which may have a bridging comprising a straight chain constituted by 1–2 carbon atoms (e.g. cyclopentyl, cyclohexyl, cycloheptyl, cyclooctyl, tetrahydropyranyl, tetrahydrothiapyranyl, piperidinyl, indanyl, tetrahydronaphthalenyl, bicyclo[2.2.1]heptyl, etc., each of which may be substituted);

(3) a phenyl-lower ($C_{1-4}$) alkyl which may have 1 to 3 substituents selected from halogen, an optionally halogenated lower ($C_{1-4}$) alkyl or an optionally halogenated lower ($C_{1-4}$) alkoxy;

(4) a phenyl which may have 1 to 3 substituents selected from halogen, an optionally halogenated lower ($C_{1-4}$) alkyl or an optionally halogenated lower ($C_{1-4}$) alkoxy; and (5) a 5- to 6-membered aromatic heterocyclic ring (e.g. furan, thiophene, pyrrole, pyridine, etc.) which may have 1 to 3 substituents selected from halogen, an optionally halogenated lower ($C_{1-4}$) alkyl, an optionally halogenated lower ($C_{1-4}$) alkoxy, an optionally halogenated lower ($C_{1-4}$) alkoxy-lower ($C_{1-4}$) alkoxy, phenyl-lower ($C_{1-4}$) alkyl, cyano or hydroxy group.

In the above formula (I), examples of the "nitrogen-containing heterocyclic ring" in-the "optionally substituted nitrogen-containing heterocyclic ring group which may contain a sulfur atom or an oxygen atom as ring constituting atoms and wherein a nitrogen atom may form a quaternary ammonium (preferably, optionally substituted nitrogen-containing heterocyclic ring group which may contain a sulfur atom or an oxygen atom as ring constituting atoms)" include a 5- to 6-membered aromatic heterocyclic ring which may contain 1 to 3 hetero-atoms consisting of 1 to 2 kinds of hetero-atoms selected from an oxygen atom, a sulfur atom and a nitrogen atom other than one nitrogen atom such as pyrrole, imidazole, pyrazole, thiazole, oxazole, isothiazole, isoxazole, tetrazole, pyridine, pyrazine, pyrimidine, pyridazine, triazole, etc.; 5–8 membered non-aromatic heterocyclic ring which may contain 1 to 3 hetero-atoms consisting of 1 to 2 kinds of hetero-atoms selected from an oxygen atom, a sulfur atom and a nitrogen atom other than one nitrogen atom such as pyrrolidine, pyrroline, imidazolidine, imidazoline, pyrazolidine, pyrazoline, piperidine, piperazine, oxazine, oxadiazine, thiazine, thiadiazine, morpholine, thio-morpholine, azacycloheptane, azacyclooctane (azocane), etc.; etc. These nitrogen-containing heterocyclic rings may have a bridging comprising a straight chain constituted by 1–2 carbon atoms to form a bridged nitrogen-containing heterocyclic ring azabicyclo[2.2.1]heptane, azabicyclo[2.2.2]octane (quinuclidine), etc. (preferably, piperidine having a bridging comprising a straight chain constituted by 1–2 carbon atoms, etc.).

Among the above-exemplified nitrogen-containing heterocyclic rings, pyridine, imidazole, pyrrolidine, piperidine, piperazine, morpholine, thiomorpholine, azabicyclo[2.2.2]octane (preferably, a 6-membered ring) are preferable.

The nitrogen atom of said "nitrogen-containing heterocyclic ring" may form a quaternary ammonium or may be oxidized. When the nitrogen atom of said "nitrogen-containing heterocyclic ring" forms a quaternary ammonium, examples of the counter anion of the "nitrogen-containing heterocyclic ring wherein the nitrogen atom forms a quaternary ammonium" include an anion of a halogen atom (e.g. $Cl^-$, $Br^-$, $I^-$, etc.), etc., and also an anion derived from an inorganic acid such as hydrochloric acid, hydrobromic acid, nitric acid, sulfuric acid, phosphoric acid, etc.; an anion derived from an organic acid such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.; an anion derived from an acidic amino acid such as aspartic acid, glutamic acid, etc.; etc. Among others, Cl$^-$, Br$^-$, I$^-$, etc. are preferable.

Said "nitrogen-containing heterocyclic ring" may bind to the divalent group represented by Z through either a carbon atom or a nitrogen atom, and may be 2-pyridyl, 3-pyridyl, 2-piperidinyl, etc. which binds to the divalent group represented by Z through a carbon atoms. Preferably, the "nitrogen-containing heterocyclic ring" binds to the divalent group represented by Z through a nitrogen atom, as exemplified by the following formulas:

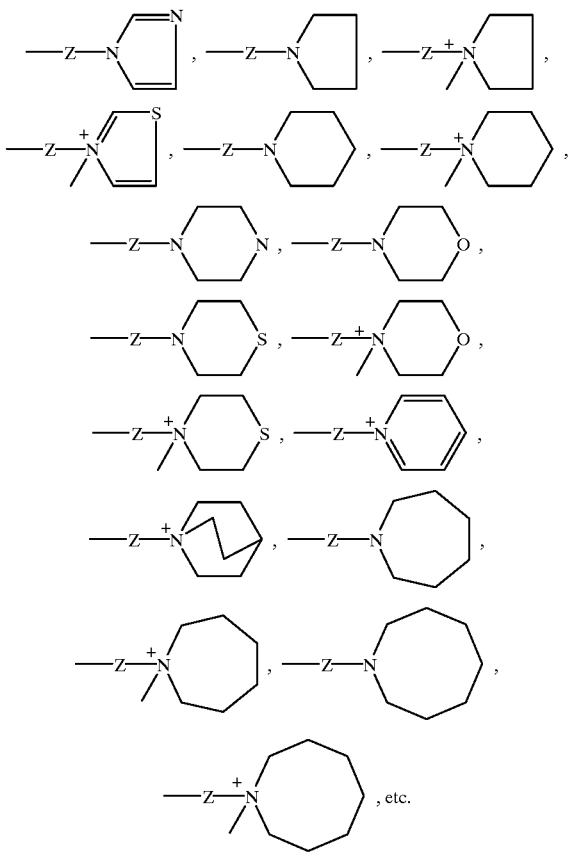

Examples of the substituents, which said "nitrogen containing heterocyclic ring" may have, include halogen (e.g. fluorine, chlorine, bromine, iodine, etc.), an optionally substituted lower ($C_{1-4}$) alkyl, an optionally substituted lower ($C_{1-4}$) alkoxy, an optionally substituted phenyl, an optionally substitutedmono- or di-phenyl-lower ($C_{1-4}$) alkyl, an optionally substituted $C_{3-7}$ cycloalkyl, cyano, nitro, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxycarbonyl, carbamoyl, mono-$C_{1-4}$ alkylcarbamoyl, di-$C_{1-4}$ alkylcarbamoyl, etc.), lower ($C_{1-4}$) alkoxy-carbonyl, formyl, lower ($C_{2-4}$) alkanoyl, lower ($C_{1-4}$) alkylsulfonyl, an optionally substituted heterocyclic ring group (e.g. 5- to 6-membered aromatic heterocyclic ring containing 1 to 4 hetero-atoms consisting of 1 to 2 kinds of hetero-atoms selected from an oxygen atom, a sulfur atom and a nitrogen atom such as furan, thiophene, pyrrole, imidazole, pyrazole, thiazole, oxazole, isothiazole, isoxazole, tetrazole, pyridine, pyrazine, pyrimidine, pyridazine, triazole, etc.; 5- to 6-membered non-aromatic heterocyclic ring containing 1 to 4 hetero-atoms consisting of 1 to 2 kinds of hetero-atoms selected from an oxygen atom, a sulfur atom and a nitrogen atom such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, tetrahydrothiopyran, etc.; etc.), etc., and the number of the substituents is preferably 1–3.

Examples of the substituent, which the "optionally substituted lower ($C_{1-4}$) alkyl", the "optionally substituted lower ($C_{1-4}$) alkoxy", the "optionally substituted phenyl", the "optionally substituted mono- or di-phenyl-lower ($C_{1-4}$) alkyl", the "optionally substituted $C_{3-7}$ cycloalkyl" and the "optionally substituted heterocyclic ring group" as a substituent for said "nitrogen-containing heterocyclic ring" may have, include halogen (e.g. fluorine, chlorine, bromine, iodine, etc.), an optionally halogenated lower ($C_{1-4}$) alkyl, lower ($C_{3-10}$) cycloalkyl, lower ($C_{3-10}$) cycloalkenyl, an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), $C_{1-3}$ alkylenedioxy (e.g. methylenedioxy, ethylenedioxy, etc.), cyano, nitro, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), lower ($C_{1-4}$) alkoxy-carbonyl, etc., and the number of the substituents are preferably 1 to 3. In addition, the nitrogen atom in said "nitrogen-containing heterocyclic ring" may be oxidized.

In the above formula (I), preferred example of the substituents for the "nitrogen-containing heterocyclic ring" in the "optionally substituted nitrogen-containing heterocyclic ring group which may contain a sulfur atom or an oxygen atom as ring constituting atoms and wherein a nitrogen atom may form a quaternary ammonium" include (1) halogen, (2) cyano, (3) hydroxy group, (4) carboxyl group, (5) lower ($C_{1-4}$) alkoxy-carbonyl, (6) lower ($C_{1-4}$) alkyl which may be substituted with halogen, hydroxy group or lower ($C_{1-4}$) alkoxy, (7) lower ($C_{1-4}$) alkoxy which may be substituted with halogen, hydroxy group or lower ($C_{1-4}$) alkoxy, (8) phenyl which may be substituted with halogen, lower ($C_{1-4}$) alkyl, hydroxy group, lower ($C_{1-4}$) alkoxy or $C_{1-3}$ alkylenedioxy, (9) mono- or di-phenyl-lower ($C_{1-4}$) alkyl whose benzene ring may be substituted with halogen, lower ($C_{1-4}$) alkyl, hydroxy group, lower ($C_{1-4}$) alkoxy or $C_{1-3}$ alkylenedioxy, (10) 5- to 6-membered aromatic heterocyclic ring such as furan, thiophene, pyrrole, pyridine, etc., etc.

In the above formula (I), examples of the "group binding through a sulfur atom'" represented by R$^2$ include a group of the formula: —S(O)$_m$—R$^s$ wherein m is an integer of 0–2, and R$^s$ is a substituent.

In the above formula, preferred examples of the "substituent" represented by $R^5$ include (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted aralkyl (e.g. phenyl-$C_{1-4}$ alkyl (e.g. benzyl, phenethyl, etc.), etc.);

(4) an optionally substituted aryl (e.g. phenyl, naphthyl, etc.) etc.

Examples of the substituent, which the above-mentioned (1) optionally substituted alkyl, (2) optionally substituted cycloalkyl, (3) optionally substituted aralkyl and (4) an optionally substituted aryl may have, include halogen (e.g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g. trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

In the above formula (I), examples of the "hydrocarbon group" in the "optionally substituted hydrocarbon group" represented by $R^5$ and $R^6$ of the "group of the formula:

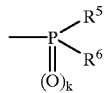

wherein k is 0 or 1, and when k is 0, a phosphorus atom may form a phosphonium (preferably, a phosphorus atom does not form a phosphonium); and $R^5$ and $R^6$ are independently an optionally substituted hydrocarbon group, an optionally substituted hydroxy group or an optionally substituted amino group (preferably, an optionally substituted hydrocarbon group or an optionally substituted amino group), and $R^5$ and $R^6$ may bind to each other to form a cyclic group together with the adjacent phosphorus atom" represented by $R^2$ include (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted alkenyl (e.g. $C_{2-10}$ alkenyl such as allyl, crotyl, 2-pentenyl, 3-hexenyl, etc., preferably lower ($C_{2-6}$) alkenyl, etc.);

(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(5) an optionally substituted alkynyl (e.g. $C_{2-10}$ alkynyl such as ethynyl, 1-propynyl, 2-propynyl, 1-butynyl, 2-pentynyl, 3-hexynyl, etc., preferably lower ($C_{2-6}$) alkynyl, etc.);

(6) an optionally substituted aralkyl (e.g. phenyl-$C_{1-4}$ alkyl (e.g. benzyl, phenethyl, etc.), etc.);

(7) an optionally substituted aryl (e.g. phenyl, naphthyl, etc.); etc.

Examples of the substituents, which the above-mentioned (1) optionally substituted alkyl, (2) optionally substituted cycloalkyl, (3) optionally substituted alkenyl, (4) optionally substituted cycloalkenyl, (5) optionally substituted alkynyl, (6) optionally substituted aralkyl and (7) optionally substituted aryl may have, include halogen (e.g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-6}$ alkylcarbamoyl, etc.), an optionally halogenated $C_{1-4}$ alkyl (e.g. trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the "optionally substituted hydroxy group" represented by $R^5$ and $R^6$ include a hydroxy group which may have (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted alkenyl (e.g. $C_{2-10}$ alkenyl such as allyl, crotyl, 2-pentenyl, 3-hexenyl, etc., preferably lower ($C_{2-6}$) alkenyl, etc.);

(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(5) an optionally substituted aralkyl (e.g. phenyl-$C_{1-4}$ alkyl (e.g. benzyl, phenethyl, etc.), etc.);

(6) formyl or an optionally substituted acyl (e.g. $C_{2-4}$ alkanoyl (e.g. acetyl, propionyl, butyryl, isobutyryl, etc.), $C_{1-4}$ alkylsulfonyl (e.g. methanesulfonyl, ethanesulfonyl, etc.), etc.);

(7) an optionally substituted aryl (e.g. phenyl, naphthyl, etc.); etc.

Examples of the substituents, which the above-mentioned (1) optionally substituted alkyl, (2) optionally substituted cycloalkyl, (3) optionally substituted alkenyl, (4) optionally substituted cycloalkenyl, (5) optionally substituted aralkyl, (6). optionally substituted acyl and (7) optionally substituted aryl may have, include halogen (e.g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g. trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the "optionally substituted amino group" represented by $R^5$ and $R^6$ include an amino group which may have (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted alkenyl (e.g. $C_{2-10}$ alkenyl such as allyl, crotyl, 2-pentenyl,3-hexenyl, etc., preferably lower ($C_{2-6}$)alkenyl, etc.);

(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(5) formyl or an optionally substituted acyl (e.g. $C_{2-4}$ alkanoyl (e.g. acetyl, propionyl, butyryl, isobutyryl, etc.), $C_{1-4}$ alkylsulfonyl (e.g. methanesulfonyl, ethanesulfonyl, etc.), etc.);

(6) an optionally substituted aryl (e.g. phenyl, naphthyl, etc.); etc.

Examples of the substituents, which the above-mentioned (1) optionally substituted alkyl, (2) optionally substituted cycloalkyl, (3) optionally substituted alkenyl, (4) optionally substituted cycloalkenyl, (5)optionally substituted acyl and (6) optionally substituted aryl may have, include halogen (e.g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5-to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g. trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

In the above formula, the groups $R^5$ and $R^6$ may bind to each other to form a cyclic group (preferably, 5- to 7-membered ring) together with the adjacent phosphorus atom. Said cyclic group may have a substituent. Examples of the substituent include halogen (e.g. fluorine, chlorine, bromine, iodine, etc.), nitro, cyano, hydroxy group, an optionally substituted thiol group (e.g. thiol, $C_{1-4}$ alkylthio, etc.), an optionally substituted amino group (e.g. amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g. trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

In the above formula (I), examples of the counter anion, when the phosphorus atom forms a phosphonium, include an anion of a halogen atom (e.g. $Cl^-$, $Br^-$, $I^-$, etc.), etc., and also an anion derived from an inorganic acid such as hydrochloric acid, hydrobromic acid, nitric acid, sulfuric acid, phosphoric acid, etc.; an anion derived from an organic acid such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.; an anion derived from an acidic amino acid such as aspartic acid, glutamic acid, etc.; etc. Among others, $Cl^-$, $Br^-$, $I^-$, etc. are preferable.

As the group $R^2$, (1) an optionally substituted amino group wherein a nitrogen atom may form a quaternary ammonium (preferably, an optionally substituted amino group), (2) an optionally substituted nitrogen-containing heterocyclic ring group which may contain a sulfur atom or an oxygen atom as ring constituting atoms and wherein a nitrogen atom may form a quaternary ammonium (preferably, an optionally substituted nitrogen-containing heterocyclic ring group which may contain a sulfur atom or an oxygen atom as ring constituting atoms) and (3) a group of the formula:

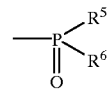

wherein $R^5$ and $R^6$ are independently an optionally substituted hydrocarbon group, and $R^5$ and $R^6$ may bind to each other to form a cyclic group together with the adjacent phosphorus atom are preferable.

As the group $R^2$, (1) an optionally substituted amino group in which a nitrogen atom does not form a quaternary ammonium is preferable, and a group of the formula: —NRR' wherein R and R' are independently an optionally substituted aliphatic (acyclic and alicyclic) hydrocarbon group or an optionally substituted alicyclic (non-aromatic) heterocyclic ring group is more preferable.

Examples of the "optionally substituted aliphatic hydrocarbon group" and the "optionally substituted alicyclic heterocyclic ring group" represented by R or R' include the "optionally substituted aliphatic (non-aromatic) hydrocarbon group" (e.g. alkyl, cycloalkyl, alkenyl, cycloalkenyl, etc., each of which may be substituted) and the "optionally substituted alicyclic heterocyclic ring group" (e.g. an optionally substituted 5- to 6-membered non-aromatic heterocyclic ring, etc.), respectively exemplified by the substituents for the "optionally substituted amino" represented by $R^2$.

Among them, as the group R, an optionally substituted acyclic hydrocarbon group (e.g. alkyl, alkenyl, etc., each of which may be substituted) is preferable, an optionally substituted $C_{1-6}$ alkyl group is more preferable, and an optionally substituted methyl is most preferable; and as the group R', an optionally substituted acyclic hydrocarbon group (e.g. alkyl, alkenyl, etc., each of which may be substituted; more preferably, an optionally substituted $C_{1-6}$ alkyl group; further more preferably, an optionally substituted ethyl), an optionally substituted alicyclic hydrocarbon group (e.g. cycloalkyl, cycloalkenyl, etc., each of which may be substituted; more preferably, an optionally substituted $C_{3-8}$ cycloalkyl group; further more preferably, an optionally substituted cyclohexyl) or an optionally substituted alicyclic (non-aromatic) heterocyclic ring group (more preferably, an optionally substituted saturated heterocyclic ring group (preferably 6-membered ring group); further more preferably, an optionally substituted tetrahydropyranyl, an optionally substituted tetrahydrothiopyranyl or an optionally substituted piperidyl: most preferably, an optionally substituted tetrahydropyranyl) is preferable.

Among them, as the group R', an optionally substituted alicyclic hydrocarbon group or an optionally substituted alicyclic (non-aromatic) heterocyclic ring group is preferable.

Examples of the salts of the compound represented by the formula (I) include a pharmaceutically acceptable salt such as a salt with inorganic base, a salt with organic base, a salt with inorganic acid, a salt with organic acid, a salt with basic or acidic amino acid, etc. Examples of the salt with the inorganic base include a salt with alkali metal (e.g. sodium, potassium, etc.), alkaline earth metal (e.g. calcium, magnesium, etc.), aluminum, ammonium, etc. Examples of the salt with the organic base include a salt with trimethylamine, triethylamine, pyridine, picoline, ethanolamine, diethanolamine, triethanolamine, dicyclohexylamine, N,N'-dibenzylethylenediamine, etc. Examples of the salt with the inorganic acid include a salt with hydrochloric acid, hydrobromic acid, nitric acid, sulfuric acid, phosphoric acid, etc. Examples of the salt with the organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Examples of the salt with the basic amino acid include a salt with arginine, lysine, ornithine, etc. Examples of the salt with the acidic amino acid include a salt with aspartic acid, glutamic acid, etc.

The compound of the formula (I) of the present invention may be hydrated or solvated. When the compound of the formula (I) of the present invention exists as configuration isomer, diastereomer, conformer, etc., it is possible to isolate individual isomers with per se known separation and purification method, if desired. When the compound of the formula (I) of the present invention is racemate, it can be separated into (S)-compound and (R)-compound with usual optical resolution and individual optical isomers and a mixture thereof are included in the scope of the present invention.

The pro-drug of the compound of the formula (I) or a salt thereof of the present invention [hereinafter, referred to as Compound (I)] means a compound which is converted to Compound (I) under the physiological condition or with a reaction due to an enzyme, an gastric acid, etc. in the living body, that is, a compound which is converted to Compound (I) with oxidation, reduction, hydrolysis, etc. according to an enzyme; a compound which is converted to Compound (I) with gastric acid, etc.; etc.

Examples of the pro-drug of Compound (I) include a compound wherein an amino group of Compound (I) is substituted with acyl, alkyl, phosphoric acid, etc. (e.g. a compound wherein an amino group of Compound (I) is substituted with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl, etc.); a compound wherein an hydroxy group of Compound (I) is substituted with acyl, alkyl, phosphoric acid, boric acid, etc. (e.g. a compound wherein an hydroxy group of Compound (I) is substituted with acetyl, palmitoyl, propanoyl, pivaloyl, succinyl, fumaryl, alanyl, dimethylaminomethylcarbonyl, etc.); a compound wherein a carboxyl group of Compound (I) is modified with ester, amide, etc. (e.g. a compound wherein a carboxyl group of Compound (I) is modified with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.); etc. These pro-drug can be produced by per se known method from Compound (I).

The pro-drug of Compound (I) may be a compound which is converted into Compound (I) under the physiological conditions as described in "Pharmaceutical Research and Development", Vol. 7 (Drug Design), pages 163–198 published in 1990 by Hirokawa Publishing Co. (Tokyo, Japan).

Compound (I) may be labeled with isotope (e.g. $^3H$, $^{14}C$, $^{35}S$, $^{125}I$, etc.), etc.

The present compound of the formula (I) or a salt thereof (hereinafter, "Compound (I)" include the compound of the formula (I) and its salt) alone or as an admixture with a pharmaceutically acceptable carrier (e.g. solid formulations such as tablets, capsules, granules, powders, etc.; liquid formulations such as syrups, injections, etc.) may be orally or non-orally administered.

Examples of non-oral formulations include injections, drops, suppositories, pessaries, etc. In particular, pessary is useful for the prevention of infectious disease of HIV.

Examples of the carriers include various organic or inorganic carriers which are generally used in this field. For example, an excipient, a lubricant, a binder, an disintegrating agent, etc. are used in the solid formulations, and a solvent, a solubilizer, a suspending agent, a isotonizing agent, a buffer, a soothing agent, etc. are used in the liquid formulations. In addition, if desired, an appropriate additive such as a preservative, an antioxidant, a colorant, a sweetener, etc. may be used in the above formulations.

Examples of the excipient include lactose, sucrose, D-mannitol, starch, crystalline cellulose, light silic acid anhydride, etc. Examples of the lubricant include magnesium stearate, calcium stearate, talc, colloidal silica, etc. Examples of the binder include crystalline cellulose, sucrose, D-mannitol, dextrin, hydroxypropyl cellulose, hydroxypropylmethyl cellulose, polyvinylpyrrolidone, etc. Examples of the disintegrating agent include starch, carboxymethyl cellulose, carboxymethyl cellulose calcium, croscarmellose sodium, sodium carboxymethyl starch, etc. Examples of the solvent include water for injection, alcohol, propyleneglycol, macrogol, sesame oil, corn oil, etc. Examples of the solubilizer include polyethyleneglycol, propyleneglycol, D-mannitol, benzyl benzoate, ethanol, trisaminomethane, cholesterol, triethanolamine, sodium carbonate, sodium citrate, etc. Examples of the suspending agent include surfactants such as stearyl triethanolamine, sodium laurylsulfate, laurylaminopropionic acid, lecithin, benzalkonium chloride, benzetonium chloride, glycerin monostearate, etc.; hydrophilic polymers such as polyvinylalcohol, polyvinylpyrrolidone, sodium carboxymethyl cellulose, methyl cellulose, hydroxymethyl cellulose, hydroxyethyl cellulose, hydroxypropyl cellulose, etc.; etc. Examples of the isotonizing agent include sodium chloride, glycerin, D-mannitol, etc. Examples of the buffer include a buffer solution of phosphate, acetate, carbonate, citrate, etc. Examples of the soothing agent include benzylalcohol, etc. Examples of the preservative include paraoxybenzoic acid esters, chlorobutanol, benzylalcohol, phenethylalcohol, dehydroacetic acid, sorbic acid, etc. Examples of the antioxidant include sulfites, ascorbic acid, etc.

The present invention further provides production methods of the compound of the formula (I) or a salt thereof.

The compound of the formula (I) or a salt thereof can be produced in accordance with per se known methods, for example, the methods described below, the methods described in JP-A-73476/1996, or analogous methods thereto, etc.

A salt of the compound of the formulas (II), (II'), (III), (IV), (V), (I-1), (I-2), (I-3) and (I-4) may be similar to that of the compound of the formula (I).

In the following reaction steps, when the starting compounds have, as substituents, an amino group, a carboxyl group and/or hydroxy group, these groups may be protected by ordinary protective groups such as those generally employed in peptide chemistry, etc. After the reaction, if necessary, the protective groups may be removed to obtain the desired compound.

Examples of the amino-protective group include an optionally substituted $C_{1-6}$ alkylcarbonyl (e.g. acetyl, propionyl, etc.), formyl, phenylcarbonyl, $C_{1-6}$ alkyloxycarbonyl (e.g. methoxycarbonyl, ethoxycarbonyl, t-butoxycarbonyl, etc.), aryloxycarbonyl (e.g. phenoxycarbonyl, etc.), $C_{7-10}$ aralkyloxycarbonyl (e.g. benzyloxycarbonyl, etc.), trityl, phthaloyl, etc. These protective groups may be substituted by 1 to 3 substituents such as halogen atom (e.g. fluorine, chlorine, bromine, iodine, etc.), $C_{1-6}$ alkylcarbonyl (e.g. acetyl, propionyl, butyryl, etc.), nitro group, etc.

Examples of the carboxyl-protective group include an optionally substituted $C_{1-6}$ alkyl (e.g. methyl, ethyl, propyl, isopropyl, butyl, tert-butyl, etc.), phenyl, trityl, silyl, etc. These protective groups may be substituted by 1 to 3 substituents such as halogen atom (e.g. fluorine, chlorine, bromine, iodine, etc.), $C_{1-6}$ alkylcarbonyl (e.g. acetyl, propionyl, butyryl, etc.), formyl, nitro group, etc.

Examples of the hydroxy-protective group include an optionally substituted $C_{1-6}$ alkyl (e.g. methyl, ethyl, propyl, isopropyl, butyl, tert-butyl, etc.), phenyl, $C_{7-10}$ aralkyl (e.g. benzyl, etc.), $C_{1-6}$ alkylcarbonyl (e.g. acetyl, propionyl, etc.), formyl, phenyloxycarbonyl, $C_{7-10}$ aralkyloxycarbonyl (e.g. benzyloxycarbonyl, etc.), pyranyl, furanyl, silyl, etc. These protective groups may be substituted by 1 to 4 substituents such as halogen atom (e.g. fluorine, chlorine, bromine, iodine, etc.), $C_{1-6}$ alkyl, phenyl, $C_{7-10}$ aralkyl, nitro group, etc.

These protective group may be introduced or removed by per se known methods (e.g. a method described in Protective Groups in Organic Chemistry (J. F. W. McOmie et al.; Plenum Press Inc.) or the methods analogous thereto. For example, employable method for removing the protective groups is a method using an acid, a base, reduction, ultraviolet ray, hydrazine, phenylhydrazine, sodium N-methyldithiocarbamate, tetrabutylammonium fluoride, palladium acetate, etc.

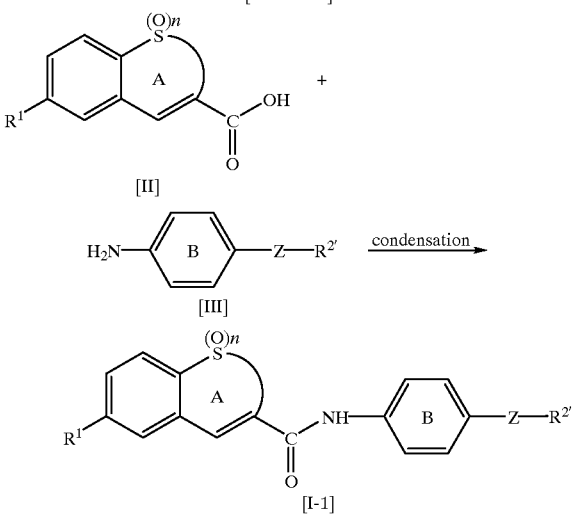

[Method A]

wherein each symbol is as defined above.

This production method is carried out by reacting the compound [II], a salt or a reactive derivative thereof with the aniline derivative [III] or a salt thereof to obtain the anilide Compound [I-1].

The condensation reaction of the compounds [II] and [III] is carried out by usual methods for peptide synthesis. Said methods for peptide synthesis are employed according to optional known methods, for example, methods described in "Peptide Synthesis" written by M. Bodansky and M. A. Ondetti, Interscience, New York, 1966; "The Proteins", volume 2, written by F. M. Finn and K. Hofmann, H. Nenrath and R. L. Hill edition, Academic Press Inc., New York, 1976; "peputido-gosei no kiso to jikken (Basis and Experiment of Peptide Synthesis)" written by Nobuo Izumiya et al., Maruzen K. K. ,1985; etc., as well as azide method, chloride method, acid anhydride method, mixed acid anhydride method, DCC method, active ester method, method using Woodward reagent K, carbonyldiimidazole method, oxidation-reduction method, DCC/HONB method, etc. and in addition WSC method, method using diethyl cyanophosphate (DEPC), etc.

The condensation reaction can be carried out in a solvent. Examples of the solvents to be employed in the reaction include anhydrous or hydrous N,N-dimethylformamide (DMF), dimethylsulfoxide (DMSO), pyridine, chloroform, dichloromethane, tetrahydrofuran (THF), dioxane, acetonitrile, or a suitable mixture of these solvents.

Usually, about 1–2 moles of the Compound [III] are used per 1 mole of the Compound [II]. The reaction temperature is generally about −20° C. to about 50° C., preferably about −10° C., to about 30° C. and the reaction time is generally about 1 to about 100 hours, preferably about 2 to about 40 hours.

The thus obtained anilide derivative [I-1] can be isolated and purified by known separation and purification methods such as concentration, concentration under reduced pressure, extraction, crystallization, recrystallization, solvent convert, chromatography, etc.

In addition, the compound of the formula (II'):

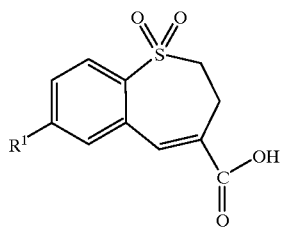

wherein $R^1$ is as defined above or a salt thereof is a novel compound and useful as an intermediate for producing the compound of the formula (I) or a salt thereof.

[Method B]

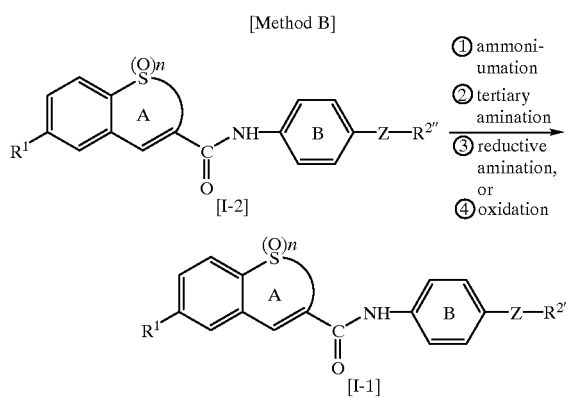

① When the group $R^{2''}$ in Compound [I-2] is, for example, a tertiary amine residue, Compound [I-1] wherein the group $R^{2'}$ is an quaternary ammonium can be produced by reacting Compound [I-2] with halogenated alkyl or halogenated aralkyl. Examples of the halogen atom include chlorine, bromine, iodine, etc. and usually about 1 to 5 moles of the halogenated alkyl (e.g. halogenated lower ($C_{1-6}$) alkyl, etc.) or halogenated aralkyl (e.g. halogenated lower ($C_{1-4}$) alkyl-phenyl, etc.) is used per mole of Compound [I-2]. The reaction is carried out in an inert solvent such as toluene, benzene, xylene, dichloromethane, chloroform, 1,2-dichloroethane, dimethylformamide (DMF), dimethylacetamide, etc., or a suitable mixture of these solvents. The reaction temperature is generally about 10° C. to about 160° C., preferably about 20° C. to about 120° C. and the reaction time is generally about 1 hour to about 100 hours, preferably about 2 hours to about 40 hours. This reaction is preferably carried out under inert gas (e.g. nitrogen, argon, etc.) atmosphere.

② When the group $R^{2''}$ in Compound [I-2] is, for example, a secondary amine residue, Compound [I-1] wherein the group $R^{2'}$ is a tertiary amino can be produced by reacting Compound [I-2] with halogenated alkyl or halogenated aralkyl. Examples of a halogen atom include chlorine, bromine, iodine, etc. and usually about 1 to 2 moles of the halogenated alkyl or halogenated aralkyl is used per mole of Compound [I-2]. If necessary, the reaction smoothly proceeds by addition of about once to 3 times moles of a base such as triethylamine, diisopropylethylamine, pyridine, lithium hydride, sodium hydride, sodium methoxide, sodium ethoxide, sodium carbonate, potassium carbonate, sodium hydrogen carbonate and further sodium iodide, potassium iodide, etc.

This tertiary amination reaction is carried out in an inert solvent such as methanol, ethanol, propanol, isopropanol, n-butanol, tetrahydrofuran, diethylether, dimethoxyethane, 1,4-dioxane, toluene, benzene, xylene, dichloromethane, chloroform, 1,2-dichloroethane, dimethylformamide (DMF), dimethylsulfoxide (DMSO), pyridine, etc., or a suitable mixture of these solvents. The reaction temperature is generally about 0° C. to 180° C., and the reaction time is generally about 1 hour to about 40 hours. This reaction is preferably carried out under inert gas (e.g. nitrogen, argon, etc.) atmosphere.

③ When the group $R^{2''}$ in Compound [I-2] is, for example, a secondary amine residue, Compound [I-1] wherein the group $R^{2'}$ is a tertiary amino can be produced by reacting Compound [I-2] with aldehyde compound in the presence of a reductive amination reagent such as triacetoxysodium boron hydride, cyanosodium boron hydride, sodium boron hydride, etc.

The conditions of this reductive amination reaction varies depending on the reagent to be used. For example, when triacetoxysodium boron hydride is used, reaction is carried out in an inert solvent such as dichloromethane, chloroform, 1,2-dichloroethane, tetrahydrofuran, diethylether, dioxane, acetonitrile, dimethylformamide (DMF), etc., or a suitable mixture of these solvents. In this case, about 1 to 2 moles of the reagent is used per mole of Compound [I-2]. The reaction temperature is generally about 0° C. to about 80° C., and the reaction time is generally about 1 hour to about 40 hours. This reaction is preferably carried out under inert gas (e.g. nitrogen, argon, etc.) atmosphere.

④ When the group $R^{2''}$ in Compound [I-2] is, for example, a sulfide residue or a tertiary amine residue, Compound [I-1] wherein the group $R^{2'}$ is a sulfinyl group, a sulfonyl group or an amine oxide group can be produced by reacting Compound [I-2] with an oxidizing agent such as m-chloroperbenzoic acid (m-CPBA), perbenzoic acid, p-nitroperbenzoic acid, magnesium monoperoxyphthalate, peracetic acid, hydrogen peroxide, sodium periodate, potassium periodate, etc. The conditions of this oxidation reaction varies depending on the oxidizing agent to be used. For example, when m-chloroperbenzoic acid is used, reaction is carried out in an inert solvent such as dichloromethane, chloroform, 1,2-dichloroethane, diethylether, tetrahydrofuran, acetone, ethyl acetate, etc., or a suitable mixture of these solvents. Usually, about 1–3 moles of oxidizing agent is used per mole of Compound [I-2]. The reaction temperature is generally about −50° C. to about 100° C. (preferably −25° C. to 25° C.), and the reaction time is generally about 1 hour to about 40 hours.

[Method C]

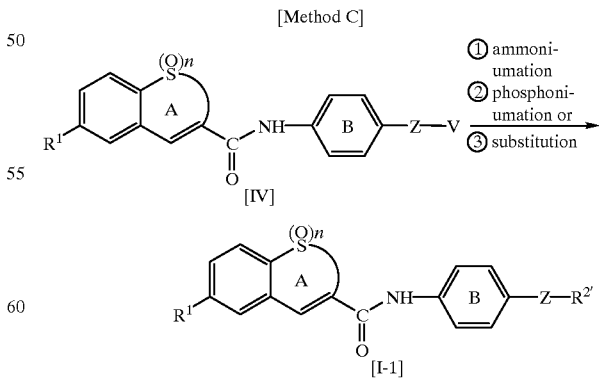

wherein V in the Compound [IV] is a halogen atom (chlorine, bromine, iodine, etc.), or a sulfonyloxy group (methane-sulfonyloxy group, trifluoromethanesulfonyloxy group, benzenesulfonyloxy group, toluenesulfonyloxy group, etc.), and the other symbols are as defined above.

② Compound [I-1] wherein the group $R^{2'}$ is a quaternary ammonium can be produced by reacting Compound [IV] and a tertiary amine. The reaction is carried out in an inert solvent such as toluene, benzene, xylene, dichloromethane, chloroform, 1,2-dichloroethane, dimethylformamide (DMF), dimethylacetamide, etc., or a suitable mixture of these solvents. Usually, about 1–3 moles of the tertiary amine is used per mole of Compound [IV]. The reaction temperature is generally about 10° C. to about 120° C., and the reaction time is generally about 1 hour to about 40 hours. This reaction is preferably carried out under inert gas (e.g. nitrogen, argon, etc.) atmosphere.

② Compound [I-1] wherein the group $R^{2'}$ is a quaternary phosphonium can be produced by reacting Compound [IV] and a tertiary phosphine. The reaction is carried out in an inert solvent such as toluene, benzene, xylene, dichloromethane, chloroform, 1,2-dichloroethane, acetonitrile, dimethylformamide (DMF), or a suitable mixture of these solvents. Usually, about 1–2 moles of the tertiary phosphine is used per mole of Compound [IV]. The reaction temperature is generally about 20° C. to about 150° C., and the reaction time is generally about 1 hour to about 50 hours. This reaction is preferably carried out under inert gas (e.g. nitrogen, argon, etc.) atmosphere.

③ Compound [I-1] wherein the group $R^{2'}$ is a secondary or tertiary amino group or a thio group can be produced by reacting Compound [IV] and primary or secondary amine compound or thiol compound. Usually, about 1 to 3 moles of the primary or secondary amine compound or the thiol compound is used per mole of Compound [IV]. If necessary, the reaction smoothly proceeds by addition of about once to 3 times moles of a base such as triethylamine, diisopropylethylamine, pyridine, lithium hydride, sodium hydride, sodium methoxide, sodium ethoxide, sodium carbonate, potassium carbonate, sodium hydrogen carbonate and further sodium iodide, potassium iodide, etc. This substitution reaction is carried out in an inert solvent such as methanol, ethanol, propanol, isopropanol, n-butanol, tetrahydrofuran, diethylether, dimethoxyethane, 1,4-dioxane, toluene, benzene, xylene, dichloromethane, chloroform, 1,2-dichloroethane, dimethylformamide (DMF),dimethylsulfoxide (DMSO), pyridine, etc., or a suitable mixture of these solvents. The reaction temperature is generally about –10° C. to about 180° C., and the reaction time is generally about 1 hour to about 40 hours. The reaction is carried out preferably under inert gas (e.g. nitrogen, argon, etc.) atmosphere.

[Method D]

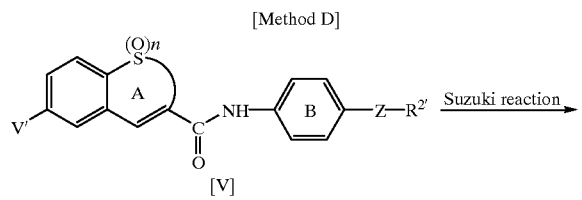

[V]

-continued

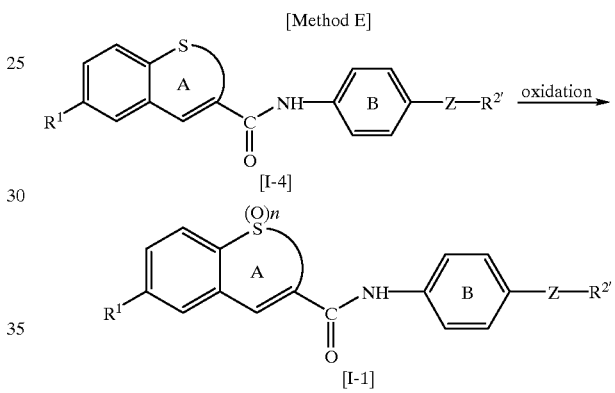

wherein V' is a halogen atom (bromine, iodine, etc.) or a sulfonyloxy group (trifluoromethanesulfonyloxy group, etc.), and the other symbols are as defined above.

Compound (I-3) wherein the group $R^{1'}$ is a 5- to 6-membered aromatic ring group can be produced by subjecting Compound [V] to, for example, Suzuki reaction [cross condensation reaction of aryl borate with e.g. aryl halide or aryloxytrifluoromethanesulfonate in the presence of palladium catalyst; A. Suzuki et al., Synth. Commun. 1981, 11, 513]. Usually, about 1–1.5 times moles of aryl borate is used per mole of Compound [V].

[Method E]

wherein each symbol is as defined above.

The Compound [I-1] can be produced by reacting the Compound [1-4] with an oxidizing agent such as m-chloroperbenzoic acid (m-CPBA), perbenzoic acid, p-nitroperbenzoic acid, magnesium monoperoxyphthalate, peracetic acid, hydrogen peroxide, sodium periodate, potassium periodate, etc. The conditions of this oxidation reaction varies depending on the oxidizing agent to be used. For example, when m-chloroperbenzoic acid is used, reaction is carried out in an inert solvent such as dichloromethane, chloroform, 1,2-dichloroethane, diethylether, tetrahydrofuran, acetone, ethyl acetate, etc., ora suitable mixture of these solvents. Usually, about 1–3 moles of oxidizing agent is used per mole of Compound [I-4]. The reaction temperature is generally about –50° C. to about 100° C. (preferably –25° C. to 25° C., and the reaction time is generally about 1 hour to about 40 hours.

The thus obtained anilide derivative [I-1] or [1-3] can be isolated and purified by known separation and purification methods such as concentration, concentration under reduced pressure, extraction, crystallization, recrystallization, solvent convert, chromatography, etc.

Compound [II] used as a starting material can be produced by a known method (e.g. method described in JP-A-73476/1996, etc.) or the methods analogous thereto. For example, Compound [II] can be produced by a method described in the following Reaction Scheme I or II, a method described in the following Reference Examples or the methods analogous thereto.

Reaction Scheme I

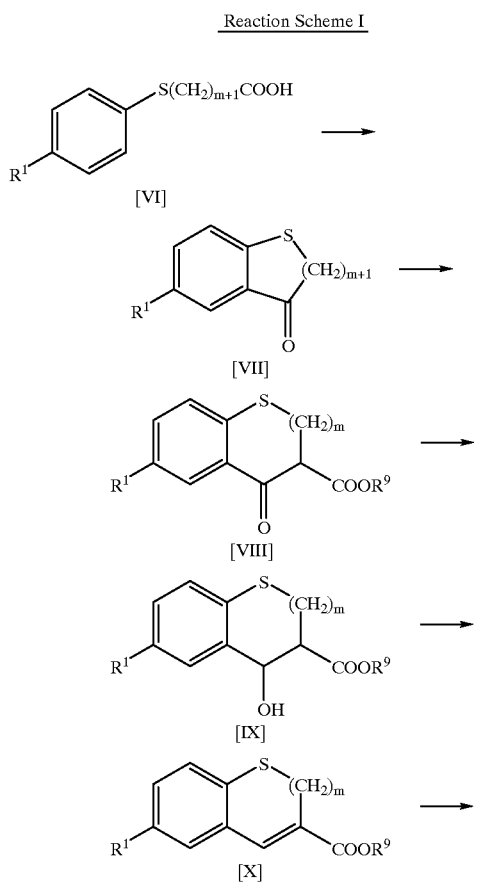

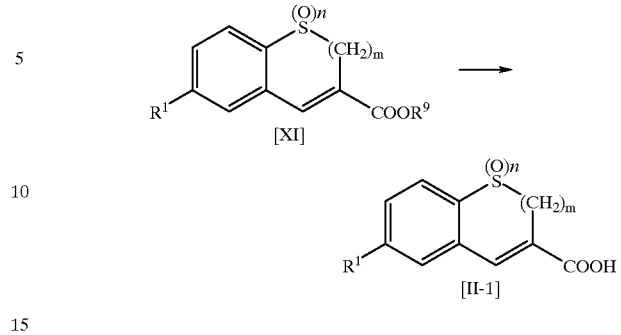

wherein $R^9$ is a $C_{1-4}$ alkyl group, m is an integer of 1 or 2, and the other symbols are as defined above.

In this reaction, the compound of the formula [VI] is heated with a polyphosphoric acid, or Compound [VI] is converted to acid chloride with thionyl chloride, oxalyl chloride, phosphorous oxychloride, phosphorous pentachloride, etc., followed by subjecting the resulting acid chloride to usual Friedel-Crafts reaction and cyclizing the same to produce Compound [VII]. Compound [VII] is reacted with carbonate ester in the presence of a base to produce ketoester [VIII]. Compound [VIII] is subjected to reduction with catalytic hydrogenation or sodium boron hydride, etc. to produce Compound [IX]. Compound [IX] is subjected to dehydration and ester hydrolysis by per se known method to produce Compound [X]. Compound [X] is converted to Compound [XI] with oxidation, and Compound [XI] is subjected to ester hydrolysis to produce unsaturated carboxylic acid [II-1].

Reaction Scheme II

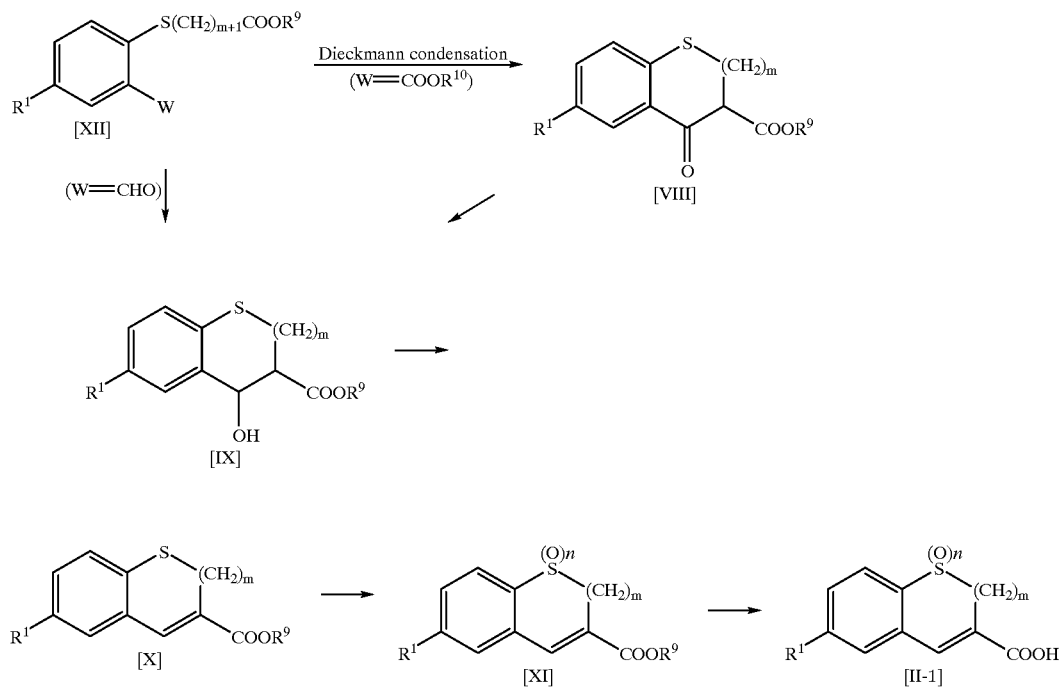

wherein $R^{10}$ is a $C_{1-4}$ alkyl group and the other symbols are as defined above.

The Compound [VIII] or [IX] can be produced by subjecting the Compound [VII] to Dieckmann condensation (J. P. Schaefer and J. J. Bloomfield, Org. Reactions, 1967, 15, 1). Compound [VIII] or [IX] is subjected to the reactions as described in Reaction Scheme I to produce 10 unsaturated carboxylic acid [II-1].

Compound [III] can be produced by a known method (e.g. method described in JP-A-73476/1996, etc.) or the methods analogous thereto. For example, Compound [III] can be produced by a method described in the following Reaction Scheme III, a method described in the following Reference Examples or the methods analogous thereto.

Reaction Scheme III

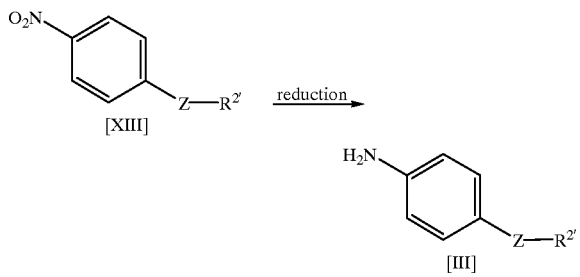

The reduction of Compound [XIII] can be carried out by per se known methods, for example, reduction with metal, reduction with metal hydride, reduction with metal hydride complex compound, reduction with diborane or substituted borane, catalytic hydrogenation, etc. That is, this reaction is carried out by treating Compound [XIII] with reduction agent. Examples of the reduction agent include metal such as reduced iron, zinc powder, etc.; alkali metal boron hydride (e.g. sodium boron hydride, lithium boron hydride, etc.); metal hydride complex compound such as aluminum lithium hydride, etc.; metal hydride such as sodium hydride etc.; organic tin compound (triphenyltin hydride, etc.), metal complex compound and metal salt such as nickel compound, zinc compound etc.; catalytic reduction agent using hydrogen and transit metal catalyst such as palladium, plutonium, rhodium, etc.; diborane; etc. Among others, as the reduction agent, catalytic reduction agent using hydrogen and transit metal catalyst such as palladium, plutonium, rhodium, etc.; reduced iron, etc. are preferable. The reaction is carried out in a solvent which does not affect the reaction. Examples of the solvent include benzene, toluene, xylene, chloroform, carbon tetrachloride, dichloromethane, 1,2-dichloroethane, 1,1,2,2-tetrachloroethane, diethylether, tetrahydrofuran, dioxane, methanol, ethanol, propanol, isopropanol, 2-methoxyethanol, N,N-dimethylformamide, acetic acid, or a suitable mixture of these solvents, etc. The solvent is appropriately selected depending on kind of the reduction agent. The reaction temperature is generally about −20° C. to about 150° C., preferably about 0° C. to about 100° C., and the reaction time is generally about 1 to about 24 hours.

The resulting Compound [III] can be separated and purified with known separation and purification methods such as concentration, concentration under reduced pressure, extraction, crystallization, was recrystallized with, solvent conversion, chromatography, etc.

The compound of the formula (I) or a salt thereof of the present invention may be used in combination with other drugs for the treatment or prevention of infectious disease of HIV (in particular, a pharmaceutical composition for the treatment or prevention of AIDS). In this case, these drugs can be formulated by mixing individually or simultaneously with pharmaceutically acceptable carriers, excipients, binders, diluents or the like, which can be administered orally or non-orally as a pharmaceutical composition for the treatment or prevention of infectious disease of HIV. In the case of formulating these effective components individually, while the individually formulated agents can be administered in the form of their mixture prepared by using e.g. a diluent when administered, the individually formulated agents can also be administered separately or simultaneously or with time intervals to the one and same subject. A kit for administering the individually formulated effective components in the form of their mixture prepared by using e.g. a diluent when administered (e.g. a kit for injection which comprises two or more ampoules each comprising a powdery component and a diluent for mixing and dissolving two or more components when administered, etc.), a kit for administering the individually formulated agents simultaneously or with time intervals to the one and the same subject (e.g. a kit for tablets to be administered simultaneously or with time intervals, characterized by having two or more tablets each comprising an agent and said tablets being put in one or separate bags and, if necessary, a column to describe time to be administered of each agent, etc.), etc. are also included by the pharmaceutical composition of the present invention.

Examples of the other pharmaceutical agent for the treatment or prevention of infectious disease of HIV to be used in combination with the compound of the formula (I) or a salt thereof of the present invention include nucleotide reverse transcriptases inhibitor such as zidovudine, didanosine, zalcitabine, lamivudine, stavudine, abacavir, adefovir, adefovir dipivoxil, fozivudine tidoxil, etc.; non-nucleotide reverse transcriptases inhibitor (including an agent having anti-oxidation activity such as immunocal, oltipraz, etc.) such as nevirapine, delavirdine, efavirenz, loviride, immunocal, oltipraz, etc.; protease inhibitors such as saquinavir, ritonavir, indinavir, nelfinavir, amprenavir, palinavir, lasinavir, etc.; etc.

As the nucleotide reverse transcriptase inhibitor, zidovudine, didanosine, zalcitabine, lamivudine, stavudine, abacavir, etc. are preferable; as the non-nucleotide reverse transcriptase inhibitor, nevirapine, delavirdine, efavirenz, etc. are preferable; and as the protease inhibitor, saquinavir, ritonavir, indinavir, nelfinavir, amprenavir, etc. are preferable.

The compound of the formula (I) or a salt thereof of the present invention may be used in combination with, for example, CXCR4 antagonist (CXCR4 being a second receptor of T cell-tropic HIV-1) such as AMD-3100, etc., antibody against HIV-1 surface antigen, HIV-1 vaccine, etc., in addition to the above-mentioned protease inhibitor, reverse transcriptase inhibitor, etc.

The compound of the formula (I) or a salt thereof of the present invention has potent CCR antagonistic activity (in particular, potent CCR5 antagonistic activity) and therefore can be used for the treatment or prevention of various infectious diseases of HIV, for example, AIDS in human. The compound of the formula (I) or a salt thereof of the present invention is of low toxicity and safely used as CCR5 antagonist for the treatment or prevention of AIDS and also for the prevention of the progression of AIDS.

The dose per day of the compound of the formula (I) or a salt thereof varies depending on the condition and body weight of a patient, administration route, etc. Typical daily dose per adult patient (body weight: 50 Kg) for oral administration is about 5–1000 mg, preferably about 10–600 mg, more preferably about 10–300 mg, and in particular about 15–150 mg, as active ingredient [the compound of the formula (I) or a salt thereof] and the compound of the formula (I) or a salt thereof is administered once or 2–3 times par day.

When the compound of the formula (I) or a salt thereof is used in combination with a reverse transcriptase inhibitor and/or a protease inhibitor, the dose of the reverse transcriptase inhibitor or the protease inhibitor ranges, for example, from about 1/200–1/2 or more of usual dose to about 2–3 times or less of usual dose. In case that two or more drugs are used in combination, each dose of the drugs is appropriately adjusted if one drug affects metabolism of the other drug, while each dose of the drugs when they are used in combination is generally the same as the dose when they are used alone.

Typical daily dose of the reverse transcriptase inhibitor and the protease inhibitor is as follows:

zidovudine: 100 mg didanosine: 125–200 mg zalcitabine: 0.75 mg lamivudine: 150 mg stavudine: 30–40 mg saquinavir: 600 mg ritonavi: 600 mg indinavir: 800 mg nelfinavir: 750 mg In case of combination use of the compound of the formula (I) or a salt thereof with a reverse transcriptase inhibitor and/or a protease inhibitor preferred embodiments are shown below.

① A drug containing about 10–300 mg of the compound of the formula (I) or a salt thereof and a drug containing about 50–200 mg of zidovudine to one adult patient (body weight: 50 Kg) are administered. Each of the drugs may be administered to the one and the same subject simultaneously or with time intervals of 12 hours or less.

② drug containing about 10–300 mg of the compound of the formula (I) or a salt thereof and a drug containing about 300–1200 mg of saquinavir to one adult patient (body weight: 50 Kg) are administered. Each of the drugs may be administered to the one and the same subject simultaneously or with time intervals of 12 hours or less.

BEST MODE FOR CARRYING OUT THE INVENTION

The present invention is hereinafter described in more detail by means of the following Test Example, Formulation Example, Reference Example and Working Example, which are mere examples of the present invention and are not construed as limitative to the present invention.

The following gene manipulation is carried out in accordance with methods described in textbook (Maniatis et al., Molecular Cloning, Cold Spring Harbor Laboratory, 1989) or protocol attached to reagents.

Test Example (1) Cloning of Human CCR5 Chemokine Receptor

Cloning of CCR5 gene was carried out by PCR (polymerase chain reaction) from human spleen cDNA. With using 0.5 ng of spleen cDNA (Toyobo, QUICK-Clone cDNA) as template, PCR was performed in DNA Thermal Cycler 480 (Perkin-Elmer) (reaction conditions: 30 cycles of 95° C. for 1 minute, 60° C. for 1 minute, and 75° C. for 5 minutes) by adding primer set, 5'-CAGGATCCGA TGGATTATCAAGTGTCAAGTCCAA-3' (25 pmol) and 5'-TCTAGATCACAAGCCCACAGATATTTCCTGCTCC-3' (25 pmol), which were designed referring to nucleotide sequence of CCR5 gene reported by Samson et al. (Biochemistry, 35(11), 3362–3367 (1996)) and by using TaKaRa EX Taq (TakaraShuzo). The resultant PCR product was subjected to agarose gel. electrophoresis to collect about 1.0 kb DNA fragment, which was subjected to Original TA Cloning Kit (Funakoshi) to carry out cloning of CCR5 gene.

(2) Preparation of Plasmid for Expression of Human CCR5

The plasmid obtained in the above (1) was digested with restriction enzymes XbaI (Takara Shuzo) and BamHI (Takara Shuzo) and subjected to agarose gel electrophoresis to collect about 1.0 kb DNA fragment. The DNA fragment was mixed with plasmid pcDNA3.1 (Funakoshi) for expression in animal cells, said plasmid being digested with XbaI and BamHI, and they were ligated with DNA Ligation Kit Ver.2 (Takara Shuzo). The resulting plasmid was subjected to transformation of competent cell of E. coli JM109 (Takara Shuzo) to obtain plasmid pCKR5.

(3) Introduction of Plasmid for Expression of Human CCR5 into CHO-K1 cell and Expression of said Plasmid in CHO-K1 cell CHO-K1 cells were grown in 750 ml of tissue culture flask (Becton Dickinson) using Ham's F12 medium (Nihon Pharmaceutical) containing 10% fetal calf serum (Life Tech Oriental) and took off with 0.5 g/L trypsin-0.2 g/L EDTA (Life Tech Oriental). The cells were washed with PBS (Life Tech Oriental), centrifuged (1000 rpm, 5 minutes), and suspended in PBS. With using Gene Pulser (Bio-Rad Laboratories), DNA was introduced into the cells under the conditions shown below. That is, to the cuvette of 0.4 cm gap were added $8\times10^6$ cells and 10 µg of plasmid pCKR5 for expression of human CCR5, and electroporation was carried out under 0.25 kV of voltage and 960 µF of capacitance. The cells were transferred into Ham's F12 medium (Nihon Pharmaceutical) containing 10% fetal calf serum, and cultivated for 24 hours. The cells were again took off and centrifuged, and suspended in Ham's F12 medium (Nihon Pharmaceutical) containing 10% fetal calf serum and 500 µg/ml of geneticin (Life Tech Oriental). The suspension was diluted to give $10^4$ cells/ml of the suspension, which was inoculated on 96 well plate (Becton Dickinson) to give geneticin resistant cells. The resulting geneticin resistant cells were cultivated in 96 well plate (Becton Dickinson), and cells expressing CCR5 were selected from the geneticin resistant cells. That is, in assay buffer (Ham's F12 medium containing 0.5% BSA and 20 mM HEPES (Wako Pure Chemical, pH7.2) to which was added 200 pM of [$^{125}$I]-RANTES (Amersham) as ligand, binding reaction was carried out at room temperature for 40 minutes, and the buffer was washed with cooled PBS. To the buffer was added 50 µl/well of 1M NaOH, and the mixture was stirred. Radioactivity was determined with γ-counter to select CHO/CCR5 cells which specifically bind to the ligand.

(4) Evaluation of Test Compounds Based on CCR5 Antagonistic Activity

The CHO/CCR5 were inoculated on 96 well microplate ($5\times10^4$ cells/well) and cultivated for 24 hours. The medium was removed by means of suction, and to each well was added assay buffer containing Test Compound (1 µM) and then 100 pM of [$^{125}$I]-RANTES (Amersham) as ligand. Binding assay was carried out at room temperature for 40 minutes, and assay buffer was removed by means of suction. Each well was washed twice with cooled PBS, and 200 µl of Microscint-20 (Packard Instrument, Inc.) was added to each well. Radio-activity was determined with Top-Count Micro Scintillation Counter (Packard Instrument, Inc.).

According to the method described above, inhibition rate of Test Compound (whose number is referred to in the following Examples) to CCR5 binding. The results are shown in Table 1.

TABLE 1

| Compound Number | Inhibition Rate (%) |
|---|---|
| 4 | 91 |
| 27 | 100 |
| 29 | 100 |
| 30 | 99 |
| 44 | 96 |
| 54 | 99 |
| 73 | 94 |
| 74 | 94 |
| 75 | 95 |
| 84 | 97 |
| 97 | 92 |
| 98 | 98 |
| 111 | 95 |
| 123 | 94 |
| 124 | 97 |
| 125 | 92 |
| 129 | 95 |

(5) Inhibitory Effect on HIV-1 Infection to MAGI-CCR5 Cell

The plasmid where β-galactosidase gene was ligated downstream of HIV-1 LTR was introduced into CD4 positive HeLa cell, to which human CCR5 was further introduced to obtain transformant MAGI-CCR5. By using said transformant MAGI-CCR5, degree of HIV-1 infection was calculated from β-galactosidase activity (blue color due to decomposition of 5-bromo-4-chloro-3-indolyl-β-D-galactopyranoside). Specifically, MAGI-CCR5 cells were suspended in DMEM medium containing 10% serum to prepare $5 \times 10^4$ cells/ml suspension. To each well of 96 well plate was inoculated 200 $\mu$l of the suspension, and the cells were cultivated at 37° C. overnight. The medium was removed by means of suction, and to the residue was added 100 $\mu$l of the above medium containing 1.6 $\mu$M of Test Compound and 100 $\mu$l of the above medium containing 300PFU of HIV-1 BA-L cells. The cells were cultivated at 37° C. for 2 days. The medium was removed by means of suction. To the residue was added 200 $\mu$l of cell fixative (PBS containing 1% formaldehyde and 0.2% glutaraldehyde), and the mixture was allowed to stand at room temperature for 5 minutes and washed twice with PBS. To the mixture was added 100 $\mu$l of staining solution (PBS containing 4 $\mu$M potassium ferrocyanide, 4 $\mu$M potassium ferricyanade, 2 $\mu$M $MgCl_2$ and 0.4 mg/ml X-gal), and the mixture was allowed to stand at 37° C. for 50 minutes and washed twice with PBS. The number of blue cells was counted by microscope and defined as the number of cells infected with HIV-1. According to this method, inhibition rate on HIV-1 infection was determined. The results are shown in Table 2.

TABLE 2

| Compound No. | Inhibition Rate (%) |
|---|---|
| 30 | 91 |
| 29 | 91 |
| 97 | 87 |
| 98 | 91 |

The pharmaceutical composition for antagonizing CCR5 (e.g. a medicament for the treatment or prevention of infectious disease of HIV, a medicament for the treatment or prevention of AIDS, etc.) comprising the compound of the formula (I) or a salt thereof of the present invention, as an active ingredient, can be prepared, for example, by the following prescriptions:

1. Capsule

| (1) Compound obtained in Working Example 4 | 40 mg |
|---|---|
| (2) lactose | 70 mg |
| (3) fine crystalline cellulose | 9 mg |
| (4) magnesium stearate | 1 mg |
| 1 capsule | 120 mg |

(1), (2), (3) and ½ of (4) are mixed and then granulated. To the granules is added the remainder of (4), and the whole is filled into a gelatin capsule.

2. Tablet

| (1) Compound obtained in Working Example 4 | 40 mg |
|---|---|
| (2) lactose | 58 mg |
| (3) corn starch | 18 mg |
| (4) fine crystalline cellulose | 3.5 mg |
| (5) magnesium stearate | 0.5 mg |
| 1 tablet | 120 mg |

(1), (2), (3), ⅔ of (4) and ½ of (5) are mixed and then granulated. To the granules are added the remainders of (4) and (5), followed by subjecting the mixture to compression molding.

3. Capsule

| (1) Compound obtained in working Example 115 | 40 mg |
|---|---|
| (2) lactose | 70 mg |
| (3) fine crystalline cellulose | 9 mg |
| (4) magnesium stearate | 1 mg |
| 1 capsule | 120 mg |

(1), (2), (3) and ½ of (4) are mixed and then granulated. To the granules is added the remainder of (4), and the whole is filled into a gelatin capsule.

4. Tablet

| (1) Compound obtained in Working Example 115 | 40 mg |
|---|---|
| (2) lactose | 58 mg |
| (3) corn starch | 18 mg |
| (4) fine crystalline cellulose | 3.5 mg |
| (5) magnesium stearate | 0.5 mg |
| 1 tablet | 120 mg |

(1), (2), (3), ⅔ of (4) and ½ of (5) are mixed and then granulated. To the granules are added the remainders of (4) and (5), followed by subjecting the mixture to compression molding.

WORKING EXAMPLE

Working Example 1 (Production of Compound 1)

To a solution of 7-(4-morpholinophenyl)-1,1-dioxo-2,3-dihydro-1-benzothiepine-4-carboxylic acid (177 mg; purity: about 50%) and 1-hydroxybenzotriazole (HOBt) (90 mg) in DMF (5 ml) was added at room temperature 1-ethyl-3-(3'-dimethylaminopropyl)carbodiimide hydrochloride (WSC) (127 mg), and the mixture was stirred for 1 hour. To the mixture were added a solution of 4-[N-methyl-N-(tetrahydropyran-4-yl)aminomethyl]aniline (107 mg) and triethylamine (0.12 ml) in DMF (5 ml) and a piece of 4-dimethylaminopyridine, and the mixture was stirred for 64 hours. The mixture was concentrated under reduced pressure, and to the residue was added water. The mixture was extracted with dichloromethane, and the organic layer was washed with saturated brine and dried with magnesium sulfate. The solvent was evaporated under reduced pressure, and the residue was purified with column chromatography (ethanol/ethyl acetate=1:1) and recrystallized from ethanol/diethylether to give yellow crystals of N-[4-[N-methyl-N-(tetrahydropyran-4-yl)aminomethyl]phenyl]-7-(4-morpholinophenyl)-1,1-dioxo-2,3-dihydro-1-benzothiepine-4-carboxamide (Compound 1) (31.6 mg).

$^1$H-NMR (200 MHz, CDCl$_3$) δ 1.38–1.84 (4H, m), 2.23 (3H, s), 2.58–2.80 (1H, m), 3.10–3.45 (8H, m), 3.61 (2H, s), 3.67–3.78 (2H, m), 3.83–3.94 (4H, m), 3.99–4.09 (2H, m), 7.00 (2H, d, J=8.8 Hz), 7.19–7.38 (3H, m), 7.49–7.60 (4H, m), 7.62–7.71 (2H, m), 7.89–7.95 (1H, m), 8.19 (1H, d, J=8.4 Hz). IR (KBr) 3277, 1659, 1603, 1522, 1313, 1234, 1124, 928, 820 cm$^{-1}$;

Working Example 2 (Production of Compound 2)

To a solution of N-[4-[N-methyl-N-(tetrahydropyran-4-yl)aminomethyl]phenyl]-7-(4-morpholinophenyl)-1,1-dioxo-2,3-dihydro-1-benzothiepine-4-carboxamide (36 mg) in ethanol/methanol (10/5 ml) was added at room temperature concentrated hydrochloric acid (0.5 ml), and the mixture was stirred for a few minutes. Insoluble materials were filtered off, and the filtrate was concentrated under reduced pressure. To the residue was added diethylether, and precipitated solid was collected by filtration, which was washed with diethylether to give yellow powder of N-[4-[N-methyl-N-(tetrahydropyran-4-yl)aminomethyl]phenyl]-7-(4-morpholinophenyl)-1,1-dioxo-2,3-dihydro-1-benzothiepine-4-carboxamide dihydrochloride (Compound 2) (34 mg).

$^1$H-NMR (200 MHz, DMSO-d$_6$) δ 1.65–2.18 (4H, m), 2.60 (3H, s), 3.01–3.12 (2H, m), 3.16–3.51 (7H, m), 3.62–3.87 (6H, m), 3.93–4.07 (2H, m), 4.10–4.22 (1H, m), 4.39–4.51 (1H, m), 7.08 (2H, d, J=8.8 Hz), 7.53–7.58 (3H, m), 7.72 (2H, d, J=8.8 Hz), 7.80–7.92 (3H, m), 8.02–8.10 (2H, m), 10.42 (1H, br s).

Working Example 3 (Production of Compound 3)

To a solution of 7-(4-methoxyphenyl)-1,1-dioxo-2,3-dihydro-1-benzothiepine-4-carboxylic acid (150 mg) in THF (10 ml) were added at room temperature oxalyl chloride (0.2 ml) and a drop of DMF, and the mixture was stirred for 1 hour. The solvent was evaporated under reduced pressure, and the residue was dissolved in THF (20 ml). To the solution were added dropwise at 0° C. 4-[N-methyl-N-(tetrahydropyran-4-yl)aminomethyl]aniline (107 mg) and triethylamine (0.12 ml), and the mixture was stirred at room temperature for 4 hours. The mixture was added to vigorously stirred water to stop the reaction, and the mixture was extracted with ethyl acetate. The organic layer was washed with saturated brine, dried with magnesium sulfate and concentrated under reduced pressure, and the residue was purified with column chromatography (ethanol/ethyl acetate=1:2) and recrystallized from ethanol to give colorless crystals of 7-(4-methoxyphenyl)-N-[4-[N-methyl-N-(tetrahydropyran-4-yl)aminomethyl]phenyl]-1,1-dioxo-2,3-dihydro-1-benzothiepine-4-carboxamide (Compound 3) (161.1 mg).

m.p. 247–249° C.; $^1$H-NMR (200 MHz, CDCl$_3$) δ 61.68–1.83 (4H, m), 2.21 (3H, s), 2.52–2.74 (1H, m), 3.16 (2H, d, J=6.6 Hz), 3.31–3.44 (2H, m), 3.58 (2H, s), 3.69–3.76 (2H, m), 3.87 (3H, s), 3.98–4.10 (2H, m), 7.02 (2H, d, J=8.8 Hz), 7.30–7.35 (3H, m), 7.52–7.57 (4H, m), 7.62–7.70 (2H, m), 7.91 (1H, br s), 8.20 (1H, d, J=8.0 Hz). IR (KBr) 3246, 1655, 1633, 1605, 1518, 1410, 1317, 1294, 1250, 1171, 1128, 825 cm$^{-1}$; Anal. for C$_{31}$H$_{34}$N$_2$O$_5$S; Calcd. C, 70.56; H, 6.97; N, 7.26; Found. C, 70.43; H, 6.83; N, 7.22.

Working Example 4 (Production of Compound 4)

To a suspension of 7-(4-ethoxyphenyl)-1,1-dioxo-2,3-dihydro-1-benzothiepine-4-carboxylic acid (16.90 g) in THF (340 ml) and DMF (2 ml) was added at room temperature thionyl chloride (3.62 ml), and the mixture was stirred for 2 hours. The mixture was added at room temperature to a suspension of 4-[N-methyl-N-(tetrahydropyran-4-yl)aminomethyl]aniline 2hydrochloride (15.21 g) and triethylamine (40 ml) in THF (150 ml) for 1 hour, and the mixture was stirred for 4 hours. The mixture was concentrated under reduced pressure, and precipitated colorless crystals were collected by filtration, which were washed with water, ethanolethyl acetate and diisopropylether to give crude crystals (21.90 g). The crude crystals were purified with recrystallization from THF/ethanol to give colorless crystals of 7-(4-ethoxyphenyl)-N-[4-[N-methyl-N-(tetrahydropyran-4-yl)aminomethyl]phenyl]-1,1-dioxo-2,3-dihydro-1-benzothiepine-4-carboxamide (Compound 4) (21.02 g).

m.p. 243–246° C.; $^1$H-NMR (200 MHz, CDCl$_3$) δ 1.45 (3H, t, J=7.0 Hz), 1.67–1.80 (4H, m), 2.21 (3H, s), 2.55–2.72 (1H, m), 3.13–3.20 (2H, m), 3.28–3.44 (2H, m), 3.58 (2H, s), 3.69–3.76 (2H, m), 3.97–4.08 (2H, m), 4.10 (2H, q, J=7.0 Hz), 7.06 (2H, d, J=8.8 Hz), 7.31–7.35 (3H, m), 7.52–7.57 (4H, m), 7.63–7.70 (2H, m), 7.89 (1H, br s), 8.20 (1H, d, J=8.0 Hz). IR (KBr) 3428, 1657, 1635, 1603, 1518, 1410, 1317, 1294, 1246, 1128, 827 cm$^{-1}$; Anal. for C$_{32}$H$_{36}$N$_2$O$_5$S; Calcd. C, 68.55; H, 6.47; N, 5.00; Found. C, 68.68; H, 6.50; N, 4.92.

Working Example 5 (Production of Compound 4)

To a solution of 7-(4-ethoxyphenyl)-1,1-dioxo-2,3-dihydro-1-benzothiepine-4-carboxylic acid (150 mg) in THF (10 ml) were added at room temperature oxalyl chloride (0.18 ml) and a drop of DMF, and the mixture was stirred for 1 hour. The solvent was evaporated under reduced pressure, and the residue was dissolved in THF (20 ml). To the solution were added dropwise at 0° C. 4-[N-methyl-N-(tetrahydropyran-4-yl)aminomethyl]aniline (102 mg) and triethylamine (0.12 ml), and the mixture was stirred at room temperature for 4 hours. The mixture was added to vigorously stirred water to stop the reaction and extracted with ethyl acetate. The organic layer was washed with saturated brine, dried with magnesium sulfate and concentrated under reduced pressure, and the residue was purified with column chromatography (ethanol/ethyl acetate=1:2) and recrystallized from ethanol to give colorless crystals of 7-(4- ethoxyphenyl)-N-[4-[N-methyl-N-(tetrahydropyran-4-yl) aminomethyl]phenyl]-1,1-dioxo-2,3-dihydro-1-benzothiepine-4-carboxamide (Compound 4) (134 mg). $^1$H-NMR (200 MHz, CDCl$_3$) δ 1.45 (3H, t, J=7.0 Hz), 1.67–1.80 (4H, m), 2.21 (3H, s), 2.55–2.72 (1H, m), 3.13–3.20 (2H, m), 3.28–3.44 (2H, m), 3.58 (2H, s), 3.69–3.76 (2H, m), 3.97–4.08 (2H, m), 4.10 (2H, q, J=7.0 Hz), 7.06 (2H, d, J=8.8 Hz), 7.31–7.35 (3H, m), 7.52–7.57 (4H, m), 7.63–7.70 (2H, m), 7.89 (1H, br s), 8.20 (1H, d, J=8.0 Hz). IR (KBr) 3428, 1657, 1635, 1603, 1518, 1410, 1317, 1294, 1246, 1128, 827 cm$^{-1}$; Anal. for C$_{32}$H$_{36}$N$_2$O$_5$S; Calcd. C, 68.55; H, 6.47; N, 5.00; Found. C, 68.16; H, 6.52; N, 5.13.

Working Example 6 (Production of Compound 5)

To a solution of 7-(4-ethoxyphenyl)-N-[4-[N-methyl-N-(tetrahydropyran-4-yl)aminomethyl]phenyl]-1,1-dioxo-2,3-dihydro-1-benzothiepine-4-carboxamide (2.5 g) in THF (125 ml) was added at room temperature 6N hydrochloric acid (1.5 ml), and the mixture was stirred for 0.5 hour and concentrated under reduced pressure. To the mixture was added diethylether, colorless crystals were collected by filtration to give crude crystals (2.61 g), which were purified with recrystallization from 90% ethanol to give colorless crystals of 7-(4-ethoxyphenyl)-N-[4-[N-methyl-N-(tetrahydropyran-4-yl)aminomethyl]phenyl]-1,1-dioxo-2,3-dihydro-1-benzothiepine-4-carboxamide hydrochloride (Compound 5) (2.33 g).

m.p. 255° C. (dec.); $^1$H-NMR (200 MHz, CDCl$_3$) δ 1.45 (3H, t, J=7.0 Hz), 1.53–1.86 (2H, m), 1.93–2.21 (2H, m), 2.48 (3H, br s), 2.94–3.35 (5H, m), 3.70–3.76 (2H, m), 3.78–3.99 (3H, m), 4.10 (2H, q, J=7.0 Hz), 4.16–4.35 (1H, m), 7.00 (2H, d, J=8.8 Hz), 7.57–7.70 (5H, m), 7.87–7.92 (1H, m), 8.00–8.08 (3H, m), 8.18 (1H, d, J=8.4 Hz), 9.72–9.83 (1H, m). Anal. for C$_{32}$H$_{37}$N$_2$O$_5$SCl.0.5 H$_2$O; Calcd. C, 63.40; H, 6.32; N, 4.62; Cl, 5.85; Found. C, 63.36; H, 6.10; N, 4.49; Cl, 5.76.

Working Example 7 (Production of Compound 6)

To a solution of 7-(3,4-methylenedioxyphenyl)-1,1-dioxo-2,3-dihydro-1-benzothiepine-4-carboxylic acid (150 mg) in THF (10 ml) were added at room temperature oxalyl chloride (0.07 ml) and a drop of DMF, and the mixture was stirred for 1 hour. The solvent was evaporated under reduced pressure, and the residue was dissolved in THF (20 ml). To the solution were added dropwise at 0° C. 4-[N-methyl-N-(tetrahydropyran-4-yl)aminomethyl]aniline (102 mg) and triethylamine (0.12 ml), and the mixture was stirred at room temperature for 16 hours. The mixture was added to vigorously stirred water to stop the reaction and extracted with ethyl acetate. The organic layer was washed with saturated brine, dried with magnesium sulfate and concentrated under reduced pressure, and the residue was purified with column chromatography (ethanol/ethyl acetate=1:2) and recrystallized from ethanol to give colorless crystals of 7-(3,4-methylenedioxyphenyl)-N[4-[N-methyl-N-(tetrahydropyran-4-yl)aminomethyl]phenyl]-1,1-dioxo-2,3-dihydro-1-benzothiepine-4-carboxamide (Compound 6) (133 mg).

m.p. 245–248° C.; $^1$H-NMR (200 MHz, CDCl$_3$) δ 1.66–1.83 (4H, m), 2.21 (3H, s), 2.52–2.74 (1H, m), 3.17 (2H, t, J=7.0 Hz), 3.29–3.45 (2H, m), 3.58 (2H, s), 3.70–3.76 (2H, m), 3.96–4.10 (2H, m), 6.05 (2H, s), 6.92 (1H, d, J=8.8 Hz), 7.07–7.12 (2H, m), 7.31–7.35 (3H, m), 7.52–7.67 (4H, m), 7.89 (1H, br s), 8.20 (1H, d, J=8.0 Hz). IR (KBr) 3259, 1651, 1597, 1512, 1477, 1319, 1294, 1232, 1128, 1036, 930, 810 cm$^{-1}$; Anal. for C$_{31}$H$_{32}$N$_2$O$_6$S; Calcd. C, 66.41; H, 5.75; N, 5.00; Found. C, 66.34; H, 5.75; N, 4.85.

Working Example 8 (Production of Compound 7)

To a solution of 7-(4-chlorophenyl)-1,1-dioxo-2,3-dihydro-1-benzothiepine-4-carboxylic acid (150 mg) in THF (10 ml) were added at room temperature oxalyl chloride (0.08 ml) and a drop of DMF, and the mixture was stirred for 1 hour. The solvent was evaporated under reduced pressure, and the residue was dissolved in THF (15 ml). The solution was added dropwise at 0° C. to a solution of 4-[N-methyl-N-(tetrahydropyran-4-yl)aminomethyl]aniline (104 mg) and triethylamine (0.12 ml) in THF (5 ml), and the mixture was stirred at room temperature for 19 hours. To the mixture was added water, and the mixture was extracted with ethyl acetate. The organic layer was washed with saturated brine, dried with magnesium sulfate and concentrated under reduced pressure, and the residue was purified with column chromatography (ethanol/ethyl acetate=1:2) and recrystallized from ethanol/diisopropylether to give colorless crystals of 7-(4-chlorophenyl)-N-[4-[N-methyl-N-(tetrahydropyran-4-yl)aminomethyl]phenyl]-1,1-dioxo-2,3-dihydro-1-benzothiepine-4-carboxamide (Compound 7) (154.8 mg).

m.p. 247–250° C.; $^1$H-NMR (200 MHz, CDCl$_3$) δ 1.62–1.85 (4H, m), 2.21 (3H, s), 2.52–2.73 (1H, m), 3.14–3.21 (2H, m), 3.29–3.44 (2H, m), 3.57 (2H, s), 3.69–3.76 (2H, m), 3.97–4.10 (2H, m), 7.31–7.35 (3H, m), 7.45–7.56 (6H, m), 7.63–7.72 (2H, m), 7.90 (1H, br s), 8.24 (1H, d, J=8.0 Hz). IR (KBr) 3246, 1655, 1601, 1529, 1410, 1317, 1294, 1130, 818 cm$^{-1}$; Anal. for C$_{30}$H$_{31}$N$_2$O$_4$SCl; Calcd. C, 65.38; H, 5.67; N, 5.08; Found. C, 65.54; H, 5.56; N, 4.98.

Working Example 9 (Production of Compound 8)

To a solution of 7-(4-fluorophenyl)-1,1-dioxo-2,3-dihydro-1-benzothiepine-4-carboxylic acid (150 mg) in THF (10 ml) were added at room temperature oxalyl chloride (0.08 ml) and a drop of DMF, and the mixture was stirred for 1 hour. The solvent was evaporated under reduced pressure, and the residue was dissolved in THF (15 ml). The solution was added dropwise at 0 to a solution of 4-[N-methyl-N-(tetrahydropyran-4-yl)aminomethyl]aniline (109 mg) and triethylamine (0.13 ml) in THF (5 ml), and the mixture was stirred at room temperature for 24 hours. To the mixture was added water, and the mixture was extracted with ethyl acetate. The organic layer was washed with saturated brine, dried with magnesium sulfate and concentrated under reduced pressure, and the residue was purified with column chromatography (ethanol/ethyl acetate=1:3) and recrystallized from ethanol to give colorless crystals of 7-(4-fluorophenyl)-N-[4-[N-methyl-N-(tetrahydropyran-4-yl)aminomethyl]phenyl]-1,1-dioxo-2,3-dihydro-1-benzothiepine-4-carboxamide (Compound 8) (128.5 mg).

m.p. 219–221° C.; $^1$H-NMR (200 MHz, CDCl$_3$) δ 1.52–1.83 (4H, m), 2.21 (3H, s), 2.53–2.75 (1H, m), 3.14–3.21 (2H, m), 3.30–3.45 (2H, m), 3.58 (2H, s), 3.71–3.78 (2H, m), 3.99–4.10 (2H, m), 7.15–7.24 (2H, m), 7.31–7.35 (3H, m), 7.52–7.70 (6H, m), 7.95 (1H, br s), 8.23 (1H, d, J=8.6 Hz). IR (KBr) 3273, 1655, 1601, 1516, 1410, 1311, 1128, 825 cm$^{-1}$; Anal. for C$_{30}$H$_{31}$N$_2$O$_4$SF.0.5 H$_2$O; Calcd. C, 66.28; H, 5.93; N, 5.15; Found. C, 66.56; H, 5.90; N, 5.13.

Working Example 10 (Production of Compound 9)

To a solution of 7-(4-trifluoromethylphenyl)-1,1-dioxo-2,3-dihydro-1-benzothiepine-4-carboxylic acid (180 mg) in THF (10 ml) were added at room temperature oxalyl chloride (0.8 ml) and a drop of DMF, and the mixture was stirred for 1 hour. The solvent was evaporated under reduced pressure, and the residue was dissolved in THF (10 ml). The solution was added at 0° C. to a solution of 4-[N-methyl-N-(tetrahydropyran-4-yl)aminomethyl]aniline (114 mg) and triethylamine (0.13 ml) in THF (5 ml), and the mixture was stirred at room temperature for 14 hours. To the mixture was added water, and the mixture was extracted with dichloromethane. The organic layer was washed with saturated brine, dried with magnesium sulfate and concentrated under reduced pressure, and precipitated crystals were recrystallized from ethanol to give colorless crystals of N-[4-[N-methyl-N-(tetrahydropyran- 4-yl)aminomethyl]phenyl]-7-(4-trifluoromethylphenyl)-1,1-dioxo-2,3-dihydro-1-benzothiepine-4-carboxamide (Compound 9) (208.9 mg).

m.p. 270–272° C.; $^1$H-NMR (200 MHz, DMSO-$d_6$) δ 1.37–1.61 (2H, m), 1.63–1.78 (2H, m), 2.10 (3H, s), 2.46–2.67 (1H, m), 3.07–3.13 (2H, m), 3.18–3.35 (2H, m), 3.52 (2H, s), 3.75–3.96 (4H, m), 7.27 (2H, d, J=8.5 Hz), 7.56 (1H, s), 7.67 (2H, d, J=8.5 Hz), 7.90 (2H, d, J=8.4 Hz), 7.97–8.06 (3H, m), 8.14–8.18 (2H, m). IR (KBr) 3245, 1654, 1636, 1601, 1529, 1410, 1325, 1294, 1173, 1130, 1072, 827 cm$^{-1}$; Anal. for $C_{31}H_{31}N_2O_4SF_3$; Calcd. C, 63.68 H, 5.34; N, 4.79; Found. C, 63.64; H, 5.30; N, 4.70.

Working Example 11 (Production of Compound 10)

To a solution of 7-(4-ethylphenyl)-1,1-dioxo-2,3-dihydro-1-benzothiepine-4-carboxylic acid (180 mg) in THF (10 ml) were added at room temperature oxalyl chloride (0.09 ml) and a drop of DMF, and the mixture was stirred for 1 hour. The solvent was evaporated under reduced pressure, and the residue was dissolved in THF (15 ml). The solution was added dropwise at 0° C. to a solution of 4-[N-methyl-N-(tetrahydropyran-4-yl)aminomethyl]aniline (128 mg) and triethylamine (0.15 ml) in THF (5 ml), and the mixture was stirred at room temperature for 64 hours. To the mixture was added water, and the mixture was extracted with ethyl acetate. The organic layer was washed with saturated brine, dried with magnesium sulfate and concentrated under reduced pressure, and precipitated crystals were recrystallized from ethanol to give pale yellow crystals of 7-(4-ethylphenyl)-N-[4-[N-methyl-N-(tetrahydropyran-4-yl)aminomethyl]phenyl]-1,1-dioxo-2,3-dihydro-1-benzothiepine-4-carboxamide (Compound 10) (173.6 mg).

m.p. 257–260° C.; $^1$H-NMR (200 MHz, CDCl$_3$) δ 1.29 (3H, t, J=6.7 Hz), 1.56–1.83 (4H, m), 2.21 (3H, s), 2.54–2.71 (1H, m), 2.72 (2H, q, J=6.7 Hz), 3.17 (2H, t, J=6.7 Hz), 3.31–3.44 (2H, m), 3.58 (2H, s), 3.70–3.76 (2H, m), 3.98–4.11 (2H, m), 7.31–7.35 (5H, m), 7.54 (2H, d, J=8.0 Hz), 7.55 (2H, d, J=8.4 Hz), 7.66 (1H, s), 7.71 (1H, dd, J=8.4 Hz), 7.92 (1H, br s), 8.21 (1H, d, J=8.4 Hz). IR (KBr) 3248, 1657, 1635, 1599, 1525, 1410, 1317, 1294, 1128, 824 cm$^{-1}$; Anal. for $C_{32}H_{36}N_2O_4S$; Calcd. C, 70.56; H, 6.66; N, 5.14; Found. C, 70.30; H, 6.73; N, 5.29.

Working Example 12 (Production of Compound 11)

To a solution of 7-(4-isopropylphenyl)-1,1-dioxo-2,3-dihydro-1-benzothiepine-4-carboxylic acid (180 mg) in THF (10 ml) were added at room temperature oxalyl chloride (0.09 ml) and a drop of DMF, and the mixture was stirred for 1 hour. The solvent was evaporated under reduced pressure, and the residue was dissolved in THF (15 ml). The solution was added dropwise at 0° C. to a solution of 4-[N-methyl-N-(tetrahydropyran-4-yl)aminomethyl]aniline (122 mg) and triethylamine (0.14 ml) in THF (5 ml), and the mixture was stirred at room temperature for 20 hours. To the mixture was added water, and the mixture was extracted with ethyl acetate. The organic layer was washed with saturated brine, dried with magnesium sulfate and concentrated under reduced pressure, and the residue was purified with column chromatography (ethanol/ethyl acetate=1:3) and recrystallized from ethanol to give colorless crystals of 7-(4-isopropylphenyl)-N-[4-[N-methyl-N-(tetrahydropyran-4-yl)aminomethyl]phenyl]-1,1-dioxo-2,3-dihydro-1-benzothiepine-4-carboxamide (Compound 11) (189.8 mg, 67%).

m.p. 240–247° C.; $^1$H-NMR (200 MHz, CDCl$_3$) δ 1.30 (6H, d, J=7.0 Hz), 1.52–1.83 (4H, m), 2.21 (3H, s), 2.55–2.77 (1H, m), 2.90–3.04 (1H, m), 3.17 (2H, t, J=6.6 Hz), 3.37 (2H, dt, J=2.8, 11.0 Hz), 3.58 (2H, s), 3.70–3.76 (2H, m), 3.98–4.09 (2H, m), 7.31–7.38 (5H, m), 7.52–7.58 (4H, m), 7.66–7.73 (2H, m), 7.98 (1H, br s), 8.21 (1H, d, J=8.4 Hz). IR (KBr) 3251, 1655, 1601, 1525, 1410, 1317, 1296, 1130, 821 cm$^{-1}$; Anal. for $C_{33}H_{38}N_2O_4S$; Calcd. C, 70.94; H, 6.86; N, 5.01; Found. C, 70.89; H, 6.61; N, 7.75.

Working Example 13 (Production of Compound 12)

To a solution of 7-(4-tert-butylphenyl)-1,1-dioxo-2,3-dihydro-1-benzothiepine-4-carboxylic acid (180 mg) in THF (1 ml) were added at room temperature oxalyl chloride (0.09 ml) and a drop of DMF, and the mixture was stirred for 1 hour. The solvent was evaporated under reduced pressure, and the residue was dissolved in tetrahydrofuran (15 ml). The solution was added dropwise at 0° C. to a solution of 4-[N-methyl-N-(tetrahydropyran-4-yl)aminomethyl]aniline (119 mg) and triethylamine (0.14 ml) in THF (5 ml), and the mixture was stirred at room temperature for 16 hours. To the mixture was added water, and the mixture was extracted with ethyl acetate. The organic layer was washed with saturated brine, dried with magnesium sulfate and concentrated under reduced pressure, and precipitated crystals were recrystallized from ethanol to give colorless crystals of 7-(4-tert-butylphenyl)-N-[4-[N-methyl-N-(tetrahydropyran-4-yl)aminomethyl]phenyl]-1,1-dioxo-2,3-dihydro-1-benzothiepine-4-carboxamide (Compound 12) (209.8 mg).

m.p. 247–249° C.; $^1$H-NMR (200 MHz, CDCl$_3$) δ 1.37 (9H, s), 1.52–1.83 (4H, m), 2.21 (3H, s), 2.54–2.74 (1H, m), 3.13–3.20 (2H, m), 3.29–3.45 (2H, m), 3.58 (2H, s), 3.68–3.79 (2H, m), 3.98–4.10 (2H, m), 7.31–7.35 (3H, m), 7.46–7.60 (6H, m), 7.66 (1H, d, J=1.8 Hz), 7.71 (1H, dd, J=8.0, 1.8 Hz), 7.99 (1H, br s), 8.21 (1H, d, J=8.0 Hz). IR (KBr) 3278, 1655, 1599, 1512, 1313, 1300, 1130, 821 cm$^{-1}$; Anal. for $C_{34}H_{40}N_2O_4S \cdot 0.2\ H_2O$; Calcd. C, 70.85; H, 7.07; N, 4.86; Found. C, 70.60; H, 6.91; N, 4.78.

Working Example 14 (Production of Compound 13)

To a solution of 7-[4-(1-pyrrolidinyl)phenyl]-1,1-dioxo-2,3-dihydro-1-benzothiepine-4-carboxylic acid (75 mg) in DMF (5 ml) was added at room temperature thionyl chloride (0.1 ml), and the mixture was stirred for 1 hour. The solvent was evaporated under reduced pressure, and the residue was dissolved in dichloromethane (10 ml). The solution was added dropwise at 0° C. to a solution of 4-[N-methyl-N-(tetrahydropyran-4-yl)aminomethyl]aniline (53 mg) and triethylamine (0.5 ml) in dichloromethane (5 ml), and the mixture was stirred at room temperature for 16 hours. To the mixture was added water, and the mixture was extracted with dichloromethane. The organic layer was washed with saturated brine, dried with magnesium sulfate and concentrated under reduced pressure, and the residue was purified with column chromatography (ethanol/ethyl acetate=1:2) to give yellow crystals of N-[4-[N-methyl-N-(tetrahydropyran-4-yl)aminomethyl]phenyl]-7-[4-(1-pyrrolidinyl)phenyl]-1,1-dioxo-2,3-dihydro-1-benzothiepine-4-carboxamide (Compound 13) (36.3 mg).

$^1$H-NMR (200 MHz, DMSO-d$_6$) δ 1.42–1.67 (4H, m), 1.89–2.04 (4H, m), 2.10 (3H, s), 2.45–2.68 (1H, m), 2.98–3.10 (2H, m), 3.17–3.36 (6H, m),3.52 (2H, s), 3.69–3.81 (2H, m), 3.83–3.96 (2H, m), 6.65 (2H, d, J=8.6 Hz), 7.27 (2H, d, J=8.0 Hz), 7.52 (1H, s), 7.61–7.71 (4H, m), 7.76–7.84 (1H, m), 7.98–8.02 (2H, m), 10.16 (1H, s). IR (KBr) 3278, 1657, 1606, 1525, 1379, 1315, 1294, 1167, 1128, 812 cm$^{-1}$;

Working Example 15 (Production of Compound 14)

To a solution of 7-(4-piperidinophenyl)-1,1-dioxo-2,3-dihydro-1-benzothiepine-4-carboxylic acid (200 mg) in DMF (10 ml) was added at room temperature thionyl chloride (0.1 ml), and the mixture was stirred for 1 hour. The solvent was evaporated under reduced pressure, and the residue was dissolved in dichloromethane (15 ml). The solution was added dropwise at 0° C. to a solution of 4-[N-methyl-N-(tetrahydropyran-4-yl)aminomethyl]aniline (125 mg) and triethylamine (0.5 ml) in dichloromethane (5 ml), and the mixture was stirred at room temperature for 16 hours. The mixture was added to water, and the mixture was extracted with dichloromethane. The organic layer was washed with saturated brine, dried with magnesium sulfate and concentrated under reduced pressure, and the residue was purified with column chromatography (ethanol/ethyl acetate=1:4) to give yellow crystals of N-[4-[N-methyl-N-(tetrahydropyran-4-yl)aminomethyl]phenyl]-7-(4-piperidinophenyl)-1,1-dioxo-2,3-dihydro-1-benzothiepine-4-carboxamide (Compound 14) (39.5 mg).

$^1$H-NMR (200 MHz, DMSO-d$_6$) δ 1.39–1.77 (10H, m), 2.10 (3H, s), 2.46–2.70 (1H, m), 3.01–3.11 (2H, m), 3.17–3.35 (6H, m), 3.52 (2H, s), 3.72–3.81 (2H, m), 3.83–3.97 (2H, m), 7.05 (2H, d, J=8.8 Hz), 7.27 (2H, d, J=8.4 Hz), 7.53 (1H, s), 7.67 (2H, d, J=8.4 Hz), 7.68 (2H, d, J=8.8 Hz), 7.84 (1H, dd, J=8.2, 2.2 Hz), 8.01–8.05 (2H, m), 10.17 (1H, s). IR (KBr) 3280, 1657, 1603, 1522, 1315, 1292, 1238, 1126, 818 cm$^{-1}$.

Working Example 16 (Production of Compound 15)

To a solution of 7-(4-morpholinophenyl)-1,1-dioxo-2,3-dihydro-1-benzothiepine-4-carboxylic acid hydrochloride (200 mg) and 1-hydroxybenzotriazole (0.12 g) in DMF (5 ml) was added at room temperature 1-ethyl-3-(3'-dimethylaminopropyl)carbodiimide hydrochloride (0.18 g), and the mixture was stirred for 1 hour. To the mixture was added a solution of 4-[N-(4,4-ethylenedioxycyclohexyl)-N-methylaminomethyl]aniline (0.19 g) and triethylamine (0.2 ml) in DMF (3 ml) and stirred for 64 hours. The mixture was concentrated under reduced pressure, and to the residue was added water. The mixture was extracted with ethyl acetate, and the organic layer was washed with saturated brine and dried with magnesium sulfate. The solvent was evaporated under reduced pressure, and the residue was purified with column chromatography (ethanol/ethyl acetate=1:1) to give yellow crystals of N-[4-[N-(4,4-ethylenedioxycyclohexyl)-N-methylaminomethyl]phenyl]-7-(4-morpholinophenyl)-1,1-dioxo-2,3-dihydro-1-benzothiepine-4-carboxamide (Compound 15) (119 mg).

$^1$H-NMR (200 MHz, CDCl$_3$) δ 1.51–1.75 (4H, m), 1.77–1.91 (4H, m), 2.20 (3H, s), 2.44–2.65 (1H, m), 3.11–3.20 (2H, m), 3.23–3.28 (4H, m), 3.57 (2H, s), 3.69–3.75 (2H, m), 3.87–3.91 (4H, m), 3.95 (4H, s), 7.00 (2H, d, J=8.8 Hz), 7.30–7.35 (3H, m), 7.51–7.58 (4H, m), 7.64 (1H, br s), 7.65–7.73 (1H, m), 7.88–7.93 (1H, m), 8.18 (1H, d, J=7.6 Hz). IR (KBr) 3346, 1653, 1608, 1520, 1410, 1310, 1238, 1165, 1126, 928, 819 cm$^{-1}$.

Working Example 17 (Production of Compound 16)

To a solution of 7-(4-methoxyphenyl)-1,1-dioxo-2,3-dihydro-1-benzothiepine-4-carboxylic acid (170 mg) in THF (10 ml) were added at room temperature oxalyl chloride (0.09 ml) and a drop of DMF, and the mixture was stirred for 1 hour and concentrated under reduced pressure. The residue was dissolved in THF (15 ml). The solution was added dropwise at 0 to a solution of 4-[N-(4,4-ethylenedioxycyclohexyl)-N-methylaminomethyl]aniline (0.15 g) and triethylamine (0.14 ml) in THF (5 ml), and the mixture was stirred at room temperature for 21 hours. To the mixture was added water, and the mixture was extracted with ethyl acetate. The organic layer was washed with saturated brine and dried with magnesium sulfate. The solvent was evaporated under reduced pressure, and the residue was purified with column chromatography (ethanol/ethyl acetate=1:1) and recrystallized from ethanol/ethyl acetate) to give pale yellow crystals of N-[4-[N-(4,4-ethylenedioxycyclohexyl)-N-methylaminomethyl]phenyl]-7-(4-methoxyphenyl)- 1,1-dioxo-2,3-dihydro-1-benzothiepine-4-carboxamide (Compound 16) (164.2 mg).

m.p. 222–228° C.; $^1$H-NMR (200 MHz, CDCl$_3$) δ 1.45–1.90 (8H, m), 2.20 (3H, s), 2.45–2.63 (1H, m), 3.13–3.20 (2H, m), 3.56 (2H, s), 3.69–3.76 (2H, m), 3.88 (3H, s), 3.95 (4H, s), 7.02 (2H, d, J=8.6 Hz), 7.30–7.35 (3H, m), 7.52–7.70 (6H, m), 7.92 (1H, br s), 8.20 (1H, d, J=8.0 Hz). IR (KBr) 3356, 1651, 1608, 1518, 1311, 1292, 1252, 1126, 824 cm$^{-1}$; Anal. for C$_{34}$H$_{38}$N$_2$O$_6$S; Calcd. C, 67.75; H, 6.35; N, 4.65; Found. C, 67.48; H, 6.15; N, 4.47.

Working Example 18 (Production of Compound 17)

To a solution of N-[4-[N-(4,4-ethylenedioxycyclohexyl)-N-methylaminomethyl]phenyl]-7-(4-methoxyphenyl)-1,1-dioxo-2,3-dihydro-1-benzothiepine-4-carboxamide (112 mg) in THF (20 ml) was added at room temperature 3N hydrochloric acid (1 ml), and the mixture was stirred for 18 hours. To the mixture was added saturated sodium bicarbonate solution, and the mixture was extracted with ethyl acetate. The organic layer was washed with saturated brine, dried with magnesium sulfate and concentrated under reduced pressure to give colorless solid, which was recrystallized from ethyl acetate/hexane to give colorless crystals of 7-(4-methoxyphenyl)-N-[4-[N-methyl-N-(4-oxocyclohexyl)aminomethyl]phenyl]-1,1-dioxo-2,3-dihydro-1-benzothiepine-4-carboxamide (Compound 17) (77.6 mg).

m.p. 214–218° C.; $^1$H-NMR (200 MHz, CDCl$_3$) δ 1.77–2.14 (4H, m), 2.24 (3H, s), 2.26–2.58 (4H, m), 2.80–2.96 (1H, m), 3.13–3.20 (2H, m), 3.61 (2H, s), 3.70–3.76 (2H, m), 3.87 (3H, s), 7.02 (2H, d, J=8.8 Hz), 7.32–7.36 (3H, m), 7.53–7.70 (6H, m), 7.97 (1H, br s), 8.20 (1H, d, J=8.4 Hz). IR (KBr) 3280, 1713, 1657, 1603, 1518, 1313, 1296, 1252, 1128, 825 cm$^{-1}$; Anal. for C$_{32}$H$_{34}$N$_2$O$_5$S.0.5 H$_2$O; Calcd. C, 67.70; H, 6.21; N, 4.93; Found. C, 67.58; H, 5.97; N, 4.66.

Working Example 19 (Production of Compound 18)

To a solution of 7-(4-ethoxyphenyl)-1,1-dioxo-2,3-dihydro-1-benzothiepine-4-carboxylic acid (180 mg) in THF (10 ml) were added at room temperature oxalyl chloride (0.09 ml) and a drop of DMF, and the mixture was stirred for 1 hour. The mixture was concentrated under reduced pressure, and the residue was dissolved in THF (10 ml). The solution was added dropwise at 0° C. to a solution of 4-[N-(4,4-ethylenedioxycyclohexyl)-N-methylaminomethyl]aniline [0.153 g (0.553 mmol)] and triethylamine (0.14 ml) in THF (5 ml), and the mixture was stirred at room temperature for 16 hours. To the mixture was added water, and the mixture was extracted with ethyl acetate. The organic layer was washed with saturated brine and dried with magnesium sulfate. The solvent was evaporated under reduced pressure to give crude crystals, which were recrystallized from ethanol/diisopropylether to give colorless crystals of 7-(4-ethoxyphenyl)-N-[4-[N-(4,4-ethylenedioxycyclohexyl)-N-methylaminomethyl]phenyl]-1,1-dioxo-2,3-dihydro-1-benzothiepine-4-carboxamide (Compound 18) (187 mg).

m.p. 220–223° C.; $^1$H-NMR (200 MHz, CDCl$_3$) δ 1.46 (3H, t, J=7.0 Hz), 1.51–1.92 (8H, m), 2.21 (3H, s), 2.46–2.64 (1H, m), 3.17 (2H, t, J=7.0 Hz), 3.57 (2H, s), 3.73 (2H, t, J=7.0 Hz), 3.95 (4H, s), 4.10 (2H, q, J=7.0 Hz), 7.01 (2H, d, J=9.0 Hz), 7.28–7.38 (3H, m), 7.49–7.59 (4H, m), 7.61–7.72 (2H, m), 7.87–7.94 (1H, m), 8.21 (1H, d, J=8.2 Hz). IR (KBr) 3346, 1651, 1518, 1311, 1292, 1250, 1164, 1126, 822 cm$^{-1}$; Anal. for C$_{35}$H$_{40}$N$_2$O$_6$S.0.2 H$_2$O; Calcd. C, 67.76; H, 6.56; N, 4.52; Found. C, 67.66; H, 6.32; N, 4.36.

Working Example 20 (Production of Compound 19)

To a solution of 7-(4-ethoxyphenyl)-N-[4-[N-(4,4-ethylenedioxycyclohexyl)-N-methylaminomethyl]phenyl]-1,1-dioxo-2,3-dihydro-1-benzothiepine-4-carboxamide (140 mg) in THF (20 ml) was added at room temperature 3N hydrochloric acid (1 ml), and the mixture was stirred for 40 hours. To the mixture was added saturated sodium bicarbonate solution, and the mixture was extracted with ethyl acetate. The organic layer was washed with saturated brine, dried with magnesium sulfate and concentrated under reduced pressure to give colorless solid, which was recrystallized from ethyl acetate/hexane to give colorless crystals of 7-(4-ethoxyphenyl)-N-[4-[N-methyl-N-(4-oxocyclohexyl)aminomethyl]phenyl]-1,1-dioxo-2,3-dihydro-1-benzothiepine-4-carboxamide (Compound 19) (101.1 mg).

m.p. 195° C. (dec.); $^1$H-NMR (200 MHz, CDCl$_3$) δ 1.45 (3H, t, J=7.0 Hz), 1.83–2.17 (4H, m), 2.24 (3H, s), 2.26–2.59 (4H, m), 2.80–2.98 (1H, m), 3.13–3.20 (2H, m), 3.62 (2H, s), 3.69–3.76 (2H, m), 4.10 (2H, q, J=7.0 Hz), 7.01 (2H, d, J=8.8 Hz), 7.32–7.36 (3H, m), 7.52–7.70 (6H, m), 7.96 (1H, br s), 8.20 (1H, d, J=8.4 Hz). IR (KBr) 3278, 1713, 1657, 1603, 1520, 1313, 1298, 1248, 1128, 824 cm$^{-1}$; Anal. for C$_{33}$H$_{36}$N$_2$O$_5$S.1.0 H$_2$O; Calcd. C, 67.10; H, 6.48; N, 4.74; Found. C, 66.97; H, 6.09; N, 4.72.

Working Example 21 (Production of Compound 20)

To a solution of 7-(3,4-methylenedioxyphenyl)-1,1-dioxo-2,3-dihydro-1-benzoxepine-4-carboxylic acid (180 mg) in THF (10 ml) were added at room temperature oxalyl chloride (0.09 ml) and a drop of DMF, and the mixture was stirred for 1 hour and concentrated under reduced pressure. The residue was dissolved in THF (15 ml), and the solution was added dropwise at 0° C. to a solution of 4-[N-(4,4-ethylenedioxycyclohexyl)-N-methylaminomethyl]aniline (0.153 g) and triethylamine (0.14 ml) in THF (5 ml). The mixture was stirred at room temperature for 15 hours. To the mixture was added water, and the mixture was extracted with ethyl acetate. The organic layer was washed with saturated brine and dried with magnesium sulfate. The solvent was evaporated under reduced pressure, and the residue was purified with column chromatography (ethanol/ethyl acetate=1:1) and recrystallized from ethanol/diisopropylether to give pale yellow crystals of N-[4-[N-(4,4-ethylenedioxycyclohexyl)-N-methylaminomethyl]phenyl]-7-(3,4-methylenedioxyphenyl)-1,1-dioxo-2,3-dihydro-1-benzothiepine-4-carboxamide (Compound 20) (153.1mg).

m.p. 214–215° C.; $^1$H-NMR (200 MHz, CDCl$_3$) δ 1.45–1.92 (8H, m), 2.20 (3H, s), 2.43–2.62 (1H, m), 3.17 (2H, t, J=7.0 Hz), 3.57 (2H, s), 3.69–3.76 (2H, m), 3.95 (4H, s), 6.04 (2H, s), 6.92 (1H, d, J=8.6 Hz), 7.07–7.12 (2H, m), 7.31–7.35 (3H, m), 7.51–7.66 (4H, m), 7.88 (1H, br s), 8.19 (1H, d, J=8.4 Hz). IR (KBr) 3327, 1649, 1514, 1314, 1292, 1238, 1128, 1109, 930, 818 cm$^{-1}$; Anal. for C$_{34}$H$_{36}$N$_2$O$_7$S.0.1 H$_2$O; Calcd. C, 66.02; H, 5.90; N, 4.53; Found. C, 65.98; H, 5.78; N, 4.23.

Working Example 22 (Production of Compound 21)

To a solution of N-[4-[N-(4,4-ethylenedioxycyclohexyl)-N-methylaminomethyl]phenyl]-7-(3,4-methylenedioxyphenyl)-1,1-dioxo-2,3-dihydro-1-benzothiepine-4-carboxamide (100 mg) in THF (10 ml) was added at room temperature 3N hydrochloric acid (1 ml), and the mixture was stirred for 39 hours. To the mixture was added saturated sodium bicarbonate solution, and the mixture was extracted with ethyl acetate. The organic layer was washed with saturated brine, dried with magnesium sulfate and concentrated under reduced pressure to give colorless solid which were recrystallized from ethyl acetate to give colorless crystals of 7-(3,4-methylenedioxyphenyl)-N-[4-[N-methyl-N-(4-oxocyclohexyl)aminomethyl]phenyl]-1,1-dioxo-2,3-dihydro-1-benzothiepine-4-carboxamide (Compound 21) (56.8 mg).

m.p. 219–223° C.; $^1$H-NMR (200 MHz, CDCl$_3$) δ 1.83–2.17 (4H, m), 2.24 (3H, s), 2.29–2.59 (4H, m), 2.81–2.98 (1H, m), 3.16 (2H, t, J=6.9 Hz), 3.61 (2H, s), 3.73 (2H, t, J=6.9 Hz), 6.05 (2H, s), 6.92 (1H, d, J=8.4 Hz), 7.07–7.12 (2H, m), 7.32–7.36 (3H, m), 7.54–7.59 (3H, m), 7.64 (1H, dd, J=8.0, 2.0 Hz), 7.98 (1H, br s), 8.19 (1H, d, J=8.0 Hz). IR (KBr) 3280, 1716, 1659, 1599, 1510, 1479, 1410, 1317, 1292, 1234, 1128, 1041, 812 cm$^{-1}$; Anal. for C$_{32}$H$_{32}$N$_2$O$_6$S.0.5 H$_2$O; Calcd. C, 66.08; H, 5.72; N, 4.82; Found. C, 66.36; H, 5.73; N, 4.78.

Working Example 23 (Production of Compound 22)

To a solution 7-(4-chlorophenyl)-1,1-dioxo-2,3-dihydro-1-benzothiepine-4-carboxylic acid (250 mg) in THF (10 ml) were added at room temperature oxalyl chloride (0.13 ml) and a drop of DMF, and the mixture was stirred for 1 hour and concentrated under reduced pressure. The residue was dissolved in THF (15 ml), and the solution was added dropwise at 0° C. to a solution of 4-[N-(4,4-ethylenedioxycyclohexyl)-N-methylaminomethyl]aniline (0.238 g) and triethylamine (0.2 ml) in THF (5 ml). The mixture was stirred at room temperature for 20 hours. To the mixture was added water, and the mixture was extracted with ethyl acetate. The organic layer was washed with saturated brine and dried with magnesium sulfate. The solvent was evaporated under reduced pressure, and the residue was purified with column chromatography (ethanol/ethyl acetate=1:2) and recrystallized from ethanol to give colorless crystals of 7-(4-chlorophenyl)-N-[4-[N-(4,4-ethylenedioxycyclohexyl)-N-methylaminomethyl]phenyl]-1,1-dioxo-2,3-dihydro-1-benzothiepine-4-carboxamide (Compound 22) (286.8 mg).

m.p. 224–228° C.;

$^1$H-NMR (200 MHz, CDCl$_3$) δ 1.44–1.90 (8H, m), 2.20 (3H, s), 2.42–2.64 (1H, m ), 3.12–3.23 (2H, m), 3.56 (2H, s), 3.70–3.77 (2H, m), 3.95 (4H, s), 7.31–7.35 (3H, m), 7.45–7.57 (6H, m), 7.63–7.73 (2H, m), 7.90 (1H, br s), 8.24 (1H, d, J=8.4 Hz). IR (KBr) 3336, 1672, 1518, 1308, 1282, 1165, 1126, 1097, 820 cm$^{-1}$; Anal. for C$_{33}$H$_{35}$N$_2$O$_5$SCl; Calcd. C, 65.28; H, 5.81; N, 4.61; Found. C, 65.18; H, 5.70; N, 4.60.

Working Example 24 (Production of Compound 23)

To a solution of 7-(4-chlorophenyl)-N-[4-[N-(4,4-ethylenedioxycyclohexyl)-N-methylaminomethyl]phenyl]-1,1-dioxo-2,3-dihydro-1-benzothiepine-4-carboxamide (180 mg) in THF (15 ml) was added at room temperature 3N hydrochloric acid (1 ml), and the mixture was stirred for 7 days. To the mixture was added saturated sodium bicarbonate solution, and the mixture was extracted with ethyl acetate. The organic layer was washed with saturated brine, dried with magnesium sulfate and concentrated under reduced pressure to give colorless solid, which was recrystallized from ethyl acetate to give colorless crystals of 7-(4-chlorophenyl)-N-[4-[N-methyl-N-(4-oxocyclohexyl)aminomethyl]phenyl]-1,1-dioxo-2,3-dihydro-1-benzothiepine-4-carboxamide (Compound 23) (85.9 mg).

m.p. 197–200° C.; $^1$H-NMR (200 MHz, CDCl$_3$) δ 1.79–2.20 (4H, m), 2.25 (3H, s), 2.29–2.62 (4H, m), 2.84–3.03 (1H, m), 3.18 (2H, t, J=7.0 Hz), 3.63 (2H, s), 3.70–3.78 (2H, m), 7.30–7.72 (11H, m), 7.84–8.02 (1H, m), 8.24 (1H, d, J=8.4 Hz). IR (KBr) 3277, 1714, 1653, 1599, 1529, 1410, 1319, 1128, 820 cm$^{-1}$; Anal. for C$_{31}$H$_{31}$N$_2$O$_4$SCl.0.75 H$_2$O; Calcd. C, 64.57; H, 5.68; N, 4.86; Found. C, 64.49; H, 5.40; N, 4.92.

Working Example 25 (Production of Compound 24)

To a solution of 7-(4-morpholinophenyl)-1,1-dioxo-2,3-dihydro-1-benzothiepine-4-carboxylic acid (150 mg) and 1-hydroxybenzotriazole (101 mg) in DMF (5 ml) was added at room temperature 1-ethyl-3-(3'-dimethylaminopropyl)carbodiimide hydrochloride (144 mg), and the mixture was stirred for 2 hours. To the mixture were added a solution of ethyl 3-[N-(4-aminobenzyl)-N-methylamino]propionate (133 mg) and triethylamine (0.1 ml) in DMF (5 ml) and a piece of 4-dimethylaminopyridine, and the mixture was stirred for 20 hours and concentrated under reduced pressure. To the residue was added water, and the mixture was extracted with dichloromethane. The organic layer was washed with saturated brine and dried with magnesium sulfate. The solvent was evaporated under reduced pressure, and the residue was purified with column chromatography (ethanol/ethyl acetate=1:9) and recrystallized from ethyl acetate/hexane to give yellow crystals of N-[4-[N-(2-ethoxycarbonylethyl)-N-methylaminomethyl]phenyl]-7-(4-morpholinophenyl)-1,1-dioxo-2,3-dihydro-1-benzothiepine-4-carboxamide (Compound 24) (133.6 mg).

m.p. 209–211° C.; $^1$H-NMR (200 MHz, CDCl$_3$) δ 1.26 (3H, t, J=7.2 Hz), 2.21 (3H, s), 2.49–2.55 (2H, m), 2.72–2.79 (2H, m), 3.10–3.20 (2H, m), 3.23–3.28 (4H, m), 3.51 (2H, s), 3.69–3.76 (2H, m), 3.87–3.92 (4H, m), 4.15 (2H, q, J=7.2 Hz), 7.00 (2H, d, J=9.2 Hz), 7.25–7.37 (3H, m), 7.53–7.58 (4H, m), 7.63–7.72 (2H, m), 7.96 (1H, s), 8.19 (1H, d, J=8.0 Hz). IR (KBr) 3334, 1732, 1651, 1605, 1520, 1311, 1238, 1165, 1126, 930, 818 cm$^{-1}$; Anal. for C$_{34}$H39N$_3$O$_6$S; Calcd. C, 66.10; H, 6.36; N, 6.80; Found. C, 65.84; H, 6.44; N, 6.81.

Working Example 26 (Production of Compound 25)

To a solution of 7-(4-trifluoromethoxyphenyl)-1,1-dioxo-2,3-dihydro-1-benzothiepine-4-carboxylic acid (180 mg) in THF (5 ml) were added at room temperature oxalyl chloride (0.08 ml) and a drop of DMF, and the mixture was stirred for 1 hour. The solvent was evaporated under reduced pressure, and the residue was dissolved in DMF (4 ml). The solution was added dropwise at 0° C. to a solution of 4-[N-methyl-N-(tetrahydropyran-4-yl)aminomethyl]aniline (109 mg) and triethylamine (0.19 ml) in THF (5 ml), and the mixture was stirred at room temperature for 18 hours. To the mixture was added water, and the mixture was extracted with ethyl acetate. The organic layer was washed with saturated brine, dried with magnesium sulfate and concentrated under reduced pressure, and the residue was purified with column chromatography (ethanol/ethyl acetate=1:3) and recrystallized from ethanol to give colorless crystals of N-[4-[N-methyl-N-(tetrahydropyran-4-yl)aminomethyl]phenyl]-7-(4-trifluoromethoxyphenyl)-1,1-dioxo-2,3-dihydro-1-benzothiepine-4-carboxamide (Compound 25) (137.0 mg).

m.p. 261–263° C.; $^1$H-NMR (200 MHz, CDCl$_3$) δ 1.52–1.82 (4H, m), 2.21 (3H, s), 2.52–2.74 (1H, m), 3.15–3.22 (2H, m), 3.31–3.45 (2H, m), 3.58 (2H, s), 3.71–3.78 (2H, m), 3.98–4.12 (2H, m), 7.27–7.35 (5H, m), 7.55 (2H, d, J=8.8 Hz), 7.61–7.65 (3H, m), 7.70 (1H, dd, J=8.1, 1.8 Hz), 7.93 (1H, br s), 8.25 (1H, d, J=8.1 Hz). IR (KBr) 3242, 1657, 1633, 1601, 1518, 1412, 1317, 1294, 1265, 1215, 1169, 1130 cm$^{-1}$; Anal. for C$_{31}$H$_{31}$N$_2$O$_5$SF$_3$; Calcd. C, 61.99; H, 5.20; N, 4.66; Found. C, 61.95; H, 5.01; N, 4.59.

Working Example 27 (Production of Compound 26)

To a solution of 7-(3,4-dichlorophenyl)-1,1-dioxo-2,3-dihydro-1-benzothiepine-4-carboxylic acid (180 mg) in THF (10 ml) were added at room temperature thionyl chloride (0.08 ml) and a drop of DMF, and the mixture was stirred for 1 hour. The solvent was evaporated under reduced pressure, and the residue was dissolved in THF (15 ml). The solution was added dropwise at 0° C. to a solution of 4-[N-methyl-N-(tetrahydropyran-4-yl)aminomethyl]aniline (114 mg) and triethylamine (0.2 ml) in THF (2 ml), and the mixture was stirred at room temperature for 16 hours. To the mixture was added water, and the mixture was extracted with ethyl acetate. The organic layer was washed with saturated brine, dried with magnesium sulfate and concentrated under reduced pressure, and the residue was purified with column chromatography (ethanol/ethyl acetate=1:4) and recrystallized from ethanol to give colorless crystals of 7-(3,4-dichlorophenyl)-N-[4-[N-methyl-N-(tetrahydropyran-4-yl)aminomethyl]phenyl]-1,1-dioxo-2,3-dihydro-1-benzothiepine-4-carboxamide (Compound 26) (155.0 mg).

m.p. 235–237° C.; $^1$H-NMR (200 MHz, CDCl$_3$) δ 1.56–1.78 (4H, m), 2.21 (3H, s), 2.55–2.73 (1H, m), 3.17 (2H, t, J=6.6 Hz), 3.31–3.44 (2H, m), 3.57 (2H, s), 3.73 (2H, t, J=6.6 Hz), 3.98–4.10 (2H, m), 7.30–7.35 (3H, m), 7.43 (1H, dd, J=8.4, 2.2 Hz), 7.52–7.69 (6H, m), 7.96 (1H, br s), 8.25 (1H, d, J=8.2 Hz). IR (KBr) 3253, 1655, 1633, 1601, 1529, 1467, 1410, 1317, 1296, 1130, 818 cm$^{-1}$; Anal. for C$_{30}$H$_{30}$N$_2$O$_4$SCl$_2$; Calcd. C, 61.54; H, 5.16; N, 4.78; Found. C, 61.71; H, 5.14; N, 4.77.

Working Example 28 (Production of Compound 27)

To a solution of 7-(4-propylphenyl)-1,1-dioxo-2,3-dihydro-1-benzothiepine-4-carboxylic acid (200 mg) in THF (5 ml) were added at room temperature thionyl chloride (0.09 ml) and a drop of DMF, and the mixture was stirred for 1 hour. The solvent was evaporated under reduced pressure, and the residue was dissolved in THF (12 ml). The solution was added dropwise at 0° C. to a solution of 4-[N-methyl-N-(tetrahydropyran-4-yl)aminomethyl]aniline[122 mg (0.55 mmol)] and triethylamine (0.14 ml) in THF (2 ml), and the mixture was stirred at room temperature for 4 hours. To the mixture was added water, and the mixture was extracted with ethyl acetate. The organic layer was washed with saturated brine, dried with magnesium sulfate and concentrated under reduced pressure to give pale yellow crystals, which were recrystallized from ethanol to give colorless crystals of N-[4-[N-methyl-N-(tetrahydropyran-4-yl)aminomethyl]phenyl]-7-(4-propylphenyl)-1,1-dioxo-2,3-dihydro-1-benzothiepine-4-carboxamide (Compound 27) (195.0 mg).

m.p. 247–250° C.; $^1$H-NMR (200 MHz, CDCl$_3$) δ 0.98 (3H, t, J=7.3 Hz), 1.56–1.83 (6H, m), 2.21 (3H, s), 2.52–2.74 (3H, m), 3.18 (2H, t, J=6.6 Hz), 3.31–3.44 (2H, m), 3.58 (2H, s), 3.70–3.76 (2H, m), 3.97–4.10 (2H, m), 7.28–7.35 (5H, m), 7.52 (2H, d, J=8.4 Hz), 7.55 (2H, d, J=8.4 Hz), 7.66–7.73 (2H, m), 7.94 (1H, br s), 8.21 (1H, d, J=8.0 Hz). IR (KBr) 3250, 1657, 1635, 1599, 1525, 1410, 1315, 1296, 1165, 1130 cm$^{-1}$; Anal. for C$_{33}$H$_{38}$N$_2$O$_4$S; Calcd. C, 70.94; H, 6.86; N, 5.01; Found. C, 70.99; H, 6.51; N, 5.05.

Working Example 29 (Production of Compound 28)

To a solution of 7-(4-isopropoxyphenyl)-1,1-dioxo-2,3-dihydro-1-benzothiepine-4-carboxylic acid (400 mg) in THF (10 ml) were added at room temperature thionyl chloride (0.094 ml) and a drop of DMF, and the mixture was stirred for 1 hour. The solvent was evaporated under reduced pressure, and the residue was dissolved in THF (10 ml). The solution was added dropwise at 0° C. to a solution of 4-[N-methyl-N-(tetrahydropyran-4-yl)aminomethyl]aniline (260 mg) and triethylamine (0.45 ml) in THF (2 ml), and the mixture was stirred at room temperature for 18 hours. To the mixture was added water, and the mixture was extracted with ethyl acetate. The organic layer was washed with saturated brine, dried with magnesium sulfate and concentrated under reduced pressure to give pale yellow crystals, which were recrystallized from ethanol to give pale yellow crystals of 7-(4-isopropoxyphenyl)-N-[4-[N-methyl-N-(tetrahydropyran-4-yl)aminomethyl]phenyl]-1,1-dioxo-2,3-dihydro-1-benzothiepine-4-carboxamide (Compound 28) (367.1 mg).

m.p. 245–247° C.; $^1$H-NMR (200 MHz, CDCl$_3$) δ 1.38 (6H, d, J=5.8 Hz), 1.59–1.84 (4H, m), 2.21 (3H, s), 2.54–2.76 (1H, m), 3.16 (2H, t, J=7.0 Hz), 3.31–3.44 (2H, m), 3.58 (2H, s), 3.69–3.76 (2H, m), 3.99–4.10 (2H, m), 4.56–4.69 (1H, m), 6.99 (2H, d, J=8.8 Hz), 7.31–7.35 (3H, m), 7.53 (2H, d, J=8.8 Hz), 7.55 (2H, d, J=8.8 Hz), 7.62–7.69 (2H, m), 7.93 (1H, br s), 8.19 (1H, d, J=8.4 Hz). IR (KBr) 3248, 1655, 1603, 1515, 1410, 1317, 1292, 1248, 1171, 1128, 825 cm$^{-1}$; Anal. for C$_{33}$H$_{38}$N$_2$O$_5$S; Calcd. C, 68.96; H, 6.66; N, 4.87; Found. C, 68.70; H, 6.34; N, 4.86.

Working Example 30 (Production of Compound 29)

To a suspension of 7-(4-propoxyphenyl)-1,1-dioxo-2,3-dihydro-1-benzothiepine-4-carboxylic acid (170 mg) in THF (5 ml) were added at room temperature thionyl chloride (0.07 ml) and a drop of DMF, and the mixture was stirred for 1 hour. The solvent was evaporated under reduced pressure, and the residue was dissolved in THF (10 ml). The solution was added dropwise at room temperature to a solution of 4-[N-methyl-N-(tetrahydropyran-4-yl)aminomethyl]aniline (111 mg) and triethylamine (0.18 ml) in THF (2 ml), and the mixture was stirred at room temperature for 21 hours. To the mixture was added water, and the mixture was extracted with ethyl acetate. The organic layer was washed with saturated brine, dried with magnesium sulfate and concentrated under reduced pressure, and the residue was purified with column chromatography (ethanol/ethyl acetate=1:3) and recrystallized from ethanol to give pale yellow crystals of N-[4-[N-methyl-N-(tetrahydropyran-4-yl)aminomethyl]phenyl]-7-(4-propoxyphenyl)-1,1-dioxo-2,3-dihydro-1-benzothiepine-4-carboxamide (Compound 29) (147.6 mg).

m.p. 244–247° C.; $^1$H-NMR (200 MHz, CDCl$_3$) δ 1.06 (3H, t, J=7.4 Hz), 1.57–1.90 (6H, m), 2.21 (3H, s), 2.54–2.75 (1H, m), 3.13–3.20 (2H, m), 3.31–3.44 (2H, m), 3.58 (2H, s), 3.69–3.76 (2H, m), 3.98 (2H, t, J=6.6 Hz), 3.99–4.11 (2H, m), 7.01 (2H, d, J=8.8 Hz), 7.31–7.35 (3H, m), 7.52–7.56 (4H, m), 7.62 (1H, d, J=1.8 Hz), 7.67 (1H, dd, J=8.0, 1.8 Hz), 7.92 (1H, br s), 8.19 (1H, d, J=8.0 Hz). IR (KBr) 3280, 1657, 1603, 1520, 1315, 1294, 1250, 1130, 822 cm$^{-1}$, Anal. for C$_{33}$H$_{38}$N$_2$O$_5$S; Calcd. C, 68.96; H, 6.66; N, 4.87; Found. C, 68.72; H, 6.70; N, 4.88.

Working Example 31 (Production of Compound 30)

To a solution of 7-(4-butoxyphenyl)-1,1-dioxo-2,3-dihydro-1-benzothiepine-4-carboxylic acid (180 mg) in THF (5 ml) were added at room temperature thionyl chloride (0.07 ml) and a drop of DMF, and the mixture was stirred for 1 hour. The solvent was evaporated under reduced pressure, and the residue was dissolved in THF (10 ml). The solution was added dropwise at room temperature to a solution of 4-[N-methyl-N-(tetrahydropyran-4-yl)aminomethyl]aniline (114 mg) and triethylamine (0.2 ml) in THF (2 ml), and the mixture was stirred at room temperature for 3 hours. To the mixture was added water, and the mixture was extracted with ethyl acetate. The organic layer was washed with saturated brine, dried with magnesium sulfate and concentrated under reduced pressure, and the residue was purified with column chromatography (ethanol/ethyl acetate=1:4) and recrystallized from ethanol to give pale yellow crystals of 7-(4-butoxyphenyl)-N-[4-[N-methyl-N-(tetrahydropyran-4-yl)aminomethyl]phenyl]-1,1-dioxo-2,3-dihydro-1-benzothiepine-4-carboxamide (Compound 30) (138.6 mg).

m.p. 233–236° C.; $^1$H-NMR (200 MHz, CDCl$_3$) δ 1.00 (3H, t, J=7.3 Hz), 1.40–1.87 (8H, m), 2.21 (3H, s), 2.55–2.72 (1H, m), 3.16 (2H, t, J=6.8 Hz), 3.31–3.42 (2H, m), 3.58 (2H, s), 3.72 (2H, t, J=6.8 Hz), 3.98–4.10 (2H, m), 4.02 (2H, t, J=6.4 Hz), 7.00 (2H, d, J=8.8 Hz), 7.30–7.35 (3H, m), 7.54

(2H, d, J=8.8 Hz), 7.55 (2H, d, J=8.8 Hz), 7.62–7.69 (2H, m), 7.93 (1H, br s), 8.19 (1H, d, J=8.0 Hz). IR (KBr) 3280, 1659, 1603, 1518, 1315, 1294, 1250, 1128, 825 cm$^{-1}$; Anal. for $C_{34}H_{40}N_2O_5S$; Calcd. C, 69.36; H, 6.85; N, 4.76; Found. C, 69.20; H, 6.75; N, 4.94.

Working Example 32 (Production of Compound 31)

To a suspension of 6-(4-methylphenyl)-1,1-dioxo-1,2-dihydro-2H-thiochromene-3-carboxylic acid (178 mg, 0.567 mmol) and HOBt(115 mg, 0.85 mmol) in acetonitrile (5 ml) was added WSC (163 mg, 0.85 mmol), and the mixture was stirred for 1 hour. To the mixture was added a solution of 4-[N-methyl-N-(tetrahydropyran-4-yl)aminomethyl]aniline (187 mg, 0.85 mmol) and triethylamine (0.16 ml, 1.13 mmol) in acetonitrile (1 ml), and the mixture was stirred for 15 hours. The solvent was evaporated, and the residue was diluted with ethyl acetate. The mixture was washed with water and saturated brine, and dried with magnesium sulfate. The solvent was evaporated, and the residue was subjected to silica gel column chromatography to give, from the fraction eluted with ethyl acetate/ethanol (2:1), 6-(4-methylphenyl)-N-(4-((N-methyl-N-tetrahydropyran-4-ylamino)methyl)phenyl-1,1-dioxo-1,2-dihydro-2H-thiochromene-3-carboxamide (Compound 31) (89.4 mg, 31%) as brown powder.

m.p. 197° C. (decomp.). $^1$H-NMR (DMSO-d$_6$) δ: 7.96–8.02 (3H, m), 7.86 (1H, s), 7.65–7.71(4H, m), 7.25–7.38 (4H, m), 4.57(2H, s), 3.81–4.00 (2H, m), 3.54 (2H, s), 3.20–3.32 (2H, m), 2.50–2.72 (1H, m), 2.39 (3H, s), 2.12 (3H, s).

Working Example 33 (Production of Compound 32)

To a suspension of 7-(4-methylphenyl)-1,1-dioxo-2,3-dihydro-1-benzothiepine-4-carboxylic acid (325 mg, 0.991 mmol) in THF(10 ml) were added at 0° C. oxalyl chloride (0.26 ml, 2.97 mmol) and DMF (1 drop), and the mixture was stirred at room temperature for 1.5 hours. The solvent was evaporated, and the residue was dissolved in THF (8 ml). To the solution was added dropwise a solution of 4-(N-(3-ethoxycarbonylethyl)-N-methyl)aminomethyl) aniline (257 mg, 1.09 mmol) and triethylamine (0.42 ml, 2.97 mmol) in THF (2 ml) at 0, and the mixture was stirred at room temperature for 17 hours. To the mixture was added water, and the mixture was extracted with ethyl acetate. The extract was washed with saturated brine and dried with magnesium sulfate. The solvent was evaporated, and the residue was subjected to silica gel column chromatography to give, from the fraction eluted with ethyl acetate, N-(4-(N-(3-ethoxycarbonylethyl)-N-methyl)aminomethyl) phenyl-7-(4-methylphenyl)-1,1-dioxo-2,3-dihydro-1-benzothiepine-4-carboxamide (Compound 32) (310 mg, 57%), which was recrystallized from acetone/ethanol to give colorless crystals having m.p. 180° C.

$^1$H-NMR (CDCl$_3$) δ: 8.20 (1H, d, J=8.0), 7.98 (1H, br s), 7.64–7.71 (2H, m), 7.47–7.57 (4H, m), 7.26–7.36 (4H, m), 4.15 (2H, q, J=7.4), 3.72 (2H, t, J=6.7), 3.51 (2H, s), 3.16 (2H, t, J=6.7), 2.76 (2H, t, J=7.0), 2.52 (2H, t, J=7.0), 2.42 (3H, s), 2.21 (3H, s), 1.26 (3H, t, J=7.4).

Working Example 34 (Production of Compound 33)

To a suspension of 6-(4-methylphenyl)- 1,1-dioxo-1,2-dihydro-2H-thiochromene-3-carboxylic acid (115 mg, 0.494 mmol) in THF (5 ml) were added oxalyl chloride (0.13 ml, 1.48 mmol) and DMF (1 drop), and the mixture was stirred at room temperature for 1 hour. The solvent was evaporated under reduced pressure, and the residue was dissolved in THF (5 ml). To the solution was added a solution of 4-(N-(2-methoxyethyl)-N-methyl)aminomethylaniline (127 mg, 0.543 mmol) and triethylamine (0.21 ml, 1.48 mmol) in THF (2 ml), and the mixture was stirred for 15 hours. To the mixture was added water, and the mixture was extracted with ethyl acetate. The extract was washed with saturated brine and dried with magnesium sulfate. The solvent was evaporated, and the residue was subjected to silica gel column chromatography to give, from the fraction eluted with ethyl acetate/ethanol (4:1), N-(4-(N-(4-methoxyethyl)-N-methyl)aminomethyl)phenyl-6-(4-methylphenyl)-1,1-dioxo-1,2-dihydro-2H-thiochromene-3-carboxamide (Compound 33) (110 mg, 42%) as dark green crystals.

m.p. 138° C. $^1$H-NMR (CDCl$_3$) δ: 8.19 (1H, br s), 7.90 (2H, d, J=8.4), 7.56 (2H, dd, J=8.0, 8.1), 7.32–7.48 (5H, m), 7.17–7.22 (4H, m), 4.21 (2H, s), 3.44 (2H, s), 3.43 (2H, t, J=5.6), 3.25 (3H, s), 2.51 (2H, t, J=5.6), 2.32 (3H, s), 2.17 (3H, s). Anal. Calcd for $C_{28}H_{30}N_2O_4S.0.5\ H_2O$: C; 67.31, H; 6.25, N; 5.61. Found: C; 67.61, H; 5.98, N; 5.33.

Working Example 35 (Production of Compound 34)

To a solution of 7-(4-methylphenyl)-N-(4-((N-methyl-N-tetrahydropyran-4-ylamino)methyl)phenyl-1,1-dioxo-2,3-dihydro-1-benzothiepine-4-carboxamide (137 mg, 0.258 mmol) in DMF (2 ml) was added methyl iodide (0.02 ml, 0.284 mmol), and the mixture was stirred for 16 hours. The solvent was evaporated to give powder, which was washed with hexane to give dimethyl (N-(7-(4-methylphenyl)-1,1-dioxo-2,3-dihydro-1-benzothiepine-4-carbonyl-4-aminobenzyl)-N-(tetrahydropyran-4-yl)ammonium chloride (Compound 34) (164 mg, 95%) as brown powder.

m.p. 170–171° C.; $^1$H-NMR (DMSO-d$_6$) δ: 9.46 (1H, s), 8.04–8.11 (2H, m), 7.84–7.86 (3H, m), 7.72 (2H, d, J=8.4), 7.52–7.61 (2H, m), 7.36 (2H, d, J=7.4), 4.47 (2H, s), 4.00–4.14 (2H, m), 3.83 (2H, t, J=6.2), 3.50–3.71 (1H, m), 2.88 (6H, s), 2.38 (3H, s), 2.10–2.22 (2H, m), 1.79–2.00 (2H, m). Anal. Calcd for $C_{32}H_{37}IN_2O_4S.H_2O$: C; 55.65, H; 5.69, N; 4.06. Found: C; 55.65, H; 5.64, N; 4.17.

Working Example 36 (Production of Compound 35)

To a solution of 7-(4-methylphenyl)-N-(4-((N-methyl-N-(3-pentyl)amino)methyl)phenyl-1,1-dioxo-2,3-dihydro-1-benzothiepine-4-carboxamide (119 mg, 0.321 mmol) in DMF (2 ml) was added methyl iodide (0.025 ml, 0.353 mmol), and the mixture was stirred for 16 hours. The solvent was evaporated to give powder, which was washed with hexane to give dimethyl (N-(1,1-dioxo-7-(4-methylphenyl)-2,3-dihydro-1-benzothiepine-4-carbonyl-4-aminobenzyl)-N-(3-pentyl)ammonium chloride (Compound 35) (114 mg, 95%).

m.p. 150–151° C.; $^1$H-NMR (CDCl$_3$) δ: 9.48 (1H, br s), 8.22 (1H, br s), 8.13 (2H, d, J=8.0), 7.86–7.92 (2H, m), 7.45–7.76 (4H, m), 7.24–7.29 (2H, m), 4.74 (2H, s), 3.76 (2H, t, J=5.2), 3.20–3.37 (1H, m), 3.02 (2H, t, J=5.2), 2.98 (6H,s), 2.38 (3H, s), 1.50–1.80 (4H, m), 1.08 (6H, t, J=7.4). Anal. Calcd for $C_{32}H_{39}IN_2O_3S.1.5\ H_2O$: C; 56.06, H; 6.17, N; 4.09. Found: C; 55.47, H; 5.90, N; 4.38.

Working Example 37 (Production of Compound 36)

To a solution of 7-(4-methylphenyl)-N-(4-((N-methyl-N-tetrahydropyran-4-yl)aminomethyl)phenyl)-2,3-dihydro-1- benzothiepine-4-carboxamide (0.2 g) in dichloromethane (50 ml) was added at −30° C. to −10° C. 70% mCPBA (0.1 g), and the mixture was stirred at −30° C. to −10° C. for 1 hour. To the mixture was added an aqueous solution of sodium thiosulfate, and the mixture was concentrated and extracted with ethyl acetate. The organic layer was washed with sodium hydrogen carbonate solution, water and saturated brine, and dried with anhydrous magnesium sulfate. Under reduced pressure, the solvent was evaporated, and the residue was purified with silica gel column chromatography (methanol/dichloromethane) to give crude crystals, which were recrystallized from ethyl acetate/hexane to give 7-(4-methylphenyl)-N-(4-((N-methyl-N-tetrahydropyran-4-yl) aminomethyl)phenyl)-1-oxo-2,3-dihydro-1-benzothiepine-4-carboxamide (Compound 36) (0.04 g) as colorless crystals.

mp 191–192° C.; $^1$H-NMR(δ ppm, CDCl$_3$) 1.65–1.80 (4H, m), 2.22 (3H, s), 2.41 (3H, s), 2.55–2.90 (2H, m), 3.10–3.25 (1H, m), 3.35–3.50 (3H, m), 3.58 (2H, s), 3.81–3.95 (1H, m), 4.01–4.11 (2H, m), 7.25 (2H, d, J=8.0Hz), 7.33 (2H, d, J=8.5 Hz), 7.45 (2H, d, J=8.0 Hz), 7.52 (1H, s), 7.61 (2H, d, J=8.5 Hz), 7.70 (1H, dd, J=2.0, 8.2 Hz), 7.97 (1H, d, J=8.0 Hz), 8.26 (1H, s). IR(KBr) ν: 2948, 2845, 1663 cm$^{-1}$.

Working Example 38 (Production of Compound 37)

In dichloromethane (10 ml) was suspended 7-(4-methylphenyl)-1,1-dioxo-2,3-dihydro-1-benzothiepine-4-carboxylic acid (0.3 g), and to the suspension were added under ice-cooling oxalyl chloride (0.25 ml) and dimethylformamide (catalytic amount). The mixture was stirred at room temperature for 2 hours, and the solvent was evaporated. The residue was dissolved in tetrahydrofuran (20 ml), and the solution was added dropwise to a solution of 4-(N-methyl-N-(tetrahydropyran-4-yl)aminomethyl)aniline (0.22 g) and triethylamine (0.38 ml) in tetrahydrofuran (25 ml) under ice-cooling. Under nitrogen atmosphere, the mixture was stirred overnight at room temperature, and the solvent was evaporated. To the residue was added water, and the mixture was extracted with ethyl acetate. The organic layer was washed with water and saturated brine, and dried with anhydrous magnesium sulfate. Under reduced pressure, the solvent was evaporated to give crude crystals, which were recrystallized from ethyl acetate/hexane to give 7-(4-methylphenyl)-N-(4-((N-methyl-N-tetrahydropyran-4-yl) aminomethyl)phenyl)-1,1-dioxo-2,3-dihydro-1-benzothiepine-4-carboxamide (Compound 39) (0.22 g) as pale yellow crystals.

mp 234–235° C. (dec.). $^1$H-NMR(δppm, CDCl$_3$) 1.67–1.75 (4H, m), 2.21 (3H, s), 2.42 (3H, s), 2.57–2.70 (1H, m), 3.17 (2H, t, J=6.8 Hz), 3.37 (2H, dt, J=2.6, 11.2 Hz), 3.58 (2H, s), 3.73 (2H, t, J=6.8 Hz), 4.01–4.11 (2H, m), 7.27–7.36 (4H, m), 7.49–7.57 (4H, m), 7.65 (1H, s), 7.70 (1H, dd, J=2.0, 8.2 Hz), 7.94 (1H, s), 8.21 (1H, d, J=8.2 Hz). IR(KBr) ν: 2946, 2845, 1667 cm$^{-1}$. Anal. Calcd. for C$_{31}$H$_{34}$N$_2$O$_4$S: C, 70.16; H, 6.46; N, 5.28. Found C, 69.95; H, 6.22; N, 5.16.

Working Example 39 (Production of Compound 38)

To a suspension of 7-(4-methylphenyl)-1,1-dioxo-2,3-dihydro-1-benzothiepine-4-carboxylic acid (0.25 g) in dichloromethane (8 ml) were added, under ice-cooling, oxalyl chloride (0.2 ml) and dimethylformamide (catalytic amount), and the mixture was stirred at room temperature for 2 hours. The solvent was evaporated, and the residue was dissolved in tetrahydrofuran (15 ml). The solution was added dropwise to a solution of 4-((N-methyl-N-(pentan-3-yl))aminomethyl)aniline (0. 17 g) and triethylamine (0.32 ml) in tetrahydrofuran (15 ml), under ice-cooling. Under nitrogen atmosphere, the mixture was stirred overnight at room temperature, and the solvent was evaporated. To the residue was added water, and the mixture was extracted with ethyl acetate. The organic layer was washed with water and saturated brine, and dried with anhydrous magnesium sulfate. Under reduced pressure, the solvent was evaporated to give crude crystals, which were recrystallized from ethyl acetate/hexane to give N-(4-((N-methyl-N-(pentan-3-yl)) aminomethyl)phenyl)-7-(4-methylphenyl)-1,1-dioxo-2,3-dihydro-1-benzothiepine-4-carboxamide (Compound 38) (0.13 g) as colorless crystals.

mp 130–131° C.; $^1$H-NMR(δppm, CDCl$_3$) 0.94 (6H, t, J=7.3 Hz), 1.27–1.58 (4H, m), 2.15 (3H, s), 2.28–2.38 (1H, m), 2.42 (3H, s), 3.17 (2H, t, J=6.8 Hz), 3.58 (2H, s), 3.72 (2H, t, J=6.8 Hz), 7.27–7.37 (4H, m), 7.49–7.56 (4H, m), 7.66–7.72 (2H, m), 7.97 (1H, s), 8.21 (1H, d, J=8.0 Hz). IR(KBr) ν: 2963, 2930, 1663 cm$^{-1}$. Anal. Calcd. for C$_{31}$H$_{36}$N$_2$O$_3$S.0.5 H$_2$O: C, 70.83; H, 7.09; N, 5.33. Found C, 70.77; H, 6.76; N, 5.45.

Working Example 40 (Production of Compound 39)

In dichloromethane (5 ml) was suspended 7-(4-methylphenyl)-1,1-dioxo-2,3-dihydro-1-benzothiepine-4-carboxylic acid (0.3 g). To the suspension were added, under ice-cooling, oxalyl chloride (0.25 ml) and dimethylformamide (catalytic amount), and the mixture was stirred at room temperature for 2 hours. The solvent was evaporated, and the residue was dissolved in tetrahydrofuran (20 ml). The solution was added dropwise to a solution of N-(4-aminobenzyl) sarcosine methyl ester (0.21 g) and triethylamine (0.38 ml) in tetrahydrofuran (10 ml), under ice-cooling. Under nitrogen atmosphere, the mixture was stirred at room temperature overnight. The solvent was evaporated, and to the residue was added water. The mixture was extracted with ethyl acetate, and the organic layer was washed with water and saturated brine, and dried with anhydrous magnesium sulfate. Under reduced pressure, the solvent was evaporated, and the residue was purified with silica gel column chromatography (ethyl acetate/hexane) to give crude crystals, which were recrystallized from ethyl acetate/hexane to give N-(4-((N-methoxycarbonylmethyl-N-methyl)aminomethyl) phenyl)-7-(4-methylphenyl)-1,1-dioxo-2,3-dihydro-1-benzothiepine-4-carboxamide (Compound 39) (0.22 g) as colorless crystals.

mp 136–143° C.; $^1$H-NMR(δ ppm, CDCl$_3$) 2.39 (3H, s), 2.43 (3H, s), 3.17 (2H, t, J=6.6 Hz), 3.27 (2H, s), 3.66 (2H, s), 3.69–3.76 (2H, m), 3.72 (3H, s), 7.28–7.37 (4H, m), 7.48–7.58 (4H, m), 7.65 (1H, s), 7.70 (1H, dd, J=1.6, 8.4 Hz), 7.93 (1H, s), 8.21 (1H, d, J=8.4 Hz). IR(KBr) ν: 2932, 1744 cm$^{-1}$. Anal. Calcd. for C$_{29}$H$_{30}$N$_2$O$_5$S: C, 67.16; H, 5.83; N, 5.40. Found C, 66.94; H, 5.94; N, 5.20.

Working Example 41 (Production of Compound 40)

In THF (6.5 ml) was dissolved 7-(5-methyl-2-thienyl)-1,1-dioxo-2,3-dihydro-1-benzothiepine-4-carboxylic acid (166 mg), and to the solution were added, under ice-cooling and stirring, oxalyl chloride (0.087 ml) and DMF (one drop). The mixture was stirred at room temperature for 2 hours. Under reduced pressure, the solvent was evaporated, and the residue was dissolved in THF (6 ml). The solution was added dropwise, under ice-cooling, to a stirred solution of 4-[N-methyl-N-(tetrahydropyran-4-yl)aminomethyl]aniline (135 mg) and triethylamine (0.2 ml) in THF (4 ml), and the mixture was stirred at room temperature for 13 hours. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give N-[4-[N-methyl-N-(tetrahydropyran-4-yl)aminomethyl]phenyl]-7-(5-methyl-2-thienyl)-1,1-dioxo-2,3-dihydro-1-benzothiepine-4-carboxamide (Compound 40) (113 mg).

m.p. 229–231° C.; $^1$H-NMR (200 MHz, CDCl$_3$) δ 1.60–1.82 (4H, m), 2.21 (3H, s), 2.54 (3H, s), 2.65 (1H, m), 3.37 (2H, td, J=11.4, 3.0 Hz), 3.57 (2H, s), 3.70 (2H, m), 4.01–4.07 (2H, m), 6.79 (1H, dd, J=3.6, 1.0 Hz), 7.24–7,34 (3H, m), 7.53–7.64 (4H, m), 8.01 (1H, s), 8.11 (1H, d, J=8.4 Hz); IR (KBr) 1659, 1526, 1410, 1318, 1292, 1128, 806 cm$^{-1}$.

Working Example 42 (Production of Compound 41)

In THF (16 ml) was dissolved 7-(4-methyl-2-thienyl)-1,1-dioxo-2,3-dihydro-1-benzothiepine-4-carboxylic acid (400 mg), and to the stirred solution were added under ice-cooling oxalyl chloride (0.21 ml) and DMF (one drop). The mixture was stirred at room temperature for 2 hours. Under reduced pressure, the solvent was evaporated, and the residue was dissolved in THF (6 ml). The solution was added dropwise to a stirred solution of 4-[N-methyl-N-(tetrahydropyran-4-yl)aminomethyl]aniline (352 mg) and triethylamine (0.5 ml) in THF (10 ml), under ice-cooling, and the mixture was stirred at room temperature, for 15 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give N-[4-[N-methyl-N-(tetrahydropyran-4-yl) aminomethyl]phenyl]-7-(4-methyl-2-thienyl)-1,1-dioxo-2,3-dihydro-1-benzothiepine-4-carboxamide (Compound 41) (355 mg).

m.p. 232–234° C.; $^1$H-NMR (200 MHz, CDCl$_3$) δ 1.57–1.83 (4H, m), 2.21 (3H, s), 2.54 (3H, s), 2.65 (1H, m), 3.13 (2H, t, J=6.6 Hz), 3.38 (2H, td, J=11.4,2.8 Hz), 3.57 (2H, s), 3.70 (2H, t, J=6.6 Hz), 4.00–4.08 (2H, m), 7.00(1H, s), 7.23–7.34 (3H, m), 7.53–7.64 (4H, m), 8.10 (2H, d, J=8.0 Hz); IR (KBr) 1643, 1518, 1408, 1319, 1294, 817 cm$^{-1}$.

Working Example 43 (Production of Compound 42)

In THF (8.0 ml) was dissolved 7-(5-chloro-2-thienyl)-1,1-dioxo-2,3-dihydro-1-benzothiepine-4-carboxylic acid (200 mg), and to the stirred solution were added under ice-cooling oxalyl chloride (0.075 ml) and DMF (one drop). The mixture was stirred at room temperature for 2 hours. Under reduced pressure, the solvent was evaporated, and the residue was dissolved in THF (8 ml). The solution was added dropwise to a stirred solution of 4-[N-methyl-N-(tetrahydropyran-4-yl)aminomethyl]aniline (153 mg) and triethylamine (0.20 ml) in THF (6 ml), under ice-cooling, and the mixture was stirred at room temperature for 16 hours. The reaction solution was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1)and recrystallized from ethanol to give 7-(5-chloro-2-thienyl)-N-[4-[N-methyl-N-(tetrahydropyran-4-yl)aminomethyl]phenyl]-1,1-dioxo-2,3-dihydro-1-benzothiepine-4-carboxamide (Compound 42) (90 mg).

m.p. 221–222° C.; $^1$H-NMR (200 MHz, CDCl$_3$) δ 1.60–1.83 (4H, m), 2.22 (3H, s), 2.67 (1H, m), 3.14 (2H, m), 3.37 (2H, td, J=11.4,2.6 Hz), 3.59 (2H, s), 3.71 (2H, m), 4.00–4.08 (2H, m), 6.97 (1H, d, J=4.0 Hz), 7.22 (1H,J=4.0 Hz), 7.33 (3H, d, J=8.8 Hz), 7.51–7.61 (4H, m), 8.00 (1H, s), 8.14 (1H, d, J=8.0 Hz); IR (KBr) 1655, 1528, 1410, 1318, 1294, 1130, 819 cm$^{-1}$; Anal. for $C_{28}H_{29}ClN_2O_4S_2$; Calcd. C, 60.36; H, 5.25; N, 5.03; Found. C, 60.56; H, 5.37; N, 4.93.

Working Example 44 (Production of Compound 43)

In THF (8 ml) was dissolved 7-[(4-methylthio)phenyl]-1,1-dioxo-2,3-dihydro-1-benzothiepine-4-carboxylic acid (133 mg), and to the stirred solution were added at room temperature oxalyl chloride (0.065 ml) and DMF (one drop). The mixture was stirred at room temperature for 2 hours. Under reduced pressure, the solvent was evaporated, and the residue was dissolved in THF (6 ml). The solution was added dropwise to a stirred solution of 4-[N-methyl-N-(tetrahydropyran-4-yl)aminomethyl]aniline (100 mg) and triethylamine (0.15 ml) in THF (6 ml), under ice-cooling, and the mixture was stirred at room temperature for 2 hours. The reaction solution was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give N-[4-[N-methyl-N-(tetrahydropyran-4-yl)aminomethyl] phenyl]-7-[(4-methylthio)phenyl]-1,1-dioxo-2,3-dihydro-1-benzothiepine-4-carboxamide (Compound 43) (80 mg).

m.p. 249–252° C.; $^1$H-NMR (200 MHz, CDCl$_3$) δ (3H, t, J=7.2 Hz), 1.58–2.00 (4H, m), 2.32 (3H, s), 2.54 (3H, s), 2.87 (1H, m), 3.16 (2H, t, J=6.6 Hz), 3.30 (2H, td, J=11.4,2.6 Hz), 3.74 (4H, m), 3.94–4.10 (2H, m), 7.27–7.81 (12H, m), 8.20 (1H, d, J=8.4 Hz); IR (KBr) 1653, 1530, 1410, 1318, 1294, 1130, 812 cm$^{-1}$.

Working Example 45 (Production of Compound 44)

In THF (4 ml) was dissolved 7-[(4-ethylthio)phenyl]-1,1-dioxo-2,3-dihydro-1-benzothiepine-4-carboxylic acid (130 mg), and to the stirred solution were added at room temperature thionyl chloride (0.035 ml) and DMF (0.02 ml). The mixture was stirred at room temperature for 1 hour. Under reduced pressure, the solvent was evaporated, and the residue was dissolved in THF (6 ml). The solution was added dropwise to a stirred solution of 4-[N-methyl-N-(tetrahydropyran-4-yl)aminomethyl]aniline (130 mg) and triethylamine (0.3 ml) in THF (6 ml), under ice-cooling, and the mixture was stirred at room temperature for 4 hours. The reaction solution was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/

1) and recrystallized from ethanol to give 7-[(4-ethylthio) phenyl]-N-[4-[N-methyl-N-(tetrahydropyran-4-yl) aminomethyl]phenyl]-1,1-dioxo-2,3-dihydro-1-benzothiepine-4-carboxamide (Compound 44) (82 mg).

m.p. 232–233° C.; $^1$H-NMR (200 MHz, CDCl$_3$) δ 1.37 (3H, t, J=7.2 Hz), 1.58–1.82 (4H, m), 2.21 (3H, s), 2.66 (1H, m), 3.02 (2H, q, J=7.2 Hz), 3.16 (2H, m), 3.37 (2H, td, J=11.4,2.6 Hz), 3.58 (2H, s), 3.72 (2H, m), 4.00–4.08 (2H, m), 7.30–7.70 (11H, m), 8.01 (1H, s), 8.20 (1H, d, J=8.0 Hz); IR (KBr) 1655, 1522, 1410, 1315, 1294, 1130, 816 cm$^{-1}$.

Working Example 46 (Production of Compound 45)

In THF (10 ml) was dissolved 7-[(4-ethylsulfonyl) phenyl]-1,1-dioxo-2,3-dihydro-1-benzothiepine-4-carboxylic acid (250 mg), to the stirred solution were added at room temperature thionyl chloride (0.054 ml) and DMF (one drop). The mixture was stirred at room temperature for 1 hour. Under reduced pressure, the solvent was evaporated, and the residue was dissolved in THF (8 ml). The solution was added dropwise to a stirred solution of 4-[N-methyl-N-(tetrahydropyran-4-yl)aminomethyl]aniline (167 mg) and triethylamine (0.43 ml) in THF (8 ml), under ice-cooling, and the mixture was stirred at room temperature for 2 hours. The reaction solution was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[(4-ethylsulfonyl)phenyl]-N-[4-[N-methyl-N-(tetrahydropyran-4-yl)aminomethyl]phenyl]-1,1-dioxo-2,3-dihydro-1-benzothiepine-4-carboxamide (Compound 45) (105 mg).

m.p. 210–211° C.; $^1$H-NMR (200 MHz, CDCl$_3$) δ 1.32 (3H, t, J=7.2 Hz), 1.56–1.83 (4H, m), 2.21 (3H, s), 2.65 (1H, m), 3.16 (2H, q, J=7.2 Hz), 3.19 (2H, m), 3.37 (2H, td, J=11.4, 3.0 Hz), 3.58 (2H, s), 3.74 (2H, m), 4.01–4.07 (2H, m), 7.33 (2H, d, J=8.4 Hz), 7.38 (1H, s), 7.55 (2H, d, J=8.4 Hz), 7.69–7.80 (4H, s), 7.99–8.05 (3H, m), 8.29 (2H, d, J=8.0 Hz); IR (KBr) 1659, 1530, 1410, 1313, 1294, 1146, 747, 733 cm$^{-1}$.

Working Example 47 (Production of Compound 46)

In THF (10 ml) was dissolved 1,1-dioxo-7-[(4-propylthio) phenyl]-2,3-dihydro-1-benzothiepine-4-carboxylic acid (400 mg), and to the stirred solution were added at room temperature thionyl chloride (0.089 ml) and DMF (one drop). The mixture was stirred at room temperature for 1 hour. Under reduced pressure, the solvent was evaporated, and the residue was dissolved in THF (8 ml). The solution was added dropwise to a stirred solution of 4-[N-methyl-N-(tetrahydropyran-4-yl)aminomethyl]aniline (280 mg) and triethylamine (0.57 ml) in THF (8.4 ml), under ice-cooling, and the mixture was stirred at room temperature for 2 hours. The reaction solution was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give N-[4-[N-methyl-N-(tetrahydropyran-4-yl)aminomethyl] phenyl]-1,1-dioxo-7-[(4-propylthio)phenyl]-2,3-dihydro-1-benzothiepine-4-carboxamide (Compound 46) (298 mg).

m.p. 220–220° C.; $^1$H-NMR (200 MHz, CDCl$_3$) δ 1.06 (3H, t, J=7.2 Hz), 1.60–1.81 (6H, m), 2.21 (3H, s), 2.65 (1H, m), 2.97 (2H, t, J=7.4 Hz), 3.17 (2H, m), 3.37 (2H, td, J=11.2,2.8 Hz), 3.58 (2H, s), 3.72 (2H, m), 4.00–4.09 (2H, m), 7.29–7.70 (11H, m), 7.95 (1H, s), 8.21 (1H, d, J=8.0 Hz); Anal. for C$_{33}$H$_{38}$N$_2$O$_4$S$_2$; Calcd. C, 67.09; H, 6.48; N, 4.74; Found. C, 67.15; H, 6.27; N, 4.98; IR (KBr) 1660, 1516, 1410, 1314, 1294, 1130, 816 cm$^{-1}$.

Working Example 48 (Production of Compound 47)

In THF (10 ml) was dissolved 7-[(4-butylthio)phenyl]-1,1-dioxo-2,3-dihydro-1-benzothiepine-4-carboxylic acid (400 mg), and to the stirred solution were added at room temperature thionyl chloride (0.086 ml) and DMF (one drop). The mixture was stirred at room temperature for 1 hour. Under reduced pressure, the solvent was evaporated, and the residue was dissolved in THF (8 ml). The solution was added dropwise to a stirred solution of 4-[N-methyl-N-(tetrahydropyran-4-yl)]aniline (270 mg) and triethylamine (0.55 ml) in THF (8.1 ml), under ice-cooling, and the mixture was stirred at room temperature for 2 hours. The reaction solution was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[(4-butylthio) phenyl]-N-[4-[N-methyl-N-(tetrahydropyran-4-yl) aminomethyl]phenyl]-1,1-dioxo-2,3-dihydro-1-benzothiepine-4-carboxamide (Compound 47) (267 mg).

m.p. 207–209° C.; $^1$H-NMR (200 MHz, CDCl$_3$) δ 0.95 (3H, t, J=7.0 Hz), 1.42–1.75 (8H, m), 2.21 (3H, s), 2.65 (1H, m), 2.99 (2H, t, J=7.2 Hz), 3.16 (2H, m), 3.37 (2H, td, J=11.2,3.0 Hz), 3.57 (2H, s), 3.72 (2H, m), 4.01–4.09 (2H, m), 7.30–7.70 (11H, m), 7.96 (1H, s), 8.21 (1H, d, J=8.2 Hz); IR (KBr) 1653, 1530, 1410, 1318, 1294, 1130, 816 cm$^{-1}$; Anal. for C$_{34}$H$_{40}$N$_2$O$_4$S$_2$; Calcd. C, 67.52; H, 6.67; N, 4.63; Found. C, 67.66; H, 6.52; N, 4.87.

Reference Example 1

To a suspension of methyl 7-bromo-2,3-dihydro-1-benzothiepine-4-calboxylate (3.00 g) in acetic acid (30 ml) was added at room temperature 30% hydrogen peroxide solution (4.5 ml), and the mixture was refluxed for 1 hour. The reaction mixture was added to a stirred water, and precipitated crystals were collected by filtration. The crystals were washed with water and diisopropylether to give colorless crystals of methyl 7-bromo-1,1-dioxo-2,3-dihydro-1-benzothiepine-4-carboxylate (3.06 g).

m.p. 162–164° C.; $^1$H-NMR (200 MHz, CDCl$_3$) δ 3.11 (2H, t, J=6.5 Hz), 3.62 (2H, t, J=6.5 Hz), 3.87 (3H, s), 7.64–7.76 (3H, m), 8.03 (1H, d, J=8.4 Hz). IR (KBr) 1718, 1288, 1263, 1165, 1128, 1090, 797, 748 cm$^{-1}$; Anal. for C$_{12}$H$_{11}$O$_4$SBr; Calcd. C, 43.52; H, 3.35; Found. C, 43.52; H, 3.18.

Reference Example 2

To a solution of methyl 7-bromo-2,3-dihydro-1-benzothiepine-4-carboxylate (0.8 g) in THF (10 ml) was added at 0° C. 70% 3-chloroperbenzoic acid (1.45 g), and the mixture was stirred at 0° C. for 30 minutes and further at room temperature for 1 hour. To the mixture was added an aqueous solution of sodium thiosulfate, and the mixture was stirred for a few minutes and extracted with ethyl acetate. The organic layer was washed with saturated brine, dried with magnesium sulfate and concentrated under reduced pressure, and the residue was purified with column chromatography (ethyl acetate/hexane=1:1) and recrystallized from ethyl acetate/hexane to give pale yellow crystals of methyl 7-bromo-1,1-dioxo-2,3-dihydro-1-benzothiepine-4-carboxylate (827 mg). $^1$H-NMR (200 MHz, CDCl$_3$) δ 3.11 (2H, t, J=6.5 Hz), 3.62 (2H, t, J=6.5 Hz), 3.87 (3H, s), 7.64–7.76 (3H, m), 8.03 (1H, d, J=8.4 Hz). IR (KBr) 1718, 1288, 1263, 1165, 1128, 1090, 797, 748 cm$^{-1}$; Anal. for C$_{12}$H$_{11}$O$_4$SBr; Calcd. C, 43.52; H, 3.35; Found. C, 43.39; H, 3.38.

Reference Example 3

Under argon atmosphere, a mixture of methyl 7-bromo-1,1-dioxo-2,3-dihydro-1-benzothiepine-4-carboxylate (0.7 g), 4-morpholinophenyl borate (481 mg) and potassium carbonate (0.59 g) in toluene/ethanol/water (20/2/2 ml) was stirred at room temperature for 1 hour. To the mixture was added tetrakistriphenylphosphinepalladium (0.12 g), and the mixture was refluxed for 20 hours and cooled. To the mixture was added water, and the mixture was extracted with ethyl acetate. The organic layer was washed with saturated brine, dried with magnesium sulfate and concentrated under reduced pressure, and precipitated solid was recrystallized from ethyl acetate/hexane to give yellow crystals of methyl 7-(4-morpholinophenyl)-1,1-dioxo-2,3-dihydro-1-benzothiepine-4-carboxylate (617.6 mg).

m.p. 215–217° C.; $^1$H-NMR (200 MHz, CDCl$_3$) δ 3.10–3.17 (2H, m), 3.23–3.28 (4H, m), 3.61–3.67 (2H, m), 3.87 (3H, s), 3.84–3.95 (4H, m), 7.00 (2H, d, J=8.8 Hz), 7.56 (2H, d, J=8.8 Hz), 7.66–7.74 (2H, m), 7.91 (1H, s), 8.18 (1H, d, J=8.8 Hz). IR (KBr) 1705, 1605, 1520, 1309, 1290, 1238, 1165, 1126, 928, 816, 752 cm$^{-1}$; Anal. for C$_{22}$H$_{23}$NO$_5$S; Calcd. C, 63.90; H, 5.61; N, 3.39; Found. C, 63.89; H, 5.74; N, 3.51.

Reference Example 4

To a solution of methyl 7-(4-morpholinophenyl)-1,1-dioxo-2,3-dihydro-1-benzothiepine-4-carboxylate (550 mg) in ethanol/THF (15 ml/15 ml) was added at room temperature 1N sodium hydroxide solution (1.6 ml), and the mixture was stirred for 18 hours. To the mixture was added 1N hydrochloric acid (1.6 ml), and the mixture was concentrated under reduced pressure. Precipitated crystals were collected by filtration and washed with 2-propanol and diethylether to give yellow crystals of 7-(4-morpholinophenyl)-1,1-dioxo-2,3-dihydro-1-benzothiepine-4-carboxylic acid (268.9 mg). The mother liquor was concentrated, and the resulting solid was collected by filtration (177 mg). (Second crystals, Purity: about 50%)

$^1$H-NMR (200 MHz, DMSO-d$_6$) δ 2.89–3.02 (2H, m), 3.15–3.26 (4H, m), 3.68–3.82 (6H, m), 7.06 (2H, d, J=9.0 Hz), 7.74 (2H, d, J=9.0 Hz), 7.83–7.91 (2H, m), 7.99–8.08 (2H, m). IR (KBr) 3408, 1711, 1678, 1605, 1520, 1290, 1236, 1167, 1124, 928, 820, 746 cm$^{-1}$; Anal. for C$_{21}$H$_{21}$NO$_5$S.0.5 H$_2$O; Calcd. C, 61.75; H, 5.43; N, 3.43; Found. C, 61.60; H, 5.65; N, 3.50.

Reference Example 5

A mixture of methyl 7-(4-morpholinophenyl)-1,1-dioxo-2,3-dihydro-1-benzothiepine-4-carboxylate (100 mg) and 6N hydrochloric acid (10 ml) was stirred at 70° C. for 4 hours and concentrated under reduced pressure. To the residue was added 2-propanol, and the resulting solid was collected by filtration and washed with 2-propanol and diethylether to give yellow powder of 7-(4-morpholinophenyl)-1,1-dioxo-2,3-dihydro-1-benzothiepine-4-carboxylic acid hydrochloride (89.3 mg).

$^1$H-NMR (200 MHz, DMSO-d$_6$) δ 2.89–3.02 (2H, m), 3.15–3.26 (4H, m), 3.68–3.82 (4H, m), 7.06 (2H, d, J=9.0 Hz), 7.74 (2H, d, J=9.0 Hz), 7.83–7.91 (2H, m), 7.99–8.08 (2H, m). Anal. for C$_{21}$H$_{21}$NO$_5$S.HCl; Calcd. C, 57.86; H, 5.09; N, 3.21; Found. C, 57.47; H, 5.12; N, 3.31.

Reference Example 6

To a solution of methyl 7-(4-methoxyphenyl)-2,3-dihydro-1-benzothiepine-4-carboxylate (0.60 g) in THF (10 ml) was added at 0° C. 70% 3-chloroperbenzoic acid (1.0 g), and the mixture was stirred at 0° C. for 30 minutes and then at room temperature for 2 hours. To the mixture was added an aqueous solution of sodium thiosulfate, and the mixture was stirred for a few minutes and extracted with dichloromethane. The organic layer was washed with sodium bicarbonate solution and saturated brine, dried with magnesium sulfate and concentrated under reduced pressure to give solid, which was recrystallized from ethyl acetate/hexane to give colorless crystals of methyl 7-(4-methoxyphenyl)-1,1-dioxo-2,3-dihydro-1-benzothiepine-4-carboxylate (584.5 mg).

m.p. 191–193° C.; $^1$H-NMR (200 MHz, CDCl$_3$) δ 3.11–3.17 (2H, m), 3.61–3.68 (2H, m), 3.87 (3H, s), 3.88 (3H, s), 7.02 (2H, d, J=9.0 Hz), 7.57 (2H, d, J=9.0 Hz), 7.66–7.70 (2H, m), 7.92 (1H, s), 8.20 (1H, d, J=8.6 Hz). IR (KBr) 1713, 1603, 1516, 1437, 1286, 1248, 1171, 1128, 1030, 820, 750, 606 cm$^{-1}$; Anal. for C$_{19}$H$_{18}$O$_5$S; Calcd. C, 63.67; H, 5.06; Found. C, 63.88; H, 5.14.

Reference Example 7

To a solution of methyl 7-(4-methoxyphenyl)-1,1-dioxo-2,3-dihydro-1-benzothiepine-4-carboxylate (463 mg) in 1,2-dimethoxyethane (30 ml) was added 6N hydrochloric acid (30 ml), and the mixture was refluxed for 18 hours and concentrated under reduced pressure to give crystals, which were collected by filtration. The crystals washed with 2-propanol and hexane to give pale yellow crystals of 7-(4-methoxyphenyl)-1,1-dioxo-2,3-dihydro-1-benzothiepine-4-carboxylic acid (384 mg).

m.p. 250° C. (dec.); $^1$H-NMR (200 MHz, DMSO-d$_6$) δ 2.91–3.01 (2H, m), 3.71–3.78 (2H, m), 3.83 (3H, s), 7.08 (2H, d, J=8.8 Hz), 7.80 (2H, d, J=8.8 Hz), 7.84–7.91 (2H, m), 8.03–8.07 (2H, m). IR (KBr) 2978, 1682, 1608, 1520, 1292, 1255, 1165, 1130, 824 cm$^{-1}$; Anal. for C$_{18}$H$_{16}$O$_5$S; Calcd. C, 62.78; H, 4.68; Found. C, 62.51; H, 4.50.

Reference Example 8

Under argon atmosphere, a mixture of methyl 7-bromo-1,1-dioxo-2,3-dihydro-1-benzothiepine-4-carboxylate (0.80 g), 4-ethoxyphenyl borate (0.44 g) and potassium carbonate (0.67 g) in toluene/ethanol/water (20/2/2 ml) was stirred at room temperature for 1 hour. To the mixture was added tetrakistriphenylphosphinepalladium (0.14 g), and the mixture was refluxed for 16 hours, cooled, extracted with ethyl acetate, washed with saturated brine, dried with magnesium sulfate and concentrated under reduced pressure. The resulting solid was recrystallized from ethyl acetate/hexane to give pale yellow crystals of methyl 7-(4-ethoxyphenyl)-1,1-dioxo-2,3-dihydro-1-benzothiepine-4-carboxylate (739.5 mg).

m.p. 173–175° C.; $^1$H-NMR (200 MHz, CDCl$_3$) δ 1.46 (3H, t, J=7.0 Hz), 3.11–3.17 (2H, m), 3.61–3.68 (2H, m), 3.87 (3H, s), 4.10 (2H, q, J=7.0 Hz), 7.00 (2H, d, J=8.8 Hz), 7.55 (2H, d, J=8.8 Hz), 7.64–7.72 (2H, m), 7.91 (1H, s), 8.19 (1H, d, J=8.4 Hz). IR (KBr) 1713, 1608, 1518, 1292, 1250, 1225, 1167, 1132, 1038, 829, 757 cm$^{-1}$; Anal. for C$_{20}$H$_{20}$O$_5$S; Calcd. C, 64.50; H, 5.41; Found. C, 64.21; H, 5.26.

Reference Example 9

To a solution of methyl 7-(4-ethoxyphenyl)-1,1-dioxo-2,3-dihydro-1-benzothiepine-4-carboxylate (600 mg) in 1,2-dimethoxyethane (40 ml) was added 6N hydrochloric acid (30 ml), and the mixture was refluxed for 7 hours and concentrated under reduced pressure. To the residue was added 2-propanol, and precipitated crystals were collected by filtration. The crystals were dissolved in THF, and the solution was concentrated to give crystals, which were collected by filtration to give pale yellow crystals of 7-(4-ethoxyphenyl)-1,1-dioxo-2,3-dihydro-1-benzothiepine-4-carboxylic acid (507.5 mg).

m.p. 278° C. (dec.); $^1$H-NMR (200 MHz, DMSO-d$_6$) δ 1.36 (3H, t, J=7.0 Hz), 2.94–3.00 (2H, m), 3.71–3.78 (2H, m), 4.10 (2H, q, J=7.0 Hz), 7.06 (2H, d, J=8.8 Hz), 7.78 (2H, d, J=8.8 Hz), 7.83–7.92 (2H, m), 8.03–8.07 (2H, m). IR (KBr) 3039, 1676, 1608, 1518, 1294, 1250, 1165, 1130, 827, 746 cm$^{-1}$; Anal. for C$_{19}$H$_{18}$O$_5$S; Calcd. C, 63.67; H, 5.06; Found. C, 63.73; H, 5.28.

Reference Example 10

To a solution of methyl 7-(3,4-methylenedioxyphenyl)-2,3-dihydro-1-benzothiepine-4-carboxylate (0.80 g) in THF (10 ml) was added at 0° C. 70% 3-chloroperbenzoic acid (1.22 g), and the mixture was stirred at 0° C. for 15 minutes and then at room temperature for 2 hours. To the mixture was added an aqueous solution of sodium thiosulfate, and the mixture was stirred for a few minutes and extracted with dichloromethane. The organic layer was washed with sodium bicarbonate solution and saturated brine, dried with magnesium sulfate and concentrated under reduced pressure to give solid, which was recrystallized from THF/isopropanol to give colorless crystals of methyl 7-(3,4-methylenedioxyphenyl)-1,1-dioxo-2,3-dihydro-1-benzothiepine-4-carboxylate (763.3 mg).

m.p. 185–187° C.; $^1$H-NMR (200 MHz, CDCl$_3$) δ 3.11–3.17 (2H, m), 3.61–3.65 (2H, m), 3.87 (3H, s), 6.05 (2H, s), 6.92 (1H, dd, J=7.3, 1.1 Hz), 7.08–7.13 (2H, m), 7.62–7.66 (2H, m), 7.90 (1H, br s), 8.20 (1H, d, J=8.8 Hz). IR (KBr) 1714, 1481, 1277, 1252, 1232, 1130, 1036, 804, 754 cm$^{-1}$; Anal. for C$_{19}$H$_{16}$O$_6$S; Calcd. C, 61.28; H, 4.33; Found. C, 61.41; H, 4.56.

Reference Example 11

To a solution of methyl 7-(3,4-methylenedioxyphenyl)-1,1-dioxo-2,3-dihydro-1-benzothiepine-4-carboxylate (500 mg) in 1,2-dimethoxyethane (50 ml) was added 6N hydrochloric acid (30 ml), and the mixture was refluxed for 5 hours and concentrated under reduced pressure. Precipitates were collected by filtration and washed with 2-propanol and diethylether to give pale yellow crystals of 7-(3,4-methylenedioxyphenyl)-1,1-dioxo-2,3-dihydro-1-benzothiepine-4-carboxylic acid (415.7 mg).

m.p. 254° C. (dec.); $^1$H-NMR (200 MHz, DMSO-d$_6$) δ 2.97 (2H, t, J=6.6 Hz), 3.71–3.78 (2H, m), 6.10 (2H, s), 7.05 (1H, d, J=8.0 Hz), 7.34 (1H, dd, J=8.0, 1.8 Hz), 7.50 (1H, d, J=1.8 Hz), 7.82–7.90 (2H, m), 8.01–8.06 (2H, m). IR (KBr) 3439, 1678, 1479, 1290, 1234, 1128, 1038 cm$^{-1}$; Anal. for C$_{18}$H$_{14}$O$_6$S.0.2 H$_2$O; Calcd. C, 59.73; H, 4.01; Found. C, 59.82; H, 3.95.

Reference Example 12

Under argon atmosphere, methyl 7-bromo-1,1-dioxo-2,3-dihydro-1-benzothiepine-4-carboxylate (0.70 g), a mixture of 4-chlorophenyl borate (0.38 g) and potassium carbonate (0.59 g) in toluene/ethanol/water (20/2/2 ml) was stirred at room temperature for 1 hour. To the mixture was added tetrakistriphenylphosphinepalladium (0.12 g), and the mixture was refluxed for 20 hours, cooled, extracted with ethyl acetate, washed with saturated brine, dried with magnesium sulfate and concentrated under reduced pressure. The residue was purified with column chromatography (ethyl acetate/hexane=1:1) and recrystallized from ethyl acetate/hexane to give to give pale yellow crystals of methyl 7-(4-chlorophenyl)-1,1-dioxo-2,3-dihydro-1-benzothiepine-4-carboxylate (466 mg).

m.p. 168–170° C.; $^1$H-NMR (200 MHz, CDCl$_3$) δ 3.15 (2H, t, J=6.2 Hz), 3.62–3.68 (2H, m), 3.88 (3H, s), 7.44–7.57 (4H, m), 7.67–7.70 (2H, m), 7.91 (1H, s), 8.24 (1H, d, J=8.6 Hz). IR (KBr) 1720, 1296, 1275, 1248, 1223, 1194, 1165, 1132, 1090, 822, 752 cm$^{-1}$; Anal. for C$_{18}$H$_{15}$O$_4$SCl; Calcd. C, 59.59; H, 4.17; Found. C, 59.77; H, 4.14.

Reference Example 13

To a solution of methyl 7-(4-chlorophenyl)-1,1-dioxo-2,3-dihydro-1-benzothiepine-4-carboxylate (0.95 g) in 1,2-dimethoxyethane (50 ml) was added 6N hydrochloric acid (30 ml), and the mixture was stirred at 70° C. for 64 hours. The mixture was cooled to room temperature, extracted with ethylacetate, saturated brine, dried with magnesium sulfate and concentrated under reduced pressure. Precipitated crystals were collected by filtration, and the crystals was washed with diisopropylether and hexane to give pale yellow crystals of 7-(4-chlorophenyl)-1,1-dioxo-2,3-dihydro-1-benzothiepine-4-carboxylic acid (804.9 mg).

m.p. 288° C. (dec.); $^1$H-NMR (200 MHz, DMSO-d$_6$) δ 2.95–3.01 (2H, m), 3.73–3.80 (2H, m), 7.59 (2H, d, J=8.4 Hz), 7.85–7.96 (4H, m), 8.10 (1H, d, J=8.0 Hz), 8.14 (1H, s). IR (KBr) 2987, 1697, 1142, 1294, 1165, 1134, 1093, 818 cm$^{-1}$; Anal. for C$_{17}$H$_{13}$O$_4$SCl; Calcd. C, 58.54 H, 3.76; Found. C, 58.55; H, 3.85.

Reference Example 14

Under argon atmosphere, a mixture of methyl 7-bromo-1,1-dioxo-2,3-dihydro-1-benzothiepine-4-carboxylate (1.0 g), 4-fluorophenyl borate (0.465 g) and potassium carbonate (0.84 g) in toluene/ethanol/water (30/3/3 ml) was stirred at room temperature for 1 hour. To the mixture was added tetrakistriphenylphosphinepalladium (0.17 g), and the mixture was refluxed for 20 hours, cooled, extracted with ethyl acetate, saturated brine, dried with magnesium sulfate and concentrated under reduced pressure. The residue was purified with column chromatography (ethyl acetate/hexane=1:1) and recrystallized from ethyl acetate/hexane=1:1 to give pale yellow crystals of methyl 7-(4-fluorophenyl)-1,1-dioxo-2,3-dihydro-1-benzothiepine-4-carboxylate (656.3 mg).

m.p. 180–183° C.; $^1$H-NMR (200 MHz, CDCl$_3$) δ 3.12–3.19 (2H, m), 3.62–3.69 (2H, m), 3.88 (3H, s), 7.15–7.24 (2H, m), 7.55–7.70 (4H, m), 7.91 (1H, br s), 8.23 (1H, d, J=9.2 Hz). IR (KBr) 1718, 1692, 1514, 1279, 1242, 1201, 1161, 1130, 831, 752, 604, 519 cm$^{-1}$; Anal. for C$_{18}$H$_{15}$O$_4$SF; Calcd. C, 62.42; H, 4.36; Found. C, 62.38; H, 4.40.

Reference Example 15

To a solution of methyl 7-(4-fluorophenyl)-1,1-dioxo-2,3-dihydro-1-benzothiepine-4-carboxylate (0.55 g) in 1,2-dimethoxyethane (20 ml) was added 6N hydrochloric acid (10 ml), and the mixture was refluxed for 29 hours, cooled to room temperature, extracted with ethyl acetate, saturated brine, dried with magnesium sulfate and concentrated under reduced pressure to give crystals, which were collected by filtration. The crystals were washed with diisopropylether and hexane to give pale yellow crystals of 7-(4-fluorophenyl)-1,1-dioxo-2,3-dihydro-1-benzothiepine-4-carboxylic acid (490.7 mg).

m.p. 260° C. (dec.); $^1$H-NMR (200 MHz, DMSO-d$_6$) δ 2.98 (2H, t, J=7.0 Hz), 3.76 (2H, d, J=7.0 Hz), 7.32–7.40 (2H, m), 7.85–7.94 (4H, m), 8.07–8.11 (2H, m). IR (KBr) 2939, 1687, 1514, 1296, 1161, 1132, 824 cm$^{-1}$; Anal. for C$_{17}$H$_{13}$O$_4$SF; Calcd. C, 61.44; H, 3.94; Found. C, 61.20; H, 4.09.

Reference Example 16

Under argon atmosphere, a mixture of methyl 7-bromo-1,1-dioxo-2,3-dihydro-1-benzothiepine-4-carboxylate (1.00 g), 4-trifluoromethylphenyl borate (0.63 g) and potassium carbonate (0.84 g) in toluene/ethanol/water (30/3/3 ml) was stirred at room temperature for 1 hour. To the mixture was added tetrakistriphenylphosphinepalladium (0.174 g), and the mixture was refluxed for 16 hours, cooled, extracted with ethyl acetate, washed with saturated brine, dried with magnesium sulfate and concentrated under reduced pressure. The residue was purified with column chromatography (ethyl acetate/hexane=1:2) to give pale yellow crystals of methyl 7-(4-trifluoromethylphenyl)-1,1-dioxo-2,3-dihydro-1-benzothiepine-4-carboxylate (704.7 mg).

m.p. 168–170° C.; $^1$H-NMR (200 MHz, CDCl$_3$) δ 3.13–3.20 (2H, m), 3.63–3.70 (2H, m), 3.88 (3H, s), 7.67–7.80 (6H, m), 7.92 (1H, br s), 8.28 (1H, d, J=8.4 Hz). IR (KBr) 1714, 1325, 1248, 1169, 1130, 1070, 831, 750 cm$^{-1}$; Anal. for C$_{19}$H$_{15}$O$_4$SF$_3$; Calcd. C, 57.57; H, 3.81; Found. C, 57.62; H, 3.66.

Reference Example 17

To a solution of methyl 7-(4-trifluoromethylphenyl)-1,1-dioxo-2,3-dihydro-1-benzothiepine-4-carboxylate (600 mg) in 1,2-dimethoxyethane (40 ml) was added at room temperature 6N hydrochloric acid (20 ml), and the mixture was refluxed for 22 hours, cooled to room temperature and extracted with ethyl acetate/THF. The organic layer was washed with saturated brine, dried with magnesium sulfate and concentrated under reduced pressure to give crystals, which were collected by filtration. The crystals were washed with hexane to give colorless crystals of 7-(4-trifluoromethylphenyl)-1,1-dioxo-2,3-dihydro-1-benzothiepine-4-carboxylic acid (439.5 mg).

m.p. >300° C.; $^1$H-NMR (200 MHz, DMSO-d$_6$) δ 2.96–3.02 (2H, m), 3.75–3.82 (2H, m), 7.87–8.17 (7H, m), 8.22 (1H, d, J=1.6 Hz). IR (KBr) 2985, 1695, 1325, 1294, 1171, 1132, 1117, 1072, 829 cm$^{-1}$; Anal. for C$_{18}$H$_{13}$O$_4$SF$_3$; Calcd. C, 56.54; H, 3.43; Found. C, 56.43; H, 3.55.

Reference Example 18

Under argon atmosphere, a mixture of methyl 7-bromo-1,1-dioxo-2,3-dihydro-1-benzothiepine-4-carboxylate (0.80 g), 4-ethylphenyl borate (0.40 g) and potassium carbonate (0.67 g) in toluene/ethanol/water (30/3/3 ml) was stirred at room temperature for 1 hour. To the mixture was added tetrakistriphenylphosphinepalladium (0.14 g), and the mixture was refluxed for 15 hours, cooled, extracted with ethyl acetate, washed with saturated brine, dried with magnesium sulfate and concentrated under reduced pressure. The residue was purified with column chromatography (ethyl acetate/hexane=1:1) to give pale yellow crystals of methyl 7-(4-ethylphenyl)-1,1-dioxo-2,3-dihydro-1-benzothiepine-4-carboxylate (732 mg).

m.p. 173–176° C.; $^1$H-NMR (200 MHz, CDCl$_3$) δ 1.29 (3H, t, J=7.5 Hz), 2.72 (2H, q, J=7.5 Hz), 3.11–3.18 (2H, m), 3.62–3.68 (2H, m), 3.87 (3H, s), 7.33 (2H, d, J=8.1 Hz), 7.54 (2H, d, J=8.1 Hz), 7.66–7.74 (2H, m), 7.92 (1H, br s), 8.21 (1H, d, J=8.4 Hz). IR (KBr) 1714, 1315, 1294, 1277, 1252, 1223, 1165, 1130, 825, 750 cm$^{-1}$; Anal. for C$_{20}$H$_{20}$O$_4$S; Calcd. C, 67.39; H, 5.66; Found. C, 67.36; H, 5.63.

Reference Example 19

To a solution of methyl 7-(4-ethylphenyl)-1,1-dioxo-2,3-dihydro-1-benzothiepine-4-carboxylate (600 mg) in 1,2-dimethoxyethane (20 ml) was added 6N hydrochloric acid (10 ml), and the mixture was refluxed for 24 hours, cooled to room temperature and extracted with ethyl acetate. The organic layer was washed with saturated brine, dried with magnesium sulfate and concentrated under reduced pressure to give crystals, which were collected by filtration. The crystals were washed with hexane to give pale yellow crystals of 7-(4-ethylphenyl)-1,1-dioxo-2,3-dihydro-1-benzothiepine-4-carboxylic acid (501.2 mg).

m.p. 260–265° C.; $^1$H-NMR (200 MHz, DMSO-d$_6$) δ 1.29 (3H, t, J=7.6 Hz), 2.73 (2H, q, J=7.6 Hz), 3.17 (2H, t, J=6.6 Hz), 3.67 (2H, t, J=6.6 Hz), 7.34 (2H, d, J=8.4 Hz), 7.55 (2H, d, J=8.4 Hz), 7.70–7.78 (2H, m), 8.02 (1H, s), 8.24 (1H, d, J=8.8 Hz). IR (KBr) 2966, 1675, 1290, 1163, 1128, 824, 744 cm$^{-1}$; Anal. for C$_{19}$H$_{18}$O$_4$S; Calcd. C, 66.65; H, 5.30; Found. C, 66.47; H, 5.41.

Reference Example 20

Under argon atmosphere, a mixture of methyl 7-bromo-2,3-dihydro-1-benzothiepine-4-carboxylate (0.80 g), 4-isopropylphenyl borate (0.44 g) and potassium carbonate (0.67 g) in toluene/ethanol/water (30/3/3 ml) was stirred at room temperature for 1 hour. To the mixture was added tetrakistriphenylphosphinepalladium (0.14 g), and the mixture was refluxed for 20 hours, cooled, extracted with ethyl acetate, washed with saturated brine, dried with magnesium sulfate and concentrated under reduced pressure. The residue was purified with column chromatography (ethyl acetate/hexane=1:2) to give pale yellow crystals of methyl 7-(4-isopropylphenyl)-1,1-dioxo-2,3-dihydro-1-benzothiepine-4-carboxylate (774.7 mg).

m.p. 142–144° C.; $^1$H-NMR (200 MHz, CDCl$_3$) δ 1.30 (6H, d, J=6.6 Hz), 2.90–3.06 (1H, m), 3.12–3.18 (2H, m), 3.62–3.68 (2H, m), 3.87 (3H, s), 7.36 (2H, d, J=8.2 Hz), 7.55 (2H, d, J=8.2 Hz), 7.69–7.73 (2H, m), 7.92 (1H, br s), 8.22 (1H, d, J=8.8 Hz). IR (KBr) 1713, 1315, 1294, 1277, 1252, 1223, 1196, 1167, 1130, 825, 752 cm$^{-1}$; Anal. for C$_{21}$H$_{22}$O$_4$S; Calcd. C, 68.08; H, 5.99; Found. C, 68.04; H, 6.15.

Reference Example 21

To a solution of methyl 7-(4-isopropylphenyl)-1,1-dioxo-2,3-dihydro-1-benzothiepine-4-carboxylate (600 mg) in 1,2-dimethoxyethane (20 ml) was added at room temperature 6N hydrochloric acid (10 ml), and the mixture was refluxed for 24 hours, cooled to room temperature and extracted with ethyl acetate. The organic layer was washed with saturated brine, dried with magnesium sulfate and concentrated under reduced pressure to give crystals, which were collected by filtration. The crystals were washed with hexane to give colorless crystals of 7-(4-isopropylphenyl)-1,1-dioxo-2,3-dihydro-1-benzothiepine-4-carboxylic acid (555.2 mg).

m.p. 282° C. (dec.); $^1$H-NMR (200 MHz, CDCl$_3$) δ 1.30 (6H, d, J=7.0 Hz), 2.92–3.05 (1H, m), 3.13–3.20 (2H, m), 3.63–3.70 (2H, m), 7.36 (2H, d, J=8.5 Hz), 7.56 (2H, d, J=8.2 Hz), 7.69–7.78 (2H, m), 8.01 (1H, br s), 8.24 (1H, d, J=8.8 Hz). IR (KBr) 2962, 1676, 1294, 1167, 1132, 824, 748 cm$^{-1}$; Anal. for C$_{20}$H$_{20}$O$_4$S.0.2 H$_2$O; Calcd. C, 66.72; H, 5.71; Found. C, 66.63; H, 5.79.

Reference Example 22

Under argon atmosphere, a mixture of methyl 7-bromo-1,1-dioxo-2,3-dihydro-1-benzothiepine-4-carboxylate (0.80 g), 4-tert-butylphenyl borate (0.47 g) and potassium carbonate (0.67 g) in toluene/ethanol/water (30/3/3 ml) was stirred at room temperature for 1 hour. To the mixture was added tetrakistriphenylphosphinepalladium (0.14 g), and the mixture was refluxed for 16 hours, cooled, extracted with ethyl acetate, washed with saturated brine, dried with magnesium sulfate and concentrated under reduced pressure. The residue was purified with column chromatography (ethyl acetate/hexane=1:1) and recrystallized from ethyl acetate/diisopropylether to give colorless crystals of methyl 7-(4-tert-butylphenyl)-1,1-dioxo-2,3-dihydro-1-benzothiepine-4-carboxylate (793.6 mg).

m.p. 170–172° C.; $^1$H-NMR (200 MHz, CDCl$_3$) δ 1.38 (9H, s), 3.12–3.18 (2H, m), 3.62–3.69 (2H, m), 3.88 (3H, s), 7.49–7.59 (4H, m), 7.70–7.74 (2H, m), 7.92 (1H, br s), 8.22 (1H, d, J=8.8 Hz). IR (KBr) 1713, 1319, 1296, 1277, 1244, 1198, 1169, 1128, 827, 752 cm$^{-1}$; Anal. for C$_{22}$H$_{24}$O$_4$S; Calcd. C, 68.72; H, 6.29; Found. C, 68.67; H, 6.31.

Reference Example 23

To a solution of methyl 7-(4-tert-butylphenyl)-1,1-dioxo-2,3-dihydro-1-benzothiepine-4-carboxylate (400 mg) in 1,2-dimethoxyethane (20 ml) was added 6N hydrochloric acid (10 ml), and the mixture was stirred at 70° C. for 55 hours, cooled to room temperature and extracted with ethyl acetate. The organic layer was washed with saturated brine, dried with magnesium sulfate and concentrated under reduced pressure to give crystals, which were collected by filtration and washed with hexane to give pale yellow crystals of 7-(4-tert-butylphenyl)-1,1-dioxo-2,3-dihydro-1-benzothiepine-4-carboxylic acid (362.7 mg).

m.p. 289–291° C.; $^1$H-NMR (200 MHz, DMSO-d$_6$) δ 1.33 (9H, s), 2.94–3.01 (2H, m), 3.73–3.79 (2H, m), 7.54 (2H, d, J=8.6 Hz), 7.76 (2H, d, J=8.6 Hz), 7.89–7.93 (2H, m), 8.06–8.11 (2H, m). IR (KBr) 2962, 1689, 1292, 1165, 1132, 824, 748 cm$^{-1}$; Anal. for C$_{21}$H$_{22}$O$_4$S; Calcd. C, 68.08; H, 5.99; Found. C, 67.93; H, 5.69.

Reference Example 24

Under argon atmosphere, a mixture of methyl 7-bromo-1,1-dioxo-2,3-dihydro-1-benzothiepine-4-carboxylate (0.80 g), 4-(1-pyrrolidinyl)phenyl borate (508 mg) and potassium carbonate (0.67 g) in toluene/ethanol/water (30/3/3 ml) was stirred at room temperature for 1 hour. To the mixture was added tetrakistriphenylphosphinepalladium (0.14 g), and the mixture was refluxed for 17 hours, cooled, extracted with ethyl acetate, washed with saturated brine, dried with magnesium sulfate and concentrated under reduced pressure to give crystals, which were collected by filtration. The crystals were washed with diisopropylether to give yellow crystals of methyl 7-[4-(1-pyrrolidinyl)phenyl]-1,1-dioxo-2,3-dihydro-1-benzothiepine-4-carboxylate (323 mg).

m.p. 227° C. (dec.); $^1$H-NMR (200 MHz, CDCl$_3$) δ 2.00–2.11(4H, m), 3.09–3.16 (2H, m), 3.29–3.41 (4H, m), 3.61–3.67 (2H, m), 3.87 (3H, s), 6.65 (2H, d, J=8.8 Hz), 7.54 (2H, d, J=8.8 Hz), 7.65–7.69 (2H, m), 7.91 (1H, br s), 8.15 (1H, d, J=9.2 Hz). IR (KBr) 1714, 1608, 1585, 1529, 1385, 1313, 1279, 1252, 1163, 1128, 808, 754 cm$^{-1}$; Anal. for C$_{22}$H$_{23}$NO$_4$S; Calcd. C, 66.48; H, 5.83; N, 3.52; Found. C, 66.74; H, 5.82; N, 3.38.

Reference Example 25

To methyl 7-[4-(1-pyrrolidinyl)phenyl]-1,1-dioxo-2,3-dihydro-1-benzothiepine-4-carboxylate (270 mg) was added 6N hydrochloric acid (30 ml), and the mixture was stirred at 70° C. for 7 hours and concentrated under reduced pressure. To the residue was added 2-propanol to give crystals, which were collected by filtration. The crystals were washed with 2-propanol and hexane to give yellow crystals of 7-[4-(1-pyrrolidinyl)phenyl]-1,1-dioxo-2,3-dihydro-1-benzothiepine-4-carboxylic acid hydrochloride (204 mg).

m.p. 283° C. (dec.); $^1$H-NMR (200 MHz, DMSO-d$_6$) δ 1.86–2.03 (4H, m), 2.95 (2H, t, J=6.3 Hz), 3.23–3.36 (4H, m), 3.69–3.75 (2H, m), 6.67 (2H, d, J=8.7 Hz), 7.70 (2H, d, J=8.7 Hz), 7.80–7.86 (2H, m), 7.97–8.01 (2H, m). IR (KBr) 2883, 1701, 1389, 1319, 1288, 1196, 1171, 1128, 822 cm$^{-1}$; Anal. for C$_{21}$H$_{22}$NO$_4$SCl.0.5 H$_2$O; Calcd. C, 58.80; H, 5.40; N, 3.27; Found. C, 59.02; H, 5.27; N, 3.20.

Reference Example 26

Under argon atmosphere, a mixture of methyl 7-bromo-1,1-dioxo-2,3-dihydro-1-benzothiepine-4-carboxylate (0.80 g), 4-piperidinophenyl borate (0.55 g) and potassium carbonate (0.67 g) in toluene/ethanol/water (30/3/3 ml) was stirred at room temperature for 1 hour. To the mixture was added tetrakistriphenylphosphinepalladium (0.14 g), and the mixture was refluxed for 15 hours, cooled, extracted with ethyl acetate, washed with saturated brine, dried with magnesium sulfate and concentrated under reduced pressure to give crystals, which were recrystallized from ethyl acetate to give yellow crystals of methyl 7-(4-piperidinophenyl)-1,1-dioxo-2,3-dihydro-1-benzothiepine-4-carboxylate (0.85 g).

m.p. 202–204° C.; $^1$H-NMR (200 MHz, CDCl$_3$) δ 1.59–1.80 (6H, m), 3.10–3.16 (2H, m), 3.23–3.34 (4H, m), 3.61–3.67 (2H, m), 3.87 (3H, s), 7.01 (2H, d, J=9.0 Hz), 7.54 (2H, d, J=9.0 Hz), 7.65–7.70 (2H, m), 7.91 (1H, br s), 8.17 (1H, d, J=8.8 Hz). IR (KBr) 1707, 1605, 1585, 1518, 1435, 1298, 1240, 1511, 1124, 816, 741 cm$^{-1}$; Anal. for C$_{23}$H$_{25}$NO$_4$S; Calcd. C, 67.13; H, 6.12; N, 3.40; Found. C, 67.12; H, 6.36; N, 3.52.

Reference Example 27

To methyl 7-(4-piperidinophenyl)-1,1-dioxo- 2,3-dihydro-1-benzothiepine-4-carboxylate (600 mg) was added 6N hydrochloric acid (60 ml), and the mixture was stirred at 70° C. for 5 hours and concentrated under reduced pressure. To the residue was added ethanol, and to the mixture were added 8N sodium hydroxide solution and 1N sodium hydroxide solution to make the solution pH 6–7. The mixture was concentrated under reduced pressure to give solid, which was collected by filtration and washed with water, 2-propanol, acetone and diisopropylether to give yellow powder of 7-(4-piperidinophenyl)-1,1-dioxo-2,3-dihydro-1-benzothiepine-4-carboxylic acid (549.5 mg).

$^1$H-NMR (200 MHz, DMSO-d$_6$) δ 1.45–1.60 (6H, m), 2.96 (2H, t, J=6.7 Hz), 3.12–3.46 (4H, m), 3.69–3.75 (2H, m), 7.03 (2H, d, J=8.8 Hz), 7.69 (2H. d, J=8.8 Hz), 7.78–7.87 (2H, m), 7.99–8.03 (2H, m). IR (KBr) 2937, 1680, 1605, 1587, 1520, 1292, 1240, 1128, 818, 744 cm$^{-1}$.

Reference Example 28

Under argon atmosphere, A mixture of methyl 7-bromo-1,1-dioxo-2,3-dihydro-1-benzothiepine-4-carboxylate (0.80 g), 4-trifluoromethoxyphenyl borate (0.55 g) and potassium carbonate (0.67 g) in toluene/ethanol/water (30/3/3 ml) was stirred at room temperature for 1 hour. To the mixture was added tetrakistriphenylphosphinepalladium (0.14 g), and the mixture was refluxed for 20 hours, cooled, extracted with ethyl acetate, washed with saturated brine, dried with magnesium sulfate and concentrated under reduced pressure. The residue was purified with column chromatography (ethyl acetate/hexane=1:2) to give pale yellow crystals of methyl 7-(4-trifluoromethoxyphenyl)-1,1-dioxo-2,3-dihydro-1-benzothiepine-4-carboxylate (638.5 mg).

m.p. 142–143° C.; $^1$H-NMR (200 MHz, CDCl$_3$) δ 3.13–3.19 (2H, m), 3.62–3.69 (2H, m), 3.88 (3H, s), 7.35 (2H, d, J=8.0 Hz), 7.60–7.73 (4H, m), 7.92 (1H, br s), 8.25 (1H, d. J=8.8 Hz). IR (KBr) 1713, 1514, 1257, 1215, 1165, 1130, 837, 754 cm$^{-1}$; Anal. for C$_{19}$H$_{15}$O$_5$SF$_3$; Calcd. C, 55.34; H, 3.67; Found. C, 55.48; H, 3.63.

Reference Example 29

To a solution of methyl 7-(4-trifluoromethoxyphenyl)-1,1-dioxo-2,3-dihydro-1-benzothiepine-4-carboxylate (450 mg) in 1,2-dimethoxyethane (10 ml) was added at room temperature 6N hydrochloric acid (5 ml), and the mixture was refluxed for 24 hours, cooled to room temperature and extracted with ethyl acetate. The organic layer was washed with saturated brine, dried with magnesium sulfate and concentrated under reduced pressure to give crystals, which were collected by filtration. The crystals were washed with hexane to give colorless crystals of 7-(4-trifluoromethoxyphenyl)-1,1-dioxo-2,3-dihydro-1-benzothiepine-4-carboxylic acid (390.3 mg).

m.p. 284–285° C.; $^1$H-NMR (200 MHz, DMSO-d$_6$) δ 2.95–3.02 (2H, m), 3.74–3.80 (2H, m), 7.52 (2H, d, J=8.0 Hz), 7.89–7.99 (4H, m), 8.09–8.16 (2H, m). IR (KBr) 3047, 1693, 1269, 1215, 1165, 1132 cm$^{-1}$; Anal. for C$_{18}$H$_{13}$O$_5$SF$_3$; Calcd. C, 54.27 H, 3.29; Found. C, 54.22; H, 3.20.

Reference Example 30

Under argon atmosphere, a mixture of methyl 7-bromo-1,1-dioxo-2,3-dihydro-1-benzothiepine-4-carboxylate (0.80 g), 3,4-dichlorophenyl borate (0.54 g) and potassium carbonate (0.67 g) in toluene/ethanol/water (30/3/3 ml) was stirred at room temperature for 1 hour. To the mixture was added tetrakistriphenylphosphinepalladium (0.14 g), and the mixture was refluxed for 18 hours, cooled, extracted with ethyl acetate, washed with saturated brine, dried with magnesium sulfate and concentrated under reduced pressure. The residue was purified with column chromatography (ethyl acetate/hexane=1:2→1:1) to give pale yellow crystals of methyl 7-(3,4-dichlorophenyl)-1,1-dioxo-2,3-dihydro-1-benzothiepine-4-carboxylate (631.3 mg).

$^1$H-NMR (200 MHz, CDCl$_3$) δ 3.13–3.19 (2H, m), 3.62–3.69 (2H, m), 3.88 (3H, s), 7.45 (1H, dd, J=8.2, 2.0 Hz), 7.58 (1H, d, J=8.2 Hz), 7.66–7.71 (3H, m), 7.91 (1H, br s), 8.26 (1H, d, J=8.2 Hz). IR (KBr) 1707, 1321, 1275, 1252, 1171, 1130, 750 cm$^{-1}$.

Reference Example 31

To a solution of methyl 7-(3,4-dichlorophenyl)-1,1-dioxo-2,3-dihydro-1-benzothiepine-4-carboxylate (450 mg) in 1,2-dimethoxyethane (10 ml) was added 6N hydrochloric acid (10 ml), and the mixture was refluxed for 64 hours, cooled to room temperature and extracted with ethyl acetate. The organic layer was washed with saturated brine, dried with magnesium sulfate and concentrated under reduced pressure to give crystals, which were collected by filtration to give colorless crystals of 7-(3,4-dichlorophenyl)-1,1-dioxo-2,3-dihydro-1-benzothiepine-4-carboxylic acid (395.5 mg).

$^1$H-NMR (200 MHz, DMSO-d$_6$) δ 2.94–3.02 (2H, m), 3.73–3.80 (2H, m), 7.78 (1H, d, J=8.4 Hz), 7.83–7.91 (2H, m), 7.97–8.02 (1H, m), 8.10 (1H, d, J=8.0 Hz), 8.18 (1H, d, J=2.2 Hz), 8.23–8.27 (1H, m). IR (KBr) 2985, 1672, 1468, 1415, 1,319, 1292, 1173, 1133, 820 cm$^{-1}$.

Reference Example 32

Under argon atmosphere, a mixture of methyl 7-bromo-1,1-dioxo-2,3-dihydro-1-benzothiepine-4-carboxylate (0.80 g), 4-propylphenyl borate (0.435 g) and potassium carbonate (0.67 g) in toluene/ethanol/water (25/2.5/2.5 ml) was stirred at room temperature for 1 hour. To the mixture was added tetrakistriphenylphosphinepalladium (0.14 g), and the mixture was refluxed for 18 hours, cooled, extracted with ethyl acetate, washed with saturated brine, dried with magnesium sulfate and concentrated under reduced pressure. Precipitated crystals were collected by filtration and the crystals were washed with ethyl acetate, diisopropylether and hexane to give colorless crystals of methyl 7-(4-propylphenyl)-1,1-dioxo-2,3-dihydro-1-benzothiepine-4-carboxylate (557.2 mg).

m.p. 155–156° C.; $^1$H-NMR (200 MHz, CDC$_3$) δ 0.98 (3H, t, J=7.4 Hz), 1.63–1.77 (2H, m), 2.66 (2H, t, J=7.6 Hz), 3.11–3.18 (2H, m), 3.61–3.68 (2H, m), 3.87 (3H, s), 7.30 (2H, d, J=8.4 Hz), 7.54 (2H, d, J=8.4 Hz), 7.69–7.73 (2H, m), 7.92 (1H, br s), 8.22 (1H, d, J=8.8 Hz). IR (KBr) 1709, 1313, 1290, 1248, 1165, 1130, 748 cm$^{-1}$; Anal. for C$_{21}$H$_{22}$O$_4$S; Calcd. C, 68.08; H, 5.99; Found. C, 68.13; H, 5.89.

Reference Example 33

To a solution of methyl 7-(4-propylphenyl)-1,1-dioxo-2,3-dihydro-1-benzothiepine-4-carboxylate (450 mg) in 1,2-dimethoxyethane (15 ml) was added 6N hydrochloric acid (7.5 ml), and the mixture was refluxed for 40 hours, cooled to room temperature and extracted with ethyl acetate. The organic layer was washed with saturated brine, dried with magnesium sulfate and concentrated under reduced pressure to give crystals, which were collected by filtration and recrystallized from THF/diisopropylether to give colorless crystals of 7-(4-propylphenyl)-1,1-dioxo-2,3-dihydro-1-benzothiepine-4-carboxylic acid (433.6 mg).

$^1$H-NMR (200 MHz, DMSO-d$_6$) δ 0.92 (3H, t, J=7.3 Hz), 1.58–1.69 (2H, m), 2.58–2.66 (2H, m), 2.93–3.01 (2H, m), 3.72–3.79 (2H, m), 7.34 (2H, d, J=8.2 Hz), 7.74 (2H, d, J=8.2 Hz), 7.88–7.93 (2H, m), 8.06–8.09 (2H, m). IR (KBr) 3012, 1678, 1408, 1321, 1298, 1167, 1132 cm$^{-1}$.

Reference Example 34

Under argon atmosphere, a mixture of methyl 7-bromo-1,1-dioxo-2,3-dihydro-1-benzothiepine-4-carboxylate (0.80 g), 4-isopropoxyphenyl borate (0.48 g) and potassium carbonate (0.67 g) in toluene/ethanol/water (25/2.5/2.5 ml) was stirred at room temperature for 1 hour. To the mixture was added tetrakistriphenylphosphinepalladium (0.14 g), and the mixture was refluxed for 13 hours, cooled, extracted with ethyl acetate, washed with saturated brine, dried with magnesium sulfate and concentrated under reduced pressure. The residue was purified with column chromatography (ethyl acetate/hexane=1:2) to give colorless crystals of methyl 7-(4-isopropoxyphenyl)-1,1-dioxo-2,3-dihydro-1-benzothiepine-4-carboxylate (606.5 mg).

m.p. 140–142° C.; $^1$H-NMR (200 MHz, CDCl$_3$) δ 1.38 (6H, d, J=6.2 Hz), 3.11–3.17 (2H, m), 3.61–3.68 (2H, m), 3.87 (3H, s), 4.57–4.69 (1H, m), 6.99 (2H, d, J=9.0 Hz), 7.54 (2H, d, J=9.0 Hz), 7.66–7.70 (2H, m), 7.91 (1H, br s), 8.19 (1H, d, J=8.8 Hz). IR (KBr) 1709, 1516, 1309, 1288, 1246, 1165, 1128, 829, 750 cm$^{-1}$; Anal. for C$_{21}$H$_{22}$O$_5$S; Calcd. C, 65.27; H, 5.74; Found. C, 65.13; H, 5.83.

Reference Example 35

To a solution of methyl 7-(4-isopropoxyphenyl)-1,1-dioxo-2,3-dihydro-1-benzothiepine-4-carboxylate (250 mg) in 1,2-dimethoxyethane (10 ml) was added 6N hydrochloric acid (3 ml), and the mixture was stirred at 70° C. for 18 hours. To the mixture were added 1,2-dimethoxyethane (10 ml) and 6N hydrochloric acid (5 ml), and the mixture was stirred at 70° C. for 4 days, cooled to room temperature and extracted with ethyl acetate. The organic layer was washed with saturated brine; dried with magnesium sulfate and concentrated under reduced pressure to give crystals, which were collected by filtration. The crystals were washed with hexane to give colorless crystals of 7-(4-isopropoxyphenyl)-1,1-dioxo-2,3-dihydro-1-benzothiepine-4-carboxylic acid (230.3 mg).

$^1$H-NMR (200 MHz, DMSO-d$_6$) δ 1.30 (6H, d, J=5.8 Hz), 2.93–3.00 (2H, m), 3.71 (2H, m), 4.63–4.7.8 (1H, m), 7.04 (2H, d, J=8.8 Hz), 7.76 (2H, d, J=8.8 Hz), 7.84–7.91 (2H, m), 8.03–8.07 (2H, m). IR (KBr) 2977, 1676, 1608, 1513, 1292, 1246, 1165, 1130, 951, 829, 746 cm$^{-1}$.

Reference Example 36

Under argon atmosphere, a mixture of methyl 7-bromo-1,1-dioxo-2,3-dihydro-1-benzothiepine-4-carboxylate (0.70 g), 4-propoxyphenyl borate (0.38 g) and potassium carbonate (0.58 g) in toluene/ethanol/water (20/2/2 ml) was stirred at room temperature for 1 hour. To the mixture was added tetrakistriphenylphosphinepalladium (0.12 g), and the mixture was refluxed for 18 hours, cooled, extracted with ethyl acetate, washed with saturated brine, dried with magnesium sulfate and concentrated under reduced pressure. The residue was purified with column chromatography (ethyl acetate/hexane=1:2→1:1) to give pale yellow crystals of methyl 7-(4-propoxyphenyl)-1,1-dioxo-2,3-dihydro-1-benzothiepine-4-carboxylate (616.4 mg).

m.p. 153–155° C.; $^1$H-NMR (200 MHz, CDCl$_3$) δ 1.07 (3H, t, J=7.5 Hz), 1.76–1.93 (2H, m), 3.11–3.17 (2H, m), 3.61–3.68 (2H, m), 3.87 (3H, s), 3.99 (2H, t, J=6.6 Hz), 7.01 (2H, d, J=9.0 Hz), 7.55 (2H, d, J=9.0 Hz), 7.66–7.70 (2H, m), 7.91 (1H, br s), 8.20 (1H, d, J=8.4 Hz). IR (KBr) 1718, 1608, 1518, 1315, 1281, 1248, 1223, 1163, 1132, 831, 754 cm$^{-1}$; Anal. for C$_{21}$H$_{22}$O$_5$S; Calcd. C, 65.27; H, 5.74; Found. C, 65.35; H, 5.63.

Reference Example 37

To a solution of methyl 7-(4-propoxyphenyl)-1,1-dioxo-2,3-dihydro-1-benzothiepine-4-carboxylate (400 mg) in 1,2-dimethoxyethane (10 ml) was added 6N hydrochloric acid (5 ml), and the mixture was refluxed for 2 days, cooled to room temperature and concentrated under reduced pressure to give crystals, which were collected by filtration. The crystals were washed with water, 2-propanol and diisopropylether to give colorless crystals of 7-(4-propoxyphenyl)-1,1-dioxo-2,3-dihydro-1-benzothiepine-4-carboxylic acid (346.1 mg).

m.p. 270–273° C.; $^1$H-NMR (200 MHz, DMSO-d$_6$) δ 1.00 (3H, t, J=7.5 Hz), 1.65–1.86 (2H, m), 2.93–3.00 (2H, m), 3.71–3.78 (2H, m), 4.00 (2H, t, J=6.6 Hz), 7.06 (2H, d, J=8.7 Hz), 7.78 (2H, d, J=8.7 Hz), 7.83–7.93 (2H, m), 8.03–8.07 (2H, m). IR (KBr) 2972, 1676, 1608, 1518, 1292, 1250, 1163, 1128, 827, 746 cm$^{-1}$; Anal. for C$_{20}$H$_{20}$O$_5$S; Calcd. C, 64.50; H, 5.41; Found. C, 64.34; H. 5.48.

Reference Example 38

Under argon atmosphere, a mixture of methyl 7-bromo-1,1-dioxo-2,3-dihydro-1-benzothiepine-4-carboxylate (0.70 g), 4-butoxyphenyl borate (0.45 g) and potassium carbonate (0.58 g) in toluene/ethanol/water (20/2/2 ml) was stirred at room temperature for 1 hour. To the mixture was added tetrakistriphenylphosphinepalladium (0.12 g), and the mixture was refluxed for 20 hours, cooled, extracted with ethyl acetate, washed with saturated brine, dried with magnesium sulfate and concentrated under reduced pressure. The residue was purified with column chromatography (ethyl acetate/hexane=1:1) to give colorless crystals of methyl 7-(4-butoxyphenyl)-1,1-dioxo-2,3-dihydro-1-benzothiepine-4-carboxylate (672.6 mg).

m.p. 123–125° C.; $^1$H-NMR (200 MHz, CDCl$_3$) δ 1.00 (3H, t, J=7.1 Hz), 1.45–1.62 (2H, m), 1.74–1.88 (2H, m), 3.11–3.18 (2H, m), 3.61–3.68 (2H, m), 3.87 (3H, s), 4.03 (2H, t, J=6.4 Hz), 7.01 (2H, d, J=8.8 Hz), 7.55 (2H, d, J=8.8 Hz), 7.64–7.72 (2H, m), 7.91 (1H, br 2), 8.19 (1H, d, J=8.8 Hz). IR (KBr) 1714, 1516, 1317, 1294, 1248, 1223, 1165, 1132, 824, 750 cm$^{-1}$; Anal. for C$_{22}$H$_{24}$O$_5$S; Calcd. C, 65.98; H, 6.04; Found. C, 66.27; H, 5.78.

Reference Example 39

To a solution of methyl 7-(4-butoxyphenyl)-1,1-dioxo-2,3-dihydro-1-benzothiepine-4-carboxylate (500 mg) in 1,2-dimethoxyethane (10ml) was added 6N hydrochloric acid (5 ml), and the mixture was refluxed for 16 hours. To the mixture were added 1,2-dimethoxyethane (5 ml) and 6N hydrochloric acid (2 ml), and the mixture was refluxed for 4 hours, cooled to room temperature and extracted with ethyl acetate. The organic layer was washed with saturated brine, dried with magnesium sulfate and concentrated under reduced pressure to give crystals, which were collected by filtration. The crystals were washed with diisopropylether to give colorless crystals of 7-(4-butoxyphenyl)-1,1-dioxo-2,3-dihydro-1-benzothiepine-4-carboxylic acid (388.9 mg).

m.p. 244–247° C.; $^1$H-NMR (200 MHz, DMSO-d$_6$) δ 0.95 (3H, t, J=7.1 Hz), 1.35–1.56 (2H, m), 1.64–1.81 (2H, m), 2.93–3.00 (2H, m), 3.71–3.78 (2H, m), 4.04 (2H, t, J=6.6 Hz), 7.06 (2H, d, J=8.8 Hz), 7.77 (2H, d, J=8.8 Hz), 7.85–7.90 (2H, m), 8.03–8.07 (2H, m). IR (KBr) 2958, 1676, 1608, 1518, 1408, 1292, 1252, 1163, 1128, 827, 746 cm$^{-1}$; Anal. for C$_{22}$H$_{22}$O$_5$S; Calcd. C, 65.27; H, 5.74; Found. C, 65.28; H, 5.70.

Reference Example 40

To a solution of ethyl 6-(4-methylphenyl)-1,2-dihydro-2H-thiochromene-3-carboxylate (1.03 g, 3.32 mmol) in dichloromethane (20 ml) was added at 0° C. m-chloroperbenzoic acid (1.73 g, 6.98 mmol), and the mixture was stirred for 20 minutes and then at room temperature for 20 minutes. The mixture was neutralized with saturated sodium hydrogen carbonate solution and extracted with dichloromethane. The organic layer was dried with magnesium sulfate, and the solvent was evaporated to give colorless powder, which was washed with ethanol to give ethyl 6-(4-methylphenyl)-1,1-dioxo-1,2-dihydro-2H-thiochromene-3-carboxylate (0.95 g, 84%). A part of the product was recrystallized from ethyl acetate to give colorless flake crystals.

m.p. 174° C.; $^1$H-NMR (CDCl$_3$) δ: 8.09 (1H, d, J=8.0), 7.87 (1H, s), 7.80 (1H, dd, J=8.0, 1.8), 7.70 (1H, d, J=1.8), 7.41 (2H, d, J=8.0), 7.31 (2H, d, J=8.0),4.35 (2H, q, J=7.4), 4.29 (2H, d, J=1.8), 2.43 (3H, 5), 1.39 (3H, t, J=7.4). Anal. Calcd for C$_{19}$H$_{18}$O$_4$S.0.25 H$_2$O: C: 65.78, H; 5.37. Found: C; 65.93, H; 5.26.

Reference Example 41

To a solution of ethyl 6-(4-methylphenyl)-1,1-dioxo-1,2-dihydro-2H-thiochromene-3-carboxylate (0.90 g, 2.63 mmol) in tetrahydrofuran (10 ml) and acetonitrile (10 ml) was added dropwise 1N sodium hydroxide (3 ml), and the mixture was stirred for 1 hour. The reaction solution was distributed to diethylether and water, and the aqueous layer was made pH 3 with 6N hydrochloric acid and extracted with ethyl acetate. The organic layer was washed with saturated brine and dried with magnesium sulfate. The solvent was evaporated to give crude carboxylic acid as brown powder, which was washed with ethanol to give 6-(4-methylphenyl)-1,1-dioxo-1,2-dihydro-2H-thiochromene-3-carboxylic acid (0.24 g, 29%) as pale yellow powder.

$^1$H-NMR (CDCl$_3$) δ: 7.95–7.99 (3H, m), 7.69 (2H, d, J=8.2), 7.35 (2H, d, J=8.2), 4.45 (2H, s), 3.78 (3H, s).

Reference Example 42

To a solution of methyl 7-(4-methylphenyl)-2,3-dihydro-1-benzothiepine-4-carboxylate (1.5 g) in dichloromethane (25 ml) was added, under ice-cooling, 70% mCPBA (2.4 g), and the mixture was stirred at room temperature for 1 hour. To the solution was added an aqueous solution of sodium thiosulfate, and the mixture was concentrated and extracted with ethyl acetate. The organic layer was washed with sodium hydrogen carbonate solution, water and saturated brine, and dried with anhydrous magnesium sulfate. Under reduced pressure, the solvent was evaporated to give methyl 7-(4-methylphenyl)-1,1-dioxo-2,3-dihydro-1-benzothiepine-4-carboxylate (1.6 g) as colorless crystals.

mp 203–204° C.; $^1$H-NMR(δ ppm, CDCl$_3$) 2.43 (3H, s), 3.15 (2H, t, J=6.6 Hz), 3.65 (2H, t, J=6.6 Hz), 3.88 (3H, s), 7.31 (2H, d, J=8.3 Hz), 7.52 (2H, d, J=8.3 Hz), 7.69–7.74 (2H, m), 7.92 (1H, s), 8.22 (1H, d, J=8.8 Hz). IR(KBr) ν: 2951, 1713 cm$^{-1}$. Anal. Calcd. for C$_{19}$H$_{18}$O$_4$S: C, 66.65; H, 5.30. Found C, 66.47; H, 5.33.

Reference Example 43

To methyl 7-(4-methylphenyl)-1,1-dioxo-2,3-dihydro-1-benzothiepine-4-carboxylate (1.6 g) was added 1N sodium hydroxide solution (50 ml), methanol (200 ml) and diethylether (100 ml), and the mixture was stirred overnight, concentrated and extracted with water. The aqueous layer was washed with ethyl acetate, made acidic with 1N hydrochloric acid and extracted with ethyl acetate. The organic layer was washed with water and saturated brine, and dried with anhydrous magnesium sulfate. The solvent was evaporated to give 7-(4-methylphenyl)-1,1-dioxo-2,3-dihydro-1-benzothiepine-4-carboxylic acid (1.5 g; purity about 70%) as colorless powder.

$^1$H-NMR(δ ppm, CDCl$_3$) 2.43 (3H, s), 3.14 (2H, t, J=6.6 Hz), 3.66 (2H, t, J=6.6 Hz), 7.26–7.33 (2H, m), 7.47–7.57 (2H, m), 7.70–7.74 (2H, m), 7.95 (1H, s), 8.21 (1H, d, J=8.8 Hz).

Reference Example 44

In toluene/ethanol/water (10/1/1.2 ml) was dissolved methyl 7-bromo-1,1-dioxo-2,3-dihydro-1-benzothiepine-4-carboxylate (870 mg), and to the solution were added 5-methyl-2-thienyl borate (530 mg) and potassium carbonate (1.02 g). The mixture was stirred at room temperature for 30 minutes, and to the mixture was added tetrakistriphenylphosphinepalladium (152 mg). The mixture was stirred at 100° C. for 16 hours, cooled to room temperature, extracted with ethyl acetate, washed with saturated brine and dried with magnesium sulfate. Under reduced pressure, the solvent was evaporated, and the residue was purified with silica gel column chromatography (hexane/ethyl acetate=3/1) to give methyl 7-(5-methyl-2-thienyl)-1,1-dioxo-2,3-dihydro-1-benzothiepine-4-carboxylate (210 mg).

$^1$H-NMR (200 MHz, CDCl$_3$) δ 2.54 (3H, d, J=1.0 Hz), 3.12 (2H, m), 3.63 (2H, m), 3.89 (3H, s), 6.79 (1H, dd, J=3.6, 1.0 Hz), 7.26 (1H, d, J=3.6 Hz), 7.61–7.66 (2H, m), 7.86 (1H, s), 8.12 (1H, d, J=8.8 Hz).

Reference Example 45

In 1,2-dimethoxyethane (10.5 ml) was dissolved methyl 7-(5-methyl-2-thienyl)-1,1-dioxo-2,3-dihydro-1-benzothiepine-4-carboxylate (210 mg), and to the solution was added 6N hydrochloric acid (6.3 ml). The mixture was stirred at 100° C. for 14 hours, cooled to room temperature, extracted with ethyl acetate, washed with saturated brine and dried with magnesium sulfate. Under reduced pressure, the solvent was evaporated to give 7-(5-methyl-2-thienyl)-1,1-dioxo-2,3-dihydro-1-benzothiepine-4-carboxylic acid (180 mg).

$^1$H-NMR (200 MHz, DMSO-d$_6$) δ 2.49 (3H, s), 2.93 (2H, m), 3.72 (2H, m), 6.89 (1H, d, J=3.6 Hz), 7.59 (1H, d, J=3.6 Hz), 7.72–7.81 (2H, m), 8.05 (1H, s), 7.98 (2H, d, J=8.0 Hz).

Reference Example 46

In toluene/ethanol/water (10/1/1.2 ml) was dissolved methyl 7-bromo-1,1-dioxo-2,3-dihydro-1-benzothiepine-4-carboxylate (800 mg), and to the solution were added 4-methyl-2-thienyl borate (524 mg) and potassium carbonate (935 mg). The mixture was stirred at room temperature for 30 minutes, and to the mixture was added tetrakistriphenylphosphinepalladium (152 mg). The mixture was stirred at 100° C. for 16 hours and cooled to room temperature. To the mixture was added water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=3/1) to give methyl 7-(4-methyl-2-thienyl)-1,1-dioxo-2,3-dihydro-1-benzothiepine-4-carboxylate (510 mg).

$^1$H-NMR (200 MHz, CDCl$_3$) δ 2.31 (3H, m), 3.09 (2H, m), 3.63 (2H, t, J=6.6 Hz), 3.87 (3H, s), 7.00 (1H, m), 7.27 (1H, m), 7.64–7.70 (2H, m), 7.86 (1H, s), 8.13 (1H, d, J=10.8 Hz).

Reference Example 47

In 1,2-dimethoxyethane (15.3 ml) was dissolved methyl 7-(4-methyl-2-thienyl)-1,1-dioxo-2,3-dihydro-1-benzothiepine-4-carboxylate. (510 mg), and to the solution was added 6N hydrochloric acid (10.2 ml). The mixture was stirred at 100° C. for 15 hours and cooled to room temperature. Under reduced pressure, the solvent was evaporated. To the residue,were added ethyl acetate and potassium carbonate solution, and the mixture was extracted with water. To the solution was added 6N hydrochloric acid, and the solution was made pH 4–5, extracted with ethyl acetate, washed with saturated brine and dried with magnesium sulfate. Under reduced pressure, the solvent was evaporated to give 7-(4-methyl-2-thienyl)-1,1-dioxo-2,3-dihydro-1-benzothiepine-4-carboxylic acid (459 mg).

$^1$H-NMR (200 MHz, DMSO-$d_6$) δ 2.51 (3H, s), 2.95 (2H, t, J=6.6 Hz), 3.74 (2H, t, J=6.6 Hz), 6.91 (1H, d, J=3.6 Hz), 7.61 (1H, d, J=3.6 Hz), 7.73–7.94 (2H, m), 8.05 (1H, s), 8.00 (2H, d, J=8.4 Hz).

Reference Example 48

In toluene/ethanol/water (10/1/1.2 ml) was dissolved methyl 7-bromo-1,1-dioxo-2,3-dihydro-1-benzothiepine-4-carboxylate (750 mg), and to the solution were added 5-chloro-2-thienyl borate (736 mg) and potassium carbonate (1.0 g). The mixture was stirred at room temperature for 30 minutes, and to the mixture was added tetrakistriphenylphosphinepalladium (210 mg). The mixture was stirred at 100° C. for 15 hours, cooled to room temperature, extracted with ethyl acetate, washed with saturated brine and dried with magnesium sulfate. Under reduced pressure, the solvent was evaporated, and the residue was purified with silica gel column chromatography (hexane/ethyl acetate=3/1) to give methyl 7-(5-chloro-2-thienyl)-1,1-dioxo-2,3-dihydro-1-benzothiepine-4-carboxylate (350 mg).

$^1$H-NMR (200 MHz, CDCl$_3$) δ 3.13 (2H, m), 3.64 (2H, t, m), 3.87 (3H, s), 3.88 (3H, s), 6.98 (1H, d, J=4.2 Hz), 7.44 (1H, d, J=4.2 Hz), 7.60–7.64 (2H, m), 7.86 (1H, s), 8.17 (1H, d, J=8.6 Hz).

Reference Example 49

In 1,2-dimethoxyethane (11.5 ml) was dissolved methyl 7-(5-chloro-2-thienyl)-1,1-dioxo-2,3-dihydro-1-benzothiepine-4-carboxylate (230 mg), and to the mixture was added 6N hydrochloric acid (9.2 ml). The mixture was stirred at 100° C. for 16 hours, cooled to room temperature, extracted with ethyl acetate, washed with saturated brine and dried with magnesium sulfate. Under reduced pressure, the solvent was evaporated to give 7-(5-chloro-2-thienyl)-1,1-dioxo-2,3-dihydro-1-benzothiepine-4-carboxylic acid (200 mg).

$^1$H-NMR (200 MHz, DMSO-$d_6$) δ 2.96 (2H, m), 3.75 (2H, t, m), 7.25 (2H, d, J=4.0 Hz), 7.70 (2H, d, J=4.0 Hz), 7.79–7.84 (2H, m), 8.03 (1H, d, J=8.4 Hz), 8.09 (1H, s).

Reference Example 50

In toluene (21.7 ml) was dissolved methyl 7-bromo-1,1-dioxo-2,3-dihydro-1-benzothiepine-4-carboxylate (900 mg), and to the solution was added tetrakistriphenylphosphinepalladium (243 mg). The mixture was stirred for 15 minutes, and to the mixture were added 4-(methylthio)phenyl borate (1.82 g), 2N sodium carbonate (2.7 ml) and methanol (5.4 ml). The mixture was stirred at 75° C. for 4 hours, cooled to room temperature, extracted with ethyl acetate, washed with saturated brine and dried with magnesium sulfate. Under reduced pressure, the solvent was concentrated, and the residue was purified with silica gel column chromatography (hexane/ethyl acetate=2/1) to give methyl 7-[(4-methylthio)phenyl]-1,1-dioxo-2,3-dihydro-1-benzothiepine-4-carboxylate (340 mg).

$^1$H-NMR (200 MHz, CDCl$_3$) δ 2.55 (3H, s), 2.97 (2H, m), 3.75 (2H, m), 7.39 (2H, d, J=8.6 Hz), 7.79 (2H, d, J=8.6 Hz), 7.91 (2H, d, J=8.6 Hz), 8.05 (1H, s), 8.10 (1H, d, J=9.8 Hz).

Reference Example 51

In 1,2-dimethoxyethane (10 ml) and 6N hydrochloric acid (10 ml) was dissolved methyl 7-[(4-methylthio)phenyl]-1,1-dioxo-2,3-dihydro-1-benzothiepine-4-carboxylate (330 mg), and the mixture was stirred at 100° C. for 18 hours, cooled to room temperature, extracted with ethyl acetate, washed with saturated brine and dried with magnesium sulfate. Under reduced pressure, the solvent was evaporated to give 7-[(4-methylthio)phenyl]-1,1-dioxo-2,3-dihydro-1-benzothiepine-4-carboxylic acid (133 mg).

$^1$H-NMR (200 MHz, DMSO-$d_6$) δ 2.54 (3H, s), 3.06 (2H, q, J=7.4 Hz), 3.75 (2H, t, J=6.4 Hz), 7.43 (2H, d, J=8.4 Hz), 7.79 (2H, d, J=8.4 Hz), 7.89–7.95 (2H, m), 8.06–8.12 (2H, m).

Reference Example 52

In toluene/ethanol/water (10/1/1.2 ml) was dissolved methyl 7-bromo-1,1-dioxo-2,3-dihydro-1-benzothiepine-4-carboxylate (1.16 g), and to the solution were added 4-(ethylthio)phenyl borate (1.28 g) and potassium carbonate (1.45 g). The mixture was stirred at room temperature for 30 minutes, and to the mixture was added tetrakistriphenylphosphinepalladium (243 mg). The mixture was stirred at 100° C. for 20 hours, cooled to room temperature, extracted with ethyl acetate, washed with saturated brine and dried with magnesium sulfate. Under reduced pressure, the solvent was evaporated, and the residue was purified with silica gel column chromatography (hexane/ethyl acetate=2/1) to give methyl 7-[(4-ethylthio)phenyl]-1,1-dioxo-2,3-dihydro-1-benzothiepine-4-carboxylate (330 mg).

$^1$H-NMR (200 MHz, CDCl$_3$) δ 1.37 (3H, t, J=7.4 Hz), 3.02 (2H, q, J=7.4 Hz), 3.15 (2H, m), 3.65 (2H, m), 3.87 (3H, s), 7.40 (2H, m), 7.54 (2H, m), 7.71 (2H, m), 7.91 (1H.s), 8.22 (1H, d, J=8.8 Hz).

Reference Example 53

In 1,2-dimethoxyethane (10 ml) and 6N hydrochloric acid (10 ml) was dissolved methyl 7-[(4-ethylthio)phenyl]-1,1-dioxo-2,3-dihydro-1-benzothiepine-4-carboxylate (200 mg), and the mixture was stirred at 100° C. for 14 hours, cooled to room temperature, extracted with ethyl acetate, washed with saturated brine and dried with magnesium sulfate. Under reduced pressure, the solvent was evaporated to give 7-[(4-ethylthio)phenyl]-1,1-dioxo-2,3-dihydro-1-benzothiepine-4-carboxylic acid (135 mg).

$^1$H-NMR (200 MHz, DMSO-$d_6$) δ 1.28 (3H, t, J=7.4 Hz), 2.98 (2H, m), 3.06 (2H, q, J=7.4 Hz), 3.75 (2H, m), 7.43 (2H, d, J=8.4 Hz), 7.79 (2H, d, J=8.4 Hz), 7.89–7.95 (2H, m), 8.06–8.12 (2H, m).

Reference Example 54

In THF (35 ml) was dissolved methyl 7-[(4-ethylthio)phenyl]-1,1-dioxo-2,3-dihydro-1-benzothiepine-4-carboxylatem (870 mg), and to the solution was added, under ice-cooling, 70% m-chloroperbenzoic acid (mCPBA) (1.11 g). The mixture was stirred for 1 hour, and to the mixture was added saturated sodium bicarbonate solution. The mixture was extracted with ethyl acetate, washed with saturated brine and dried with magnesium sulfate. Under reduced pressure, the solvent was evaporated to give methyl 7-[(4-ethylsulfonyl)phenyl]-1,1-dioxo-2,3-dihydro-1-benzothiepine-4-carboxylate (880 mg).

$^1$H-NMR (200 MHz, CDCl$_3$) δ 1.33 (3H, t, J=7.4 Hz), 3.19 (2H, q, J=7.4 Hz), 3.17 (2H, m), 3.67 (2H, m), 3.88 (3H, s), 7.72–7.83 (3H, m), 7.93 (1H.s), 8.02–8.07 (3H, m), 8.30 (1H, d, J=8.8 Hz).

Reference Example 55

In 1,2-dimethoxyethane (35 ml) and 6N hydrochloric acid (26 ml) was dissolved methyl 7-[(4-ethylsulfonyl)phenyl]-

1,1-dioxo-2,3-dihydro-1-benzothiepine-4-carboxylate (870 mg), and the solution was stirred at 100° C. for 12 hours, cooled to room temperature, extracted with ethyl acetate, washed with saturated brine and dried with magnesium sulfate. Under reduced pressure, the solvent was evaporated to give 7-[(4-ethylsulfonyl)phenyl]-1,1-dioxo-2,3-dihydro-1-benzothiepine-4-carboxylic acid (690 mg).

$^1$H-NMR (200 MHz, DMSO-d$_6$) δ 1.15 (3H, t, J=7.4 Hz), 3.00 (2H, m), 3.37 (2H, q, J=7.4 Hz), 3.79 (2H, m), 7.92 (2H, s), 8.00–8.18 (5H, m), 8.25 (1H, s).

Reference Example 56

In DMF (96 ml) was dissolved 4-bromobenzenethiol (12.0 g), and to the solution was added at room temperature potassium carbonate (11.4 g) and then added dropwise 1-iodopropane (6.6 ml). The mixture was stirred for 2 hours and added to water, and the mixture was extracted with ethyl acetate, washed with saturated brine and dried with magnesium sulfate. Under reduced pressure, the solvent was evaporated, and the residue was (14.1g) dissolved in THF (126 ml). To the solution was added dropwise at −78° C. 1.6N n-butyllithium/hexane (42 ml), and the mixture was stirred for 1 hour. To the mixture was added dropwise a solution of trimethyl borate (19 g) in THF (40 ml), and the mixture was stirred for 30 minutes and allowed to warm to room temperature. To the mixture was added 10% sulfuric acid (70 ml), and the mixture was stirred for 15 minutes, extracted with ethyl acetate, washed with saturated brine and dried with magnesium sulfate. Under reduced pressure, the solvent was concentrated, and the residue washed with hexane/isopropylether to give 4-(propylthio)phenyl borate (6.0 g).

$^1$H-NMR (200 MHz, CDCl$_3$) δ 1.08 (2H, t, J=7.0 Hz), 1.60–1.82 (3H, m), 7.38 (2H, d, J=8.2 Hz), 8.10 (2H, d, J=8.2 Hz).

Reference Example 57

In toluene/ethanol/water (10/1/1.2 ml) was dissolved methyl 7-bromo-1,1-dioxo-2,3-dihydro-1-benzothiepine-4-carboxylate (780 mg), and to the solution were added 4-(propylthio)phenyl borate (743 mg) and potassium carbonate (716 mg). The mixture was stirred at room temperature for 30 minutes. To the mixture was added tetrakistriphenylphosphinepalladium (136 mg), and the mixture was stirred at 90° C. for 14 hours, cooled to room temperature, extracted with ethyl acetate, washed with saturated brine and dried with magnesium sulfate. Under reduced pressure, the solvent was evaporated, and the residue was purified with silica gel column chromatography (hexane/ethyl acetate=2/1) to give methyl 1,1-dioxo-7-[(4-propylthio)phenyl]-2,3-dihydro-1-benzothiepine-4-carboxylate (798 mg).

$^1$H-NMR (200 MHz, CDCl$_3$) δ 1.06 (3H, t, J=7.2 Hz), 1.73 (2H, m), 2.97 (2H, t, J=7.2 Hz), 3.15 (2H, m), 3.65 (2H, m), 3.87 (3H, s), 7.37–7.43 (2H, s), 7.49–7.55 (2H, m), 7.91 (1H, s), 8.21 (1H, d, J=8.4 Hz).

Reference Example 58

In 1,2-dimethoxyethane (23 ml) and 6N hydrochloric acid (7.7 ml) was dissolved methyl 1,1-dioxo-7-[(4-propylthio)phenyl]-2,3-dihydro-1-benzothiepine-4-carboxylate (770 mg), and the mixture was stirred at 100° C. for 16 hours, cooled to room temperature, extracted with ethyl acetate, washed with saturated brine and dried with magnesium sulfate. Under reduced pressure, the solvent was evaporated to give 1,1-dioxo-7-[(4-propylthio)phenyl]-2,3-dihydro-1-benzothiepine-4-carboxylic acid (700 mg).

$^1$H-NMR (200 MHz, DMSO-d) δ 1.00 (3H, t, J=7.4 Hz), 1.64 (2H, m), 2.99 (2H, m), 3.76 (2H, m), 7.43 (2H, d, J=8.6 Hz), 7.89 (1H, s), 7.94 (1H, s), 8.10 (2H, m), 8.08 (2H, m).

Reference Example 59

In DMF (96 ml) was dissolved 4-bromobenzenethiol (12.0 g), and to the solution was added at room temperature potassium carbonate (11.4 g) and then added dropwise 1-iodobutane (13.9 g). The mixture was stirred for 2 hours and added to water, and the mixture was extracted with ethyl acetate, washed with saturated brine and dried with magnesium sulfate. Under reduced pressure, the solvent was evaporated, and the residue (14.3 g) was dissolved in THF (130 ml). To the solution was added dropwise at −78° C. 1.6N n-butyllithium/hexane (40 ml), and the mixture was stirred for 1 hour. To the mixture was added dropwise a solution of trimethyl borate (18.1 g) in THF (40 ml), and the mixture was stirred for 30 minutes and allowed to warm to room temperature. To the mixture was added 10% sulfuric acid (70 ml), and the mixture was stirred for 15 minutes, extracted with ethyl acetate, washed with saturated brine and dried with magnesium sulfate. Under reduced pressure, the solvent was concentrated, and the residue washed with hexane/isopropylether to give 4-(butylthio)phenyl borate (6.1 g).

$^1$H-NMR (200 MHz, CDCl$_3$) δ 0.96 (3H, t, J=7.2 Hz), 1.40–1.60 (2H, m), 1.67–1.79 (2H, m), 3.12 (2H, t, J=7.2 Hz), 7.63 (2H, d, J=8.4z), 8.09 (2H, d, J=8.4 Hz).

Reference Example 60

In toluene/ethanol/water (10/1/1.2 ml) was dissolved methyl 7-bromo-1,1-dioxo-2,3-dihydro-1-benzothiepine-4-carboxylate (730 mg), and to the solution were added 4-(butylthio)phenyl borate (780 mg) and potassium carbonate (620 mg). The mixture was stirred at room temperature for 30 minutes. To the mixture was added tetrakistriphenylphosphinepalladium (127 mg), and the mixture was stirred at 90° C. for 16 hours, cooled to room temperature, extracted with ethyl acetate, washed with saturated brine and dried with magnesium sulfate. Under reduced pressure, the solvent was evaporated, and the residue was purified with silica gel column chromatography (hexane/ethyl acetate=2/1) to give methyl 7-[(4-butylthio)phenyl]-1,1-dioxo-2,3-dihydro-1-benzothiepine-4-carboxylate (680 mg).

$^1$H-NMR (200 MHz, CDC$_3$) δ 0.95 (3H, t, J=7.2 Hz), 1.43–1.74 (2H, m), 2.99 (2H, t, J=7.4 Hz), 3.15 (2H, m), 3.65 (2H, m), 3.87 (3H, s), 7.38–7.43 (2H, m), 7.52–7.55 (2H, m), 7.67–7.72 (2H, m), 7.91 (1H, s), 8.22 (1H, d, J=11.2 Hz).

Reference Example 61

In 1,2-dimethoxyethane (20 ml) and 6N hydrochloric acid (6.7 ml) was dissolved methyl 7-[(4-butylthio)phenyl]-1,1-dioxo-2,3-dihydro-1-benzothiepine-4-carboxylate (670 mg), and the mixture was stirred at 100° C. for 16 hours, cooled to room temperature, extracted with ethyl acetate, washed with saturated brine and dried with magnesium sulfate. Under reduced pressure, the solvent was evaporated to give 7-[(4-butylthio)phenyl]-1,1-dioxo-2,3-dihydro-1-benzothiepine-4-carboxylic acid (620 mg).

$^1$H-NMR (200 MHz, DMSO-d$_6$) δ 0.90 (3H, t, J=7.2 Hz), 1.14–1.65 (4H, m), 2.97 (2H, m), 3.04 (2H, t, J=7.2 Hz), 3.76 (2H, m), 7.43 (2H, d, J=8.4 Hz), 7.78 (2H, d, J=8.4 Hz), 7.89–97.95 (2H, m), 8.10–8.14 (2H, m).

Reference Example 62

A solution of methyl 7-bromo-1,1-dioxo-2,3-dihydro-1-benzothiepine-4-carboxylate (700 mg) in 1,2- dimethoxyethane (15 ml) and 6N hydrochloric acid was refluxed for 18 hours and cooled to room temperature. The solvent was evaporated under reduced pressure to give colorless crystals, which were collected by filtration. The crystals were washed with water, 2-propanol and diisopropylether to give colorless crystals of 7-bromo-1,1-dioxo-2,3-dihydro-1-benzothiepine-4-carboxylic acid (634 mg).

m.p. 290–300° C.; $^1$H-NMR (200 MHz, DMSO-d$_6$) δ 2.91–2.97 (2H, m), 3.73–3.80 (2H, m), 7.73 (1H, s), 7.84 (1H, dd, J=8.4, 2.0 Hz), 7.94 (1H, d, J=8.4 Hz), 8.08 (1H, d, J=2.0 Hz). IR (KBr) 3088, 1680, 1419, 1286, 1165, 1133, 1097, 793, 744 cm$^{-1}$; Anal. for $C_{11}H_9O_4SBr$ Calcd. C, 41.66; H, 2.86: Found. C, 41.82; H, 3.02.

Reference Example 63

To a suspension of 7-bromo-1,1-dioxo-2,3-dihydro-1-benzothiepine-4-carboxylic acid (4.47 g) in THF (90 ml) were added at room temperature thionyl chloride (1.03 ml) and DMF (1 ml), and the mixture was stirred for 1 hour and added dropwise to a solution of 4-[[N-methyl-N-(tetrahydropyran-4-yl)amino]methyl]aniline (3.41 g) and triethylamine (7.9 ml) in THF (30 ml), at 0° C. The mixture was stirred for 3 hours and concentrated under reduced pressure, to which were added water. Precipitated colorless crystals were collected by filtration, and the crystals were washed with water, ethanol, 2-propanol and diisopropylether to give colorless crystals of 7-bromo-N-[4-[[N-methyl-N-(tetrahydropyran-4-yl)amino]methyl]phenyl]-1,1-dioxo-2,3-dihydro-1-benzothiepine-4-carboxamide (4.94 g).

m.p. 232–235° C.; $^1$H-NMR (200 MHz, CDCl$_3$) δ 1.54–1.83 (4H, m), 2.21 (3H, s), 2.54–2.73 (1H, m), 3.11–3.18 (2H, m), 3.30–3.44 (2H, m), 3.58 (2H, s), 3.66–3.73 (2H, m), 3.99–4.10 (2H, m), 7.19 (1H, s), 7.33 (2H, d, J=8.3 Hz), 7.53 (2H, d, J=8.3 Hz), 7.62–7.71 (2H, m), 7.88 (1H, br s), 8.04 (1H, d, J=8.4 Hz). IR (KBr) 3259, 1657, 1633, 1603, 1529, 1410, 1319, 1296, 1132 cm$^{-1}$; Anal. for $C_{24}H_{27}N_2O_4SBr$; Calcd. C, 55.49; H, 5.24; N, 5.39; Found. C, 55.56; H, 4.98; N, 5.22.

Reference Example 64

To a mixture of 4-bromo-2-chlorophenol (10.81 g) and potassium carbonate (8.65 g) in DMF (10 ml) was added at room temperature ethyl iodide (4.17 ml), and the mixture was stirred for 68 hours. To the mixture was added water, and the mixture was extracted with hexane. The organic layer was washed with saturated brine and dried with magnesium sulfate. Under reduced pressure, the solvent was evaporated to give pale yellow oil of 4-bromo-2-chloro-1-ethoxybenzene (12.28 g).

To a solution of 4-bromo-2-chloro-1-ethoxybenzene (12.0 g) in diethylether (100 ml) was added dropwise at −78° C. a solution of 1.6M n-butyllithium in hexane (35 ml), and the mixture was stirred for 1 hour. To the mixture was added dropwise a solution of trimethyl borate (17 ml) in diethylether (20 ml), and the mixture was allowed to warm to room temperature and then stirred at room temperature for 2 hours. To the mixture was added dropwise 10% sulfuric acid (100 ml), and the mixture was stirred for 1 hour and extracted with ethyl acetate. The organic layer was washed with saturated brine and dried with magnesium sulfate. The solvent was evaporated under reduced pressure to give colorless crystals, which were collected by filtration and washed with hexane to give colorless crystals of 3-chloro-4-ethoxyphenyl borate (4.44 g).

$^1$H-NMR (200 MHz, CDCl$_3$) δ 1.53 (3H, t, J=7.0 Hz), 4.21 (2H, q, J=7.0 Hz), 7.02 (1H, d, J=8.2 Hz), 8.05 (1H, dd, J=8.2, 1.8 Hz), 8.14 (1H, d, J=1.8 Hz).

Reference Example 65

To a mixture of 4-bromo-2-fluorophenol (10 g) and potassium carbonate (8.7 g) in DMF (100 ml) was added at room temperature ethyl iodide (4.2 ml), and the mixture was stirred for 68 hours. To the mixture was added water, and the mixture was extracted with hexane. The organic layer was washed with saturated brine and dried with magnesium sulfate. The solvent was evaporated under reduced pressure to give pale yellow oil of 4-bromo-1-ethoxy-3-fluorobenzene (11.46 g).

To a solution of 4-bromo-1-ethoxy-3-fluorobenzene (11.10 g) in diethylether (100 ml) was added dropwise at −78° C. a solution of 1.6M n-butyllithium in hexane (35 ml), and the mixture was stirred for 1 hour. To the mixture was added dropwise a solution of trimethyl borate (17 ml) in diethylether (20 ml), and the mixture was allowed to warm to room temperature and stirred at room temperature for 2 hours. To the mixture was added dropwise 10% sulfuric acid (100 ml), and the mixture was stirred for 1 hour and extracted with ethyl acetate. The organic layer was washed with saturated brine and dried with magnesium sulfate. The solvent was evaporated under reduced pressure to give colorless crystals, which were collected by filtration and washed with hexane to give colorless crystals of 4-ethoxy-3-fluorophenyl borate (4.660).

$^1$H-NMR (200 MHz, CDCl$_3$) δ 1.51 (3H, t, J=7.0 Hz), 4.20 (2H, q, J=7.0 Hz), 7.06 (1H, dd, J=8.0, 8.0 Hz), 7.82–7.93 (2H, m).

Reference Example 66

To a solution of boron tribromide (25 g) in dichloromethane (100 ml) was added dropwise at 0° C. a solution of 3,4-dimethoxybromobenzene (10.0 g) in dichloromethane (20 ml), and the mixture was stirred at room temperature for 15 hours and then added to ice/water to stop the reaction. The mixture was extracted with diethylether, and the organic layer was washed with saturated brine, dried with magnesium sulfate and concentrated under reduced pressure to give colorless crystals of 4-bromocathechol (8.43 g).

To a mixture of 4-bromocathechol (8.43 g) and potassium carbonate (15.4 g) in DMF (80 ml) was added at room temperature ethyl iodide (7.5 ml), and the mixture was stirred for 15 hours. To the mixture was added water, and the mixture was extracted with hexane. The organic layer was washed with water and saturated brine, dried with magnesium sulfate and concentrated under reduced pressure, and the residue purified with silica gel column chromatography (ethyl acetate/hexane=1:4) to give yellow oil of 4-bromo-1,2-diethoxybenzene (10.06 g).

$^1$H-NMR (200 MHz, CDCl$_3$) δ 1.44 (3H, t, J=7.0 Hz), 1.45 (3H, t, J=7.0 Hz), 4.06 (2H, q, J=7.0 Hz), 4.07 (2H, q, J=7.0 Hz), 6.74 (1H, d, J=8.8 Hz), 6.97–7.02 (2H, m). IR (neat) 1585, 1500, 1477, 1396, 1252, 1219, 1134, 1041, 845, 795 cm$^{-1}$.

Reference Example 67

To a mixture of 4-bromophenol (15 g), sodium iodide (13.0 g) and potassium carbonate (14.4 g) in DMF (200 ml) was added at room temperature 2-chloroethylmethyl ether (9 ml), and the mixture was stirred at 80° C. for 3 days. To the mixture was added water, and the mixture was extracted with diethylether. The organic layer was washed with water and saturated brine, dried with magnesium sulfate and concentrated under reduced pressure to give orange oil of 1-bromo-4-(2-methoxyethoxy)benzene (17.44 g).

$^1$H-NMR (200 MHz, CDCl$_3$) δ 3.45 (3H, s), 3.72–3.77 (2H, m), 4.06–4.11 (2H, m), 6.81 (2H, d, J=8.9 Hz), 7.37 (2H, d, J=8.9 Hz). IR (neat) 1587, 1489, 1454, 1284, 1246, 1128, 1061, 824 cm$^{-1}$.

Reference Example 68

To a mixture of 1,4-benzodioxane (5.0 g) and sodium carbonate (5.9 g) in hexane (100 ml) was added dropwise at room temperature a solution of bromine (1.9 ml) in hexane (20 ml) for 1 hour and the mixture was stirred for 1 hour. To the mixture was added an aqueous solution of sodium thiosulfate, and the mixture was extracted with ethyl acetate. The organic layer was washed with saturated brine, dried with magnesium sulfate and concentrated under reduced pressure to give orange oil of 6-bromo-2,3-dihydro-1,4-benzodioxine (7.48 g).

Under argon atmosphere, to a solution of 6-bromo-2,3-dihydro-1,4-benzodioxine (7.48 g) in THF (50 ml) was added dropwise at –78° C. a solution of 1.6M n-butyllithium in hexane (20 ml), and the mixture was stirred for 1 hour. To the mixture was added dropwise a solution of trimethyl borate (12 ml) in THF (12 ml), and the mixture was allowed to gradually warm to room temperature and then stirred at room temperature for 2 hours. To the mixture was added dropwise 10% sulfuric acid (100 ml), and the mixture was stirred for 30 minutes and extracted with ethyl acetate. The organic layer was washed with water and saturated brine, dried with magnesium sulfate and concentrated under reduced pressure. Precipitated colorless crystals were collected by filtration and washed with diisopropylether to give colorless crystals of 2,3-dihydro-1,4-benzodioxin-6-yl borate (2.02 g).

$^1$H-NMR (200 MHz, CDCl$_3$) δ 4.24–4.37 (4H, m), 6.97 (1H, d, J=8.4 Hz), 7.68–7.73 (2H, m).

Reference Example 69

To a mixture of 2,3-dihydrobenzofuran (11.06 g) and sodium carbonate (14.8 g) in hexane (100 ml) was added dropwise at 0° C. a solution of bromine (4.8 ml) in hexane (20 ml) for 1.5 hours, and the mixture was stirred at room temperature for 1 hour. To the mixture was added water, and the mixture was extracted with hexane. The organic layer was washed with saturated brine, dried with magnesium sulfate and concentrated under reduced pressure to give gray crystals of 5-bromo-2,3-dihydrobenzofuran (17.64 g).

$^1$H-NMR (200 MHz, CDCl$_3$) δ 3.20 (2H, t, J=8.8 Hz), 4.57 (2H, t, J=8.8 Hz), 6.66 (1H, d, J=8.4 Hz), 7.17–7.30 (2H, m).

Reference Example 70

To a mixture of 4-bromo-2-fluoroaniline (10.0 g), potassium carbonate (21.8 g) and sodium iodide (15.8 g) in DMF (100 ml) was added at room temperature bis (2-chloroethyl) ether (7.53 g), and the mixture was stirred at 90 for 4 days. To the mixture was added bis(2-chloroethyl) ether (1 ml), and the mixture was stirred for 2 days. To the mixture was added water, and the mixture was extracted with ethyl acetate. The organic layer was washed with water and saturated brine, dried with magnesium sulfate and concentrated under reduced pressure, and the residue was purified with silica gel column chromatography (ethyl acetate/hexane=1:5) to give orange oil (9.19 g). The oil was dissolved in THF (100 ml), and to the solution was added triethylamine (2.5 ml). To the mixture was added at 0° C. acetyl chloride (1.3 ml), and the mixture was stirred for 1 hour. To the mixture was added water, and the mixture was extracted with ethyl acetate. The organic layer was washed with saturated brine, dried with magnesium sulfate and concentrated under reduced pressure, the residue was purified with silica gel column chromatography (ethyl acetate/hexane=1:4) to remove an acetyl compound and to give yellow oil of 4-(4-bromo-3-fluorophenyl)morpholine (6.89 g).

$^1$H-NMR (200 MHz, CDCl$_3$) δ 3.03–3.08 (4H, m), 3.84–3.89 (4H, m), 6.76–6.85 (1H, m), 7.16–7.26 (2H, m). IR (neat) 1565, 1497, 1450, 1257, 1236, 1209, 1119, 935, 866, 808 cm$^{-1}$.

Reference Example 71

Under argon atmosphere, a solution of 6-iode-3,4-dihydro-2H-1-benzopyran (10.15 g) in diethylether (80 ml)was added dropwise at –78° C. a solution of 1.6M n-butyllithium in hexane (27 ml), and the mixture was stirred for 1 hour. To the mixture was added dropwise a solution of trimethyl borate (14 ml) in diethylether (14 ml). The reaction mixture was allowed to gradually warm to room temperature, and the mixture was stirred at room temperature for 2 hours. To the mixture was added dropwise 1N hydrochloric acid (100 ml), and the mixture was stirred for 1 hour and extracted with ethyl acetate. The organic layer was washed with saturated brine, dried with magnesium sulfate and concentrated under reduced pressure. To the residue was added hexane and diisopropylether to give crystals, which were collected by filtration and washed with hexane to give colorless crystals of 3,4-dihydro-2H-1-benzopyran-6-yl borate (2.00 g).

$^1$H-NMR (200 MHz, CDCl$_3$) δ 1.97–2.15 (2H, m), 2.91 (2H, t, J=6.2 Hz), 4.27 (2H, t, J=5.1 Hz), 6.90 (1H, d, J=8.2 Hz), 7.90 (1H, d, J=1.4 Hz), 7.96 (1H, dd, J=8.2, 1.4 Hz).

Reference Example 72

To a solution of 7-bromo-3,4-dihydro-1-benzoxepin-5 (2H)-one (20.0 g) in trifluoroacetic acid (32 ml) was added at room temperature triethylsilane (29.2 ml), and the mixture was stirred for 2 hours and concentrated under reduced pressure. To the residue was added water, and the mixture was extracted with ethyl acetate. The organic layer was washed with saturated sodium bicarbonate solution and saturated brine, dried with magnesium sulfate and concentrated under reduced pressure. The residue was distilled under reduced pressure (0.8 mmHg/123° C.) to give colorless oil. The obtained oil (13.12 g) was dissolved in ethanol (200 ml), and to the solution was added platinum oxide (0.4 g). The mixture was stirred under hydrogen atmosphere for 24 hours. The catalyst was removed by filtration, and the filtrate was concentrated under reduced pressure. The residue was purified with silica gel column chromatography (hexane→ethyl acetate/hexane=1:19) to give colorless oil of 7-bromo-2,3,4,5-tetrahydro-1-benzoxepine (9.61 g).

Under argon atmosphere, to a solution of 7-bromo-2,3,4, 5-tetrahydro-1-benzoxepine (9.61 g) in THF (50 ml) was added dropwise at –78° C. a solution of 1.6M n-butyllithium in hexane (29 ml), and the mixture was stirred for 1 hour. To the mixture was added dropwise a solution of trimethyl borate (14 ml) in THF (14 ml). The reaction mixture was allowed to gradually warm to room temperature and the mixture was stirred at room temperature for 2 hours. To the mixture was added dropwise 1N hydrochloric acid (100 ml), and the mixture was stirred for 1 hour and extracted with ethyl acetate. The organic layer was washed with water and saturated brine, dried with magnesium sulfate and concentrated under reduced pressure. Precipitated colorless crystals were collected by filtration, which were washed with hexane to give colorless crystals of 2,3,4,5-tetrahydro-1-benzoxepin-7-yl borate (3.18 g).

$^1$H-NMR (200 MHz, CDCl$_3$) δ 1.72–1.88 (2H, m), 1.93–2.11 (2H, m), 2.91–3.04 (2H, m), 3.99–4.14 (2H, m), 7.10 (1H, d, J=7.8 Hz), 7.99–8.04 (2H, m).

Reference Example 73

A solution of 5-bromo-2-hydroxyacetophenone 10.0 g (46.5 milli mole), acetone (17 ml) and pyrrolidine (3.9 ml) in toluene (100 ml) was refluxed for 4 hours. To the mixture was added acetone (17 ml), and the mixture was refluxed for 15 hours. To the mixture was added 1N hydrochloric acid (100 ml), and the mixture was extracted with ethyl acetate. The organic layer was washed with water and saturated brined, dried with magnesium sulfate and concentrated under reduced pressure. The residue was purified with silica gel column chromatography (ethyl acetate/hexane=1:7) to give yellow oil of 6-bromo-2,2-dimethyl-2,3-dihydro-4H-1-benzopyran-4-one (7.57 g).

$^1$H-NMR (200 MHz, CDCl$_3$) δ 1.46 (6H, s), 2.72 (2H, s), 6.83 (1H, d, J=8.8 Hz), 7.54 (1H, dd, J=8.8, 2.6 Hz), 7.97 (1H, d, J=2.6 Hz). IR (neat) 1689, 1597, 1464, 1414, 1373, 1319, 1282, 1225, 1167, 1132, 1066, 926, 827 cm$^{-1}$.

Reference Example 74

TO a solution of 6-bromo-2,2-dimethyl-2,3-dihydro-4H-1-benzopyran-4-one (7.57 g) in trifluoroacetic acid (21.4 ml) was added at room temperature triethylsilane (10.4 ml), and the mixture was stirred for 4 days. To the mixture was added triethylsilane (7.1 ml), and the mixture was stirred at 50° C. for 24 hours. To the mixture was added at 0° C. 12N sodium hydroxide solution to make the solution alkaline, and the mixture was extracted with diethylether. The organic layer was washed with saturated brine, dried with magnesium sulfate and concentrated under reduced pressure. The residue was purified with silica gel column chromatography (hexane) to give colorless oil of 6-bromo-2,2-dimethyl-3,4-dihydro-2H-1-benzopyran (10.77 g).

Under argon atmosphere, to a solution of 6-bromo-2,2-dimethyl-3,4-dihydro-2H-1-benzopyran (10.77 g) in THF (50 ml) was added dropwise at −78° C. a solution of 1.6M n-butyllithium in hexane (18 ml), and the mixture was stirred for 1 hour. To the mixture was added dropwise trimethyl borate (7.5 ml) in THF (7.5 ml). The reaction mixture was allowed to gradually warm to room temperature, and the mixture was stirred at room temperature for 2 hours. To the mixture was added dropwise 1N hydrochloric acid (100 ml), and the mixture was stirred for 1 hour and extracted with ethyl acetate. The organic layer was washed with water and saturated brine, dried with magnesium sulfate and concentrated under reduced pressure. The residue was purified with silica gel column chromatography (ethyl acetate/hexane=1:4→1:2) to give colorless crystals of 2,2-dimethyl-3,4-dihydro-2H-1-benzopyran-6-yl borate (170 mg).

$^1$H-NMR (200 MHz, CDCl$_3$) δ 1.38 (6H, s), 1.87 (2H, t, J=6.9 Hz), 2.90 (2H, t, J=6.9 Hz), 6.89 (1H, d, J=8.0 Hz), 7.94–7.98 (2H, m).

Reference Example 75

To a mixture of 4-bromo-2-fluorophenol (10.07 g) and potassium carbonate (9.5 g) in DMF (100 ml) was added at room temperature 2-bromoethylethyl ether (6.0 ml), and the mixture was stirred for 18 hours. To the mixture was added 2-bromoethylethyl ether (1.2 ml), and the mixture was stirred at 55° C. for 5 hours. To the mixture was added water, and the mixture was extracted with ethyl acetate. The organic layer was washed with water (thrice) and saturated brine (once), and dried with magnesium sulfate. The solvent was evaporated under reduced pressure to give pale yellow oil of 4-bromo-1-(2-ethoxyethoxy)-2-fluorobenzene (13.79 g).

$^1$H-NMR (200 MHz, CDCl$_3$) δ 1.24 (3H, t, J=7.0 Hz), 3.60 (2H, q, J=7.0 Hz), 3.78–3.83 (2H, m), 4.14–4.19 (2H, m), 6.84–6.92 (1H, m), 7.15–7.27 (2H, m). IR (neat) 1502, 1306, 1269, 1207, 1130, 1055, 866 cm$^{-1}$.

Reference Example 76

Under argon atmosphere, to a suspension of magnesium (1.34 g) in THF (30 ml) was added dropwise at room temperature a solution of 4-bromo-1-(2-ethoxyethoxy)-2-fluorobenzene (13.79 g) and 1,2-dibromoethane (1 ml) in THF (50 ml) for 1 hour, and the mixture was stirred at 60° C. for 1 hour. The reaction mixture was cooled to −78° C., to which was added dropwise a solution of trimethyl borate (17.6 ml) in THF (20 ml) for 30 minutes. The mixture was allowed to warm to room temperature and the mixture was stirred at room temperature for 2 hours. To the mixture was added 1N hydrochloric acid (100 ml), and the mixture was stirred for 1 hour, extracted with ethyl acetate, washed with saturated brine, dried with magnesium sulfate and concentrated under reduced pressure. The residue was washed with silica gel column chromatography (ethyl acetate/hexane= 1:1→2:1) to give colorless crystals of 4-(2-ethoxyethoxy)-3-fluorophenyl borate (1.40 g).

$^1$H-NMR (200 MHz, CDCl$_3$) δ 1.26 (3H, t, J=7.2 Hz), 3.64 (2H, q, J=7.2 Hz), 3.85–3.90 (2H, m), 4.26–4.31 (2H, m), 7.06–7.14 (1H, m), 7.82–7.94 (2H, m).

Reference Example 77

To a mixture of 3,4-dihydro-2H-1,5-benzodioxepine (8.86 g) and sodium carbonate (9.4 g) in hexane (100 ml) was added dropwise at room temperature a solution of bromine. (3.0 ml) in hexane (30 ml) for 2.5 hours, and the mixture was stirred for 24 hours. To the mixture was added water, and the mixture was extracted with ethyl acetate. The organic layer was washed with saturated brine, dried with magnesium sulfate and concentrated under reduced pressure to give orange oil. To the obtained oil (13.39 g) in acetic acid (50 ml) was added sodium acetate (4.1 g), and then was added dropwise a solution of bromine (1.3 ml) in acetic acid (25 ml) for 1 hour. The mixture was stirred for 24 hours and concentrated under reduced pressure. To the residue was added water, and the mixture was extracted with ethyl acetate. The organic layer was washed with saturated brine, dried with magnesium sulfate and concentrated under reduced pressure. The residue was purified with silica gel column chromatography (ethyl acetate/hexane=1:4) to give orange oil of 7-bromo-3,4-dihydro-2H-1,5-benzodioxepine (13.17 g).

To a solution of 7-bromo-3,4-dihydro-2H-1,5-benzodioxepine (13.17 g) in THF (60 ml) was added dropwise at −78° C. a solution of 1.6M n-butyllithium in hexane (40 ml), and the mixture was stirred for 1 hour. To the mixture was added dropwise a solution of trimethyl borate (19 ml) in THF (19 ml) for 1 hour, and the mixture was stirred at −78° C. for 1 hour. The reaction mixture was allowed to warm to room temperature and the mixture was stirred at room temperature for 2 hours. To the mixture was added dropwise 1N hydrochloric acid (100 ml), and the mixture was stirred for 1 hour and extracted with ethyl acetate. The organic layer was washed with water and saturated brine and dried with magnesium sulfate. The solvent was evaporated under reduced pressure to precipitate pale yellow crystals, which were collected by filtration and washed with hexane to give pale yellow crystals of 3,4-dihydro-2H-1,5-benzodioxepin-7-yl borate (2.99 g).

$^1$H-NMR (200 MHz, CDCl$_3$) δ 2.17–2.31 (2H, m), 4.26–4.35 (4H, m), 7.06 (1H, d, J=7.8 Hz), 7.76–7.80 (2H, m).

Reference Example 78

To a mixture of 4-bromo-2-chlorophenol (15.92 g) and potassium carbonate (15.9 g) in DMF (100 ml) was added at room temperature 2-bromoethylethyl ether (9.51 ml), and the mixture was stirred at 60° C. for 18 hours. To the mixture was added water, and the mixture was extracted with diethylether. The organic layer was washed with saturated brine and dried with magnesium sulfate. The solvent was evaporated under reduced pressure to give pale yellow oil of 4-bromo-2-chloro-1-(2-ethoxyethoxy)benzene (21.76 g).

$^1$H-NMR (200 MHz, CDCl$_3$) δ 1.24 (3H, t, J=7.1 Hz), 3.63 (2H, q, J=7.1 Hz), 3.80–3.85 (2H, m), 4.13–4.18 (2H, m), 6.84 (1H, d, J=8.8 Hz), 7.31 (1H, dd, J=8.8, 2.6 Hz), 7.49 (1H, d, J=2.6 Hz). IR (neat) 1481, 1290, 1263, 1250, 1124, 1056, 802 cm$^{-1}$.

Reference Example 79

To a solution of 4-bromo-2-chloro-1-(2-ethoxyethoxy)benzene (21.76 g) in diethylether/THF (80/80 ml) was added dropwise at −78° C. a solution of 1.6M n-butyllithium in hexane (53 ml), and the mixture was stirred for 1 hour. To the mixture was added dropwise a solution trimethyl borate (26 ml) in THF (26 ml) for 1 hour, and the mixture was stirred at −78° C. for 1 hour. The reaction mixture was allowed to warm to room temperature, and the mixture was stirred at room temperature for 2 hours. To the mixture was added dropwise 1N hydrochloric acid (100 ml), and the mixture was stirred for 1 hour and extracted with ethyl acetate. The organic layer was washed with water and saturated brine, and dried with magnesium sulfate. The solvent was evaporated under reduced pressure to precipitate colorless crystals, which were collected by filtration and washed with diisopropyl ether to give colorless crystals of 3-chloro-4-(2-ethoxyethoxy)phenyl borate (10.24 g).

$^1$H-NMR (200 MHz, CDCl$_3$) δ 1.27 (3H, t, J=7.0 Hz), 3.68 (2H, q, J=7.0 Hz), 3.88–3.93 (2H, m), 4.26–4.31 (2H, m), 7.06 (1H, d, J=8.4 Hz), 8.06 (1H, dd, J=8.4, 1.6 Hz), 8.15 (1H, d, J=1.6 Hz).

Reference Example 80

To a solution of 4-bromophenol (15.0 g), tetrahydropyran-4-ol (9.0g) and triphenylphosphine (23.08 g) in THF (100 ml) was added dropwise at 0° C. diethyl azodicarboxylate (40% toluene solution) (38.3 g), and the mixture was stirred at room temperature for 3 days and concentrated under reduced pressure. To the residue was added diethylether, and precipitated crystals were removed by filtration. The filtrate was concentrated, and the residue was dissolved in ethyl acetate. The solution was washed with 1N sodium hydroxide solution (×3) and saturated brine, dried with magnesium sulfate and concentrated under reduced pressure. The residue was purified with silica gel column chromatography (ethyl acetate/hexane=1:4) to give colorless crystals of 4-(4-bromophenyloxy)tetrahydropyran (15.94 g).

To a solution of 4-(4-bromophenyloxy)tetrahydropyran (15.73 g) in THF (100 ml) was added dropwise at −78° C. a solution of 1.6M n-butyllithium in hexane (42 ml), and the mixture was stirred for 1 hour. To the mixture was added dropwise a solution of trimethyl borate (20 ml) in THF (20 ml) for 1 hour, and the mixture was stirred at −78° C. for 1 hour. The reaction mixture was allowed to warm to room temperature, and the mixture was stirred at room temperature for 2 hours. To the mixture was added dropwise 1N hydrochloric acid (100 ml), and the mixture was stirred for 1 hour and extracted with ethyl acetate. The organic layer was washed with water and saturated brine, and dried with magnesium sulfate. The solvent was evaporated under reduced pressure to give colorless crystals, which were collected by filtration and washed with ethyl acetate/hexane to give colorless crystals of 4-(tetrahydropyran-4-yloxy)phenyl borate (4.30 g). The mother liquor was purified with silica gel column chromatography (ethyl acetate/hexane= 1:1) to give colorless crystals of 4-(tetrahydropyran-4-yloxy)phenyl borate (2.97 g).

$^1$H-NMR (200 MHz, CDCl$_3$) δ 1.74–1.93 (2H, m), 1.98–2.15 (2H, m), 3.55–3.68 (2H, m), 3.95–4.08 (2H, m), 4.56–4.70 (1H, m), 7.02 (2H, d, J=8.6 Hz), 8.15 (2H, d, J=8.6 Hz).

Reference Example 81

To a solution of N-ethylaniline (10.0 g) in DMF (50 ml) was added dropwise at room temperature a solution of N-bromosuccinimide (14.69 g) in DMF (100 ml), and the mixture was stirred at room temperature for 19 hours. The reaction mixture was added to water, and the mixture was extracted with ethyl acetate. The organic layer was washed with saturated brine, dried with magnesium sulfate and concentrated under reduced pressure to give pale yellow oil of 4-bromo-N-ethylaniline (17.08 g).

To a solution of 4-bromo-N-ethylaniline (17.08 g) in DMF (100 ml) were added at room temperature potassium carbonate (17.1 g), sodium iodide (12.4 g) and 2-bromoethylethyl ether (10.2 ml), and the mixture was stirred at 90° C. for 24 hours. To the mixture were added 2-bromoethylethyl ether (5.0 ml), potassium carbonate (6.22 g) and sodium iodide (6.64 g), and the mixture was stirred for 2 days. To the mixture were added 2-bromoethylethyl ether (10.0 ml), potassium carbonate (17.1 g) and sodium iodide (12.4 g), and the mixture was stirred at 90° C. for 3 days. To the mixture was added water, and the mixture was extracted with ethyl acetate. The organic layer was washed with saturated brine and dried with magnesium sulfate. Under reduced pressure, the solvent was evaporated, and the residue was purified with silica gel column chromatography (ethyl acetate/hexane=1:9) to give yellow oil of 4-bromo-N-(2-propoxyethyl)-N-ethylaniline (18.11 g).

$^1$H-NMR (200 MHz, CDCl$_3$) δ 1.14 (3H, t, J=6.9 Hz), 1.20 (3H, t, J=7.0 Hz), 3.38 (2H, q, J=7.0 Hz), 3.41–3.59 (6H, m), 6.56 (2H, d, J=9.2 Hz), 7.26 (2H, d, J=9.2 Hz). IR (neat) 1591, 1498, 1394, 1373, 1352, 1267, 1192, 1115, 806 cm$^{-1}$.

Reference Example 82

Under argon atmosphere, to a suspension of magnesium (1.57 g) in THF (30 ml) was added at room temperature a piece of iodine, and then was added dropwise at 40–50° C. a solution of 4-bromo-N-(2-propoxyethyl)-N-ethylaniline (16.82 g) in THF (50 ml) for 1.5 hours. The mixture was stirred at 50° C. for 2 hours, and the reaction mixture was cooled to −78° C., to which was added dropwise a solution of trimethyl borate (20 ml) in THF (20 ml). The reaction mixture was allowed to warm to room temperature, and the mixture was stirred at room temperature for 18 hours. To the mixture was added 2N hydrochloric acid (100 ml), and the mixture was stirred for 3 hours. To the mixture was added 8N sodium hydroxide solution to make the solution pH 7–8, and the mixture was extracted with ethyl acetate, washed with saturated brine, dried with magnesium sulfate and concentrated under reduced pressure. To the residue was added hexane to give green crystals, which were collected by filtration and washed with diisopropylether and hexane to give green crystals of 4-[N-(2-ethoxyethyl)-N-ethylamino]phenyl borate (1.21 g).

$^1$H-NMR (200 MHz, CDCl$_3$) δ 1.09–1.28 (6H, m), 3.35–3.70 (8H, m), 6.76 (2H, d, J=8.8 Hz), 8.06 (2H, d, J=8.8 Hz).

Reference Example 83

To a solution of N-methylaniline (10.0 g) in DMF (100 ml) was added dropwise a solution of at room temperature N-bromosuccinimide (16.6 g) in DMF (100 ml), and the mixture was stirred at room temperature for 20 hours. The reaction mixture was added to water, and the mixture was extracted with diethylether. The organic layer was washed with water and saturated brine, dried with magnesium sulfate and concentrated under reduced pressure to give pale yellow oil of 4-bromo-N-methylaniline (18.18 g).

To a solution of 4-bromo-N-methylaniline (18.18 g) in DMF (150 ml) were added at room temperature potassium carbonate (25.8 g), sodium iodide (28.0 g) and 2-bromoethylethyl ether (21 ml), and the mixture was stirred at 90° C. for 4 days. To the mixture were added 2-bromoethylethyl ether (10.0 ml), potassium carbonate (20.0 g) and sodium iodide (13.3 g), and the mixture was stirred for 2 days. To the mixture was added water, and the mixture was extracted with ethyl acetate. The organic layer was washed with water and saturated brined and dried with magnesium sulfate. Under reduced pressure, the solvent was evaporated, and the residue was purified with silica gel column chromatography (ethyl acetate/hexane=1:19) and distilled under reduced pressure (0.7 mmHg, 131° C.) to give yellow oil of 4-bromo-N-(2-ethoxyethyl)-N-methylaniline (17.63 g).

$^1$H-NMR (200 MHz, CDCl$_3$) δ 1.18 (3H, t, J=7.0 Hz), 2.95 (3H, s), 3.43–3.60 (6H, m), 6.59 (2H, d, J=9.2 Hz), 7.28 (2H, d, J=9.2 Hz). IR (neat) 1593, 1497, 1373, 1350, 1115, 806 cm$^{-1}$.

Reference Example 84

Under argon atmosphere, to a suspension of magnesium (1.83 g) in THF (30 ml) was added at room temperature 1,2-dibromoethane (0.1 ml). and then was added dropwise a solution of 4-bromo-N-(2-ethoxyethyl)-N-methylaniline (17.63 g) in THF (30 ml) for 1 hour. The mixture was stirred at 60° C. for 2 hours and cooled to −78° C., to which was added dropwise a solution of trimethyl borate (23.0 ml) in THF (23 ml). The mixture was stirred at −78° C. for 1 hour and allowed to warm to room temperature. To the mixture was added THF (50 ml), and the mixture was stirred at room temperature for 1 hour. To the mixture was added at 0° C. 3N hydrochloric acid (50 ml), and the mixture was stirred at room temperature for 2.5 hours. To the mixture was added 2N sodium hydroxide solution to make the solution pH 7–8, and the mixture was extracted with ethyl acetate, washed with saturated brine, dried with magnesium sulfate and concentrated under reduced pressure. To the residue was added diisopropylether to give green crystals, which were collected by filtration and washed with diisopropylether to give green crystals of 4-[N-(2-ethoxyethyl)-N-methylaminolphenyl borate (8.51 g).

$^1$H-NMR (200 MHz, CDCl$_3$) δ 1.21 (3H, t, J=7.0 Hz), 3.08 (3H, s), 3.51 (2H, q, J=7.0 Hz), 3.59–3.68 (4H, m), 6.79 (2H, d, J=8.8 Hz), 8.08 (2H, d, J=8.8 Hz).

Reference Example 85

To a solution of 2-(N-ethylanilino)ethanol (17.83 g) in DMF (300 ml) was added at 0° C. sodium hydride (60%, 4.74 g), and the mixture was stirred at 0° C. for 30 minutes and at room temperature for 30 minutes. To the mixture was added propyl iodide (11.0 ml), and the mixture was stirred at 50° C. for 19 hours. To the mixture was added water, and the mixture was extracted with ethyl acetate. The organic layer was washed with water and saturated brine, dried with magnesium sulfate and concentrated under reduced pressure, and the residue was purified with silica gel column chromatography (ethyl acetate/hexane=1:19) to give colorless oil of N-ethyl-N-(2-propoxyethyl)aniline (10.18 g).

To a solution of N-ethyl-N-(2-propoxyethyl)aniline (10.18 g) in DMF (50 ml) was added at room temperature a solution of N-bromosuccinimide (7.45 g) in DMF (50 ml) for 40 minutes, and the mixture was stirred for 3 hours. To the mixture was added a solution of N-bromosuccinimide (0.2 g) in DMF (10 ml), and the mixture was stirred for 15 hours. The reaction mixture was added to water, and the mixture was extracted with diethylether. The organic layer was washed with water (twice) and saturated brine, and dried with magnesium sulfate. Under reduced pressure, the solvent was evaporated, and the residue was distilled under reduced pressure (0.7 mmHg, 134° C.) to give pale yellow oil of 4-bromo-N-ethyl-N-(2-propoxyethyl)aniline (9.49 g).

$^1$H-NMR (200 MHz, CDCl$_3$) δ 0.91 (3H, t, J=7.4 Hz), 1.14 (3H, t, J=7.1 Hz), 1.50–1.67 (2H, m), 3.31–3.60 (8H, m), 6.56 (2H, d, J=9.2 Hz), 7.26 (2H, d, J=9.2 Hz). IR (neat) 1591, 1498, 1356, 1267, 1192, 1113, 804 cm$^{-1}$.

Reference Example 86

Under argon atmosphere, to a suspension of magnesium (0.89 g) in THF (30 ml) was added at room temperature 1,2-dibromoethane (0.1 ml) and then was added at 60° C. a solution of 4-bromo-N-ethyl-N-(2-propoxyethyl)aniline (9.49 g) in THF (40 ml) for 40 minutes. The mixture was stirred for 2 hours and cooled to −78° C. To the mixture was added a solution of trimethyl borate (11 ml) in THF (11 ml) for 1 hour, and the mixture was stirred at −78° C. for 1 hour. The reaction mixture was allowed to warm to room temperature, and the mixture was stirred at room temperature for 2 hours. To the mixture was added 3N hydrochloric acid (25 ml), and the mixture was stirred for 2 hours. To the mixture was added 2N sodium hydroxide solution to make the solution pH 7–8, and the mixture was extracted with ethyl acetate, washed with saturated brine, dried with magnesium sulfate and concentrated under reduced pressure to give crystals, which were collected by filtration and washed with hexane to give green crystals of 4-[N-ethyl-N-(2-propoxyethyl)amino]phenyl borate (0.7 g). The mother liquor was purified with silica gel column chromatography (ethyl acetate/hexane=1:1) to give green crystals of 4-[N-ethyl-N-(2-propoxyethyl)amino]phenyl borate (2.1 g).

$^1$H-NMR (200 MHz, CDCl$_3$) δ: 0.93 (3H, t, J=7.5 Hz), 1.21 (3H, t, J=7.0 Hz), 1.53–1.69 (2H, m), 3.39–3.62 (8H, m), 6.76 (2H, d, J=9.0 Hz), 8.06 (2H, d, J=8.0 Hz).

Reference Example 87

To a solution of N-methylaniline (10.0 g) in DMF (100 ml) was added dropwise at room temperature a solution of N-bromosuccinimide (16.6 g) in DMF (100 ml), and the mixture was stirred for at room temperature for 20 hours. The reaction mixture was added to water, and the mixture was extracted with diethylether. The organic layer was washed with water (thrice) and saturated brine, dried with magnesium sulfate and concentrated under reduced pressure to give yellow oil of 4-bromomethylaniline (17.93 g).

To a solution of 4-bromomethylaniline (17.93 g) in DMF (300 ml) were added at room temperature potassium carbonate (52 g), sodium iodide (42 g) and 2-bromoethylethyl ether (35 ml), and the mixture was stirred at 90° C. for 4 days. To the mixture was added water, and the mixture was extracted with ethyl acetate. The organic layer was washed with water (thrice) and saturated brine, and dried with magnesium sulfate. Under reduced pressure, the solvent was evaporated, and the residue was purified with silica gel column chromatography (ethyl acetate/hexane=1:19) and distilled under reduced pressure (0.5 mmHg, 124–127° C.) to give yellow oil of 4-bromo-N-methyl-N-(2-propoxyethyl)aniline (17.95 g).

$^1$H-NMR (200 MHz, CDCl$_3$) δ 0.90(3H, t, J=7.3 Hz), 1.46–1.65 (2H, m), 2.95 (3H, s), 3.37 (2H, t, J=6.6 Hz), 3.45–3.59 (4H, m), 6.58 (2H, d, J=9.2 Hz), 7.28 (2H, d, J=9.2 Hz). IR (neat) 1593, 1502, 1373, 1352, 1117, 806 cm$^{-1}$.

Reference Example 88

Under argon atmosphere, to a suspension of magnesium (1.76 g) in THF (30 ml) was added at room temperature 1,2-dibromoethane (0.1 ml) and then was added a solution of 4-bromo-N-methyl-N-(2-propoxyethyl)aniline (17.95 g) in THF (30 ml) for 30 minutes. The mixture was stirred at 60° C. for 1.5 hours and cooled to −78° C., to which was added a solution of trimethyl borate (22 ml) in THF (22 ml) for 30 minutes. The mixture was stirred at −78° C. for 1 hour, allowed to warm to room temperature and stirred for 2 hours. To the mixture was added 3N hydrochloric acid (50 ml), and the mixture was stirred for 30 minutes. To the mixture was added 2N sodium hydroxide solution to make the solution pH 7–8, and the mixture was extracted with ethyl acetate, washed with saturated brine, dried with magnesium sulfate and concentrated under reduced pressure to give crystals, which were collected by filtration and washed with hexane to give green crystals of 4-[N-methyl-N-(2-propoxyethyl)amino]phenyl borate (5.18 g).

$^1$H-NMR (200 MHz, CDCl$_3$) δ 0.92 (3H, t, J=7.5 Hz), 1.49–1.68 (2H, m), 3.08 (3H, s), 3.41 (2H, t, J=6.7 Hz), 3.55–3.67 (4H, m), 6.78 (2H, d, J=8.7 Hz), 8.08 (2H, d, J=8.7 Hz).

Reference Example 89

To a solution of 4-bromo-2-ethoxyphenol (8.0 g) in DMF (50 ml) were added at room temperature potassium carbonate (7.65 g), sodium iodide (6.64 g) and 2-chloroethylpropylether (5.6 ml), and the mixture was stirred at 90° C. for 24 hours. To the mixture was added water, and the mixture was extracted with ethyl acetate. The organic layer was washed with water, 1N sodium hydroxide solution and saturated brine, dried with magnesium sulfate and concentrated under reduced pressure. The residue was purified with silica gel column chromatography (ethyl acetate/hexane=1:4) to give yellow oil of 4-bromo-2-ethoxy-1-(2-propoxyethoxy)benzene (10.33 g).

$^1$H-NMR (200 MHz, CDCl$_3$) δ 0.93 (3H, t, J=7.5 Hz), 1.43 (3H, t, J=7.0 Hz), 1.53–1.72 (2H, m), 3.50 (2H, t, J=6.8 Hz), 3.79 (2H, t, J=4.9 Hz), 4.05 (2H, q, J=7.0 Hz), 4.14 (2H, t, J=4.9 Hz), 6.80 (1H, d, J=9.2 Hz), 6.98–7.02 (2H, m). IR (neat) 1587, 1498, 1475, 1454, 1402, 1294, 1254, 1219, 1137, 1041, 934 cm$^{-1}$.

Reference Example 90

Under argon atmosphere, to a solution of 4-bromo-2-ethoxy-1-(2-propoxyethoxy)benzene (10.25 g) in THF/diethylether (30/30 ml) was added dropwise at −78° C. a solution of 1.6M n-butyllithium in hexane (23 ml), and the mixture was stirred at −78° C. for 1 hour. To the mixture was added a solution of trimethyl borate (98.1 milli mole) in THF (11 ml) for 1 hour, and the mixture was stirred at −78° C. for 1 hour and allowed to warm to room temperature. The mixture was stirred at room temperature for 2 hours. To the mixture was added 1N hydrochloric acid (100 ml), and the mixture was stirred for 30 minutes and extracted with ethyl acetate. The organic layer was washed with saturated brine, dried with magnesium sulfate and concentrated under reduced pressure to give crystals, which were collected by filtration and washed with hexane to give colorless crystals of 3-ethoxy-4-(2-propoxyethoxy)phenyl borate (3.09 g).

$^1$H-NMR (200 MHz, CDCl$_3$) δ 0.95 (3H, t, J=7.5 Hz), 1.50 (3H, t, J=6.9 Hz), 1.57–1.72 (2H, m), 3.55 (2H, t, J=6.8 Hz), 3.84–3.90 (2H, m), 4.17–4.29 (4H, m), 7.04 (1H, d, J=8.0 Hz), 7.70 (1H, d, J=1.4 Hz), 7.81 (1H, dd, J=8.0, 1.4 Hz).

Reference Example 91

To a solution of 4-bromo-2-chlorophenol (10 g) in DMF (200 ml) were added at room temperature potassium carbonate (9.99 g), sodium iodide (7.95 g) and 2-chloroethylpropylether (6.7 ml), and the mixture was stirred at 90° C. for 24 hours. To the mixture was added water, and the mixture was extracted with hexane. The organic layer was washed with water, 1N sodium hydroxide solution and saturated brine, dried with magnesium sulfate and concentrated under reduced pressure to give pale yellow oil of 4-bromo-2-chloro-1-(2-propoxyethoxy)benzene (14.91 g).

$^1$H-NMR (200 MHz, CDCl$_3$) δ 0.93 (3H, t, J=7.3 Hz), 1.54–1.70 (2H, m), 3.52 (2H, t, J=6.6 Hz), 3.82 (2H, t, J=4.9 Hz), 4.16 (2H, t, J=4.9 Hz), 6.85 (1H, d, J=8.8 Hz), 7.31 (1H, dd, J=8.8, 2.4 Hz), 7.50 (1H, d, J=2.4 Hz). IR (neat) 1584, 1483, 1452, 1290, 1265, 1250, 1128, 1086, 1066, 800 cm$^{-1}$.

Reference Example 92

Under argon atmosphere, to a solution of 4-bromo-2-chloro-1-(2-propoxyethoxy)benzene (14.91 g) in THF/diethylether (40/40 ml) was added dropwise at −78° C. a solution of 1.6M n-butyllithium in hexane (33 ml), and the mixture was stirred at −78° C. for 1 hour. To the mixture was added a solution of trimethyl borate (16.1 ml) in THF (16 ml) for 1 hour, and the mixture was stirred at −78° C. for 1 hour. The reaction mixture was allowed to warm to room temperature and then stirred at room temperature for 36 hours. To the mixture was added 1N hydrochloric acid (10 ml), and the mixture was extracted with ethyl acetate. The organic layer was washed with saturated brine, dried with magnesium sulfate and concentrated under reduced pressure. The residue was purified with silica gel column chromatography (ethyl acetate/hexane=1:1→2:1) to give colorless crystals of 3-chloro-4-(2-propoxyethoxy)phenyl borate (3.31 g).

$^1$H-NMR (200 MHz, CDCl$_3$) δ 0.96 (3H, t, J=7.3 Hz), 1.56–1.70 (2H, m), 3.57 (2H, t, J=6.6 Hz), 3.89 (2H, t, J=5.0

Hz), 4.28 (2H, t, J=5.0 Hz), 7.06 (1H, d, J=8.2 Hz), 8.05 (1H, dd, J=8.2, 1.4 Hz), 8.14 (1H, d, J=1.4 Hz).

Reference Example 93

To a solution of 4-bromo-2-methylphenol (10.46 g) in DMF (10 ml) were added at room temperature potassium carbonate (11.5 g), sodium iodide (9.97 g) and 2-chloroethylpropylether (5.6 ml), and the mixture was stirred at 90° C. for 7 days. To the mixture was added water, and the mixture was extracted with ethyl acetate. The organic layer was washed with water, 1N sodium hydroxide solution and saturated brine, dried with magnesium sulfate and concentrated under reduced pressure. The residue was purified with silica gel column chromatography (ethyl acetate/hexane=1:9) to give pale yellow oil of 4-bromo-2-methyl-1-(2-propoxyethoxy)benzene (11.7 g).

$^1$H-NMR (200 MHz, CDCl$_3$) δ 0.94 (3H, t, J=7.6 Hz), 1.52–1.71 (2H, m), 2.20 (3H, s), 3.50 (2H, t, J=6.8 Hz), 3.79 (2H, t, J=5.0 Hz), 4.09 (2H, t, J=5.0 Hz), 6.69 (IH, d, J=9.2 Hz), 7.18–7.27 (2H, m). IR (neat) 1491, 1454, 1296, 1248, 1190, 1132 cm$^{-1}$.

Reference Example 94

Under argon atmosphere, to a suspension of magnesium (1.14 g) in THF (10 ml) was added at room temperature 1,2-dibromoethane (0.05 ml), and then was added dropwise a solution of 4-bromo-2-methyl-1-(2-propoxyethoxy) benzene (11.7 g) in THF (50 ml) for 20 minutes. The mixture was stirred at 60° C. for 1.5 hours. The reaction mixture was cooled to −78° C., and to the mixture was added dropwise trimethyl borate (10.0 ml) in THF (10 ml). The mixture was stirred at −78° C. for 1 hour and allowed to warm to room temperature. To the mixture was added THF (50 ml), and the mixture was stirred at room temperature for 2 hours. To the mixture was added 1N hydrochloric acid (100 ml), and the mixture was stirred for 30 minutes, extracted with ethyl acetate, washed with saturated brine, dried with magnesium sulfate and concentrated under reduced pressure. To the residue was added diisopropylether, and precipitated green crystals were collected by filtration, which were washed with hexane to give colorless crystals of 3-methyl-4-(2-propoxyethoxy)phenyl borate (5.44 g). $^1$H-NMR (200 MHz, CDCl$_3$) δ 0.96 (3H, t, J=7.5 Hz), 1.56–1.75 (2H, m), 2.34 (3H, s), 3.55(2H, t, J=6.6 Hz), 3.86 (2H, t, J=5.0), 4.22 (2H, t, J=5.0), 6.94 (1H, d, J=8.1 Hz), 7.97 (1H, s), 8.05 (1H, d, J=8.1 Hz).

Working Example 49 (Production of Compound 48)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 m), 2,4-dimethoxyphenyl borate (116 mg) and potassium carbonate (160 mg) in toluene/ethanol/water (6/0.6/0.6 ml) was stirred at room temperature for 1 hour. To the mixture was added tetrakistriphenylphosphinepalladium (33 mg), and the mixture was refluxed for 7 hours, cooled, extracted with ethyl acetate, washed with saturated brine, dried with magnesium sulfate and concentrated under reduced pressure. The residue was purified with silica gel column chromatography (ethanol/ethyl acetate=1:3) to give crystals, which were recrystallized from ethanol to give colorless crystals of 7-(2,4-dimethoxyphenyl)-N-[4-[[N-methyl-N-(tetrahydropyran-4-yl)amino]methyl]phenyl]-1,1-dioxo-2,3-dihydro-1-benzothiepine-4-carboxamide (Compound 48) (216 mg).

m.p. 175–178° C.; $^1$H-NMR (200 MHz, CDCl$_3$) δ 1.54–1.82 (4H, m), 2.20 (3H, s), 2.55–2.74 (1H, m), 3.16 (2H, t, J=6.7 Hz), 3.31–3.43 (2H, m), 3.57 (2H, s), 3.72 (2H, t, J=6.7 Hz), 3.82 (3H, s), 3.87 (3H, s), 3.99–4.10 (2H, m), 6.57–6.62 (2H, m), 7.23–7.34 (4H, m), 7.54 (2H, d, J=8.4 Hz), 7.62–7.66 (2H, m), 7.97 (1H, br s), 8.16 (1H, d, J=8.2 Hz). IR (KBr) 3284, 1649, 1610, 1518, 1313, 1296, 1211, 1130 cm$^{-1}$; Anal. for C$_{32}$H$_{36}$N$_2$O$_6$S.0.2 H$_2$O Calcd. C, 66.23; H, 6.32; N, 4.83: Found. C, 65.93; H, 6.33; N, 4.79.

Working Example 50 (Production of Compound 49)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 3-chloro-4-ethoxyphenyl borate (127 mg) and potassium carbonate (160 mg) in toluene/ethanol/water (10/1/1 ml) was stirred at room temperature for 1 hour. To the mixture was added tetrakistriphenylphosphinepalladium (33 mg), and the mixture was refluxed for 30 hours, cooled, extracted with ethyl acetate, washed with saturated brine, dried with magnesium sulfate and concentrated under reduced pressure. The residue was purified with silica gel column chromatography (ethanol/ethyl acetate=1:4) to give crystals, which were recrystallized from ethanol to give colorless crystals of 7-(3-chloro-4-ethoxyphenyl)-N-[4-[[N-methyl-N-(tetrahydropyran-4-yl)amino]methyl]phenyl]-1,1-dioxo-2,3-dihydro-1-benzothiepine-4-carboxamide (Compound 49) (38 mg).

m.p. 201–204° C.; $^1$H-NMR (200 MHz, CDCl$_3$) δ 1.52 (3H, t, J=7.0 Hz), 1.63–1.85(4H, m), 2.21 (3H, s), 2.56–2.74 (1H, m), 3.14–3.20 (2H, m), 3.31–3.44 (2H, m), 3.58(2H, s), 3.70–3.76 (2H, m), 3.99–4.10 (2H, m), 4.18 (2H, q, J=7.0 Hz), 7.02 (1H, d, J=8.8 Hz), 7.31–7.35 (3H, m), 7.46 (1H, dd, J=8.8, 2.2 Hz), 7.55 (2H, d, J=8.8 Hz), 7.61–7.68 (3H, m), 7.91 (1H, br s), 8.21 (1H, d, J=8.0 Hz). IR (KBr) 3332, 1649, 1599, 1516, 1311, 1294, 1269, 1165, 1130, 820 cm$^{-1}$; Anal. for C$_{32}$H$_{35}$N$_2$O.SCl; Calcd. C, 64.58; H, 5.93; N, 4.71; Found. C, 64.53; H, 5.81; N, 4.70.

Working Example 51 (Production of Compound 50)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 4-ethoxy- 3-fluorophenyl borate (117 mg) and potassium carbonate (160 mg) in toluene/ethanol/water (10/1/1 ml) was stirred at room temperature for 1 hour. To the mixture was added tetrakistriphenylphosphinepalladium (33 mg), and the mixture was refluxed for 24 hours, cooled, extracted with ethyl acetate, washed with saturated brine, dried with magnesium sulfate and concentrated under reduced pressure. The residue was purified with silica gel column chromatography (ethanol/ethyl acetate=1:4) to give crystals, which were recrystallized from ethanol to give pale yellow crystals of 7-(4-ethoxy-3-fluorophenyl)-N-[4-[[N-methyl-N-(tetrahydropyran-4-yl)amino]methyl]phenyl]-1,1-dioxo-2,3-dihydro-1-benzothiepine-4-carboxamide (Compound 50) (137 mg).

m.p. 233–235° C.; $^1$H-NMR (200 MHz, CDCl$_3$) δ 1.50 (3H, t, J=6.9 Hz), 1.64–1.84 (4H, m), 2.21 (3H, s), 2.56–2.72 (1H, m), 3.14–3.20 (2H, m), 3.31–3.44 (2H, m), 3.58 (2H, s), 3.70–3.76 (2H, m), 3.98–4.11 (2H, m), 4.18 (2H, g, J=6.9 Hz), 7.02–7.11 (1H, m), 7.30–7.40 (5H, m), 7.55 (2H, d, J=8.4 Hz), 7.60 (1H, d, J=1.8 Hz), 7.66 (1H, dd, J=8.2, 1.8 Hz), 7.92 (1H, br s), 8.21 (1H, d, J=8.2 Hz). IR (KBr) 3432, 1659, 1603, 1522, 1309, 1130 cm$^{-1}$; Anal. for C$_{32}$H$_{35}$N$_2$O$_5$SF; Calcd. C, 66.42; H, 6.10; N, 4.84; Found. C, 66.16; H, 6.09; N, 4.83.

Working Example 52 (Production of Compound 51)

To a solution of 4-bromo-1,2-diethoxybenzene (9.74 g) in THF (80 ml) was added dropwise at −78° C. a solution of 1.6M n-butyllithium in hexane (27 ml), and the mixture was stirred for 1 hour. To the mixture was added dropwise a solution of trimethyl borate (14 ml) in THF (14 ml). The reaction mixture was allowed to warm to room temperature and stirred at room temperature for 2 hours. To the mixture was added dropwise 10% sulfuric acid (100 ml), and the mixture was stirred for 30 minutes and extracted with ethyl acetate. The organic layer was washed with saturated brine and dried with magnesium sulfate. The solvent was evaporated under reduced pressure to give colorless crystals, which were collected by filtration and washed with hexane to give colorless crystals of 3,4-diethoxyphenyl borate (5.22 g).

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 3,4-diethoxyphenyl borate (134 mg) and potassium carbonate (160 mg) in toluene/ethanol/water (10/1/1 ml) was stirred at room temperature for 1 hour. To the mixture was added tetrakistriphenylphosphinepalladium (33 mg), and the mixture was refluxed for 7 hours, cooled, extracted with ethyl acetate, washed with saturated brine, dried with magnesium sulfate and concentrated under reduced pressure to give crystals, which were recrystallized from ethanol to give pale yellow crystals of 7-(3,4-diethoxyphenyl)-N-[4-[[N-methyl-N-(tetrahydropyran-4-yl)amino]methyl]phenyl]-1,1-dioxo-2,3-dihydro-1-benzothiepine-4-carboxamide (Compound 51) (214 mg).

m.p. 224–226° C.; $^1$H-NMR (200 MHz, CDCl$_3$) δ 1.49 (6H, t, J=7.0 Hz), 1.66–1.83 (4H, m), 2.21 (3H, s), 2.57–2.72 (1H, m), 3.17 (2H, t, J=6.8 Hz), 3.31–3.44 (2H, m), 3.58 (2H, s), 3.72 (2H, t, J=6.8 Hz), 3.98–4.11 (2H, m), 4.16 (2H, q, J=7.0 Hz), 4.18 (2H, g, J=7.0 Hz), 6.97 (1H, d, J=8.0 Hz), 7.11–7.16 (2H, m), 7.31–7.35 (3H, m), 7.56 (2H, d, J=8.4 Hz), 7.60–7.68 (2H, m), 7.96 (1H, s), 8.18 (1H, d, J=8.4 Hz). IR (KBr) 3329, 1653, 1599, 1518, 1315, 1250, 1134, 810 cm$^{-1}$; Anal. for C$_{34}$H$_{40}$N$_2$O$_6$S.0.2 H$_2$O; Calcd. C, 67.13; H, 6.69; N, 4.60; Found. C, 67.01; H, 6.55; N, 4.48.

Working Example 53 (Production of Compound 52)

Under argon atmosphere, a mixture of 7-bromo-N-[4-[[N-methyl-N-(tetrahydropyran- 4-yl)aminomethyl]phenyl]-1,1-dioxo-2,3-dihydro-1-benzothiepine-4-carboxamide (300 mg), 3,4-dimethoxyphenyl borate (116 mg) and potassium carbonate (160 mg) in toluene/ethanol/water (10/1/1 ml) was stirred at room temperature for 1 hour. To the mixture was added tetrakistriphenylphosphinepalladium (40 mg), and the mixture was refluxed for 6 hours, cooled, extracted with ethyl acetate, washed with saturated brine, dried with magnesium sulfate and concentrated under reduced pressure to give crystals, which were recrystallized from ethanol to give colorless crystals of 7-(3,4-dimethoxyphenyl)-N-[4-[[N-methyl-N-(tetrahydropyran-4-yl)amino]methyl]phenyl]-1,1-dioxo-2,3-dihydro-1-benzothiepine-4-carboxamide (Compound 52) (112 mg).

m.p. 195–197° C.; $^1$H-NMR (200 MHz, CDCl$_3$) δ 1.67–1.84 (4H, m), 2.21 (3H, s), 2.56–2.74 (1H, m), 3.14–3.21 (2H, m), 3.31–3.44 (2H, m), 3.58 (2H, s), 3.69–3.76 (2H, m), 3.95 (3H, s), 3.97 (3H, s), 3.99–4.11 (2H, m), 6.98 (1H, d, J=8.2 Hz), 7.10 (1H, d, J=2.0 Hz), 7.18 (1H, dd, J=8.2, 2.0 Hz), 7.33 (2H, d, J=8.4 Hz), 7.37 (1H, s), 7.55 (2H, d, J=8.4 Hz), 7.62 (1H, d, J=2.0 Hz), 7.68 (1H, dd, J=8.4, 2.0 Hz), 7.95 (1H, s), 8.20 (1H, d, J=8.4 Hz). IR (KBr) 3327, 1668, 1595, 1520, 1311, 1257, 1136 cm$^{-1}$; Anal. for C$_{32}$H$_{36}$N$_2$O$_6$S.0.2 H$_2$O Calcd. C, 66.23; H, 6.32; N, 4.82; Found. C, 66.19; H, 6.52; N, 4.73.

Working Example 54 (Production of Compound 53)

To a solution of 1-bromo-4-(2-methoxyethoxy)benzene (17.0 g) in diethylether/THF (150/50 ml) was added dropwise at −78° C. a solution of 1.6M n-butyllithium in hexane (50 ml), and the mixture was stirred for 1 hour. To the mixture was added dropwise a solution of trimethyl borate (24.8 ml) in THF (25 ml). The reaction mixture was allowed to warm to room temperature and the mixture was stirred at room temperature for 2 hours. To the mixture was added dropwise 10% sulfuric acid (100 ml), and the mixture was stirred for 30 minutes and extracted with ethyl acetate. The organic layer was washed with saturated brine and dried with magnesium sulfate. The solvent was evaporated under reduced pressure. The residue was purified with silica gel column chromatography (ethyl acetate/hexane=1:1) to give colorless crystals of 4-(2-methoxyethoxy)phenyl borate (7.17 g).

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 4-(2-methoxyethoxy)phenyl borate (124 mg) and potassium carbonate, (160 mg) in toluene/ethanol/water (10/1/1 ml) was stirred at room temperature for 1 hour. To the mixture was added tetrakistriphenylphosphinepalladium (40 mg), and the mixture was refluxed for 6 hours, cooled, extracted with ethyl acetate, washed with saturated brine, dried with magnesium sulfate and concentrated under reduced pressure to give crystals, which were recrystallized from ethanol to give colorless crystals of 7-[4-(2-methoxyethoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 53) (246 mg).

m.p. 227–231° C.; $^1$H-NMR (200 MHz, CDCl$_3$) δ 1.64–1.84 (4H, m), 2.21 (3H, s), 2.55–2.74 (1H, m), 3.13–3.19 (2H, m), 3.32–3.44 (2H, m), 3.47 (3H, s), 3.58 (2H, s), 3.69–3.81 (4H, m), 3.99–4.09 (2H, m), 4.16–4.21 (2H, m), 7.04 (2H, d, J=8.8 Hz), 7.30–7.35 (3H, m), 7.52–7.56 (4H, m), 7.62–7.69 (2H, m), 7.92 (1H, s), 8.19 (1H, d, J=8.4 Hz). IR (KBr) 3246, 1655, 1605, 1518, 1410, 1315, 1294, 1254, 1167, 1128, 825 cm$^{-1}$; Anal. for C$_{33}$H$_{38}$N$_2$O$_6$S; Calcd. C, 67.10; H, 6.48; N, 4.74; Found. C, 66.85; H, 6.40; N, 4.62.

Working Example 55 (Production of Compound 54)

To a solution of 4-bromo-N,N-diethylaniline (17.0 g) in THF (150 ml) was added dropwise at −78° C. a solution of 1.6M n-butyllithium in hexane (51 ml), and the mixture was stirred for 1 hour. To the mixture was added dropwise a solution of trimethyl borate (25 ml) in THF (25 ml). The reaction mixture was allowed to warm to room temperature, and the mixture was stirred at room temperature for 2 hours. To the mixture was added dropwise 1N hydrochloric acid (200 ml), and the mixture was stirred for 1 hour. To the mixture was added saturated sodium bicarbonate solution to make the solution pH 7, and the mixture was extracted with ethyl acetate. The organic layer was washed with saturated brine and dried with magnesium sulfate. The solvent was evaporated under reduced pressure to give colorless crystals, which were collected by filtration. The crystals were washed with diisopropylether to give colorless crystals of 4-diethylaminophenyl borate (2.47 g). The mother liquor was concentrated to give gray crystals, which were collected by filtration and washed with hexane to give 4-diethylaminophenyl borate (4.00 g).

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 4-diethylaminophenyl borate (123 mg) and potassium carbonate (160 mg) in toluene/ethanol/water (10/1/1 ml) was stirred at room temperature for 1 hour. To the mixture was added tetrakistriphenylphosphinepalladium (33 mg), and the mixture was refluxed for 7 hours, cooled, extracted with ethyl acetate/THF (1:1), washed with saturated brine, dried with magnesium sulfate and concentrated under reduced pressure to give crystals, which were recrystallized from ethanol to give yellow crystals of 7-(4-diethylaminophenyl)-N-[4-[[N-methyl-N-(tetrahydropyran-4-yl)amino]methyl]phenyl]-1,1-dioxo-2,3-dihydro-1-benzothiepine-4-carboxamide (Compound 54) (198 mg).

m.p. 240–246° C.; $^1$H-NMR (200 MHz, CDCl$_3$) δ 1.21 (6H, t, J=6.9 Hz), 1.65–1.82 (4H, m), 2.21 (3H, s), 2.56–2.75 (1H, m), 3.15 (2H, t, J=7.0 Hz), 3.31–3.50 (6H, m), 3.58 (2H, s), 3.68–3.74 (2H, m), 3.98–4.08 (2H, m), 6.75 (2H, d, J=9.2 Hz), 7.31–7.35 (3H, m), 7.49–7.67 (6H, m), 7.93 (1H, br s), 8.14 (1H, d, J=8.2 Hz). IR (KBr) 3292, 1657, 1606, 1527, 1408, 1315, 1296, 1271, 1128, 812 cm$^{-1}$; Anal. for C$_{34}$H$_{41}$N$_3$O$_4$S.0.5 H$_2$O; Calcd. C, 68.42; H, 7.09; N, 7.04; Found. C, 68.39; H, 7.11; N, 7.02.

Working Example 56 (Production of Compound 55)

Under argon atmosphere, a mixture of 7-bromo-N-[4-[[N-methyl-N-(tetrahydropyran-4-yl)amino]methyl]pheny]-1,1-dioxo-2,3-dihydro-1-benzothiepine-4-carboxamide (300 mg), 2,3-dihydro-1,4-benzodioxin-6-yl borate (114 mg) and potassium carbonate (160 mg) in toluene/ethanol/water (10/1/1 ml) was stirred at room temperature for 1 hour. To the mixture was added tetrakistriphenylphosphinepalladium (33 mg), and the mixture was refluxed for 6 hours, cooled, extracted with ethyl acetate, washed with saturated brine, dried with magnesium sulfate and concentrated under reduced pressure. The residue was purified with silica gel column chromatography (ethanol/ethyl acetate=1:2) to give crystals, which were recrystallized from ethanol to give colorless crystals of 7-(2,3-dihydro-1,4-benzodioxin-6-yl)-N-[4-[[N-methyl-N-(tetrahydropyran-4-yl)amino]methyl]phenyl]-1,1-dioxo-2,3-dihydro-1-benzothiepine-4-carboxamide (Compound 55) (257 mg).

m.p. 248–251° C.; $^1$H-NMR (200 MHz, CDCl$_3$) δ 1.66–1.84 (4H, m), 2.21 (3H, s), 2.57–2.74 (1H, m), 3.17 (2H, t, J=6.9 Hz), 3.31–3.43 (2H, m), 3.58 (2H, s), 3.73 (2H, t, J=6.9 Hz), 3.99–4.10 (2H, m), 4.32 (4H, s), 6.98 (1H, d, J=8.6 Hz), 7.08–7.13 (2H, m), 7.31–7.35 (3H, m), 7.55 (2H, d, J=8.4 Hz), 7.61–7.68 (2H, m), 7.90 (1H, s), 8.19 (1H, d, J=8.4 Hz). IR (KBr) 3246, 1653, 1599, 1514, 1410, 1317, 1290, 1246, 1128, 1068, 816 cm$^{-1}$; Anal. for C$_{32}$H$_{34}$N$_2$O$_6$S; Calcd. C, 66.88; H, 5.96; N, 4.87; Found. C, 66.70; H, 6.15; N, 4.74.

Working Example 57 (Production of Compound 56)

Under argon atmosphere, to a solution of 5-bromo-2,3-dihydrobenzofuran (17.64 g) in THF (150 ml) was added dropwise at −78° C. a solution of 1.6M n-butyllithium in hexane (60 ml), and the mixture was stirred for 1 hour. To the mixture was added dropwise a solution of trimethyl borate (30 ml) in THF (30 ml). The reaction mixture was allowed to gradually warm to room temperature, and the mixture was stirred at room temperature for 2 hours. To the mixture was added dropwise 10% sulfuric acid (100 ml), and the mixture was stirred for 30 minutes and extracted with ethyl acetate. The organic layer was washed with water and saturated brine, dried with magnesium sulfate and concentrated under reduced pressure to give colorless crystals, which were collected by filtration. The crystals were washed with diisopropylether to give colorless crystals of 2,3-dihydrobenzofuran-5-yl borate (8.28 g).

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 2,3-dihydrobenzofuran-5-yl borate (104 mg) and potassium carbonate (160 mg) in toluene/ethanol/water (10/1/1 ml) was stirred at room temperature for 1 hour. To the mixture was added tetrakistriphenylphosphinepalladium (33 mg), and the mixture was refluxed for 6 hours, cooled, extracted with ethyl acetate, washed with saturated brine, dried with magnesium sulfate and concentrated under reduced pressure. The residue was purified with silica gel column chromatography (ethanol/ethyl acetate=1:3) to give crystals, which were recrystallized from ethanol to give pale yellow crystals of 7-(2,3-dihydrobenzofuran-5-yl)-N-[4-[[N-methyl-N-(tetrahydropyran-4-yl)amino]methyl]phenyl]-1,1-dioxo-2,3-dihydro-1-benzothiepine-4-carboxamide (Compound 56) (246 mg).

m.p. 214–216° C.; $^1$H-NMR (200 MHz, CDCl$_3$) δ 1.57–1.84 (4H, m), 2.21 (3H, s), 2.54–2.76 (1H, m), 3.13–3.20 (2H, m), 3.29 (2H, t, J=8.6 Hz), 3.13–3.44 (2H, m), 3.58 (2H, s), 3.69–3.76 (2H, m), 4.00–4.09 (2H, m), 4.66 (2H, t, J=8.6 Hz), 6.89 (1H, d, J=8.4 Hz), 7.31–7.40 (4H, m), 7.45 (1H, s), 7.55 (2H, d, J=8.4 Hz), 7.60 (1H, d, J=1.6 Hz), 7.65 (1H, dd, J=8.4, 1.6 Hz), 7.94 (1H, s), 8.18 (1H, d, J=8.4 Hz). IR (KBr) 3265, 1653, 1632, 1597, 1527, 1410, 1317, 1294, 1234, 1128, 818 cm$^{-1}$; Anal. for C$_{32}$H$_{40}$N$_2$O$_5$S.0.2 H$_2$O; Calcd. C, 68.35; H, 6.17; N, 4.98; Found. C, 68.24; H, 6.21; N, 4.80.

Working Example 58 (Production of Compound 57)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (500 mg), 4-methoxycarbonylphenyl borate (191 mg) and potassium carbonate (266 mg) in toluene/ethanol/water (10/1/1 ml) was stirred at room temperature for 1 hour. To the mixture was added tetrakistriphenylphosphinepalladium (56 mg), and the mixture was refluxed for 6 hours, cooled, extracted with ethyl acetate, washed with saturated brine, dried with magnesium sulfate and concentrated under reduced pressure. The residue was purified with silica gel column chromatography (ethanol/ethyl acetate=1:2→1:1) to give crystals, which were recrystallized from ethanol to give colorless crystals of 7-(4-methoxycarbonylphenyl)-N-[4-[[N-methyl-N-(tetrahydropyran- 4-yl)amino]methyl]phenyl]-1,1-dioxo-2,3-dihydro-1-benzothiepine-4-carboxamide (290 mg).

m.p. 269–273° C. (dec.); $^1$H-NMR (200 MHz, CDCl$_3$) δ 1.66–1.83 (4H, m), 2.21 (3H, s), 2.56–2.72 (1H, m), 3.15–3.22 (2H, m), 3.31–3.44 (2H, m), 3.57 (2H, s), 3.70–3.77 (2H, m), 3.96 (3H, s), 3.98–4.10 (2H, m), 7.32

(2H, d, J=8.4 Hz), 7.37 (1H, s), 7.54 (2H, d, J=8.4 Hz), 7.64–7.68 (3H, m), 7.74 (1H, dd, J=8.0, 2.0 Hz), 7.95 (1H, s), 8.16 (2H, d, J=8.4 Hz), 8.26 (1H, d, J=8.0 Hz). IR (KBr) 3280, 1722, 1657, 1603, 1524, 1410, 1317, 1290, 1130, 1109, 816 cm$^{-1}$; Anal. for $C_{32}H_{34}N_2O_6S$; Calcd. C, 66.88; H, 5.96; N, 4.87; Found. C, 66.65; H, 5.83; N, 5.03.

Working Example. 59 (Production of Compound 58)

To a solution of 7-(4-ethoxyphenyl)-N-[4-[[N-methyl-N-(tetrahydropyran-4-yl)amino]methyl]phenyl]-1,1-dioxo-2,3-dihydro-1-benzothiepine-4-carboxamide (2.5 g) in THF (200 ml) was added at room temperature methane sulfonic acid (0.29 ml), and the mixture was stirred for 0.5 hours. To the mixture was added 2-propanol, and the mixture was concentrated under reduced pressure. Precipitated crystals were dissolved at 90° C. in 2-propanol, and the mixture was cooled to room temperature and then cooled to 0° C. to give crystals, which were collected by filtration and washed with diethylether to give colorless crystals of 7-(4-ethoxyphenyl)-N-[4-[[N-methyl-N-(tetrahydropyran-4-yl)amino]methyl]phenyl]-1,1-dioxo-2,3-dihydro-1-benzothiepine-4-carboxamide methane sulfonate (Compound 58) (2.56 g).

m.p. 161–166° C.; $^1$H-NMR (200 MHz, CDCl$_3$) δ 1.45 (3H, t, J=7.0 Hz), 1.76–2.16 (4H, m), 2.56–2.65 (3H, m), 2.78 (3H, s), 3.04–3.14 (2H, m), 3.20–3.52 (3H, m), 3.72–3.85 (2H, m), 3.90–4.05 (3H, m), 4.09 (2H, q, J=7.0 Hz), 4.21–4.33 (1H, m), 7.00 (2H, d, J=8.8 Hz), 7.46 (2H, d, J=8.8 Hz), 7.59–7.68 (3H, m), 7.78–7.88 (4H, m), 8.15 (1H, d, J=8.4 Hz), 9.33 (1H, s). IR (KBr) 3427, 1664, 1605, 1520, 1294, 1248, 1217, 1165, 1126, 1039, 825 cm$^{-1}$; Anal. for $C_{33}H_{40}N_2O_8S_2$·0.5 H$_2$O; Calcd. C, 59.53; H, 6.21; N, 4.21; Found. C, 59.28; H, 6.04; N, 4.39.

Working Example 60 (Production of Compound 59)

To a solution of 7-(4-ethoxyphenyl)-N-[4-[[N-methyl-N-(tetrahydropyran-4-yl)amino]methyl]phenyl]-1,1-dioxo-2,3-dihydro-1-benzothiepine-4-carboxamide (500 mg) in THF (37.5 ml) was added at room temperature citric acid (171.1 mg), and the mixture was stirred for 1 hour and concentrated under reduced pressure. To the residue was added ethanol to give crystals, which were collected by filtration and recrystallized from water/ethanol=1:10 to give colorless crystals of 7-(4-ethoxyphenyl)-N-[4-[[N-methyl-N-(tetrahydropyran-4-yl)amino]methyl]phenyl]-1,1-dioxo-2,3-dihydro-1-benzothiepine-4-carboxamide·½ citrate (Compound 59) (413 mg).

m.p. 241–245° C. (dec.); $^1$H-NMR (200 MHz, DMSO-d$_6$) δ 1.36 (3H, t, J=7.0 Hz), 1.50–1.73 (2H, m), 1.76–1.90 (2H, m), 2.30 (3H, s), 2.58 (1H, s), 2.61 (1H, s), 2.82–3.03 (1H, m), 3.05–3.11 (2H, m), 3.22–3.51 (2H, m), 3.73–3.87 (4H, m), 3.89–4.01 (2H, m), 4.10 (2H, q, J=7.0 Hz), 7.08 (2H, d, J=8.8 Hz), 7.36 (2H, d, J=8.8 Hz), 7.54 (1H, s), 7.74 (2H, d, J=8.8 Hz), 7.76 (2H, d, J=8.8 Hz), 7.87 (1H, dd, J=8.2, 1.8 Hz), 8.04–8.09 (2H, m), 10.26 (1H, s). IR (KBr) 3336, 1726, 1664, 1603, 1522, 1317, 1292, 1248, 1168, 1128, 827 cm$^{-1}$; Anal. for $C_{35}H_{40}N_2O_{8.5}S$·1.5 H$_2$O; Calcd. C, 61.48; H, 6.34; N, 4.10; Found. C, 61.50; H, 6.11; N, 4.09.

Working Example 61 (Production of Compound 60)

To a solution of 7-(4-ethoxyphenyl)-N-[4-([N-methyl-N-(tetrahydropyran-4-yl)amino]methyl]phenyl]-1,1-dioxo-2,3-dihydro-1-benzothiepine-4-carboxamide (300 mg) in THF (22.5 ml) was added at room temperature L-(+)-tartaric acid (80 mg), and the mixture was stirred at 60° C. for 2 hours and concentrated under reduced pressure. To the residue was added ethanol, and the mixture was concentrated to give crystals, which were collected by filtration and washed with ethanol to give colorless crystals of 7-(4-ethoxyphenyl)-N-[4-[[N-methyl-N-(tetrahydropyran-4-yl)amino]methyl]phenyl]-1,1-dioxo-2,3-dihydro-1-benzothiepine-4-carboxamide·½ L-(+)-tartarate (Compound 60) (259 mg).

m.p. 245–247° C. (dec.); $^1$H-NMR (200 MHz, DMSO-d$_6$) 1.36 (3H, t, J=7.0 Hz), 1.43–1.66 (2H, m), 1.69–1.82 (2H, m), 2.17 (3H, s), 2.60–2.80 (1H, m), 3.04–3.11 (2H, m), 3.17–3.33 (2H, m), 3.62 (2H, s), 3.75–3.82 (2H, m), 3.87–3.98 (2H, m), 4.10 (2H, q, J=7.0 Hz), 4.14 (1H, s), 7.07 (2H, d, J=8.9 Hz), 7.30 (2H, d, J=8.5 Hz), 7.54 (1H, s), 7.69 (2H, d, J=8.5 Hz), 7.76 (2H, d, J=8.9 Hz), 7.87 (1H, dd, J=8.4, 1.8 Hz), 8.04 (1H, d, J=1.8 Hz), 8.07 (1H, d, J=8.4 Hz), 10.21 (1H, s). IR (KBr) 3263, 1659, 1633, 1605, 1518, 1412, 1317, 1294, 1248, 1128, 825 cm$^{-1}$; Anal. for $C_{34}H_{39}N_2O_8S$; Calcd. C, 64.23; H, 6.18; N, 4.41; Found. C, 64.21; H, 6.19; N, 4.63.

Working Example 62 (Production of Compound 61)

Under argon atmosphere, to a solution of 4-(4-bromo-3-fluorophenyl)morpholine (6.89 g) in THF (50 ml) was added dropwise at −78° C. a solution of 1.6M n-butyllithium in hexane (18.2 ml), and the mixture was stirred for 1 hour. To the mixture was added dropwise a solution of trimethyl borate (9.0 ml) in THF (9 ml). The reaction mixture was allowed to gradually warm to room temperature, and the mixture was stirred at room temperature for 2 hours. To the mixture was added dropwise 1N hydrochloric acid (100 ml), and the mixture was stirred for 30 minutes. To the mixture was added 8N sodium hydroxide solution to make the solution pH 7, and the mixture was extracted with ethyl acetate. The organic layer was washed with saturated brine, dried with magnesium sulfate and concentrated under reduced pressure to give gray crystals, which were collected by filtration. The crystals were washed with diisopropylether to give gray crystals of 3-fluoro-4-morpholinophenyl borate (0.65 g).

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 3-fluoro-4-morpholinophenyl borate (156 mg) and potassium carbonate (160 mg) in toluene/ethanol/water (10/1/1 ml) was stirred at room temperature for 1 hour. To the mixture was added tetrakistriphenylphosphinepalladium (33 mg), and the. mixture was refluxed for 6 hours, cooled, extracted with ethyl acetate and washed with saturated brine. The extract was heated at 70° C., and crystals were dissolved. The solution was dried with magnesium sulfate and concentrated under reduced pressure to give crystals, which were collected by filtration and recrystallized from ethanol to give yellow crystals of 7-(3-fluoro-4-morpholinophenyl)-N-[4-[N-methyl-N-(tetrahydropyran-4-yl)amino]methyl]phenyl]-1,1-dioxo-2,3-dihydro-1-benzothiepine-4-carboxamide (Compound 61) (149 mg).

m.p. 275–277° C. (dec.); $^1$H-NMR (200 MHz, CDCl$_3$) δ 1.64–1.85 (4H, m), 2.22 (3H, s), 2.54–2.77 (1H, m), 3.15–3.19 (6H, m), 3.28–3.44 (2H, m), 3.59 (2H, s), 3.70–3.78 (2H, m), 3.88–3.92 (4H, m), 3.98–4.10 (2H, m), 6.98–7.07 (1H, m), 7.24–7.38 (5H, m), 7.55 (2H, d, J=8.4 Hz), 7.62–7.69 (2H, m), 7.90 (1H, s), 8.21 (1H, d, J=8.0 Hz). IR (KBr) 3253, 1657, 1601, 1520, 1315, 1296, 1126 cm$^{-1}$;

Anal. for $C_{34}H_{38}N_3O_5SF \cdot 0.6\ H_2O$; Calcd. C, 64.76; H, 6.27; N, 6.66; Found. C, 64.54; H, 6.21; N. 6.75.

Working Example 63 (Production of Compound 62)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 3,4-dihydro-2H-1-benzopyran-6-yl borate (113 mg) and potassium carbonate (160 mg) in toluene/ethanol/water (10/1/1 ml) was stirred at room temperature for 1 hour. To the mixture was added tetrakistriphenylphosphinepalladium (33 mg, 0.029 mmol), and the mixture was refluxed for 6 hours, cooled, extracted with ethyl acetate, washed with saturated brine, dried with magnesium sulfate and concentrated under reduced pressure to give crystals, which were collected by filtration and recrystallized from ethanol to give pale yellow crystals of 7-(3,4-dihydro-2H-1-benzopyran-6-yl)-N-[4-[[N-methyl-N-(tetrahydropyran-4-yl)amino]methyl]phenyl]-1,1-dioxo-2,3-dihydro-1-benzothiepine-4-carboxamide (Compound 62) (149 mg).

m.p. 245–249° C.; $^1$H-NMR (200 MHz, CDCl$_3$) δ 1.67–1.83 (4H, m), 1.99–2.11(2H, m), 2.21 (3H, s), 2.52–2.75 (1H, m), 2.84–2.90 (2H, m), 3.10–3.21 (2H, m), 3.31–3.44 (2H, m), 3.58 (2H, s), 3.69–3.74 (2H, m), 3.98–4.09 (2H, m), 4.22–4.27 (2H, m), 6.90 (1H, d, J=8.4 Hz), 7.31–7.36 (5H, m), 7.55 (2H, d, J=8.4 Hz), 7.62–7.69 (2H, m), 7.90 (1H, s), 8.18 (1H, d, J=8.2 Hz). IR (KBr) 3250, 1653, 1632, 1597, 1529, 1510, 1410, 1317, 1294, 1128 cm$^{-1}$; Anal. for $C_{33}H_{36}N_2O_5S$; Calcd. C, 69.21; H, 6.34; N, 4.89; Found. C, 68.81; H, 6.46; N, 4.83.

Working Example 64 (Production of Compound 63)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 2,3,4,5-tetrahydro-1-benzoxepin-7-yl borate (122 mg) and potassium carbonate (160 mg) in toluene/ethanol/water (10/1/1 ml) was stirred at room temperature for 1 hour. To the mixture was added tetrakistriphenylphosphinepalladium (33 mg), and the mixture was refluxed for 7 hours, cooled, extracted with ethyl acetate, washed with saturated brine, dried with magnesium sulfate and concentrated under reduced pressure. The residue was purified with silica gel column chromatography (ethanol/ethyl acetate=1:1) to give crystals, which were recrystallized from ethanol to give colorless crystals of N-[4-[[N-methyl-N-(tetrahydropyran-4-yl)mino]methyl]phenyl]-7-(2,3,4,5-tetrahydro-1-benzoxepin-7-yl)-1,1-dioxo-2,3-dihydro-1-benzothiepine-4-carboxamide (Compound 63) (231 mg).

m.p. 238–242° C.; $^1$H-NMR (200 MHz, CDCl$_3$) 1.68–1.86 (6H, m), 1.94–2.08 (2H, m), 2.22 (3H, s), 2.55–2.76 (1H, m), 2.87–2.92 (2H, m), 3.17 (2H, t, J=6.8 Hz), 3.31–3.44 (2H, m), 3.59 (2H, s), 3.73 (2H, t, J=6.8 Hz), 3.97–4.11 (4H, m), 7.10 (1H, d, J=9.0 Hz), 7.31–7.39 (5H, m), 7.55 (2H, d, J=8.6 Hz), 7.63 (1H, d, J=1.8 Hz), 7.68 (1H, dd, J=8.2, 1.8 Hz), 7.93 (1H, s), 8.20 (1H, d, J=8.2 Hz). IR (KBr) 3235, 1657, 1635, 1601, 1529, 1510, 1483, 1410, 1316, 1292, 1244, 1125 cm$^{-1}$; Anal. for $C_{34}H_{38}N_2O_5S$; Calcd. C, 69.60; H, 6.53; N, 4.77; Found. C, 69.31; H, 6.53; N, 5.01.

Working Example 65 (Production of Compound 64)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 2,2-dimethyl-3,4-dihydro-2H-1-benzopyran-6-yl borate (131 mg) and potassium carbonate (160 mg) in toluene/ethanol/water (10/1/1 ml) was stirred at room temperature for 1 hour. To the mixture was added tetrakistriphenylphosphinepalladium (33 mg, 0.029 mmol), and the mixture was refluxed for 6.5 hours, cooled, extracted with ethyl acetate, washed with saturated brine, dried with magnesium sulfate and concentrated under reduced pressure to give crystals, which were collected by filtration and recrystallized from ethanol to give colorless crystals of 7-(2,2-dimethyl-3,4-dihydro-2H-1-benzopyran-6-yl)-N-[4-[[N-methyl-N-(tetrahydropyran-4-yl)amino]methyl]phenyl]-1,1-dioxo-2,3-dihydro-1-benzothiepine-4-carboxamide (Compound 64) (117 mg).

m.p. 222–226° C.; $^1$H-NMR (200 MHz, CDCl$_3$) δ 1.37 (6H, s), 1.64–1.82 (4H, m), 1.86 (2H, t, J=6.6 Hz), 2.21 (3H, s), 2.55–2.75 (1H, m), 2.82–2.88 (2H, m), 3.16 (2H, t, J=6.6 Hz), 3.31–3.44 (2H, m), 3.58 (2H, s), 3.68–3.75 (2H, m), 3.98–4.11 (2H, m), 6.89 (1H, d, J=8.8 Hz), 7.30–7.37 (5H, m), 7.55 (2H, d, J=8.4 Hz), 7.61–7.67 (2H, m), 7.93 (1H, s), 8.17 (1H, d, J=8.0 Hz). IR (KBr) 3245, 1653, 1605, 1532, 1514, 1410, 1318, 1302, 1122, 820 cm$^{-1}$; Anal. for $C_{35}H_{40}N_2O_5S \cdot 0.2\ H_2O$; Calcd. C, 69.56; H, 6.74; N, 4.64; Found. C, 69.35; H, 6.78; N, 4.76.

Working Example 66 (Production of Compound 65)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 4-(2-ethoxyethoxy)-3-fluorophenyl borate (145 mg) and potassium carbonate (160 mg) in toluene/ethanol/water (10/1/1 ml) was stirred at room temperature for 1 hour. To the mixture was added tetrakistriphenylphosphinepalladium (33 mg), and the mixture was refluxed for 7 hours, cooled, extracted with ethyl acetate, washed with saturated brine, dried with magnesium sulfate and concentrated under reduced pressure. The residue was purified with silica gel column chromatography (ethanol/ethyl acetate=1:3) to give crystals, which were recrystallized from ethanol to give colorless crystals of 7-[4-(2-ethoxyethoxy)-3-fluorophenyl]-N-[4-[[N-methyl-N-(tetrahydropyran-4-yl)amino]methyl]phenyl]-1,1-dioxo-2,3-dihydro-1-benzothiepine-4-carboxamide (Compound 65) (244 mg).

m.p. 212–214° C.; $^1$H-NMR (200 MHz, CDCl$_3$) δ 1.25 (3H, t, J=7.2 Hz), 1.68–1.82 (4H, m), 2.21 (3H, s), 2.54–2.76 (1H, m), 3.14–3.21 (.2H, m), 3.30–3.44 (2H, m), 3.58 (2H, s), 3.63 (2H, q, J=7.2 Hz), 3.70–3.76 (2H, m), 3.85 (2H, t, J=4.9 Hz), 3.98–4.10 (2H, m), 4.26 (2H, t, J=4.7 Hz), 7.06–7.15 (1H, m), 7.27–7.39 (5H, m), 7.55 (2H, d, J=8.8 Hz), 7.61–7.67 (2H, m), 7.91 (1H, s), 8.21 (1H, d, J=8.0 Hz). IR (KBr) 3243, 1651, 1630, 1599, 1526, 1410, 1318, 1294, 1281, 1128 cm$^{-1}$; Anal. for $C_{34}H_{39}N_2O_6SF$; Calcd. C, 65.57; H, 6.31; N, 4.50; Found. C, 65.28; H, 6.18; N, 4.50.

Working Example 67 (Production of Compound 66)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 3,4-dihydro-2H-1,5-benzodioxepin-7-yl borate (123 mg) and potassium carbonate (160 mg) in toluene/ethanol/water (10/1/1 ml) was stirred at room temperature for 1 hour. To the mixture was added tetrakistriphenylphosphine-palladium (33 mg), and the mixture was refluxed for 6 hours, cooled, extracted with ethyl acetate, washed with saturated brine, dried with magnesium sulfate and concentrated under reduced pressure. The residue was purified with silica gel column chromatography (ethanol/ethyl acetate=1:3) to give crystals, which were recrystallized from ethanol to give colorless crystals of 7-(3,4-dihydro-2H-1,5-benzodioxepin-7-yl)-N-[4-[[N-methyl-N-(tetrahydropyran-4-yl)amino]methyl]phenyl]-1,1-dioxo-2,3-dihydro-1-benzothiepine-4-carboxamide (Compound 66) (194 mg).

m.p. 242–245° C.; $^1$H-NMR (200 MHz, CDCl$_3$) δ 1.66–1.83 (4H, m), 2.21 (3H, S), 2.18–2.29 (2H, m), 2.55–2.72 (1H, m), 3.13–3.20 (2H, m), 3.31–3.44 (2H, m), 3.57 (2H, s), 3.68–3.75 (2H, m), 3.98–4.09 (2H, m), 4.26–4.31 (4H, m), 7.06 (1H, d, J=8.4 Hz), 7.17 (1H, dd, J=8.8, 2.2 Hz), 7.23 (1H, d, J=2.2 Hz), 7.30–7.35 (3H, m), 7.54 (2H, d, J=8.4 Hz), 7.60–7.67 (2H, m), 7.83 (1H, s), 8.19 (1H, d, J=8.4 Hz). IR (KBr) 3248, 1651, 1632, 1601, 1532, 1510, 1410, 1317, 1298, 1267, 1125 cm$^{-1}$; Anal. for C$_{33}$H$_{36}$N$_2$O$_6$S; Calcd. C, 67.33; H, 6.16; N, 4.76; Found. C, 66.96; H, 6.32; N, 4.74.

Working Example 68 (Production of Compound 67)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 3-chloro-4-(2-ethoxyethoxy)phenyl borate (156 mg) and potassium carbonate (160 mg) in toluene/ethanol/water (10/1/1 ml) was stirred at room temperature for 1 hour. To the mixture was added tetrakistriphenylphosphinepalladium (33 mg), and the mixture was refluxed for 6 hours, cooled, extracted with ethyl acetate, washed with saturated brine, dried with magnesium sulfate and concentrated under reduced pressure. The residue was purified with silica gel column chromatography (ethanol/ethyl acetate=1:3) and recrystallized from ethanol to give colorless crystals of 7-[3-chloro-4-(2-ethoxyethoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 67) (269 mg).

m.p. 203–205° C.; $^1$H-NMR (200 MHz, CDCl$_3$) δ 1.26 (3H, t, J=7.1 Hz), 1.68–1.82 (4H, m), 2.21 (3H, s), 2.55–2.76 (1H, m), 3.14–3.21 (2H, m), 3.31–3.44 (2H, m), 3.58 (2H, s), 3.66 (2H, q, J=7.1 Hz), 3.69–3.76 (2H, m), 3.85–3.90 (2H, m), 3.99–4.10 (2H, m), 4.23–4.28 (2H, m), 7.07 (1H, d, J=8.8 Hz), 7.31–7.35 (3H, m), 7.45 (1H, dd, J=8.8, 2.2 Hz), 7.54 (2H, d, J=8.4 Hz), 7.61–7.68 (3H, m), 7.78 (1H, s), 8.21 (1H. d. J=8.2 Hz). IR (KBr) 3250, 1651, 1632, 1601, 1527, 1510, 1482, 1410, 1318, 1294, 1273, 11300 cm$^{-1}$; Anal. for C$_{34}$H$_{39}$N$_2$O$_6$SC; Calcd. C, 63.89; H, 6.15; N, 4.38; Found. C, 63.73; H, 6.19; N, 4.39.

Working Example 69 (Production of Compound 68)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 4-(tetrahydropyran-4-yloxy)phenyl borate (141 mg) and potassium carbonate (160 mg) in toluene/ethanol/water (10/1/1 ml) was stirred at room temperature for 1 hour. To the mixture was added tetrakistriphenylphosphinepalladium (33 mg), and the mixture was refluxed for 6 hours, cooled, extracted with ethyl acetate, washed with saturated brine, dried with magnesium sulfate and concentrated under reduced pressure. The residue was purified with silica gel column chromatography (ethanol/ethyl acetate=1:3) to give crystals, which were recrystallized from ethanol to give colorless crystals of N-[4-[[N-methyl-N-(tetrahydropyran-4-yl)amino]methyl]phenyl]-7-[4-(tetrahydropyran-4-yloxy)phenyl]-1,1-dioxo-2,3-dihydro-1-benzothiepine-4-carboxamide (Compound 68) (274 mg).

m.p. 227–229° C.; $^1$H-NMR (200 MHz, CDCl$_3$) δ 1.63–1.92 (6H, m), 1.99–2.15 (2H, m), 2.21 (3H, s), 2.55–2.76 (1H, m), 3.13–3.21 (2H, m), 3.31–3.44 (2H, m), 3.57 (2H, s), 3.59–3.75 (4H, m), 3.95–4.11 (4H, m), 4.50–4.63 (1H, m), 7.03 (2H, d, J=8.8 Hz), 7.31–7.35 (3H, m), 7.52–7.56 (4H, m), 7.62–7.68 (2H, m), 7.79 (1H, s), 8.20 (1H, d, J=8.0 Hz). IR (KBr) 3243, 1655, 1638, 1603, 1518, 1410, 1316, 1292, 1250, 1130 cm$^{-1}$; Anal. for C$_{35}$H$_{40}$N$_2$O$_6$S; Calcd. C, 68.16; H, 6.54; N, 4.54; Found. C, 67.95; H, 6.57; N, 4.56.

Working Example 70 (Production of Compound 69)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 4-[N-(2-ethoxyethyl)-N-ethylamino]phenyl borate (410 mg) and potassium carbonate (400 mg) in toluene/ethanol/water (10/1/1 ml) was stirred at room temperature for 1 hour. To the mixture was added tetrakistriphenylphosphinepalladium (50 mg), and the mixture was refluxed for 8 hours, cooled, extracted with ethyl acetate, washed with saturated brine, dried with magnesium sulfate and concentrated under reduced pressure. The residue was purified with silica gel column chromatography (ethanol/ethyl acetate= 1:3) to give crystals, which were recrystallized from ethanol to give yellow crystals of 7-[4-[N-(2-ethoxyethyl)-N-ethylamino]phenyl]-N-[4-[[N-methyl-N-(tetrahydropyran-4-yl)amino]methyl]phenyl]-1,1-dioxo-2,3-dihydro-1-benzothiepine-4-carboxamide (Compound 69) (260 mg).

m.p. 194–197° C.; $^1$H-NMR (200 MHz, CDCl$_3$) δ 1.21 (3H, t, J=7.0 Hz), 1.22 (3H, t, J=7.0 Hz), 1.68–1.83 (4H, m), 2.21 (3H, s), 2.52–2.73 (1H, m), 3.15 (2H, t, J=6.8 Hz), 3.31–3.64 (12H, m), 3.71 (2H, t, J=6.8 Hz), 3.98–4.10 (2H, m), 6.77 (2H, d, J=9.2 Hz), 7.30–7.34 (3H, m), 7.47–7.66 (6H, m), 7.90 (1H, s), 8.13 (1H, d, J=8.4 Hz). IR (KBr) 3281, 1655, 1637, 1607, 1591, 1526, 1412, 1318, 1294, 1128, 810 cm$^{-1}$; Anal. for C$_{36}$H$_{45}$N$_3$O$_5$S.0.3 H$_2$O; Calcd. C, 67.86; H, 7.21; N, 6.59; Found. C, 67.74; H, 6.91; N, 6.67.

Working Example 71 (Production of Compound 70)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 4-[N-(2-ethoxyethyl)-N-methylamino]phenyl borate (168 mg) and potassium carbonate (176 mg) in toluene/ethanol/water (10/1/1 ml) was stirred at room temperature for 1 hour. To the mixture was added tetrakistriphenylphosphinepalladium (33 mg), and the mixture was refluxed for 8 hours, cooled, extracted with ethyl acetate, washed with saturated brine, dried with magnesium sulfate and concentrated under reduced pressure. The residue was purified with silica gel column chromatography (ethanol/ethyl acetate= 1:3) to give crystals, which were recrystallized from ethanol to give yellow crystals of 7-[4-[N-(2-ethoxyethyl)-N-methylamino]phenyl]-N-[4-[[N-methyl-N-(tetrahydropyran-4-yl)amino]methyl]phenyl]-1,1-dioxo-2,3-dihydro-1-benzothiepine-4-carboxamide (Compound 70) (235 mg).

m.p. 190–192° C.; $^1$H-NMR (200 MHz, CDCl$_3$) δ 1.20 (3H, t, J=7.0 Hz), 1.67–1.84 (4H, m), 2.21 (3H, s), 2.55–2.75

(1H, m), 3.06 (3H, s), 3.15 (2H, t, J=6.6 Hz), 3.31–3.44 (2H, m), 3.46–3.63 (8H, m), 3.68–3.74 (2H, m), 3.99–4.09 (2H, m), 6.80 (2H, d, J=9.0 Hz), 7.30–7.35 (3H, m), 7.49–7.67 (6H, m), 7.87 (1H, s), 8.14 (1H, d, J=8.0 Hz). IR (KBr) 3275, 1655, 1636, 1609, 1591, 1526, 1508, 1318, 1292, 1128, 810 cm$^{-1}$; Anal. for $C_{35}H_{43}N_3O_5S$; Calcd. C, 68.04; H, 7.02; N, 6.80; Found. C, 67.68; H, 6.72; N, 6.89.

Working Example 72 (Production of Compound 71)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (200 mg), 4-[N-ethyl-N-(2-propoxyethyl)amino]phenyl borate (290 mg) and potassium carbonate (266 mg) in toluene/ethanol/water (10/1/1 ml) was stirred at room temperature for 1 hour. To the mixture was added tetrakistriphenylphosphinepalladium (40 mg), and the mixture was refluxed for 8 hours, cooled, extracted with ethyl acetate, washed with saturated brine, dried with magnesium sulfate and was concentrated under reduced pressure. The residue was purified with silica gel column chromatography (ethanol/ethyl acetate=1:3) to give crystals, which were recrystallized from ethanol to give pale yellow crystals of 7-[4-[N-ethyl-N-(2-propoxyethyl)amino]phenyl]-N-[4-[[N-methyl-N-(tetrahydropyran-4-yl)amino]methyl]phenyl]-1,1-dioxo-2,3-dihydro-1-benzothiepine-4-carboxamide (Compound 71) (89 mg).

m.p. 172–175° C.; $^1$H-NMR (200 MHz, CDCl$_3$) δ 0.93 (3H, t, J=7.3 Hz), 1.21 (3H, t, J=7.0 Hz), 1.53–1.83 (6H, m), 2.21 (3H, s), 2.55–2.74 (1H, m), 3.12–3.19 (2H, m), 3.31–3.63 (12H, m), 3.68–3.74 (2H, m), 3.99–4.11 (2H, m), 6.77 (2H, d, J=9.0 Hz), 7.30–7.35 (3H, m), 7.48–7.69 (6H, m), 7.88 (1H, s), 8.14 (1H, d, J=8.2 Hz). IR (KBr) 3281, 1655, 1607, 1590, 1524, 1410, 1318, 1294, 1128, 810 cm$^{-1}$; Anal. for $C_{37}H_{47}N_3O_5S$; Calcd. C, 68.81; H, 7.33; N, 6.51; Found. C, 68.77; H, 7.25; N, 6.60.

Working Example 73 (Production of Compound 72)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 4-[N-methyl-N-(2-propoxyethyl)amino]phenyl borate (205 mg) and potassium carbonate (176 mg) in toluene/ethanol/water (10/1/1 ml) was stirred at room temperature for 1 hour. To the mixture was added tetrakistriphenylphosphinepalladium (40 mg), and the mixture was refluxed for 8 hours, cooled, extracted with ethyl acetate, washed with saturated brine, dried with magnesium sulfate and was concentrated under reduced pressure. The residue was purified with silica gel column chromatography (ethanol/ethyl acetate=1:4) to give crystals, which were recrystallized from ethanol to give pale yellow crystals of 7-[4-[N-methyl-N-(2-propoxyethyl)amino]phenyl]-N-[4-[[N-methyl-N-(tetrahydropyran-4-yl)amino]methyl]phenyl]-1,1-dioxo-2,3-dihydro-1-benzothiepine-4-carboxamide (Compound 72) (210 mg).

m.p. 193–194° C.; $^1$H-NMR (200 MHz, CDCl$_3$) δ 0.91 (3H, t, J=7.4 Hz), 1.53–1.83 (6H, m), 2.21 (3H, s), 2.53–2.76 (1H, m), 3.07 (3H, s), 3.16 (2H, t, J=6.8 Hz), 3.31–3.44 (4H, m), 3.58–3.62 (6H, m), 3.68–3.75 (2H, m), 3.99–4.12 (2H, m), 6.80 (2H, d, J=9.0 Hz), 7.31–7.35 (3H, m), 7.50–7.57 (4H, m), 7.61 (1H, d, J=1.7 Hz), 7.66 (1H, dd, J=8.3, 1.7 Hz), 7.87 (1H, s), 8.15 (1H, d, J=8.3 Hz). IR (KBr) 3281, 1655, 1638, 1609, 1591, 1526, 1410, 1318, 1294, 1128, 810 cm$^{-1}$; Anal. for $C_{36}H_{45}N_3O_5S$; Calcd. C, 68.43; H, 7.18; N, 6.65; Found. C, 68.50; H, 7.18; N, 6.79.

Working Example 74 (Production of Compound 73)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300mg), 3-ethoxy-4-(2-propoxyethoxy)phenyl borate (171 mg) and potassium carbonate (160 mg) in toluene/ethanol/water (10/1/1 ml) was stirred at room temperature for 1 hour. To the mixture was added tetrakistriphenylphosphinepalladium (33 mg), and the mixture was refluxed for 6 hours, cooled, extracted with ethyl acetate, washed with saturated brine, dried with magnesium sulfate and was concentrated under reduced pressure. The residue was purified with silica gel column chromatography (ethanol/ethyl acetate=1:3) to give crystals, which were recrystallized from ethanol to give colorless crystals of 7-[3-ethoxy-4-(2-propoxyethoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 73) (237 mg).

m.p. 171–172° C.; $^1$H-NMR (200 MHz, CDCl$_3$) δ 0.94 (3H, t, J=7.3 Hz), 1.47 (3H, t, J=7.0 Hz), 1.58–1.83 (6H, m), 2.21 (3H, s), 2.56–2.73 (1H, m), 3.14–3.21 (2H, m), 3.30–3.45 (2H, m), 3.52 (2H, t, J=6.8 Hz), 3.58 (2H, s), 3.68–3.75 (2H, m), 3.85 (2H, t, J=4.9 Hz), 3.99–4.10 (2H, m), 4.16 (2H, q, J=7.0 Hz), 4.23 (2H, t, J=4.9 Hz), 7.01 (1H, d, J=8.0 Hz), 7.10–7.15 (2H, m), 7.31–7.35 (3H, m), 7.55 (2H, d, J=8.4 Hz), 7.59 (1H, d, J=2.0 Hz), 7.64 (1H, dd, J=8.0, 2.0 Hz), 7.86 (1H, s), 8.18 (1H, d, J=8.0 Hz). IR (KBr) 3324, 1651, 1595, 1520, 1316, 1291, 1254, 1128, 810 cm$^{-1}$; Anal. for $C_{37}H_{46}N_2O_7S$; Calcd. C, 67.04; H, 6.99;N, 4.23; Found. C, 66.75; H, 7.02; N, 4.22.

Working Example 75 (Production of Compound 74)

Under argon atmosphere, a mixture of 7-bromo-N-[4-[[N-methyl-N-(tetrahydropyran-4-yl)amino]methyl]phenyl]-1,1-dioxo-2,3-dihydro-1-benzothiepine-4-carboxamide (300 mg), 3-chloro-4-(2-propoxyethoxy)phenyl borate (164 mg) and potassium carbonate (160 mg) in toluene/ethanol/water (10/1/1 ml) was stirred at room temperature for 1 hour. To the mixture was added tetrakistriphenylphosphinepalladium (33 mg), and the mixture was refluxed for 6 hours, cooled, extracted with ethyl acetate, washed with saturated brine, dried with magnesium sulfate and concentrated under reduced pressure to give crystals, which were collected by filtration and recrystallized from ethanol to give colorless crystals of 7-[3-chloro-4-(2-propoxyethoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 74) (255 mg).

m.p. 183–184° C.; $^1$H-NMR (200 MHz, CDCl$_3$) δ 0.95 (3H, t, J=7.4 Hz), 1.54–1.82 (6H, m), 2.21 (3H, s), 2.55–2.72 (1H, m), 3.14–3.20 (2H, m), 3.31–3.44 (2H, m), 3.55 (2H, t, J=6.8 Hz), 3.57 (2H, s), 3.69–3.75 (2H, m), 3.87 (2H, t, J=4.9 Hz), 3.99–4.09 (2H, m), 4.26 (2H, t, J=4.9 Hz), 7.07 (1H, d, J=8.6 Hz), 7.30–7.35 (3H, m), 7.45 (1H, dd, J=8.6, 2.4 Hz), 7.54 (2H, d, J=8.4 Hz), 7.60–7.67 (3H, m), 7.82 (1H, s), 8.20 (1H, d, J=8.0 Hz). IR (KBr) 3241, 1651, 1634, 1601, 1507, 1410, 1318, 1294, 1130 cm$^{-1}$; Anal. for $C_{35}H_{41}N_2O_6SCl$; Calcd. C, 64.35; H, 6.33; N, 4.29; Found. C, 64.24; H, 6.38; N, 4.25.

Working Example 76 (Production of Compound 75)

Under argon atmosphere, a mixture of 7-bromo-N-[4-[[N-methyl-N-(tetrahydropyran-4-yl)amino]methyl]phenyl]-1, 1-dioxo-2,3-dihydro-1-benzothiepine-4-carboxamide (300 mg), 3-methyl-4-(2-propoxyethoxy)phenyl borate (151 mg) and potassium carbonate (160 mg) in toluene/ethanol/water (10/1/1 ml) was stirred at room temperature for 1 hour. To the mixture was added tetrakistriphenylphosphinepalladium (33 mg), and the mixture was refluxed for 8 hours, cooled, extracted with ethyl acetate, washed with saturated brine, dried with magnesium sulfate and concentrated under reduced pressure. The residue was purified with silica gel column chromatography (ethanol/ethyl acetate=1:3) to give crystals, which were recrystallized from ethanol to give colorless crystals of 7-[3-methyl-4-(2-propoxyethoxy) phenyl]-N-[4-[[N-methyl-N-(tetrahydropyran-4-yl)amino] methyl]phenyl]- 1,1-dioxo-2,3-dihydro-1-benzothiepine-4-carboxamide (Compound 75) (261 mg).

m.p. 192–195° C.; $^1$H-NMR (200 MHz, CDCl$_3$) δ 0.95 (3H, t, J=7.3 Hz), 1.56–1.83 (6H, m), 2.21 (3H, s), 2.31 (3H, s), 2.54–2.74 (1H, m), 3.16 (2H, t, J=6.6 Hz), 3.30–3.45 (2H, m), 3.53 (2H, t, J=6.6 Hz), 3.57 (2H, s), 3.72 (2H, t, J=6.6 Hz), 3.82–3.87 (2H, m), 3.98–4.09 (2H, m), 4.16–4.21 (2H, m), 6.93 (1H, d, J=9.2 Hz), 7.30–7.43 (5H, m), 7.54 (2H, d, J=8.4 Hz), 7.62–7.68 (2H, m), 7.85 (1H, s), 8.18 (1H, d, J=8.4 Hz). IR (KBr) 3279, 1661, 1603, 1534, 1514, 1313, 1291, 1254, 1132 cm$^{-1}$; Anal. for C$_{36}$H$_{44}$N$_2$O$_6$S; Calcd. C, 68.33; H, 7.01; N, 4.43; Found. C, 68.30; H, 6.92; N, 4.45.

Working Example 77 (Production of Compound 76)

To a solution of N-[4-[[N-methyl-N-(tetrahydropyran-4-yl)amino]methyl]phenyl]-7-(4-propoxyphenyl)-1,1-dioxo-2,3-dihydro-1-benzothiepine-4-carboxamide (17.6 g) in THF (1160 ml) was added at room temperature 6N hydrochloric acid (10 ml), and the mixture was stirred for 2 hours. Precipitated crystals were collected by filtration and washed with THF and diisopropylether to give colorless crystals, which were recrystallized from ethanol/water to give colorless crystals of N-[4-[[N-methyl-N-(tetrahydropyran-4-yl) amino]methyl]phenyl]-7-(4-propoxyphenyl)-1,1-dioxo-2,3-dihydro-1-benzothiepine-4-carboxamide hydrochloride (Compound 76) (13.2 g).

m.p. 259–273° C. (dec.); $^1$H-NMR (200 MHz, DMSO-d$_6$) δ 1.00 (3H, t, J=7.3 Hz), 1.67–1.91 (4H, m), 1.94–2.16 (2H, m), 2.57–2.59 (3H, m), 3.01–3.12 (2H, m), 3.21–3.51 (3H, m), 3.76–3.83 (2H, m), 3.97–4.19 (5H, m), 4.37–4.48 (1H, m), 7.08 (2H, d, J=8.8 Hz), 7.56–7.60 (3H, m), 7.74–7.90 (5H, m), 8.05–8.09 (2H, m), 10.23–10.39 (1H, m), 10.44 (1H, s). IR (KBr) 3218, 1669, 1595, 1522, 1319, 1294, 1258, 1168, 1132, 831 cm$^{-1}$; Anal. for C$_{33}$H$_{39}$N$_2$O$_5$SCl; Calcd. C, 64.85; H, 6.43; N, 4.58; Cl, 5.80; Found. C, 64.84; H, 6.50; N, 4.34; Cl, 5.61.

Working Example 78 (Production of Compound 77)

To a suspension of 7-(4-ethoxyphenyl)-1,1-dioxo-2,3-dihydro-1-benzothiepine-4-carboxylic acid (200 mg) in THF (5 ml) were added at room temperature thionyl chloride (0.05 ml) and a drop of DMF, and the mixture was stirred for 1 hour. The solvent was evaporated under reduced pressure, and the residue was dissolved in THF (10 ml). The solution was added dropwise at room temperature to a suspension of 4-[[N-(3-ethoxypropyl)-N-methylamino]methyl]aniline dihydrochloride (181 mg) and triethylamine (0.39 ml) in THF (2 ml), and the mixture was stirred for 4 hours. To the mixture was added water, and the mixture was extracted with ethyl acetate. The organic layer was washed with saturated brine, dried with magnesium sulfate and concentrated under reduced pressure. The residue was purified with silica gel column chromatography (ethanol/ethyl acetate= 1:2) and recrystallized from ethanol to give colorless crystals of 7-(4-ethoxyphenyl)-N-[4-[[N-(3-ethoxypropyl)-N-methylamino]methyl]phenyl]-1,1-dioxo-2,3-dihydro-1-benzothiepine-4-carboxamide (Compound 77) (161 mg).

m.p. 197–198° C.; $^1$H-NMR (200 MHz, CDCl$_3$) δ 1.19 (3H, t, J=7.0 Hz), 1.45 (3H, t, J=7.0 Hz), 1.73–1.88 (2H, m), 2.19 (3H, s), 2.45 (2H, t, J=7.4 Hz), 3.16 (2H, t, J=6.8 Hz), 3.42–3.52 (6H, m), 3.71 (2H, t, J=6.8 Hz), 4.10 (2H, q, J=7.0 Hz), 7.00 (2H, d, J=8.8 Hz), 7.29–7.34 (3H, m), 7.53 (2H, d, J=8.8 Hz), 7.54 (2H, d, J=8.4 Hz), 7.60 (1H, d, J=1.8 Hz), 7.65 (1H, dd, J=8.0, 1.8 Hz), 7.95 (1H, br s), 8.18 (1H, d, J=8.0 Hz). IR (KBr) 3338, 1651, 1606, 1518, 1311, 1292, 1252, 1165, 1128, 820 cm$^{-1}$; Anal. for C$_{32}$H$_{38}$N$_2$O$_5$S; Calcd. C, 68.30; H, 6.81; N, 4.98; Found. C, 68.20; H, 6.75; N, 4.93.

Reference Example 95

In DMF (100 ml) was dissolved 4-bromobenzenethiol (10.0 g), and to the mixture was added at room temperature potassium carbonate (9.5 g). To the mixture was added dropwise 1-iodopentane (8.3 ml), and the mixture was stirred for 2 hours. The reaction mixture was added to water, and the mixture was extracted with ethyl acetate, washed with saturated brine and dried with magnesium sulfate. Under reduced pressure, the solvent was evaporated, and the residue was dissolved in THF (112 ml). To the solution was added dropwise at −78° C. 1.6M n-butyllithium/hexane (32.9 ml), and the mixture was stirred for 1 hour. To the mixture was added dropwise a solution of trimethyl borate (14.9 g) in THF (30 ml), and the mixture was stirred for 30 minutes and warmed to room temperature. To the mixture was added 10% sulfuric acid (61 ml), and the mixture was stirred for 15 minutes. The reaction solution was extracted with ethyl acetate, washed with saturated brine and dried with magnesium sulfate. Under reduced pressure, the solvent was evaporated, and the residue was washed with hexane/isopropylether to give 4-(pentylthio)phenyl borate (5.6 g).

$^1$H-NMR (200 MHz, CDCl$_3$) δ 0.92 (3H, t, J=7.0 Hz), 1.23–1.52 (4H, m), 1.65–1.81 (2H, m), 3.01 (2H, t, J=7.4 Hz), 7.38 (2H, d, J=8.4 Hz), 8.10 (2H, d, J=8.4 Hz).

Working Example 79 (Production of Compound 78)

To 7-bromo-N-[4-[[N-methyl-N-(tetrahydropyran-4-yl) amino]methyl]phenyl]-1,1-dioxo-2,3-dihydro-1-benzothiepine-4-carboxamide (310 mg) was added toluene/ethanol/water (10/1/1, 6.0 ml) and then were added 4-(pentylthio)phenyl borate (182 mg) and potassium carbonate (181 mg), and the mixture was stirred at room temperature for 30 minutes. To the mixture was added tetrakistriphenylphosphinepalladium (34 mg), and the mixture was stirred at 100° C. for 12 hours and cooled to room temperature. The mixture was added to water, and the mixture was extracted with ethyl acetate/THF, washed with saturated brine and dried with magnesium sulfate. Under reduced pressure, the solvent was evaporated, and the residue was purified with silica gel column chromatography (ethyl acetate/ethanol=3/1) and recrystallized from ethanol to give N-[4-[[N-methyl-N-(tetrahydropyran-4-yl)amino] methyl]phenyl]-7-(4-pentylthiophenyl)-1,1-dioxo-2,3-dihydro-1-benzothiepine-4-carboxamide (Compound 78) (161 mg).

m.p. 204–206° C.; $^1$H-NMR (200 MHz, CDCl$_3$) δ 0.91 (3H, t, J=7.0 Hz), 1.23–1.49 (4H, m), 1.62–1.76 (6H, m), 2.21 (3H, s), 2.65 (1H, m), 2.98 (2H, t, J=7.4 Hz), 3.12–3.20 (2H, m), 3.31–3.43 (2H, m), 3.57 (2H, s), 3.68–3.75 (2H, m), 4.00–4.08 (2H, m), 7.29–7.41 (5H, m), 7.48–7.68 (6H, m), 8.00 (1H, s), 8.20 (1H, d, J=8.0 Hz). IR(KBr) 3252, 2951, 1653, 1597, 1526, 1410,1317, 1294, 1130, 814 cm$^{-1}$; Anal. for $C_{35}H_{42}N_2O_4S_2$; Calcd. C, 67.93; H, 6.84; N, 4.53; Found. C, 67.84; H, 6.84; N, 4.52.

Reference Example 96

In DMF (100 ml) was dissolved 4-bromobenzenethiol (10.1 g), and to the solution was added at room temperature potassium carbonate (9.6 g). To the mixture was added dropwise 1-iodohexane (9.5 ml), and the mixture was stirred for 2 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=2/1) to give 1-bromo-4-(hexylthio) benzene (14.2 g). In THF (127 ml) was dissolved 1-bromo-4-(hexylthio)benzene (14.1 g), and to the solution was added dropwise at −78° C. 1.6M n-butyllithium/hexane (35.5 ml), and the mixture was stirred for 1 hour. To the mixture was added dropwise a solution of trimethyl borate (16.1 g) in THF (32 ml), and the mixture was stirred for 30 minutes and warmed to room temperature. To the mixture was added 10% sulfuric acid (70.5 ml), and the mixture was stirred for 15 minutes. The reaction mixture was extracted with ethyl acetate, washed with saturated brine and dried with magnesium sulfate. Under reduced pressure, the solvent was evaporated, and the residue was washed with hexane/isopropylether to give 4-(hexylthio)phenyl borate (6.6 g).

$^1$H-NMR (200 MHz, CDCl$_3$) δ 0.90 (3H, t, J=6.4 Hz), 1.26–1.76 (8H, m), 3.01 (2H, t, J=7.37 (2H, d, J=8.0 Hz), 8.09 (2H, d, J=8.0 Hz).

Working Example 80 (Production of Compound 79)

To 7-bromo-N-[4-[[N-methyl-N-(tetrahydropyran-4-yl) amino]methyl]phenyl]-1,1-dioxo-2,3-dihydro-1-benzothiepine-4-carboxamide (320 mg) was added toluene/ethanol/water (10/1/1, 12 ml) and then were added 4-(hexylthio)phenyl borate (199 mg) and potassium carbonate (187 mg), and the mixture was stirred at room temperature for 30 minutes. To the mixture was added tetrakistriphenylphosphinepalladium (36 mg), and the mixture was stirred at 100° C. for 14 hours and cooled to room temperature. The mixture was added to water, and the mixture was extracted with ethyl acetate/THF, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-(4-hexylthiophenyl)-N-[4-[[N-methyl-N-(tetrahydropyran-4-yl)amino]methyl]phenyl]-1,1-dioxo-2,3-dihydro-1-benzothiepine-4-carboxamide (Compound 79) (298 mg).

m.p. 205–207° C.; $^1$H-NMR (200 MHz, CDCl$_3$) δ 0.90 (3H, t, J=6.4 Hz), 1.30–1.50 (4H, m), 1.62–1.76 (6H, m), 2.20 (3H, s), 3.31–3.44 (2H, m), 3.56 (2H, s), 3.66–3.74 (2H, m), 4.00–4.08 (2H, m), 7.28–7.40 (5H, m), 7.46–7.66 (6H, m), 8.04 (1H, s), 8.18 (1H, d, J=8.0 Hz); IR(KBr) 3275, 2951, 1655, 1597, 1526, 1410, 1318, 1294, 1130, 814 cm$^{-1}$; Anal. for $C_{36}H_{44}N_2O_4S_2$; Calcd. C, 68.32; H, 7.01; N, 4.43; Found. C, 68.35; H, 7.13; N, 4.47.

Reference Example 97

In THF (200 ml) was dissolved 4-bromobenzyl alcohol (19.8 g), and to the solution was added under ice-cooling 65% sodium hydride (3.6 g). The mixture was stirred at room temperature for 30 minutes, and to the mixture was added dropwise under ice-cooling iodomethane (8.0 ml). The mixture was stirred at room temperature for 2 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=12/1) to give 1-bromo-4-(methoxymethyl) benzene (14.8 g). In THF (10 ml) was dissolved 1-bromo-4-(methoxymethyl)benzene (12.8 g), and to the mixture was added dropwise at−78° C. 1.6M n-butyllithium/hexane (42.4 ml). The mixture was stirred for 1 hour, and to the mixture was added dropwise a solution of trimethyl borate (19.2 g) in THF (38.4 ml). The mixture was stirred for30 minutes and warmed to room temperature. To the mixture was added 5% sulfuric acid (124 ml), and the mixture was stirred for 15 minutes. The reaction mixture was extracted with ethyl acetate, washed with saturated brine and dried with magnesium sulfate. Under reduced pressure, the solvent was evaporated, and the residue was washed with hexane/isopropylether to give 4-(methoxymethyl)phenyl borate (6.3 g).

$^1$H-NMR (200 MHz, CDCl$_3$) δ 3.09 (3H, s), 4.41 (2H, s), 7.27 (2H, d, J=8.0 Hz), 7.77 (2H, d, J=8.0 Hz).

Working Example 81 (Production of Compound 80)

To 7-bromo-N-[4-[[N-methyl-N-(tetrahydropyran-4-yl) amino]methyl]phenyl]-1,1-dioxo-2,3-dihydro-1-benzothiepine-4-carboxamide (220 mg) was added toluene/ethanol/water (10/1/1, 6 ml) and then were added 4-(methoxymethyl)phenyl borate (86 mg) and potassium carbonate (123 mg), and the mixture was stirred at room temperature for 30 minutes. To the mixture was added tetrakistriphenylphosphinepalladium (19 mg), and the mixture was stirred at 90° C. for 9 hours and cooled to room temperature. The mixture was added to water, and the mixture was extracted with ethyl acetate/THF, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-(4-methoxymethylphenyl)-N-[4-[[N-methyl-N-(tetrahydropyran-4-yl)amino]methyl]phenyl]-1,1-dioxo-2,3-dihydro-1-benzothiepine-4-carboxamide (Compound 80) (99 mg).

m.p. 227–229° C.; $^1$H-NMR (200 MHz, CDCl$_3$) δ 1.60–1.82 (4H, m), 2.21 (3H, s), 2.66 (1H, m), 3.13–3.22 (2H, m), 3.30–3.45 (2H, m), 3.44 (3H, s), 3.69–3.78 (2H, m), 4.00–4.08 (2H, m), 4.53 (2H, s), 7.26–7.38 (3H, m), 7.44–7.74 (8H, m), 7.92 (1H, s), 8.23 (1H, d, J=8.0 Hz); IR(KBr) 3239, 29198, 2840, 1655, 1601, 1530, 1412, 1318, 1294, 1130, 816 cm$^{-1}$; Anal. for $C_{32}H_{36}N_2O_5S$; Calcd. C, 68.55; H, 6.47; N, 5.00; Found. C, 68.37; H, 6.38; N, 5.05.

Reference Example 98

In THF (100 ml) was dissolved 4-bromophenethyl alcohol (10 g). To the mixture was added under ice-cooling 65% sodium hydride (1.7 g), and the mixture was stirred at room temperature for 30 minutes. To the mixture was added dropwise under ice-cooling iodomethane (3.7 ml), and the mixture was stirred at room temperature for 1.5 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=6/1) to give 1-bromo-4-(2-methoxyethyl)benzene (8.3 g). In THF (100 ml) was dissolved 1-bromo-4-(2-methoxyethyl) benzene (8.2 g). To the mixture was added dropwise at −78° C. 1.6M n-butyllithium/hexane (26.0 ml), and the mixture was stirred for 1 hour. To the mixture was added dropwise a solution of trimethyl borate (11.8 g) in THF (12 ml), and the mixture was stirred for 30 minutes and warmed to room temperature. To the mixture was added 10% sulfuric acid (40 ml), and the mixture was stirred for 15 minutes. The reaction mixture was extracted with ethyl acetate, washed with saturated brine and dried with magnesium sulfate. Under reduced pressure, the solvent was evaporated, and the residue was washed with hexane/isopropylether to give 4-(2-methoxyethyl)phenyl borate (3.7 g).

$^1$H-NMR (200 MHz, CDCl$_3$) δ 2.98 (2H, t, J=6.8 Hz), 3.38 (3H, s), 3.67 (2H, t, J=6.8 Hz), 7.37 (2H, d, J=7.6 Hz), 8.16 (2H, d, J=7.6 Hz).

Working Example 82 (Production of Compound 81)

To 7-bromo-N-[4-[[N-methyl-N-(tetrahydropyran-4-yl)amino]methyl]phenyl]-1,1-dioxo-2,3-dihydro-1-benzothiepine-4-carboxamide (420 mg) was added toluene/ethanol/water (10/1/1, 16.2 ml) and then were added 4-(2-methoxyethyl)phenyl borate (216 mg) and potassium carbonate (245 mg), and the mixture was stirred at room temperature for 30 minutes. To the mixture was added tetrakistriphenylphosphinepalladium (47 mg), and the mixture was stirred at 100° C. for 10 hours and cooled to room temperature. The mixture was added to water, and the mixture was extracted with ethyl acetate/THF, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[4-(2-methoxyethyl)phenyl]-N-[4-[[N-methyl-N-(tetrahydropyran-4-yl)amino]methyl]phenyl]-1,1-dioxo-2,3-dihydro-1-benzothiepine-4-carboxamide (Compound 81) (99 mg).

m.p. 216–219° C.; $^1$H-NMR (200 MHz, CDCl$_3$) δ 1.61–1.83 (4H, m), 2.21 (3H, s), 2.65 (1H, m), 3.13–3.20 (2H, m), 3.30–3.43 (2H, m), 3.38 (3H, s), 3.58 (2H, m), 3.66 (2H, s), 3.65–3.76 (2H, m), 3.98–4.08 (2H, m), 7.30–7.38 (6H, m), 7.51–7.57 (4H, m), 7.98 (1H, s), 8.20 (1H, d, J=8.2 Hz); IR(KBr) 3293, 2944, 1667,1597, 1522, 1408, 1314, 1294, 1130, 735 cm$^{-1}$; Anal. for C$_{33}$H$_{38}$N$_2$O$_5$S; Calcd. C, 68.96; H, 6.66; N, 4.87; Found. C, 68.85; H, 6.62; N, 4.83.

Reference Example 99

To methyl 7-(4-ethoxyphenyl)-2,3-dihydro-1-benzothiepine-4-carboxylate (960 mg) were added THF (19.2 ml), methanol (9.6 ml) and 1N sodium hydroxide (3.4 ml), and the mixture was stirred at room temperature for 3 hours. Under reduced pressure, the organic solvent was evaporated. To the residue was added ethyl acetate, and the mixture was extracted with water. To the mixture was added 6N hydrochloric acid (2 ml), and the mixture was extracted with ethyl acetate/THF, washed with saturated brine and dried with magnesium sulfate. Under reduced pressure, the solvent was evaporated to give 7-(4-ethoxyphenyl)-2,3-dihydro-1-benzothiepine-4-carboxylic acid (850 mg).

$^1$H-NMR (200 MHz, DMSO-d$_6$) δ 1.35 (3H, t, J=7.0 Hz), 2.85–2.92 (2H, m), 3.14–3.20 (2H, m), 4.07 (2H, q, J=7.0 Hz), 7.00 (2H, d, J=8.6 Hz), 7.48 (2H, s), 7.65 (2H, d, J=8.6 Hz), 7.79 (2H, d, J=9.6 Hz).

Reference Example 100

In THF (15.3 ml) was dissolved 7-(4-ethoxyphenyl)-2,3-dihydro-1-benzothiepine-4-carboxylic acid (510 mg). To the mixture were added under ice-cooling thionyl chloride (0.11 ml) and DMF (one drop), and the mixture was stirred at room temperature for 1 hour. To a solution of 4-[[N-methyl-N-(tetrahydropyran-4-yl)amino]methyl]aniline (389 mg) and triethylamine (0.87 ml) in THF (15.3 ml) was added the reaction mixture, and the mixture was stirred at room temperature for 2 hours. The reaction mixture added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) to give 7-(4-ethoxyphenyl)-N-[4-[[N-methyl-N-(tetrahydropyran-4-yl)amino]methyl]phenyl]-2,3-dihydro-1-benzothiepine-4-carboxamide (512 mg).

$^1$H-NMR (200 MHz, CDCl$_3$) δ 1.44 (3H, t, J=7.0 Hz), 1.63–1.86 (4H, m), 2.21 (3H, s), 2.67 (1H, m), 3.02–3.09 (2H, m), 3.24–3.44 (4H, m), 3.59 (2H, m), 4.00–4.10 (2H, m), 4.08 (2H, q, J=7.0 Hz), 6.93–7.00 (2H, m), 7.29–7.58 (10H, m), 7.79 (1H, s).

Reference Example 101

In THF (15 ml) was dissolved 7-(4-ethoxyphenyl)-N-[4-[[N-methyl-N-(tetrahydropyran-4-yl)amino]methyl]phenyl]-2,3-dihydro-1-benzothiepine-4-carboxamide (300 mg). To the mixture was added dropwise at −78° C. a solution of m-chloroperbenzoic acid (140 mg) in THF (15 ml), and the mixture was stirred at −78° C. for 30 minutes and added to an aqueous solution of saturated sodium thiosulfate. To the mixture was added saturated sodium bicarbonate solution, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1→2/1, 1% triethylamine) to give 7-(4-ethoxyphenyl)-N-[4-[[N-methyl-N-oxide-(tetrahydropyran-4-yl)amino]methyl]phenyl]-2,3-dihydro-1-benzothiepine-4-carboxamide (140 mg).

m.p. 122–126° C.; $^1$H-NMR (200 MHz, CDCl$_3$) δ 1.44 (3H, t, J=7.0 Hz), 1.80–2.01 (4H, m), 3.25 (3H, s), 3.03–3.10 (2H, m), 3.21–3.40 (4H, m), 3.74 (1H, m), 3.98–4.10 (2H, m), 4.07 (2H, q, J=7.0 Hz), 4.34 (2H, s), 6.96 (2H, d, J=8.6 Hz), 7.29–7.55 (8H, m), 7.73 (2H, d, J=8.6 Hz), 8.87 (1H, s).

Working Example 83 (Production of Compound 82)

In THF (5.2 ml) was dissolved 7-(4-ethylthiophenyl)-1,1-dioxo-2,3-dihydro-1-benzothiepine-4-carboxylic acid (260 mg). To the mixture were added at room temperature thionyl chloride (0.06 ml) and DMF (one drop), and the mixture was stirred at room temperature for 1 hour. The reaction mixture was added dropwise to a solution of 4-[[N-(3-ethoxypropyl)-N-methylamino]methyl]aniline (0.58 ml) in THF (5.2 ml), and the mixture was stirred at room temperature for 2 hours. The reaction mixture added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-(4-ethylthiophenyl)-N-[4-[[N-(3-ethoxypropyl)-N-methylamino]methyl]phenyl]-1,1-dioxo-2,3-dihydro-1-benzothiepine-4-carboxamide (Compound 82) (115 mg).

m.p. 176–179° C.; $^1$H-NMR (200 MHz, CDCl$_3$) δ 1.20 (3H, t, J=7.0 Hz), 1.37 (3H, t, J=7.4 Hz), 1.58–1.78 (2H, m), 2.20 (3H, s), 2.47 (3H, t, J=7.4 Hz), 3.02 (2H, q, J=7.4 Hz), 3.13–3.21 (2H, m), 3.42–3.53 (2H, m), 3.69–3.76 (2H, m), 7.29–7.71 (11H, m), 7.97 (1H, s), 8.21 (1H, d, J=8.0 Hz); IR(KBr) 3349, 2974, 1669, 1593, 1520, 1406, 1308, 1128, 816 cm$^{-1}$; Anal. for C$_{32}$H$_{38}$N$_2$O$_4$S$_2$; Calcd. C, 66.41; H, 6.62; N, 4.84; Found. C, 66.55; H, 6.64; N, 4.94.

Working Example 84 (Production of Compound 83)

In methylene chloride (6 ml) was dissolved 7-(4-ethoxyphenyl)-N-[4-[[N-methyl-N-(tetrahydropyran-4-yl)amino]methyl]phenyl]-2,3-dihydro-1-benzothiepine-4-carboxamide (199 mg). To the mixture was added at –30° C. m-chloroperbenzoic acid (93 mg), and the mixture was stirred at –30° C. for 30 minutes and added to an aqueous solution of saturated sodium thiosulfate. To the mixture was added saturated sodium bicarbonate solution, and the mixture was extracted with ethyl acetate, washed with saturated brine and dried with magnesium sulfate. Under reduced pressure, the solvent was evaporated, and the residue was purified with silica gel column chromatography (ethyl acetate/methanol=3/1→2/1, 1% triethylamine) to give 7-(4-ethoxyphenyl)-N-[4-[[N-methyl-N-(tetrahydropyran-4-yl)amino]methyl]phenyl]-1-oxo-2,3-dihydro-1-benzothiepine-4-carboxamide (Compound 83) (28 mg).

m.p. 192–195° C.; $^1$H-NMR (200 MHz, CDCl$_3$) δ 1.45 (3H, t, J=7.0 Hz), 1.66–2.10 (4H, m), 2.26 (3H, s), 2.60–2.92 (3H, m), 3.10–3.21 (2H, m), 3.31–3.44 (2H, m), 3.65 (2H, s), 3.81–3.95(2H, m), 4.02–4.10 (2H, m), 4.08 (2H, q, J=7.0 Hz), 6.95 (2H, d, J=8.8 Hz), 7.34–7.71 (9H, m), 7.95 (1H, d, J=8.2 Hz), 8.33–8.36 (1H, m); IR(KBr) 3247, 2944, 1659, 1607, 1518, 1248, 1020, 814 cm$^{-1}$.

Reference Example 102

In DMF (80 ml) was dissolved 4-bromophenol (10 g). To the mixture was added at room temperature potassium carbonate (16.0 g) and then were added 2-chloroethylethyl ether (8.3 ml) and sodium iodide (9.53 g), and the mixture was stirred at 90° C. for 5 hours. The reaction mixture was added to water, and the mixture was extracted with ethyl acetate, washed with 1N sodium hydroxide and saturated brine and dried with magnesium sulfate. Under reduced pressure, the solvent was evaporated, and the residue was purified with silica gel column chromatography (hexane/ethyl acetate=2/1) to give 1-bromo-4-(2-ethoxyethoxy)benzene (10.7 g). In THF (100 ml) was dissolved 1-bromo-4-(2-ethoxyethoxy)benzene (10.3 g). To the mixture was added dropwise at –78° C. 1.6M n-butyllithium/hexane (29.1 ml), and the mixture was stirred for 1 hour. To the mixture was added dropwise a solution of trimethyl borate (13.2 g) in THF (13 ml) and the mixture was stirred for 30 minutes and warmed to room temperature. To the mixture was added 10% sulfuric acid (50 ml), and the mixture was stirred for 15 minutes. The reaction mixture was extracted with ethyl acetate, washed with saturated brine and dried with magnesium sulfate. Under reduced pressure, the solvent was evaporated, and the residue was washed with hexane/isopropylether to give 4-(2-ethoxyethoxy)phenyl borate (2.52 g).

$^1$H-NMR (200 MHz, DMSO-d$_6$) δ 1.13 (3H, t, J=7.0 Hz), 3.50 (2H, q, J=7.0 Hz), 3.66–3.71 (2H, m), 4.06–4.11 (2H, m), 6.89 (2H, d, J=8.4 Hz), 7.14 (2H, d, J=8.4 Hz).

Working Example 85 (Production of Compound 84)

To 7-bromo-N-[4-[[N-methyl-N-(tetrahydropyran-4-yl)amino]methyl]phenyl]-1,1-dioxo-2,3-dihydro-1-benzothiepine-4-carboxamide (350 mg) was added toluene/ethanol/water (10/1/1, 13.6 ml) and then were added 4-(2-ethoxyethoxy)phenyl borate (226 mg) and potassium carbonate (205 mg), and the mixture was stirred at room temperature for 30 minutes. To the mixture was added tetrakistriphenylphosphinepalladium (40 mg), and the mixture was stirred at 100° C. for 9 hours and cooled to room temperature. The mixture was added to water and the mixture was extracted with ethyl acetate/THF, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[4-(2-ethoxyethoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 84) (312 mg).

m.p. 215–217° C.; $^1$H-NMR (200 MHz, CDCl$_3$) δ 1.26 (3H, t, J=7.0 Hz), 1.60–1.81 (4H, m), 2.21 (3H, s), 2.65 (1H, m), 3.13–3.21 (2H, m), 3.31–3.44 (2H, m), 3.57 (2H, s), 3.63 (2H, q, J=7.0 Hz), 3.67–3.75 (2H, m), 3.83 (2H, t, J=5.0 Hz), 3.98–4.09 (2H, m), 4.19 (2H, t, J=5.0 Hz), 7.24 (2H, d, J=8.8 Hz), 7.30 (1H, s), 7.35 (1H, s), 7.51–7.69 (6H, m), 7.81 (1H, s), 8.19 (1H, d, J=8.4 Hz); IR(KBr) 3243, 2948, 1655, 1607, 1520, 1412, 1294, 1254, 1130, 824 cm$^{-1}$; Anal. for C$_{34}$H$_{40}$N$_2$O$_6$S; Calcd. C, 67.53; H, 6.67; N, 4.63; Found. C, 67.55; H, 6.58; N, 4.71.

Reference Example 103

In DMF (120 ml) was dissolved 4-bromophenol (15 g). To the mixture was added at room temperature potassium carbonate (21.6 g) and then were added 2-chloroethylmethylsulfide (10 ml) and sodium iodide (15.6 g), and the mixture was stirred at 90° C. for 16 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=8/1) to give 1-bromo-4-(2-methylthioethoxy)benzene (4.0 g). In THF (58 ml) was dissolved 1-bromo-4-(2-methylthioethoxy)benzene (3.9 g). To the mixture was added dropwise at –78° C. 1.6M n-butyllithium/hexane (10 ml), and the mixture was stirred for 1 hour. To the mixture was added dropwise a solution of trimethyl borate (4.6 g) in THF (9.3 ml), and the mixture was stirred for 30 minutes and warmed to room temperature. To the mixture was added 10% sulfuric acid (20 ml), and the mixture was stirred for 15 minutes. The reaction mixture was extracted with ethyl acetate, washed with saturated brine and dried with magnesium sulfate. Under reduced pressure, the solvent was evaporated, and the residue was washed with hexane/isopropylether to give 4-(2-methylthioethoxy)phenyl borate (1.39 g).

$^1$H-NMR (200 MHz, CDCl$_3$) δ 2.25 (3H, s), 2.93 (2H, t, J=6.8 Hz), 4.25 (2H, t, J=6.8 Hz), 7.01 (2H, d, J=8.8 Hz), 8.16 (2H, d, J=8.8 Hz).

Working Example 86 (Production of Compound 85)

To 7-bromo-N-[4-[[N-methyl-N-(tetrahydropyran-4-yl)amino]methyl]phenyl]-1,1-dioxo-2,3-dihydro-1- benzothiepine-4-carboxamide (360 mg) was added toluene/ethanol/water (10/1/1, 14.2 ml) and then were added 4-(2-methylthioethoxy)phenyl borate (241 mg) and potassium carbonate (216 mg), and the mixture was stirred at room temperature for 30 minutes. To the mixture was added tetrakistriphenylphosphinepalladium (41 mg), and the mixture was stirred at 100° C. for 10 hours and cooled to room temperature. The mixture was added to water, and the mixture was extracted with ethyl acetate/THF, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[4-(2-methylthioethoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 85) (30 mg).

m.p. 222–224° C.; $^1$H-NMR (200 MHz, CDCl$_3$) δ 1.66–1.76 (4H, m), 2.21 (3H, s), 2.24 (3H, s), 2.65 (1H, m), 2.92 (2H, t, J=6.6 Hz), 3.12–3.20 (2H, m), 3.37 (2H, m), 3.57 (2H, s), 3.68–3.75 (2H, m), 3.87–4.01 (2H, m), 4.22 (2H, t, J=6.6 Hz), 7.02 (2H, d, J=8.8 Hz), 7.30–7.35 (2H, m), 7.51–7.67 (7H, m), 7.97 (1H, s), 8.18 (1H, d, J=8.0 Hz); IR(KBr) 3291, 2959, 1655, 1603, 1520, 1412, 1294, 1252, 1130, 824 cm$^{-1}$.

Reference Example 104

In DMF (255 ml) was dissolved 4-bromophenol (51.0 g). To the mixture was added at room temperature potassium carbonate (81.5 g) and then was added dropwise chloromethylmethyl ether (44.8 ml), and the mixture was stirred for 2 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=8/1) to give 1-bromo-4-(methoxymethoxy)benzene (61.4 g). In ether (240 ml) was dissolved 1-bromo-4-(methoxymethoxy)benzene (30 g). To the mixture was added dropwise at −78° C. 1.6M n-butyllithium/hexane (90.7 ml), and the mixture was stirred for 1 hour. To the mixture was added dropwise a solution of trimethyl borate (43.1 g) in THF (43 ml), and the mixture was stirred for 30 minutes and warmed to room temperature. To the mixture was added water (150 ml), and the mixture was stirred for 15 minutes. The reaction mixture was extracted with ethyl acetate. Under reduced pressure, the solvent was evaporated, and the residue was stirred in methanol/water (2/1, 1000 ml) for 3 days. Under reduced pressure, methanol was removed, and the residue was extracted with ethyl acetate, washed with saturated brine and dried with magnesium sulfate. Under reduced pressure, the solvent was evaporated, and the residue was washed with hexane/isopropylether to give 4-(methoxymethoxy)phenyl borate (2.4 g). $^1$H-NMR (200 MHz, CDCl$_3$) δ 3.51 (3H, s), 5.26 (2H, s), 7.14 (2H, d, J=8.4 Hz), 8.15 (2H, d, J=8.4 Hz).

Working Example 87 (Production of Compound 86)

To 7-bromo-N-[4-[[N-methyl-N-(tetrahydropyran-4-yl)amino]methyl]phenyl]-1,1-dioxo-2,3-dihydro-1-benzothiepine-4-carboxamide (500 mg) was added toluene/ethanol/water (10/1/1, 19.2 ml) and then were added 4-(methoxymethoxy)phenyl borate (262 mg) and potassium carbonate (292 mg), and the mixture was stirred at room temperature for 30 minutes. To the mixture was added tetrakistriphenylphosphinepalladium (56 mg), and the mixture was stirred 100° C. for 9 hours and cooled to room temperature. The mixture was added to water, and the mixture was extracted with ethyl acetate/THF, washed with saturated brine and dried with magnesium sulfate. Under reduced pressure, the solvent was evaporated, and the residue was purified with silica gel column chromatography (ethyl acetate/ethanol=3/1) to give 7-(4-methoxymethoxyphenyl)-N-[4-[[N-methyl-N-(tetrahydropyran-4-yl)amino]methyl]phenyl]-1,1-dioxo-2,3-dihydro-1-benzothiepine-4-carboxamide (Compound 86) (340 mg).

m.p. 227–229° C.; $^1$H-NMR (200 MHz, CDCl$_3$) δ 1.63–1.76 (4H, m), 2.21 (3H, s), 2.66 (1H, m), 3.12–3.20 (2H, m), 3.31–3.43 (2H, m), 3.51 (3H, s), 3.58 (2H, s), 3.68–3.76 (2H, m), 4.00–4.09 (2H, m), 5.24 (2H, s), 7.16 (2H, d, J=8.8 Hz), 7.30–7.36 (2H, m), 7.51–7.68 (7H, m), 8.01 (1H, s), 8.19 (1H, d, J=8.2 Hz). IR(KBr) 3260, 2953, 1655, 1601, 1518, 1410, 1315, 1294, 1238, 1130, 997, 826 cm$^{-1}$.

Reference Example 105

In toluene (104 ml) was dissolved 4-bromophenol (13 g). To the mixture was added under ice-cooling 65% sodium hydride (6.0 g), and the mixture was stirred at room temperature for 30 minutes. To the mixture was added under ice-cooling 2-chloroethyl-N,N-dimethylammonium chloride (14.1 g), and the mixture was refluxed for 2 hours and cooled to room temperature. The reaction mixture was added to water, and the mixture was extracted with ethyl acetate, washed with 1N sodium hydroxide and saturated brine and dried with magnesium sulfate. Under reduced pressure, the solvent was evaporated, and the residue was purified with silica gel column chromatography (hexane/ethyl acetate=3/1) to give N-[2-(4-bromophenoxy)-N,N-dimethylamine (11.3 g). In THF (100 ml) was dissolved N-[2-(4-bromophenoxy)-N,N-dimethylamine (11.2 g). To the mixture was added dropwise at −78° C. 1.6M n-butyllithium/hexane (31.5 ml), and the mixture was stirred for 1 hour. To the mixture was added dropwise a solution of trimethyl borate (14.3 g) in THF (10 ml), and the mixture was stirred for 30 minutes and warmed to room temperature. To the mixture was added water (56 ml), and the mixture was stirred for 15 minutes. The reaction mixture was extracted with ethyl acetate, washed with saturated brine and dried with magnesium sulfate. Under reduced pressure, the solvent was evaporated, and the residue was washed with hexane/isopropylether to give 4-[2-(dimethylamino)ethoxy]phenyl borate (1.5 g).

$^1$H-NMR (200 MHz, DMSO-d$_6$) δ 2.43 (6H, s), 2.89 (2H, m), 4.20 (2H, m), 6.88 (2H, d, J=8.2 Hz), 8.09 (2H, d, J=7.2 Hz).

Working Example 88 (Production of Compound 87)

To 7-bromo-N-[4-[[N-methyl-N-(tetrahydropyran-4-yl)amino]methyl]phenyl]-1,1-dioxo-2,3-dihydro-1-benzothiepine-4-carboxamide (500 mg) was added toluene/ethanol/water (10/1/1, 19.2 ml) and then were added 4-[(2-dimethylamino)ethoxy]phenyl borate (321 mg) and potassium carbonate (292 mg), and the mixture was stirred at room temperature for 30 minutes. To the mixture was added tetrakistriphenylphosphinepalladium (56 mg), and the mixture was stirred at 100° C. for 12 hours and cooled to room temperature. The mixture was added to water, and the mixture was extracted with ethyl acetate/THF, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[4-(2-dimethylamino)ethoxyphenyl]-N-[4-[[N-methyl-N-(tetrahydropyran-4-yl)amino]methyl]phenyl]-1,1-dioxo-2,3-dihydro-1-benzothiepine-4-carboxamide (Compound 87) (190 mg).

m.p. 227–229° C.; $^1$H-NMR (200 MHz, CDCl$_3$) δ 1.62–1.87 (4H, m), 2.21 (3H, s), 2.37 (6H, s), 2.65 (1H, m), 2.78 (2H, t, J=5.8 Hz), 3.11–3.20 (2H, m), 3.32–3.44 (2H, m), 3.58 (2H, s), 3.68–3.76 (2H, m), 4.00–4.10 (2H, m), 4.13 (2H, t, J=5.8 Hz), 7.04 (2H, d, J=8.8 Hz), 7.30–7.35 (2H, m), 7.51–7.69 (7H, m), 7.96 (1H, s), 8.19 (1H, d, J=8.4 Hz); IR(KBr) 3245, 2946, 1655, 1607, 1520, 1412, 1318, 1294, 1254, 1130, 824 cm$^{-1}$.

Reference Example 106

In 4-methyl-2-pentanone (96 ml) was dissolved 4-bromophenol (12 g). To the mixture were added at room temperature potassium carbonate (24 g) and 4-[2-(chloroethyl)]morpholine hydrochloride (16.9 g), and the mixture was refluxed for 18 hours and cooled to room temperature. The reaction mixture was added to water, and the mixture was extracted with ethyl acetate, washed with saturated brine and dried with magnesium sulfate. Under reduced pressure, the solvent was evaporated, and the residue was filtrated to give 4-[2-(4-bromophenoxy)ethyl] morpholine (16.9 g). In THF (100 ml) was dissolved 4-[2-(4-bromophenoxy)ethyl]morpholine (16.5 g). To the mixture was added dropwise at −78° C. 1.6M n-butyllithium/hexane (31.5 ml), and the mixture was stirred for 1 hour. To the mixture was added dropwise a solution of trimethyl borate (14.3 g) in THF (10 ml), and the mixture was stirred for 30 minutes and warmed to room temperature. To the mixture was added water (56 ml), and the mixture was stirred for 15 minutes. The reaction mixture was extracted with ethyl acetate, washed with saturated brine and dried with magnesium sulfate. Under reduced pressure, the solvent was evaporated, and the residue was washed with hexane/isopropylether to give 4-[2-(4-morpholino)ethoxy] phenyl borate (1.5 g).

$^1$H-NMR (200 MHz, DMSO-d$_6$) δ 2.38–2.62 (4H, m), 3.56–3.65 (6H, m), 4.10 (2H, t, J=6.2 Hz), 6.93 (2H, d, J=9.2 Hz), 7.24–7.32 (2H, m).

Working Example 89 (Production of Compound 88)

To 7-bromo-N-[4-[[N-methyl-N-(tetrahydropyran-4-yl)amino]methyl]phenyl]-1,1-dioxo-2,3-dihydro-1-benzothiepine-4-carboxamide (500 mg) was added toluene/ethanol/water (10/1/1, 19.2 ml) and then were added 4-[2-(4-morpholino)ethoxy]phenyl borate (386 mg) and potassium carbonate (292 mg), and the mixture was stirred at room temperature for 30 minutes. To the mixture was added tetrakistriphenylphosphinepalladium (56 mg), and the mixture was stirred at 100° C. for 12 hours and cooled to room temperature. The mixture was added to water, and the mixture was extracted with ethyl acetate/THF, washed with saturated brine and dried with magnesium sulfate. Under reduced pressure, the solvent was evaporated, and the residue was purified with silica gel column chromatography (ethyl acetate/ethanol=3/1) and recrystallized from ethanol to give N-[4-[[N-methyl-N-(tetrahydropyran-4-yl)amino]methyl]phenyl]-7-[4-[2-(4-morpholino)ethoxy]phenyl]-1,1-dioxo-2,3-dihydro-1-benzothiepine-4-carboxamide (Compound 88) (190 mg).

m.p. 203–206° C.; $^1$H-NMR (200 MHz, CDCl$_3$) δ 1.63–1.84 (4H, m), 2.23 (3H, s), 2.60 (4H, t, J=4.8 Hz), 2.71 (1H, m), 2.84 (2H, t, J=5.6 Hz), 3.16–3.19 (2H, m), 3.29–3.41 (2H, m), 3.62 (2H, s), 3.66–3.77 (6H, m), 3.98–4.19 (2H, m), 4.17 (2H, t, J=5.6 Hz), 7.01 (2H, d, J=8.8 Hz), 7.32–7.41 (3H, m), 7.50–7.66 (7H, m), 8.14–8.19 (2H, m); IR(KBr) 3293, 2951, 1667, 1607, 1518, 1408, 1292, 1250, 1130, 826 cm$^{-1}$; Anal. for C$_{36}$H$_{43}$N$_3$O$_6$S; Calcd. C, 66.95; H, 6.71; N, 6.51; Found. C, 66.08; H, 6.71; N, 6.54.

Working Example 90 (Production of Compound 89)

In THF/acetone (1/1, 60 ml) was dissolved 7-(4-methoxymethoxyphenyl)-N-[4-[[N-methyl-N-(tetrahydropyran-4-yl)amino]methyl]phenyl]-1,1-dioxo-2,3-dihydro-1-benzothiepine-4-carboxamide (650 mg). To the mixture was added 1N sulfuric acid (4.4 ml), and the mixture was stirred at 65° C. for 14 hours, cooled to room temperature and neutralized with saturated sodium bicarbonate solution. Under reduced pressure, the solvent was evaporated, and the residue was added to water. The mixture was extracted with ethyl acetate, washed with saturated brine and dried with magnesium sulfate. Under reduced pressure, the solvent was evaporated, and the residue was recrystallized from ethanol to give 7-(4-hydroxyphenyl)-N-[4-[[N-methyl-N-(tetrahydropyran-4-yl)amino]methyl] phenyl]-1,1-dioxo-2,3-dihydro-1-benzothiepine-4-carboxamide (Compound 89) (530 mg).

m.p. 232–234° C.; $^1$H-NMR (200 MHz, DMSO-d$_6$) δ 1.49–1.75 (4H, m), 2.11 (3H, s), 2.59 (1H, m), 3.03–3.11 (2H, m), 3.20–3.33 (2H, m), 3.53 (2H, s), 3.73–3.83 (2H, m), 3.86–3.98 (2H, m), 6.90 (2H, d, J=8.4 Hz), 7.27 (2H, d, J=8.4 Hz), 7.52 (1H, s), 7.63–7.69 (4H, m), 7.82 (1H, d, J=10.4 Hz), 8.05 (2H, d, J=8.0 Hz), 10.17 (1H, s); IR(KBr) 3223, 1655, 1599, 1524, 1410, 1318, 1128, 826 cm$^{-1}$.

Working Example 91 (Production of Compound 90)

In DMF (4.8 ml) was dissolved 7-(4-hydroxyphenyl)-N-[4-[[N-methyl-N-(tetrahydropyran-4-yl)amino]methyl] phenyl]-1,1-dioxo-2,3-dihydro-1-benzothiepine-4-carboxamide (320 mg). To the mixture was added potassium carbonate (96 mg), and the mixture was stirred at room temperature for 30 minutes. To the mixture was added t-butyl bromoacetate (0.093 ml), and the mixture was stirred at room temperature for 4 hours. The mixture was added to water, and the mixture was extracted with ethyl acetate/THF, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[4-(t-butoxycarbonylmethoxy) phenyl]-N-[4-[[N-methyl-N-(tetrahydropyran-4-yl)amino] methyl]phenyl]-1,1-dioxo-2,3-dihydro-1-benzothiepine-4-carboxamide (Compound 90) (274 mg).

m.p. 209–211° C.; $^1$H-NMR (200 MHz, CDCl$_3$) δ 1.51 (9H, s), 1.64–2.05 (4H, m), 2.23 (3H, s), 2.66 (1H, m), 3.12–3.23 (2H, m), 3.27–3.44 (2H, m), 3.58 (2H, s), 3.65–3.76 (2H, m), 3.99–4.12 (2H, m), 4.58 (2H, s), 7.00 (2H, d, J=8.8 Hz), 7.29 (1H, s), 7.35 (2H, d, J=8.8 Hz), 7.50–7.68 (6H, m), 8.18 (1H, d, J=8.0 Hz), 8.47 (1H, s); IR(KBr) 3241, 2949, 1752, 1655, 1601, 1522, 1410, 1292, 1130, 831 cm$^{-1}$; Anal. for C$_{35}$H$_{42}$N$_2$O$_7$S Calcd. C, 66.22; H, 6.67; N, 4.41: Found. C, 66.27; H, 6.59; N, 4.36.

Working Example 92 (Production of Compound 91)

In methylene chloride (6.4 ml) was dissolved 7-[4-(t-butoxycarbonylmethoxy)phenyl]-N-[4-[[N-methyl-N-

(tetrahydropyran-4-yl)amino]methyl]phenyl]-1,1-dioxo-2,3-dihydro-1-benzothiepine-4-carboxamide (160 mg). To the mixture was added trifluoroacetic acid (6.4 ml), and the mixture was stirred at room temperature for 22 hours. Under reduced pressure, the solvent was evaporated, and the residue was dissolved in ethanol/water and neutralized with saturated sodium bicarbonate solution. To the mixture was added 1N hydrochloric acid, and the precipitates were filtered, washed with water and a little amount of ethanol and dried to give 2-[4-[[4-[[[N-methyl-N-(tetrahydropyran-4-yl)amino]methyl]anilino]carbonyl]-1,1-dioxo-2,3-dihydro-1-benzothiepine- 7-yl]phenoxy]acetic.acid hydrochloride (Compound 91) (70 mg)

m.p. 172–175° C.; $^1$H-NMR (200 MHz, DMSO-d$_6$) δ 1.67–2.12 (4H, m), 2.23 (4H, s), 3.03–3.13 (2H, m), 3.20–3.55 (4H, m), 3.74–3.85 (2H, m), 3.95–4.07 (2H, m), 4.77 (2H, s), 7.07 (2H, d, J=8.6 Hz), 7.54 (d, J=8.6 Hz), 7.58 (1H, s), 7.73–7.92 (5H, m), 8.05–8.12 (2H, m); IR(KBr) 1671, 1593, 1518, 1414, 1289, 1128, 816 cm$^{-1}$.

Reference Example 107

In THF (300 ml) was dissolved 4-bromobenzonitrile (25.1 g). To the mixture was added dropwise at −100° C. 1.6M n-butyllithium/hexane (94.8 ml), and the mixture was stirred for 10 minutes. To the mixture was added dropwise trimethyl borate (26.5 g), and the mixture was allowed to warm to room temperature for 6 hours. To the mixture was added 15% hydrochloric acid (50 ml), and the mixture was stirred for minutes. The reaction mixture was extracted with ethyl acetate, washed with water (twice), washed with saturated brine and dried with magnesium sulfate. Under reduced pressure, the solvent was evaporated, and the residue was washed with hexane/isopropylether to give 4-(cyanophenyl) borate (12.5 g).

$^1$H-NMR (200 MHz, DMSO-d$_6$) δ 7.77 (2H, d, J=7.8 Hz), 7.94 (2H, d, J=8.4 Hz), 8.40 (2H, br).

Working Example 93 (Production of Compound 92)

To 7-bromo-N-[4-[[N-methyl-N-(tetrahydropyran-4-yl)amino]methyl]phenyl]-1,1-dioxo-2,3-dihydro-1-benzothiepine-4-carboxamide (400 mg) was added toluene/ethanol/water (20/5/2, 21.6 ml) and then were added 4-cyanophenyl borate (147 mg) and potassium carbonate (147 mg), and the mixture was stirred at room temperature for 30 minutes. To the mixture was added tetrakistriphenylphosphinepalladium (46 mg), and the mixture was refluxed for 6 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-(4-cyanophenyl)-N-(4-[[N-methyl-N-(tetrahydropyran-4-yl)amino]methyl]phenyl]-1,1-dioxo-2,3-dihydro-1-benzothiepine-4-carboxamide (Compound 92) (90 mg).

m.p. 233–236° C.; $^1$H-NMR (200 MHz, CDCl$_3$) δ 1.60–1.83 (4H, m), 2.21 (3H, s), 2.66 (1H, m), 3.15–3.22 (2H, m), 3.32–3.42 (2H, m), 3.58 (2H, s), 3.70–3.78 (2H, m), 7.30–7.37 (4H, m), 7.55 (2H, d, J=8.4 Hz), 7.65–7.83 (5H, m), 7.95 (1H, s), 8.29 (1H, d, J=8.0 Hz); IR(KBr) 3245, 2951, 2228, 1665, 1597, 1526, 1408, 1314, 1294, 1132, 828, 733 cm$^{-1}$.

Reference Example 108

In DMF (150 ml) was dissolved 5-bromosalicylaldehyde (18.6 g). To the mixture was added at room temperature potassium carbonate (16.6 g) and then was added iodoethane (17.3 ml), and the mixture was stirred at 90° C. for 3 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=8/1) to give 5-bromo-2-ethoxybenzaldehyde (17.2 g).

$^1$H-NMR (200 MHz, CDCl$_3$) δ 1.48 (3H, t, J=7.2 Hz), 3.13–3.20 (2H, m), 4.14 (2H, q, J=7.0 Hz), 6.87 (1H, d, J=8.8 Hz), 7.60 (1H, d, J=8.8, 2.6 Hz), 7.91 (1H, d, J=2.6 Hz), 10.41 (1H, s).

Reference Example 109

In formic acid (85.5 ml) was dissolved 5-bromo-2-ethoxybenzaldehyde (17.1 g). To the mixture was added hydroxylamine hydrochloride (7.8 g), and the mixture was refluxed for 7 hours and cooled to room temperature. Under reduced pressure, the solvent was evaporated, and the residue was washed with water and dried to give 5-bromo-2-ethoxybenzonitrile (15.8 g).

$^1$H-NMR (200 MHz, CDCl$_3$) δ 1.48 (3H, t, J=7.0 Hz), 4.14 (2H, q, J=7.0 Hz), 6.85 (1H, d, J=8.8 Hz), 7.57–7.66 (2H, m); IR(KBr) 2984, 2230, 1591, 1489, 1393, 1314, 1284, 1134, 1038, 810 cm$^{-1}$.

Reference Example 110

In THF (180 ml) was dissolved 5-bromo-2-ethoxybenzonitrile (15.8 g). To the mixture was added dropwise at −100° C. 1.6M n-butyllithium/hexane (48 ml), and the mixture was stirred for 30 minutes. To the mixture was added dropwise trimethyl borate (14.5 g), and the mixture was stirred for 20 minutes and allowed to warm to room temperature for 5 hours. To the mixture was added 4N hydrochloric acid (50 ml), and the mixture was stirred for 15 minutes. The reaction mixture was added to water, and the mixture was extracted with ethyl acetate, washed with water (twice), washed with saturated brine and dried with magnesium sulfate. Under reduced pressure, the solvent was evaporated, and the residue was washed with hexane/isopropylether to give 3-cyano-4-ethoxyphenyl borate (6.0 g).

$^1$H-NMR (200 MHz, DMSO-d$_6$) δ 1.38 (3H, t, J=7.0 Hz), 4.22 (2H, q, J=7.0 Hz), 7.20 (1H, d, J=9.2 Hz), 8.00–8.05 (1H, m), 8.18 (1H, s).

Working Example 94 (Production of Compound 93)

To 7-bromo-N-[4-[[N-methyl-N-(tetrahydropyran-4-yl)amino]methyl]phenyl]-1,1-dioxo-2,3-dihydro-1-benzothiepine-4-carboxamide (400 mg) was added toluene/ethanol/water (10/1/1, 19.2 ml) and then were added 3-cyano-4-ethoxyphenyl borate (205 mg) and potassium carbonate (251 mg), and the mixture was stirred at room temperature for 30 minutes. To the mixture was added tetrakistriphenylphosphinepalladium (48 mg), and the mixture was refluxed for 18 hours and cooled to room temperature. The mixture was added to water, and the mixture was extracted with ethyl acetate/THF, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-(4-cyano-3-ethoxyphenyl)-N-[4-[[N-methyl-N-

(tetrahydropyran-4-yl)amino]methyl]phenyl]-1,1-dioxo-2,3-dihydro-1-benzothiepine-4-carboxamide (Compound 93) (209 mg).

m.p. 244–247° C.; $^1$H-NMR (200 MHz, DMSO-d$_6$) δ 1.41 (3H, t, J=7.0 Hz), 1.45–1.73 (4H, m), 2.10 (3H, s), 2.59 (1H, m), 3.05–3.12 (2H, m), 3.21–3.30 (2H, m), 3.52 (2H, s), 3.74–3.84 (2H, m), 3.84–3.94 (2H, m), 4.28 (2H, q, J=7.0 Hz), 7.26 (2H, d, J=8.4 Hz), 7.39 (2H, d, J=9.2 Hz), 7.53 (1H, s), 7.67 (2H, d, J=8.4 Hz), 7.92–7.97 (2H, m), 8.06–8.25 (3H, m).

Reference Example 111

In DMF (160 ml) was dissolved 5-bromosalicylaldehyde (20 g). To the mixture was added at room temperature potassium carbonate (17.9 g) and then was added 1-bromopropane (10.8 ml), and the mixture was stirred at 90° C. for 3 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=6/1) to give 5-bromo-2-propoxybenzaldehyde (21.9 g).

$^1$H-NMR (200 MHz, CDCl$_3$) δ 1.07 (3H, t, J=7.4 Hz), 1.80–1.95 (2H, m), 4.03 (2H, t, J=6.4 Hz), 6.88 (1H, d, J=9.0 Hz), 7.60 (1H, dd, J=8.8, 2.6 Hz), 7.91 (1H, d, J=2.6 Hz), 10.43 (1H, s).

Reference Example 112

In formic acid (110 ml) was dissolved 5-bromo-2-propoxybenzaldehyde (21.8 g). To the mixture was added hydroxylamine hydrochloride (9.4 g), and the mixture was refluxed for 7 hours and cooled to room temperature. Under reduced pressure, the solvent was evaporated, and the residue was added to 1N potassium hydroxide. The mixture was extracted with ethyl acetate, washed with saturated brine and dried with magnesium sulfate. Under reduced pressure, the solvent was evaporated, and the residue was purified with silica gel column chromatography (hexane/ethyl acetate=8/1) to give 5-bromo-2-propoxybenzonitrile (15.8 g).

$^1$H-NMR (200 MHz, CDCl$_3$) δ 1–07 (3H, t, J=7.4 Hz), 1.80–1.95 (2H, m), 4.02 (2H, t, J=6.4 Hz), 6.85 (1H, d, J=8.8 Hz), 7.57–7.65 (2H, m); IR(KBr) 2969, 2230, 1591, 1489, 1391, 1285, 1132, 972, 812 cm$^{-1}$.

Reference Example 113

In THF (180 ml) was dissolved 5-bromo-2-propoxybenzonitrile (15.3 g). To the mixture was added dropwise at −100° C. 1.6M n-butyllithium/hexane (44 ml) and then trimethyl borate (13.2 g), and the mixture was stirred for 20 minutes and allowed to warm to room temperature for 5 hours. To the mixture was added 4N hydrochloric acid (50 ml), and the mixture was stirred for 15 minutes. The reaction mixture was added to water, and the mixture was extracted with ethyl acetate, washed with saturated brine and dried with magnesium sulfate. Under reduced pressure, the solvent was evaporated, and the residue was washed with hexane/isopropylether to give 3-cyano-4-propoxyphenyl borate (7.0 g).

$^1$H-NMR (200 MHz, DMSO-d$_6$) δ 1.01 (3H, t, J=7.4 Hz), 1.70–1.85 (2H, m), 4.11 (2H, t, J=6.4 Hz), 7.21 (1H, d, J=9.2 Hz), 8.01–8.06 (2H, m), 8.19 (2H, br).

Working Example 95 (Production of Compound 94)

To 7-bromo-N-[4-[[N-methyl-N-(tetrahydropyran-4-yl)amino]methyl]phenyl]-1,1-dioxo-2,3-dihydro-1-benzothiepine-4-carboxamide (400 mg) was added toluene/ethanol/water (10/1/1, 13.2 ml) and then were added 3-cyano-4-propoxyphenyl borate (205 mg) and potassium carbonate (234 mg), and the mixture was stirred at room temperature for 30 minutes. To the mixture were added palladium acetate (8.6 mg) and tris(2-methylphenyl)phosphine (22.4 mg), and the mixture was refluxed for 18 hours and cooled to room temperature. The mixture was added to water, and the mixture was extracted with ethyl acetate/THF, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-(4-cyano-3-propoxyphenyl)-N-[4-[[N-methyl-N-(tetrahydropyran-4-yl)amino]methyl]phenyl]-1,1-dioxo-2,3-dihydro-1-benzothiepine-4-carboxamide (Compound 94) (243 mg).

m.p. 201–203° C.; $^1$H-NMR (200 MHz, CDCl$_3$) δ 1.11 (3H, t, J=7.4 Hz), 1.65–1.78 (4H, m), 1.86–2.00 (2H, m), 2.21 (3H, s), 2.65 (1H, m), 3.14–3.22 (2H, m), 3.30–3.44 (2H, m), 3.57 (2H, s), 3.69–3–77 (2H, m), 4.00–4.10 (2H, m), 4.11 (2H, t, J=6.6 Hz), 7.08 (1H, d, J=9.0 Hz), 7.30–7.37 (3H, m), 7.53–7.63 (4H, m), 7.71–7.77 (2H, m), 8.03 (1H, s), 8.22 (1H, d, J=8.4 Hz); IR(KBr) 3301, 2944, 2228, 1667, 1607, 1510, 1408, 1314, 1291, 1128, 819, 735 cm$^{-1}$; Anal. for C$_{34}$H$_{37}$N$_3$O$_5$S Calcd. C, 68.09; H, 6.22; N, 7.01: Found. C, 67.83; H, 6.20; N, 6.89.

Working Example 96 (Production of Compound 95)

In DMF (1.6 ml) was dissolved 7-(4-hydroxyphenyl)-N-[4-[[N-methyl-N-(tetrahydropyran-4-yl)amino]methyl]phenyl]-1,1-dioxo-2,3-dihydro-1-benzothiepine-4-carboxamide (131 mg). To the mixture was added potassium carbonate (41 mg), and the mixture was stirred for 50 minutes. To the mixture was added iodoacetamide (50 mg), and the mixture was stirred at room temperature for 20 hours. The reaction mixture was added to water, and the mixture was extracted with ethyl acetate/THF, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-(4-carbamoylmethoxyphenyl)-N-[4-[[N-methyl-N-(tetrahydropyran-4-yl)amino]methyl]phenyl]-1,1-dioxo-2,3-dihydro-1-benzothiepine-4-carboxamide (Compound 95) (52 mg).

m.p. 240–243° C.; $^1$H-NMR (200 MHz, DMSO-d$_6$) δ 1.45–1.78 (4H, m), 2.21 (3H, s), 2.60 (1H, m), 3.01–3.13 (2H, m), 3.21–3.35 (2H, m), 3.53 (2H, s), 3.74–3.80 (2H, m), 3.86–3.95 (2H, m), 4.51 (2H, m), 7.10 (2H, d, J=8.8 Hz), 7.27 (2H, d, J=8.8 Hz), 7.40–7.93 (8H, m), 8.05 (1H, s), 8.22 (1H, d, J=8.4 Hz); IR(KBr) 3320, 2951, 1669, 1597, 1518, 1408, 1291, 1130, 816 cm$^{-1}$.

Reference Example 114

In DMF (108 ml) was dissolved morpholine (9.0 g). To the mixture were added at room temperature triethylamine (24 ml) and 4-bromobenzyl bromide (21.5 g), and the mixture was stirred at 80° C. for 16 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=2/1) to give 4-(4-bromobenzyl)morpholine (17.2 g).

¹H-NMR (200 MHz, CDCl₃) δ 2.38–2.45 (4H, m), 3.44 (2H, s), 3.67–3.73 (4H, m), 7.21 (2H, d, J=8.4 Hz), 7.44 (2H, d, J=8.4 Hz).

Reference Example 115

In THF (174 ml) was dissolved 4-(4-bromobenzyl)morpholine (19.3 g). To the mixture was added dropwise at −78° C. 1.6M n-butyllithium/hexane (52 ml), and the mixture was stirred for 30 minutes. To the mixture was added dropwise a solution of trimethyl borate (21.8 g) in THF (22 ml), and the mixture was stirred for 30 minutes and warmed to room temperature. To the mixture was added water (73 ml), and the mixture was stirred for 15 minutes. The reaction mixture was extracted with ethyl acetate, washed with saturated brine and dried with magnesium sulfate. Under reduced pressure, the solvent was evaporated, and the residue was washed with hexane/isopropylether to give 4-(4-morpholinomethyl)phenyl borate (5.7 g).

¹H-NMR (200 MHz, CDCl₃) δ 2.36–2.59 (4H, m), 3.48–3.81 (6H, m), 7.25–7.44 (2H, m), 7.93–8.10 (2H, m).

Working Example 97 (Production of Compound 96)

To 7-bromo-N-[4-[[N-methyl-N-(tetrahydropyran-4-yl)amino]methyl]phenyl]-1,1-dioxo-2,3-dihydro-1-benzothiepine-4-carboxamide (560 mg) was added toluene/ethanol/water (10/1/1, 18 ml) and then were added 4-(4-morpholinomethyl)phenyl borate (285 mg) and potassium carbonate (327 mg), and the mixture was stirred at room temperature for 30 minutes. To the mixture was added tetrakistriphenylphosphinepalladium (62.2 mg), and the mixture was refluxed for 14 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give N-[4-[[N-methyl-N-(tetrahydropyran-4-yl)amino]methyl]phenyl]-7-[4-(4-morpholinomethyl)phenyl]-1,1-dioxo-2,3-dihydro-1-benzothiepine-4-carboxamide (Compound 96) (377 mg).

m.p. 211–213° C.; ¹H-NMR (200 MHz, CDCl₃) δ 1.65–1.82 (4H, m), 2.21 (3H, s), 2.45–2.51 (2H, m), 2.65 (1H, m), 3.13–3.21 (2H, m), 3.31–3.45 (2H, m), 3.56 (2H, s), 3.58 (2H, s), 3.71–3.77 (2H, m), 3.98–4.10 (2H, m), 7.30–7.37 (3H, m), 7.43–7.59 (6H, m), 7.66–7.74 (2H, m), 7.91 (1H, s), 8.22 (1H, d, J=8.2 Hz); IR(KBr) 3254, 2948, 1667, 1597, 1514, 1408, 1314, 1294, 1130, 866, 735 cm⁻¹; Anal. for $C_{35}H_{41}N_3O_5S$ Calcd. C, 68.27; H, 6.71; N, 6.82: Found. C, 68.10; H, 6.74; N, 6.75.

Reference Example 116

To methyl 7-bromo-1,1-dioxo-2,3-dihydro-1-benzothiepine-4-carboxylate (5.0 g) was added toluene/ethanol/water (10/1/1, 188 ml) and then were added 4-(2-ethoxyethoxy)phenyl borate (4.1 g) and potassium carbonate (4.6 g), and the mixture was stirred at room temperature for 30 minutes. To the mixture was added tetrakistriphenylphosphinepalladium (0.7 g), and the mixture was refluxed for 14 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=2/1) to give methyl 7-[4-(2-ethoxyethoxy)phenyl]-1,1-dioxo-2,3-dihydro-1-benzothiepine-4-carboxylate (4.6 g).

¹H-NMR (200 MHz, CDCl₃) δ 1.26 (3H, t, J=7.0 Hz), 3.10–3.18 (2H, m), 3.58–3.87 (2H, m), 3.66 (2H, q, J=7.0 Hz), 3.87 (3H, s), 4.16–4.22 (2H, m), 7.04 (2H, dd, J=6.6, 1.8 Hz), 7.55 (2H, dd, J=6.6, 1.8 Hz), 7.64–7.70 (2H, m), 7.91 (1H, s), 8.19 (1H, d, J=8.8 Hz); IR(KBr) 2920, 1709, 1604,1518, 1294, 1252, 1130, 828, 752 cm⁻¹; Anal. for $C_{22}H_{24}O_6S$ Calcd. C, 63.44; H, 5.81: Found. C, 63.27; H, 5.74.

Reference Example 117

To methyl 7-[4-(2-ethoxyethoxy)phenyl]-1,1-dioxo-2,3-dihydro-1-benzothiepine-4-carboxylate (4.35 g) were added 1,2-dimethoxyethane (87 ml) and 6N hydrochloric acid (43.5 ml), and the mixture was refluxed at 100° C. for 16 hours and cooled to room temperature. The mixture was extracted with ethyl acetate, washed with saturated brine and dried with magnesium sulfate. Under reduced pressure, the solvent was evaporated to give 7-[4-(2-ethoxyethoxy)phenyl]-1,1-dioxo-2,3-dihydro-1-benzothiepine-4-carboxylic acid (3.7 g).

¹H-NMR (200 MHz, DMSO-d₆) δ 1.44 (3H, t, J=7.0 Hz), 2.91–3.04 (2H, m), 3.52 (2H, q, J=7.0 Hz), 3.70–3.77 (4H, m), 4.13–4.19 (2H, m), 7.09 (2H, d, J=8.8 Hz), 7.78 (2H, d, J=8.8 Hz), 7.85–7.92 (2H, m), 8.03 (1H, s), 8.18 (1H, s); IR(KBr) 2978, 1684, 1606, 1518, 1412, 1292, 1252, 1165, 1128, 829 cm⁻¹; Anal. for $C_{21}H_{22}O_6S$ Calcd. C, 62.67; H, 5.51: Found. C, 62.75; H, 5.60.

Working Example 98 (Production of Compound 84)

In THF (72 ml) was dissolved 7-[4-(2-ethoxyethoxy)phenyl]-1,1-dioxo-2,3-dihydro-1-benzothiepine-4-carboxylic acid (3.6 g). To the mixture were added under ice-cooling thionyl chloride (0.93 ml) and DMF (three drops), and the mixture was stirred at room temperature for 30 minutes. The reaction mixture was added dropwise to a solution of 4-[[N-methyl-N-(tetrahydropyran-4-yl)amino]methyl]aniline (2.23 g) and triethylamine (5.0 ml) in THF (67 ml), and the mixture was stirred at room temperature for 1 hour. The reaction mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[4-(2-ethoxyethoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 84) (2.4 g).

m.p. 215–217° C.; Anal. for $C_{34}H_{40}N_2O_6S$ Calcd. C, 67.53; H, 6.67; N, 4.63: Found. C, 67.24; H, 6.62; N, 4.34.

Reference Example 118

In DMF (120 ml) was dissolved 4-bromophenol (20 g). To the mixture were added potassium carbonate (24 g) and sodium iodide (19.1 g) and then was added dropwise 2-chloroethylpropylether (19 ml), and the mixture was stirred at 80° C. for 16 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=10/1) to give 1-bromo-4-(2-propoxyethoxy)benzene (23.1 g).

$^1$H-NMR (200 MHz, CDCl$_3$) δ 0.93 (3H, t, J=7.2 Hz), 1.55–1.71 (2H, m), 3.48 (2H, t, J=6.8 Hz), 3.74–3.79 (2H, m), 4.05–4.10 (2H, m), 6.77–6.83 (2H, m), 7.33–7.38 (2H, m).

Reference Example 119

To a solution of magnesium (2.17 g) in THF (43 ml) was added 1,2-dibromoethane (3 drops). While refluxing the mixture, a solution of 1-bromo-4-(2-propoxyethoxy)benzene (22 g) in THF (176 ml) was gradually added to the mixture. The mixture was stirred for 15 minutes and cooled to −78° C. To the mixture was added dropwise a solution of trimethyl borate (13.2 g) in THF (13 ml), and the mixture was stirred for 1 hour, allowed to warm to room temperature for 6 hours and stirred at room temperature for 8 hours. To the mixture was added 5% sulfuric acid (75 ml), and the mixture was stirred for 15 minutes. The reaction mixture was added to water, and the mixture was extracted with ethyl acetate, washed with saturated brine and dried with magnesium sulfate. Under reduced pressure, the solvent was evaporated, and the residue was washed with hexane/isopropylether and then hexane/ethyl acetate to give 4-(2-propoxyethoxy)phenyl borate (8.6 g).

$^1$H-NMR (200 MHz, DMSO-d$_6$) δ 0.87 (3H, t, J=7.4 Hz), 1.44–1.62 (2H, m), 3.41 (2H, t, J=6.6 Hz), 3.67–3.72 (2H, m), 4.07–4.12 (2H, m), 6.89 (2H, d, J=8.8 Hz), 7.73 (2H, d, J=8.8 Hz).

Working Example 99 (Production of Compound 97)

To 7-bromo-N-[4-[[N-methyl-N-(tetrahydropyran-4-yl)amino]methyl]phenyl]-1,1-dioxo-2,3-dihydro-1-benzothiepine-4-carboxamide (400 mg) was added toluene/ethanol/water (10/1/1, 19.2 ml) were added 4-(2-propoxyethoxy)phenyl borate (207 mg) and potassium carbonate (234 mg), and the mixture was stirred at room temperature for 30 minutes. To the mixture was added tetrakistriphenylphosphinepalladium (36 mg), and the mixture was refluxed for 8 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give N-[4-[[N-methyl-N-(tetrahydropyran-4-yl)amino]methyl]phenyl]-7-[4-(2-propoxyethoxy)phenyl]-1,1-dioxo-2,3-dihydro-1-benzothiepine-4-carboxamide (Compound 97) (218 mg).

m.p. 195–197° C.; $^1$H-NMR (200 MHz, CDCl$_3$) δ 0.95 (3H, t, J=7.2 Hz), 1.60–1.80 (6H, m), 2.21 (3H, s), 2.65 (1H, m), 3.13–3.20 (2H, m), 3.31–3.44 (2H, m), 3.52 (2H, t, J=6.8 Hz), 3.57 (2H, s), 3.68–3.75 (2H, m), 3.82 (2H, t, J=4.8 Hz), 4.10–4.20 (2H, m), 4.19 (2H, t, J=4.8 Hz), 7.04 (2H, d, J=8.8 Hz), 7.30–7.35 (3H, m), 7.51–7.68 (6H, m), 7.83 (1H, s), 8.19 (1H, d, J=8.0 Hz); IR(KBr) 3270, 2942, 1665, 1607, 1518, 1311, 1292, 1252, 1130, 826, 667 cm$^{-1}$; Anal. for C$_{35}$H$_{42}$N$_2$O$_6$S Calcd. C, 67.94; H, 6.84; N, 4.53: Found. C, 67.87; H, 6.98; N, 4.45.

Reference Example 120

In DMF (150 ml) was dissolved 4-bromophenol (25 g). To the mixture was added potassium carbonate (30 g) and then was added dropwise 2-bromoethanol (23.5 g), and the mixture was stirred at 90° C. for 6 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=2/1) to give 2-(4-bromophenoxy)-1-ethanol (15.9 g).

$^1$H-NMR (200 MHz, CDCl$_3$) δ 2.24 (1H, br), 3.91–3.91 (2H, m), 4.02–4.07 (2H, m), 6.77–6.83 (2H, m), 7.33–7.38 (2H, m).

Reference Example 121

In DMF (150 ml) was dissolved 2-(4-bromophenoxy)-1-ethanol (15.7 g). To the mixture was added under ice-cooling 65% sodium hydride (4.3 g),and the mixture was stirred at room temperature for 2 hours. To the mixture was added dropwise iodobutane (17.3 g), and the mixture was stirred for 2 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=4/1) to give 1-bromo-4-(2-butoxyethoxy)benzene (12.6 g).

$^1$H-NMR (200 MHz, CDCl$_3$) δ 0.92 (3H, t, J=7.4 Hz), 1.27–1.65 (4H, m), 3.53 (2H, t, J=6.6 Hz), 3.74–3.79 (2H, m), 4.05–4.11 (2H, m), 6.81 (2H, d, J=9.0 Hz), 7.36 (2H, d, J=9.0 Hz).

Reference Example 122

To a solution of magnesium (1.14 g) in THF (23 ml) was added 1,2-dibromoethane (3 drops). While refluxing the mixture, a solution of 1-bromo-4-(2-butoxyethoxy)benzene (12.2 g) in THF (98 ml) was gradually added dropwise to the mixture. The mixture was stirred for 15 minutes and cooled to −78° C. To the mixture was added dropwise trimethyl borate (6.9 g), and the mixture was stirred for 1 hour, allowed to warm to room temperature for 8 hours and stirred at room temperature for 6 hours. To the mixture was added 5% sulfuric acid (75 ml), and the mixture was stirred for 15 minutes. The reaction mixture was added to water, and the mixture was extracted with ethyl acetate, washed with saturated brine and dried with magnesium sulfate. Under reduced pressure, the solvent was evaporated, and the residue was washed with hexane/isopropylether and then hexane/ethyl acetate to give 4-(2-butoxyethoxy)phenyl borate (6.0 g).

$^1$H-NMR (200 MHz, DMSO-d$_6$) δ 0.88 (3H, t, J=7.2 Hz), 1.25–1.58 (2H, m), 3.45 (2H, t, J=6.6 Hz), 3.64–3.76 (2H, m), 4.03–4.16 (2H, m), 6.87–6.96 (2H, m), 7.14 (1H, d, J=8.4 Hz), 7.81 (1H, d, J=8.4 Hz).

Working Example 100 (Production of Compound 98)

To 7-bromo-N-[4-[[N-methyl-N-(tetrahydropyran-4-yl)amino]methyl]phenyl]-1,1-dioxo-2,3-dihydro-1-benzothiepine-4-carboxamide (400 mg) was added toluene/ethanol/water (10/1/1, 19.2 ml) and then were added 4-(2-butoxyethoxy)phenyl borate (221 mg) and potassium carbonate (234 mg), and the mixture was stirred at room temperature for 30 minutes. To the mixture was added tetrakistriphenylphosphinepalladium (36 mg), and the mixture was refluxed for 8 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[4-(2-butoxyethoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 98) (330 mg).

m.p. 194–196° C.; $^1$H-NMR (200 MHz, CDCl$_3$) δ 0.93 (3H, t, J=7.2 Hz), 1.33–1.55 (2H, m), 1.57–1.77 (6H, m), 2.21 (3H, s), 2.65 (1H, m), 3.16 (2H, t, J=6.4 Hz), 3.31–3.44 (2H, m), 3.52–3.59 (2H, m), 3.57 (2H, s), 3.67–3.74 (2H, m), 3.79–3.84 (2H, m), 3.98–4.08 (2H, m), 4.18 (2H, t, J=4.8 Hz), 7.03 (2H, d, J=8.8 Hz), 7.30–7.35 (3H, m), 7.50–7.66 (6H, m), 7.88 (1H, s), 8.18 (1H, d, J=8.0 Hz); IR(KBr) 3300, 2935, 2853, 1667, 1607, 1518, 1312, 1292, 1251, 1130, 826 cm$^{-1}$; Anal. for C$_{36}$H$_{44}$N$_2$O$_6$S Calcd. C, 68.33; H, 7.01; N, 4.43: Found. C, 68.33; H, 6.85; N, 4.39.

Reference Example 123

In THF (100 ml) was dissolved 3-ethoxypropanol (10 g). To the mixture were added under ice-cooling triethylamine (14.5 ml) and methanesulfonyl chloride (6.8 ml), and the mixture was stirred at room temperature for 2 hours. The reaction mixture was added to water, and the mixture was extracted with THF, washed with saturated brine and dried with magnesium sulfate. Under reduced pressure, the solvent was evaporated, and the residue was added dropwise under ice-cooling to a solution of 4-bromophenol (20.8 g) and potassium carbonate (18.2 g) in DMF (130 ml). The mixture was stirred at 90° C. for 60 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=10/1) to give 1-bromo-4-(3-ethoxypropoxy)benzene (10.8 g).

$^1$H-NMR (200 MHz, CDCl$_3$) δ 1.20 (3H, t, J=7.0 Hz), 1.98–2.08 (2H, m), 3.49 (2H, q, J=7.0 Hz), 3.58 (2H, d, J=6.0 Hz), 4.03 (2H, d, J=6.4 Hz), 6.79 (2H, d, J=9.0 Hz), 7.36 (2H, d, J=9.0 Hz).

Reference Example 124

To a solution of magnesium (1.03 g) in THF (21 ml) was added 1,2-dibromoethane (3 drops). While refluxing the mixture, a solution of 1-bromo-4-(3-ethoxypropoxy)benzene (10.5 g) in THF (84 ml) was gradually added dropwise to the mixture. The mixture was stirred for 15 minutes and cooled to −78° C. To the mixture was added dropwise a solution of trimethyl borate (6.3 g) in THF (6 ml), and the mixture was stirred for 1 hour, allowed to warm to room temperature for 6 hours and stirred at room temperature for 8 hours. To the mixture was added 5% sulfuric acid (42 ml), and the mixture was stirred for 15 minutes. The reaction mixture was added to water, and the mixture was extracted with ethyl acetate, washed with saturated brine and dried with magnesium sulfate. Under reduced pressure, the solvent was evaporated, and the residue was washed with hexane/isopropylether to give 4-(3-ethoxypropoxy)phenyl borate (5.94 g).

$^1$H-NMR (200 MHz, DMSO-d$_6$) δ 1.11 (3H, t, J=7.0 Hz), 1.89–1.98 (2H, m), 3.42 (2H, q, J=7.0 Hz), 3.50 (2H, t, J=6.2 Hz), 4.02 (2H, t, J=6.2 Hz), 6.84–6.93 (2H, m), 7.69–7.81 (2H, m).

Working Example 101 (Production of Compound 99)

To 7-bromo-N-[4-[[N-methyl-N-(tetrahydropyran-4-yl)amino]methyl]phenyl]-1,1-dioxo-2,3-dihydro-1-benzothiepine-4-carboxamide (400 mg) was added toluene/ethanol/water (10/1/1, 19.2 ml) and then were added 4-(3-ethoxypropoxy)phenyl borate (207 mg) and potassium carbonate (234 mg), and the mixture was stirred at room temperature for 30 minutes. To the mixture was added tetrakistriphenylphosphinepalladium (36 mg), and the mixture was refluxed for 12 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[4-(3-ethoxypropoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 99) (140 mg).

m.p. 214–215° C.; $^1$H-NMR (200 MHz, CDCl$_3$) δ 1.21 (3H, t, J=7.0 Hz), 1.69–1.77 (4H, m), 2.05–2.13 (2H, m), 2.21 (3H, s), 2.65 (1H, m), 3.16 (2H, t, J=6.6 Hz), 3.31–3.44 (2H, m), 3.51 (2H, q, J=7.0 Hz), 3.57 (2H, s), 3.62 (2H, t, J=6.2 Hz), 3.67–3.75 (2H, m), 3.98–4.16 (4H, m), 7.01 (2H, d, J=8.8 Hz), 7.29–7.35 (3H, m), 7.50–7.67 (6H, m), 7.86 (1H, s), 8.18 (1H, d, J=8.0 Hz); IR(KBr) 3274, 2953, 1665, 1601, 1520, 1316, 1292, 1250, 1130, 824 cm$^{-1}$; Anal. for C$_{35}$H$_{42}$N$_2$O$_6$S Calcd. C, 67.94; H, 6.84; N, 4.53: Found. C, 67.67; H, 6.77; N, 4.54.

Reference Example 125

In DMF (120 ml) was dissolved 4-bromobenzyl alcohol (10.1 g). To the mixture was added under ice-cooling 65% sodium hydride (3.6 g), and the mixture was stirred at room temperature for 3 hours. To the mixture was added dropwise at room temperature iodoethane (12.6 g), and the mixture was stirred at room temperature for 2 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=8/1) to give 1-bromo-4-(ethoxymethyl)benzene (10.1 g).

$^1$H-NMR (200 MHz, CDCl$_3$) δ 1.24 (3H, t, J=7.0 Hz), 2.53 (2H, q, J=7.0 Hz), 4.45 (2H, s), 7.22 (2H, d, J=8.6 Hz), 7.46 (2H, d, J=8.6 Hz).

Reference Example 126

In THF/ether (4/1, 100 ml) was dissolved 1-bromo-4-(ethoxymethyl)benzene (9.8 g). To the mixture was added dropwise at −78° C. 1.6M n-butyllithium/hexane (31.3 ml), and the mixture was stirred for 1 hour. To the mixture was added trimethyl borate (11.8 g), and the mixture was stirred for 30 minutes and warmed to room temperature. To the mixture was added 5% sulfuric acid (39 ml), and the mixture was stirred for 15 minutes. The reaction mixture was extracted with ethyl acetate, washed with saturated brine and dried with magnesium sulfate. Under reduced pressure, the solvent was evaporated, and the residue was washed with hexane/isopropylether to give 4-(ethoxymethyl)phenyl borate (3.05 g).

$^1$H-NMR (200 MHz, DMSO-d$_6$) δ 1.15 (3H, t, J=7.0 Hz), 3.48 (2H, q, J=7.0 Hz), 4.45 (2H, s), 7.27 (2H, d, J=8.0 Hz), 7.76 (2H, d, J=8.0 Hz).

Working Example 102 (Production of Compound 100)

To 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) was added toluene/ethanol/water (10/1/1, 19.2 ml) and then were added 4-(ethoxymethyl)phenyl borate (125 mg) and potassium carbonate (175 mg), and the mixture was stirred at room temperature for 30 minutes. To the mixture was added tetrakistriphenylphosphinepalladium (26.6 mg), and the mixture was refluxed for 14 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[4-(ethoxymethyl)phenyl]-N-[4-[[[N-methyl-N-(tetrahydropyran-4-yl)amino]methyl]phenyl]-1,1-dioxo-2,3-dihydro-1-benzothiepine-4-carboxamide (Compound 100) (245 mg).

m.p. 221–224° C.; $^1$H-NMR (200 MHz, CDCl$_3$) δ 1.28 (3H, t, J=7.0 Hz), 1.65–1.77 (4H, m), 2.21 (3H, s), 2.65 (1H, m), 3.13–3.21 (2H, m), 3.31–3.44 (2H, m), 3.57 (2H, s), 3.60 (2H, q, J=7.0 Hz), 4.00–4.09 (2H, m), 4.57 (2H, s), 7.29–7.37 (3H, m), 7.44–7.68 (8H, m), 7.88 (1H, s), 8.19 (1H, d, J=8.0 Hz); IR(KBr) 3274, 2949, 1655, 1526, 1410, 1315, 1294, 1130, 814 cm$^{-1}$; Anal. for C$_{33}$H$_{38}$N$_2$O$_5$S; Calcd. C, 68.96; H, 6.66; N, 4.87; Found. C, 68.72; H, 6.65; N, 4.86.

Reference Example 127

In DMF (120 ml) was dissolved 4-bromobenzyl alcohol (15 g). To the mixture was added under ice-cooling 65% sodium hydride (3.0 g), and the mixture was stirred at room temperature for 3 hours. To the mixture was added dropwise at room temperature 2-bromoethylethyl ether (11.4 g), and the mixture was stirred at room temperature for 3 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=10/1) to give 1-bromo-4-[(2-ethoxyethoxy)methyl]benzene (9.0 g). In THF (104 ml) was dissolved 1-bromo-4-[2-ethoxyethoxy)methyl)]benzene (8.7 g). To the mixture was added dropwise at −78° C. 1.6M n-butyllithium/hexane (23 ml), and the mixture was stirred for 1 hour. To the mixture was added dropwise trimethyl borate (8.7 g), and the mixture was stirred for 30 minutes and warmed to room temperature. To the mixture was added 5% sulfuric acid (35 ml), and the mixture was stirred for 15 minutes. The reaction mixture was extracted with ethyl acetate, washed with saturated brine and dried with magnesium sulfate. Under reduced pressure, the solvent was evaporated, and the residue was purified with silica gel column chromatography (hexane/ethyl acetate=1/2) to give 4-[(2-ethoxyethoxy)methyl]phenyl borate (2.1 g).

$^1$H-NMR (200 MHz, CDCl$_3$) δ 1.25 (3H, t, J=7.0 Hz), 3.57 (2H, q, J=7.0 Hz), 3.58–3.67 (2H, m), 4.68 (2H, s), 7.50 (2H, d, J=8.0 Hz), 8.22 (2H, d, J=8.0 Hz).

Working Example 103 (Production of Compound 101)

To 7-bromo-N-[4-[(N-methyl-N-(tetrahydropyran-4-l)amino]methyl]phenyl]-1,1-dioxo-2,3-dihydro-1-benzothiepine-4-carboxamide (400 mg) was added toluene/ethanol/water (10/1/1, 25.5 ml) and then were added 4-[(2-ethoxyethoxy)methyl]phenyl borate (260 mg) and potassium carbonate (234 mg), and the mixture was stirred at room temperature for 30 minutes. To the mixture was added tetrakistriphenylphosphinepalladium (35.5 mg), and the mixture was refluxed for 14 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[4-[(2-ethoxyethoxy)methyl]phenyl]-N-[4-[[N-methyl-N-(tetrahydropyran-4-yl)amino]methyl]phenyl]-1,1-dioxo-2,3-dihydro-1-benzothiepine-4-carboxamide (Compound 101) (282 mg).

m.p. 184–186° C.; $^1$H-NMR (200 MHz, CDCl$_3$) δ 1.24 (3H, t, J=7.0 Hz), 1.63–1.79 (4H, m), 2.20 (3H, s), 2.64 (1H, m), 3.12–3.20 (2H, m), 3.30–3.44 (2H, m), 3.50–3.61 (4H, m), 3.62–3.73 (2H, m), 3.66 (2H, s), 3.98–4.09 (2H, m), 4.64 (2H, s), 7.30–7.37 (3H, m), 7.45–7.72 (9H, m), 7.85 (1H, s), 8.22 (1H, d, J=8.0 Hz); IR(KBr) 3300, 2926, 1667, 1597, 1526, 1408, 1313, 1294, 1130, 815 cm$^{-1}$; Anal. for C$_{35}$H$_{42}$N$_2$O$_6$S Calcd. C, 67.94; H, 6.84; N, 4.53: Found. C, 67.69; H, 6.90; N, 4.53.

Reference Example 128

In DMF (150 ml) was dissolved 4-bromophenol (25 g). To the mixture was added potassium carbonate (30 g) and then was added dropwise 3-bromopropanol (26.1 g), and the mixture was stirred at 100° C. for 20 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=2/1) to give 3-(4-bromophenoxy)-1-propanol (20.6 g).

$^1$H-NMR (200 MHz, CDCl$_3$) δ 1.76 (1H, br), 1.97–2.09 (2H, m), 3.80–3.91 (2H, m), 4.08 (2H, t, J=6.0 Hz), 6.76–6.81 (2H, m), 7.33–7.40 (2H, m).

Reference Example 129

In DMF (100 ml) was dissolved 3-(4-bromophenoxy)-1-propanol (10.0 g). To the mixture was added under ice-cooling 65% sodium hydride (2.4 g), and the mixture was stirred at room temperature for 2 hours. To the mixture was added dropwise iodoethane (3.8 ml), and the mixture was stirred for 3 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=4/1) to give 1-bromo-4-(3-methoxypropoxy)benzene (8.6 g).

$^1$H-NMR (200 MHz, CDCl$_3$) δ 0.92 (3H, t, J=7.4 Hz), 1.27–1.65 (4H, m), 3.53 (2H, t, J=6.6 Hz), 3.74–3.79 (2H, m), 4.05–4.11 (2H, m), 6.81 (2H, d, J=9.0 Hz), 7.36 (2H, d, J=9.0 Hz).

Reference Example 130

To a solution of magnesium (0.89 g) in THF (17.7 ml) was added iodine (catalytic amount). While refluxing the mixture, a solution of 1-bromo-4-(3-methoxypropoxy)

benzene (8.5 g) in THF (68 ml) was gradually added dropwise to the mixture. The mixture was stirred for 1 hour and cooled to −78° C. To the mixture was added dropwise a solution of trimethyl borate (5.4 g) in THF (10.8 ml), and the mixture was stirred for 1 hour, allowed to warm to room temperature for 6 hours, and stirred at room temperature for 8 hours. To the mixture was added 5% sulfuric acid (34 ml), and the mixture was stirred for 15 minutes. The reaction mixture was added to water, and the mixture was extracted with ethyl acetate, washed with saturated brine and dried with magnesium sulfate. Under reduced pressure, the solvent was evaporated, and the residue was washed with hexane/isopropylether and then hexane/ethyl acetate to give 4-(3-methoxypropoxy)phenyl borate (4.0 g).

$^1$H-NMR (200 MHz, DMSO-$d_6$) δ 0.88 (3H, t, J=7.2 Hz), 1.25–1.58 (2H, m), 3.45 (2H, t, J=6.6 Hz), 3.64–3.76 (2H, m), 4.03–4.16 (2H, m), 6.87–6.96 (2H, m), 7.14 (1H, d, J=8.4 Hz), 7.81 (1H, d, J=8.4 Hz).

Working Example 104 (Production of Compound 102)

To 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) was added toluene/ethanol/water (10/1/1, 19.2 ml) and then were added 4-(3-methoxypropoxy)phenyl borate (145 mg) and potassium carbonate (175 mg), and the mixture was stirred at room temperature for 30 minutes. To the mixture was added tetrakistriphenylphosphinepalladium (27 mg), and the mixture was refluxed for 14 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[4-(3-methoxypropoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 102) (190 mg).

$^1$H-NMR (200 MHz, CDCl$_3$) δ 1.63–1.82 (4H, m), 2.03–2.15 (2H, m), 2.20 (3H, s), 2.64 (1H, m), 3.11–3.19 (2H, m), 3.31–3.44 (2H, m), 3.37 (3H, s), 3.55 (2H, s), 3.53–3.58 (2H, m), 3.60–3.73 (2H, m), 4.01–4.13 (2H, m), 4.12 (2H, t, J=6.2 Hz), 7.01 (2H, d, J=8.4 Hz), 7.26–7.35 (3H, m), 7.48–7.64 (6H, m), 7.94 (1H, s), 8.16 (1H, d, J=8.0 Hz); IR(KBr) 3270, 2949, 1667, 1607, 1518, 1408, 1311, 1292, 1252, 1130, 826 cm$^{-1}$; Anal. for C$_{34}$H$_{40}$N$_2$O$_6$S Calcd. C, 67.53; H, 6.67; N, 4.63: Found. C, 67.39; H, 6.38; N, 4.71.

Reference Example 131

In DMF (100 ml) was dissolved 3-(4-bromophenoxy)-1-propanol (10.0 g). To the mixture was added under ice-cooling 65% sodium hydride (2.4 g), and the mixture was stirred at room temperature for 2 hours. To the mixture was added dropwise bromopropane (5.5 ml), and the mixture was stirred for 3 hours. To the mixture was added 65% sodium hydride (0.8 g), and the mixture was stirred at 70 for 1 hour and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=5/1) to give 1-bromo-4-(3-propoxypropoxy)benzene (6.7 g).

$^1$H-NMR (200 MHz, CDCl$_3$) δ 0.92 (3H, t, J=7.4 Hz), 1.27–1.65 (4H, m), 3.53 (2H, t, J=6.6 Hz), 3.74–3.79 (2H, m), 4.05–4.11 (2H, m), 6.81 (2H, d, J=9.0 Hz), 7.36 (2H, d, J=9.0 Hz).

Reference Example 132

To a solution of magnesium (0.63 g) in THF (12.5 ml) was added iodine (catalytic amount). While refluxing the mixture, a solution of 1-bromo-4-(3-propoxypropoxy)benzene (6.7 g) in THF (53.6 ml) was gradually added dropwise to the mixture. The mixture was stirred for 1 hour and cooled to −78° C. To the mixture was added dropwise a solution of trimethyl borate (3.8 g) in THF (7.6 ml), and the mixture was stirred for 1 hour, allowed to warm to room temperature for 6 hours and stirred at room temperature for 8 hours. To the mixture was added 5% sulfuric acid (27 ml), and the mixture was stirred for 15 minutes. The reaction mixture was added to water, and the mixture was extracted with ethyl acetate, washed with saturated brine and dried with magnesium sulfate. Under reduced pressure, the solvent was evaporated, and the residue was washed with hexane/isopropylether to give 4-(3-propoxypropoxy)phenyl borate (2.0 g).

$^1$H-NMR (200 MHz, DMSO-$d_6$) δ 0.88 (3H, t, J=7.2 Hz), 1.25–1.58 (2H, m), 3.45 (2H, t, J=6.6 Hz), 3.64–3.76 (2H, m), 4.03–4.16 (2H, m), 6.87–6.96 (2H, m), 7.14 (1H, d, J=8.4 Hz), 7.81 (1H, d, J=8.4 Hz).

Working Example 105 (Production of Compound 103)

To 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) were added toluene/ethanol/water (10/1/1, 19.2 ml) and then were added 4-(3-propoxypropoxy)phenyl borate (165 mg) and potassium carbonate (175 mg), and the mixture was stirred at room temperature for 30 minutes. To the mixture was added tetrakistriphenylphosphinepalladium (27 mg), and the mixture was refluxed for 14 hours and cooled to room temperature. The mixture was added to water, and the mixture was extracted with ethyl acetate/THF, washed with, saturated brine and dried with magnesium sulfate. Under reduced pressure, the solvent was evaporated, and the residue was purified with silica gel column chromatography (ethyl acetate/ethanol=3/1) and recrystallized from ethanol to give N-[4-[[N-methyl-N-(tetrahydropyran-4-yl)amino]methyl]phenyl]-7-[4-(3-propoxypropoxy)phenyl]-1,1-dioxo-2,3-dihydro-1-benzothiepine-4-carboxamide (Compound 103) (245 mg).

$^1$H-NMR (200 MHz, CDCl$_3$) δ 0.92 (3H, t, J=7.2 Hz), 1.54–1.92 (6H, m), 2.04–2.13 (2H, m), 2.20 (3H, s), 2.64 (1H, m), 3.11–3.18 (2H, m), 3.31–3.43 (2H, m), 3.41 (2H, t, J=6.6 Hz), 3.56 (2H, s), 3.58–3.72 (4H, m), 4.00–4.11 (2H, m), 4.13 (2H, t, J=6.2 Hz), 7.01 (2H, d, J=8.8 Hz), 7.26–7.35 (3H, m), 7.48–7.63 (6H, m), 7.98 (1H, s), 8.15 (1H, d, J=8.0 Hz); IR(KBr) 3274, 2955, 1655, 1601, 1520, 1410, 1316, 1292, 1252, 1130, 822 cm$^{-1}$; Anal. for C$_{36}$H$_{44}$N$_2$O$_6$S Calcd. C, 68.33; H, 7.01; N, 4.43: Found. C, 68.34; H, 6.82; N, 4.48.

Reference Example 133

To methyl 7-bromo-1,1-dioxo-2,3-dihydro-1-benzothiepine-4-carboxylate (6.5 g) was added toluene/ethanol/water (10/1/1,188 ml) and then were added 4-(2-propoxyethoxy)phenyl borate (5.3 g) and potassium carbonate (6.0 g), and the mixture was stirred at room temperature for 30 minutes. To the mixture was added tetrakistriphenylphosphinepalladium (0.9 g), and the mixture was refluxed for 14 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=3/2) to give methyl 7-[4-(2-propoxyethoxy)phenyl]-1,1-dioxo-2,3-dihydro-1-benzothiepine-4-carboxylate (6.5 g).

m.p. 105–107° C.; $^1$H-NMR (200 MHz, CDCl$_3$) δ 0.95 (3H, t, J=7.4 Hz), 1.56–1.76 (2H, m), 3.11–3.17 (2H, m), 3.52 (2H, t, J=6.8 Hz), 3.60–3.68 (2H, m), 3.80–3.85 (2H, m), 3.87 (3H, s), 4.16–4.21 (2H, m), 7.04 (2H, d, J=8.4 Hz), 7.53–7.58 (2H, m), 7.65–7.70 (2H, m), 7.91 (1H, s), 8.20 (1H, d, J=8.8 Hz); IR(KBr) 2920, 1709, 1604, 1518, 1294, 1252, 1130, 828, 752 m$^{-1}$; Anal. for C$_{23}$H$_{26}$O$_6$S Calcd. C, 64.17; H, 6.09: Found. C, 64.20; H, 5.91.

Reference Example 134

To methyl 7-[4-(2-propoxyethoxy)phenyl]-1,1-dioxo-2,3-dihydro-1-benzothiepine-4-carboxylate (6.5 g) were added 1,2-dimethoxyethane (130 ml) and 6N hydrochloric acid (65 ml), and the mixture was refluxed at 100° C. for 18 hours, cooled to room temperature, extracted with ethyl acetate, washed with saturated brine and dried with magnesium sulfate. Under reduced pressure, the solvent was evaporated to give 7-[4-(2-propoxyethoxy)phenyl]-1,1-dioxo-2,3-dihydro- 1-benzothiepine-4-carboxylic acid (5.0 g).

m.p. 176–179° C.; $^1$H-NMR (200 MHz, DMSO-d$_6$) δ 0.88 (3H, t, J=7.4 Hz), 1.44–1.62 (2H, m), 2.93–3.00 (2H, m), 3.43 (2H, t, J=6.6 Hz), 3.70–3.81 (4H, m), 4.14–4.19 (2H, m), 7.08 (2H, d, J=8.8 Hz), 7.78 (2H, d, J=8.8 Hz), 7.86–7.90 (2H, m), 8.05 (2H, m); IR(KBr) 2978, 1684, 1606, 1518, 1412, 1292, 1252, 1165, 1128, 829 cm$^{-1}$; Anal. for C$_{22}$H$_{24}$O$_6$S Calcd. C, 63.44; H, 5.81: Found. C, 63.38; H, 5.66.

Working Example 106 (Production of Compound 97)

In THF (98 ml) was dissolved 7-[4-(2-propoxyethoxy)phenyl]-1,1-dioxo-2,3-dihydro-1-benzothiepine-4-carboxylic acid (4.9 g). To the mixture were added under ice-cooling thionyl chloride (1.3 ml) and DMF (3 drops), and the mixture was stirred at room temperature for 30 minutes. To the mixture was added dropwise a solution of 4-[[N-methyl-N-(tetrahydropyran-4-yl)amino]methyl] aniline (2.93 g) and triethylamine (6.6 ml) in THF (88 ml), and the mixture was stirred at room temperature for 1 hour. The reaction mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give N-[4-[[N-methyl-N-(tetrahydropyran-4-yl)amino]methyl] phenyl]-7-[4-(2-propoxyethoxy)phenyl]-1,1-dioxo-2,3-dihydro-1-benzothiepine-4-carboxamide (Compound 97) (2.9 g).

m.p. 195–197° C.; Anal. for C$_{35}$H$_{42}$N$_2$O$_6$S Calcd. C, 67.94; H, 6.84; N, 4.53: Found. C, 67.84; H, 6.82; N, 4.59.

Reference Example 135

In DMF (75 ml) was dissolved 4-bromophenol (7.5 g). To the mixture were added at room temperature potassium carbonate (7.2 g) and sodium iodide (6.5 g) and then was added dropwise 2-chloro-5-chloromethyl thiophene (6.5 g), and the mixture was stirred at 90° C. for 6 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=10/1) to give 4-bromophenyl (5-chloro-2-thienyl)methyl ether (8.2 g).

$^1$H-NMR (200 MHz, CDCl$_3$) δ 5.07 (2H, s), 6.79–6.87 (4H, m), 7.34–7.42 (2H, m).

Reference Example 136

In THF (97 ml) was dissolved 4-bromophenyl(5-chloro-2-thienyl)methyl ether (8.1 g). To the mixture was added at −78° C. 1.6M n-butyllithium/hexane (8.3 ml), and the mixture was stirred for 1 hour. To the mixture was added dropwise a solution of trimethyl borate (5.5 g) in THF (5.5 ml), and the mixture was stirred for 30 minutes and warmed to room temperature. To the mixture was added 5% sulfuric acid (32 ml), and the mixture was stirred for 15 minutes, extracted with ethyl acetate, washed with saturated brine and dried with magnesium sulfate. Under reduced pressure, the solvent was evaporated, and the residue was washed with hexane/isopropylether to give 4-[(5-chloro-2-thienyl)methoxy]phenyl borate (4.2 g).

$^1$H-NMR (200 MHz, DMSO-d$_6$) δ 5.24 (2H, s), 6.86 (2H, d, J=8.4 Hz), 7.01–7.11 (2H, m), 7.74 (2H, d, J=8.4 Hz).

Working Example 107 (Production of Compound 104)

To 7-bromo-N-[4-[[N-methyl-N-(tetrahydropyran-4-yl) amino]methyl]phenyl]-1,1-dioxo-2,3-dihydro-1-benzothiepine-4-carboxamide (300 mg) was added toluene/ethanol/water (10/1/1, 19.2 ml) and then were added 4-[(5-chloro-2-thienyl)methoxy]phenyl borate (186 mg) and potassium carbonate (175 mg), and the mixture was stirred at room temperature for 30 minutes. To the mixture was added tetrakistriphenylphosphinepalladium (27 mg), and the mixture was refluxed at 100° C. for 8 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=5/2) and recrystallized from ethanol to give 7-[4-[(5-chloro-2-thienyl)methoxy]phenyl]-N-[4-[[N-methyl-N-(tetrahydropyran-4-yl)amino]methyl] phenyl]-1,1-dioxo-2,3-dihydro-1-benzothiepine-4-carboxamide (Compound 104) (137 mg).

m.p. 207–210° C.; $^1$H-NMR (200 MHz, CDCl$_3$) 1.60–1.82 (4H, m), 2.20 ()3H, s), 2.65 (1H, m), 3.15 (2H, t, J=6.2 Hz), 3.31–3.44 (2H, m), 3.57 (2H, s), 3.65–3.73 (2H, m), 3.98–4.09 (2H, m), 5.17 (2H, s), 6.83 (1H, d, J=3.8 Hz), 6.91 (1H, d, J=3.6 Hz), 7.05 (2H, d, 8.8 Hz), 7.29–7.54 (3H, m), 7.48–7.64 (6H, m), 7.98 (1H, s), 8.16 (1H, d, J=8.0 Hz); IR(KBr) 2949, 2845, 1663, 1607, 1514, 1454, 1408, 1292, 1242, 1157, 1130, 1009, 814 cm$^{-1}$.

Reference Example 137

In DMF (96 ml) was dissolved 4-bromobenzenethiol (12 g). To the mixture were added dropwise at room temperature potassium carbonate (12.3 g) and sodium iodide (10.5 g) and then was added dropwise 2-chloroethylpropylether (9.6 ml), and the mixture was stirred at 90° C. for 14 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=10/1) to give 1-bromo-4-(2-propoxyethylthio)benzene (16.9 g).

$^1$H-NMR (200 MHz, CDCl$_3$) 0.91 (3H, t, J=7.4 Hz), 1.50–1.66 (2H, m), 3.09 (2H, t, J=6.6 Hz), 3.39 (2H, t, J=7.0 Hz), 3.60 (2H, t, J=7.0 Hz), 7.20–7.26 (2H, m), 7.37–7.42 (2H, m).

Reference Example 138

To a solution of magnesium (1.53 g) in THF (23 ml) was added iodine (catalytic amount). While refluxing the mixture, a solution of 1-bromo-4-(2-propoxyethylthio) benzene (16.5 g) in THF (132 ml) was gradually added dropwise to the mixture. The mixture was stirred for 30 minutes and cooled to −78° C. To the mixture was added dropwise a solution of trimethyl borate (9.3 g) in THF (9.3 ml), and the mixture was stirred for 1 hour, allowed to warm to room temperature for 8 hours and stirred at room temperature for 6 hours. To the mixture was added 3N hydrochloric.acid (66 ml), and the mixture was stirred for 15 minutes. The reaction mixture was added to water, and the mixture was extracted with ethyl acetate, washed with saturated brine and dried with magnesium sulfate. Under reduced pressure, the solvent was evaporated, and the residue was washed with hexane/isopropylether to give 4-(2-propoxyethylthio)phenyl borate (6.5 g).

$^1$H-NMR (200 MHz, DMSO-d$_6$) δ 0.86 (3H, t, J=7.2 Hz), 1.41–1.57 (2H, m), 3.15 (2H, t, J=6.6 Hz), 3.35 (2H, t, J=6.6 Hz), 3.56 (2H, t, J=6.6 Hz), 7.27 (2H, d, J=8.0 Hz), 7.71 (2H, d, J=8.0 Hz), 7.99 (2H, br).

Working Example 108 (Production of Compound 105)

To 7-bromo-N-[4-[[N-methyl-N-(tetrahydropyran-4-yl) amino]methyl]phenyl]-1,1-dioxo-2,3-dihydro-1-benzothiepine-4-carboxamide (310 mg) was added toluene/ethanol/water (10/1/1, 19.8 ml) and then were added 4-(2-propoxyethylthio)phenyl borate (172 mg) and potassium carbonate (181 mg), and the mixture was stirred at room temperature for 30 minutes. To the mixture was added tetrakistriphenylphosphinepalladium (28 mg), and the mixture was refluxed at 100° C. for 12 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=5/2) and. recrystallized from ethanol to give N-[4-[[N-methyl-N-(tetrahydropyran-4-yl)amino] methyl]phenyl]-7-[4-(2-propoxyethylthio)phenyl]-1,1-dioxo-2,3-dihydro-1-benzothiepine-4-carboxamide (Compound 105) (220 mg).

m.p. 198–200° C.; $^1$H-NMR (200 MHz, CDCl$_3$) δ 0.92 (3H, t, J=7.4 Hz), 1.54–1.82 (6H, m), 2.21 (3H, s), 2.65 (1H, m), 3.13–3.22 (4H, m), 3.31–3.43 (2H, m), 3.47 (2H, t, J=7.0 Hz), 3.57 (2H, s), 3.67 (2H, t, J=7.0 Hz), 3.65–3.72 (2H, m), 4.01–4.09 (2H, m), 7.30–7.35 (2H, m), 7.42–7.57 (7H, m), 7.63–7.71 (2H, m), 7.87 (1H, s), 8.22 (1H, d, J=8.4 Hz); IR(KBr) 2959,2847, 1655, 1597, 1528, 1410, 1316, 1294, 1130, 816 cm$^{-1}$; Anal. for C$_{35}$H$_{42}$N$_2$O$_4$S$_2$ Calcd. C, 66.22; H, 6.67; N, 4.41: Found. C, 66.03; H, 6.72; N, 4.41.

Reference Example 139

In DMF (166 ml) was dissolved 2-(4-bromophenoxy)-1-ethanol (19.5 g). To the mixture was added under ice-cooling 65% sodium hydride (5.3 g), and the mixture was stirred at room temperature for 1.5 hours. To the mixture was added dropwise iodopentane (17.7 ml), and the mixture was stirred for 2 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=10/1) to give 1-bromo-4-(2-pentyloxyethoxy)benzene (12.0 g).

$^1$H-NMR (200 MHz, CDCl$_3$) δ 0.90 (3H, t, J=6.6 Hz), 1.25–1.37 (4H, m), 1.57–1.68 (2H, m), 3.52 (2H, t, J=6.6 Hz), 3.74–3.79 (2H, m), 4.05–4.11 (2H, m), 6.78–6.83 (2H, m), 7.33–7.39 (2H, m).

Reference Example 140

To a solution of magnesium (0.91 g) in THF (14 ml) was added iodine (catalytic amount). While refluxing the mixture, a solution of 1-bromo-4-(2-pentyloxyethoxy) benzene (11.8 g) in THF (94 ml) was gradually added dropwise to the mixture. The mixture was stirred for 30 minutes and cooled to −78° C. To the mixture was added dropwise trimethyl borate (5.7 g), and the mixture was allowed to warm to room temperature for 8 hours and stirred at room temperature for 6 hours. To the mixture was added 5% sulfuric acid (47 ml), and the mixture was stirred for 15 minutes. The reaction mixture was added to water, and the mixture was extracted with ethyl acetate, washed with saturated brine and dried with magnesium sulfate. Under reduced pressure, the solvent was evaporated, and the residue was washed with hexane/isopropylether and then hexane/ethyl acetate to give 4-(2-pentyloxyethoxy)phenyl borate (5.6 g).

$^1$H-NMR (200 MHz, DMSO-d$_6$) δ 0.86 (3H, t, J=6.6 Hz), 1.22–1.59 (6H, m), 3.44 (2H, t, J=6.6 Hz), 3.66–3.71 (2H, m), 4.05–4.13 (2H, m), 6.88 (2H, d, J=8.6 Hz), 7.72 (2H, d, J=8.6 Hz), 7.82 (2H, br).

Working Example 109 (Production of Compound 106)

To 7-bromo-N-[4-[[N-methyl-N-(tetrahydropyran-4-yl) amino]methyl]phenyl]-1,1-dioxo-2,3-dihydro-1-benzothiepine-4-carboxamide (310 mg) was added toluene/ethanol/water (10/1/1, 19.8 ml) and then were added 4-(2-pentyloxyethoxy)phenyl borate (180 mg) and potassium carbonate (181 mg), and the mixture was stirred at room temperature for 30 minutes. To the mixture was added tetrakistriphenylphosphinepalladium (28 mg), and the mixture was refluxed for 8 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=5/2) and recrystallized from ethanol to give N-[4-[[N-methyl-N-(tetrahydropyran-4-yl)amino]methyl]phenyl]-7-[4-(2-pentyloxyethoxy)phenyl]-1,1-dioxo-2,3-dihydro-1-benzothiepine-4-carboxamide (Compound 106) (188 mg).

m.p. 188–189° C.; $^1$H-NMR (200 MHz, CDCl$_3$) δ 0.90 (3H, t, J=6.6 Hz), 1.38–1.40 (4H, m), 1.56–1.77 (6H, m), 2.20 (3H, s), 2.64 (1H, m), 3.10–3.19 (2H, m), 3.30–3.44 (2H, m), 3.55 (2H, t, J=6.6 Hz), 3.56 (2H, s), 3.65–3.73 (2H, m), 3.79–3.85 (2H, m), 3.98–4.10 (2H, m), 4.15–4.21 (2H, m), 7.00–7.06 (2H, m), 7.29–7.34 (2H, m), 7.47–7.66 (7H, m), 7.95 (1H, s), 8.17 (1H, d, J=8.4 Hz); IR(KBr) 2938, 2853, 1667, 1607, 1516, 1408, 1312, 1292, 1251, 1130, 826 cm$^{-1}$; Anal. for $C_{36}H_{44}N_2O_6S$ Calcd. C, 68.70; H, 7.17; N, 4.33: Found. C, 68.64; H, 7.03; N, 4.31.

Reference Example 141

In DMF (195 ml) was dissolved 2-(4-bromophenoxy)-1-ethanol (19. 5 g). To the mixture was added under ice-cooling 65% sodium hydride (5.3 g), and the mixture was stirred at room temperature for 2 hours. To the mixture was added dropwise iodohexane (19.9 ml), and the mixture was stirred for 2 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=8/1) to give 1-bromo-4-(2-hexyloxyethoxy)benzene (16.2 g).

$^1$H-NMR (200 MHz, CDCl$_3$) δ 0.89 (3H, t, J=6.6 Hz), 1.25–1.43 (6H, m), 3.52 (2H, t, J=6.6 Hz), 3.74–3.79 (2H, m), 4.05–4.11 (2H, m), 6.78–6–84 (2H, m), 7.34–7.39 (2H, m).

Reference Example 142

To a solution of magnesium (1.19 g) in THF (14 ml) was added iodine (catalytic amount). While refluxing the mixture, a solution of 1-bromo-4-(2-hexyloxyethoxy)benzene (16.0 g) in THF (102 ml) was gradually added dropwise to the mixture. The mixture was stirred for 15 minutes and cooled to −78° C. To the mixture was added dropwise a solution of trimethyl borate (7.2 g) in THF (14 ml), and the mixture was allowed to warm to room temperature for 8 hours and stirred at room temperature for 6 hours. To the mixture was added 5% sulfuric acid (64 ml), and the mixture was stirred for 15 minutes. The reaction mixture was added to water, and the mixture was extracted with ethyl acetate, washed with saturated brine and dried with magnesium sulfate. Under reduced pressure, the solvent was evaporated, and the residue was washed with hexane/isopropylether to give 4-(2-hexyloxyethoxy)phenyl borate (6.7 g).

$^1$H-NMR (200 MHz, DMSO-d$_6$) δ 0.86 (3H, t, J=6.6 Hz), 1.18–1.59 (8H, m), 3.44 (2H, t, J=6.6 Hz), 3.66–3.71 (2H, m), 4.04–4.12 (2H, m), 6.88 (2H, d, J=8.4 Hz), 7.73 (2H, d, J=8.4 Hz).

Working Example 110 (Production of Compound 107)

To 7-bromo-N-[4-[[N-methyl-N-(tetrahydropyran-4-yl)amino]methyl]phenyl]-1,1-dioxo-2,3-dihydro-1-benzothiepine-4-carboxamide (310 mg) was added toluene/ethanol/water (10/1/1, 19.8 ml) and then were added 4-(2-hexyloxyethoxy)phenyl borate (190 mg) and potassium carbonate (181 mg), and the mixture was stirred at room temperature for 30 minutes. To the mixture was added tetrakistriphenylphosphinepalladium (28 mg), and the mixture was refluxed for 8 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=5/2) and recrystallized from ethanol to give 7-[4-(2-hexyloxyethoxy)phenyl]-N-[4-[[N-methyl-N-hexyloxyethoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 107) (200 mg).

m.p. 180–182° C.; $^1$H-NMR (200 MHz, CDCl$_3$) δ 0.89 (3H, t, J=7.2 Hz), 1.21–1.46 (6H, m), 1.57–1.82 (6H, m), 2.21 (3H, s), 2.64 (1H, m), 3.16 (2H, t, J=6.6 Hz), 3.31–3.43 (2H, m), 3.51–3.70 (2H, m), 3.57 (2H, s), 3.67–3.75 (2H, m), 3.98–4.09 (2H, m), 4.15–4.21 (2H, t, J=4.8 Hz), 7.03 (2H, d, J=8.8 Hz), 7.30–7.35 (3H, m), 7.50–7.66 (6H, m), 7.89 (1H, s), 8.18 (1H, d, J=8.4 Hz); IR(KBr) 3245, 2953, 2855, 1651, 1605, 1518, 1412, 1316, 1294, 1252, 1130, 826 cm$^{-1}$.

Working Example 111 (Production of Compound 108)

In DMF (3.8 ml) was dissolved 7-(4-hydroxyphenyl)-N-[4-[[N-methyl-N-(tetrahydropyran-4-yl)amino]methyl]phenyl]-1,1-dioxo-2,3-dihydro-1-benzothiepine-4-carboxamide (380 mg). To the mixture was added potassium carbonate (252 mg), and the mixture was stirred for 30 minutes. To the mixture was added 2-chloromethylpyridinehydrochloride (130 mg), and the mixture was stirred at room temperature for 6 hours. The reaction mixture was added to water, and the mixture was extracted with ethyl acetate/THF, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[4-(2-pyridylmethoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 108) (10 mg).

$^1$H-NMR (200 MHz, DMSO-d$_6$) δ 1.46–1.74 (4H, m), 2.10 (3H, s), 2.59 (1H, m), 3.02–3.14 (2H, m), 3.19–3.37 (2H, m), 3.52 (2H, s), 3.72–3.83 (2H, m), 3.88–3.94 (2H, m), 5.26 (2H, s), 6.90 (1H, d, J=8.4 Hz), 7.16–7.39 (5H, m), 7.53–7.89 (8H, m), 8.40–8.09 (2H, m), 8.57–8.62 (1H, m), 10.17 (1H, s).

Reference Example 143

In DMF (100 ml) was dissolved 3-bromophenol (10 g). To the mixture were added potassium carbonate (10.4 g) and bromopropane (6.0 ml), and the mixture was stirred at 60° C. for 2 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=10/1) to give 1-bromo-3-propoxybenzene (11.2 g).

$^1$H-NMR (200 MHz, CDCl$_3$) δ 1–03 (3H, t, J=7.2 Hz), 1.72–1.86 (2H, m), 3.89 (2H, t, J=6.6 Hz), 6.79–6.85 (1H, m), 7.03–7.17 (3H, m).

Reference Example 144

In THF (110 ml) was dissolved 1-bromo-3-propoxybenzene (11.0 g). To the mixture was added dropwise at −78° C. 1.6M n-butyllithium/hexane (35.2 ml), and the mixture was stirred for 1 hour. To the mixture was added dropwise a solution of trimethyl borate (10.6 g) in THF (10.6 ml), and the mixture was stirred for 30 minutes and warmed to room temperature. To the mixture was added 2N hydrochloric acid (44 ml), and the mixture was stirred for 15 minutes. The reaction mixture was extracted with ethyl acetate, washed with saturated brine and dried with magnesium sulfate. Under reduced pressure, the solvent was evaporated, and the residue was washed with hexane/isopropylether to give 3-propoxyphenyl borate (4.5 g).

$^1$H-NMR (200 MHz, DMSO-d$_6$) δ 0.99 (3H, t, J=7.4 Hz), 1.65–1.81 (2H, m), 3.91 (2H, t, J=6.6 Hz), 6.90–6.95 (1H, m), 7.18 (3H, m), 7.99 (2H, br).

Working Example 112 (Production of Compound 109)

To 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) was added toluene/ethanol/water (20/1/1, 13.9 ml) and then were added 3-propoxyphenyl borate (125 mg) and potassium carbonate (175 mg), and the mixture was stirred at room temperature for 30 minutes. To the mixture was added tetrakistriphenylphosphinepalladium (27 mg), and the mixture was refluxed for 8 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=5/2) and recrystallized from ethanol to give N-[4-[[N-methyl-N-(tetrahydropyran-4-yl)amino]methyl]phenyl]-7-(3-propoxyphenyl)-1,1-dioxo-2,3-dihydro-1-benzothiepine-4-carboxamide (Compound 109) (282 mg).

m.p. 219–221° C.; $^1$H-NMR (200 MHz, CDCl$_3$) δ 1.07 (3H, t, J=7.2 Hz), 1.63–1.90 (6H, m), 2.21 (3H, s), 2.64 (1H, m), 3.13–3.21 (2H, m), 3.31–3.44 (2H, m), 3.57 (2H, s), 3.67–3.75 (2H, m), 3.95–4.09 (2H, m), 6.98 (1H, dd, J=8.2, 2.6 Hz), 7.10–7.17 (2H, m), 7.29–7.43 (4H, m), 7.54 (2H, d, J=8.4 Hz), 7.64–7.71 (2H, m), 7.88 (1H, s), 8.20 (1H, d, J=8.4 Hz); IR(KBr) 3357, 2946, 2841, 1649, 1631, 1595, 1510, 1406, 1321, 1294, 1217, 1134, 785 cm$^{-1}$; Anal. for C$_{33}$H$_{38}$N$_2$O$_5$S Calcd. C, 68.96; H, 6.66; N, 4.87: Found. C, 68.77; H, 6.85; N, 4.88.

Reference Example 145

In DMF (140 ml) was dissolved 3-bromophenol (14 g). To the mixture were added potassium carbonate (15.7 g) and sodium iodide (12.1 g) and then was added 2-chloroethylpropylether (12.3 ml), and the mixture was stirred at 90° C. for 18 hours. There action mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=12/1) to give 1-bromo-3-(2-propoxyethoxy)benzene (11.1 g).

$^1$H-NMR (200 MHz,CDCl$_3$) δ 0.93 (3H, t, J=7.2 Hz), 1.56–1.72 (2H, m), 3.49 (2H, t, J=6.6 Hz), 3.74–3.80 (2H, m), 4.07–4.12 (2H, m), 6.81–6.89 (1H, m), 7.03–7.18 (3H, m)

Reference Example 146

To a solution of magnesium (0.99 g) in THF (9.9 ml) was added 1,2-dibromoethane (catalytic amount). To the mixture was gradually added dropwise at room temperature a solution of 1-bromo-3-(2-propoxyethoxy)benzene (10.5 g) in THF (84 ml). The mixture was stirred at 60 for 1 hour and cooled to −78° C. To the mixture was added dropwise a solution of trimethyl borate (8.5 g) in THF (17 ml), and the mixture was allowed to warm to room temperature for 8 hours and stirred at room temperature for 12 hours. To the mixture was added 2N hydrochloric acid (42 ml), and the mixture was stirred for 15 minutes. The reaction mixture was added to water, and the mixture was extracted with ethyl acetate, washed with saturated brine and dried with magnesium sulfate. Under reduced pressure, the solvent was evaporated, and the residue was washed with hexane/isopropylether and hexane/ethyl acetate to give 3-(2-propoxyethoxy)phenyl borate (3.5 g).

$^1$H-NMR (200 MHz, DMSO-d$_6$) δ 0.88 (3H, t, J=7.2 Hz), 1.46–1.63 (2H, m), 3.42 (2H, t, J=6.6 Hz), 3.67–3.73 (2H, m), 4.05–4.10 (2H, m), 6.93–6.98 (2H, m), 7.19–7.37 (2H, m), 8.00 (2H, br).

Working Example 113 (Production of Compound 110)

To 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) was added toluene/ethanol/water (20/1/1, 13.9 ml) and then were added 3-(propoxyethoxy)phenyl borate (155 mg) and potassium carbonate (176 mg), and the mixture was stirred at room temperature for 30 minutes. To the mixture was added tetrakistriphenylphosphinepalladium (27 mg), and the mixture was refluxed for 16 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=5/2) and recrystallized from ethanol to give N-[4-[[N-methyl-N-(tetrahydropyran-4-yl)amino]methyl]phenyl]-7-[3-(2-propoxyethoxy)phenyl]-1,1-dioxo-2,3-dihydro-1-benzothiepine-4-carboxamide (Compound 110) (154 mg).

m.p. 166–167° C.; $^1$H-NMR (200 MHz, CDCl$_3$) δ 0.94 (3H, t, J=7.4 Hz), 1.57–1.83 (6H, m), 2.21 (3H, s), 2.64 (1H, m), 3.18 (2H, t, J=6.6 Hz), 3.31–3.45 (2H, m), 3.51 (2H, t, J=6.6 Hz), 3.57 (2H, s), 3.68–3.75 (2H, m), 3.79–3.85 (2H, m), 4.01–4.16 (2H, m), 4.17–4.23 (2H, m), 6.97–7.03 (1H, m), 7.15–7.19 (2H, m), 7.30–7.44 (4H, m), 7.55 (2H, d, J=8.8 Hz), 7.64–7.72 (2H, m), 7.84 (1H, s), 8.21 (1H, d, J=8.2 Hz); IR(KBr) 2942, 2849, 1667, 1597, 1522, 1408, 1312, 1292, 1130 cm$^{-1}$; Anal. for C$_{35}$H$_{42}$N$_2$O$_6$S Calcd. C, 67.94; H, 6.84; N, 4.53: Found. C, 67.78; H, 6.76; N, 4.50.

Reference Example 147

In THF (150 ml) was dissolved 2-isopropoxyethanol (15 g). To the mixture were added under ice-cooling triethylamine (30.1 ml) and methanesulfonyl chloride (14.6 ml), and the mixture was stirred at room temperature for 1 hour. The reaction mixture was added to water, and the mixture was extracted with THF, washed with saturated brine and dried with magnesium sulfate. Under reduced pressure, the solvent was evaporated, and the residue was added dropwise under ice-cooling to a solution of 4-bromophenol (20.7 g) and potassium carbonate (21.5 g) in DMF (207 ml), and the mixture was stirred at 70° C. for 16 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=10/1) to give 1-bromo-4-(2-isopropoxyethoxy)benzene (16.4 g).

$^1$H-NMR (200 MHz, CDCl$_3$) δ 1.18 (3H, s), 1.21 (3H, s), 3.60–3.75 (1H, m), 4.04–4.09 (2H, m), 6.80 (2H, d, J=9.2 Hz), 7.36 (2H, d, J=9.2 Hz).

Reference Example 148

To a solution of magnesium (1.58 g) in THF (24 ml) was added 1,2-dibromoethane (catalytic amount). While refluxing the mixture, a solution of 1-bromo-4-(2-isopropoxyethoxy)benzene (10 g) in THF (80 ml) was gradually added dropwise to the mixture. The mixture was stirred at 50° C. for 1 hour and cooled to −78° C. To the mixture was added dropwise a solution of trimethyl borate (6.4 g) in THF (9.6 ml) and the mixture was stirred for 1 hour, allowed to warm to room temperature and stirred at room temperature for 8 hours. To the mixture was added 2N hydrochloric acid (40 ml), and the mixture was stirred for 15 minutes. The reaction mixture was added to water, and the mixture was extracted with ethyl acetate, washed with saturated brine and dried with magnesium sulfate. Under reduced pressure, the solvent was evaporated, and the residue was washed with hexane/isopropylether to give 4-(2-isopropoxyethoxy)phenyl borate (1.3 g).

$^1$H-NMR (200 MHz, DMSO-$d_6$) δ 1.09 (3H, s), 1.12 (3H, s), 3.55–3.71 (3H, m), 4.03–4.09 (2H, m), 6.88 (2H, d, J=8.8 Hz), 7.72 (2H, d, J=8.8 Hz).

Working Example 114 (Production of Compound 111)

To 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) was added toluene/ethanol/water (20/1/1, 13.9 ml) and then were added 4-(2-isopropoxyethoxy)phenyl borate (153 mg) and potassium carbonate (176 mg), and the mixture was stirred at room temperature for 30 minutes. To the mixture was added tetrakistriphenylphosphinepalladium (27 mg), and the mixture was refluxed for 12 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[4-(2-isopropoxyethoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 111) (159 mg).

m.p. 214–215° C.; $^1$H-NMR (200 MHz, CDCl$_3$) δ 1.20 (3H, s), 1.23 (3H, s), 1.62–1.77 (4H, m), 2.21 (3H, s), 2.67 (1H, m), 3.16 (2H, t, J=6.6 Hz), 3.31–3.44 (2H, m), 3.57 (2H, s), 3.64–3.74 (3H, m), 3.81 (2H, m), 4.00–4.18 (2H, m), 4.17 (2H, t, J=4.8 Hz), 7.03 (2H, d, J=8.8 Hz), 7.30–7.34 (3H, m), 7.50–7.67 (6H, m), 7.86 (1H, s), 8.18 (1H, d, J=8.2 Hz); IR(KBr) 3274, 2953, 1665, 1601, 1520, 1316, 1292, 1250, 1130, 824 cm$^{-1}$; Anal. for C$_{35}$H$_{42}$N$_2$O$_6$S Calcd. C, 67.94; H, 6.84; N, 4.53: Found. C, 67.67; H, 6.77; N, 4.54.

Working Example 115 (Production of Compound 112)

In THF (850 ml) was dissolved N-[4-[[N-methyl-N-(tetrahydropyran-4-yl)amino]methyl]phenyl]-7-[4-(2-propoxyethoxy)phenyl]-1,1-dioxo-2,3-dihydro-1-benzothiepine-4-carboxamide (17.3 g), and to the mixture was added at room temperature 4N hydrochloric acid/ethyl acetate (14 ml). The mixture was stirred for 1 hour. Under reduced pressure, the solvent was evaporated, and the residue was washed with ethyl acetate/acetone and recrystallized from ethanol to give N-[4-[[N-methyl-N-(tetrahydropyran-4-yl)amino]methyl]phenyl]-7-[4-(2-propoxyethoxy)phenyl]-1,1-dioxo-2,3-dihydro-1-benzothiepine-4-carboxamide hydrochloride (Compound 112) (11.2 g).

m.p. 213–215° C.; $^1$H-NMR (200 MHz, DMSO-$d_6$) δ 0.88 (3H, t, J=7.4 Hz), 1.05–1.63 (2H, m), 1.70–2.21 (4H, m), 2.58 (3H, s), 2.50–2.60 (2H, m), 3.05–3.12 (2H, m), 3.23–3.49 (4H, m), 3.43 (2H, t, J=6.6 Hz), 3.72–3.82 (2H, m), 3.94–4.03 (2H, m), 4.17 (2H, s), 4.38–4.49 (2H, m), 7.10 (2H, d, J=8.8 Hz), 7.58–7.62 (2H, m), 7.76 (2H, d, J=8.8 Hz), 7.83–7.90 (4H, m), 8.07 (2H, d, J=8.2 Hz), 10.47 (1H, s), 10.62 (1H, br). IR(KBr) 2961, 2870, 1667, 1597, 1520, 1412, 1321, 1292, 1248, 1132, 828 cm$^{-1}$; Anal. for C$_{35}$H$_{42}$N$_2$O$_6$S.HCl Calcd. C, 64.16; H, 6.61; N, 4.28: Found. C, 63.97; H, 6.55; N, 4.18.

Reference Example 149

In DMF (120 ml) was dissolved 2-bromophenol (12 g). To the mixture was added potassium carbonate (12.5 g) and then was added bromopropane (7.2 ml), and the mixture was stirred at room temperature for 3 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=12/1) to give 1-bromo-2-propoxybenzene (10.5 g).

$^1$H-NMR (200 MHz, CDCl$_3$) δ 1.08 (3H, t, J=1.4 Hz), 1.78–1.94 (2H, m), 3.98 (2H, t, J=6.6 Hz), 6.77–6.91 (2H, m), 7.19–7.29 (1H, m), 7.19–7.29 (1H, dd, J=7.6,1.8 Hz).

Reference Example 150

In THF (101 ml) was dissolved 1-bromo-2-propoxybenzene (10.1 g). To the mixture was added dropwise at −78° C. 1.6M n-butyllithium/hexane (32.3 ml), and the mixture was stirred for 1 hour. To the mixture was added dropwise a solution of trimethyl borate (9.8 g) in THF (9.8 ml), and the mixture was stirred for 30 minutes and warmed to room temperature. To the mixture was added 2N hydrochloric acid (40 ml), and the mixture was stirred for 15 minutes. The reaction mixture was extracted with ethyl acetate, washed with saturated brine and dried with magnesium sulfate. Under reduced pressure, the solvent was evaporated, and the residue was washed with hexane/isopropylether to give 2-propoxyphenyl borate (5.3 g).

$^1$H-NMR (200 MHz, DMSO-$d_6$) δ 1.00 (3H, t, J=7.2 Hz), 1.70–1.83 (2H, m), 4.00 (2H, t, J=6.6 Hz), 6.89–7.00 (2H, m), 7.33–7.42 (1H, m), 7.60 (2H, dd, J=7.2,2.0 Hz), 7.68 (2H, s).

Working Example 116 (Production of Compound 113)

To 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) was added toluene/ethanol/water (20/1/1, 13.8 ml) and then were added 2-propoxyphenyl borate (125 mg) and potassium carbonate (175 mg), and the mixture was stirred at room temperature for 30 minutes. To the mixture was added tetrakistriphenylphosphinepalladium (27 mg), and the mixture was refluxed at 100° C. for 8 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give N-[4-[[N-methyl-N-(tetrahydropyran-4-yl)amino]methyl]phenyl]-7-(2-propoxyphenyl)-1,1-dioxo-2,3-dihydro-1-benzothiepine-4-carboxamide (Compound 113) (46 mg).

m.p. 190–192° C.; $^1$H-NMR (200 MHz, CDCl$_3$) δ 0.97 (3H, t, J=7.2 Hz), 1.62–1.81 (4H, m), 2.20 (3H, s), 2.64 (1H, m), 3.18 (2H, t, J=7.0 Hz), 3.31–3.43 (2H, m), 3.57 (2H, s), 3.69–3–76 (2H, m), 3.96 (2H, t, J=7.0 Hz), 3.99–4.09 (2H, m), 6.97–7.09 (2H, m), 7.30–7.42 (5H, m), 7.51–7.56 (2H, m), 7.60–7.75 (2H, m), 7.81 (1H, s), 8.21 (1H, d, J=8.0 Hz); IR(KBr) 2938, 2920, 1667, 1599, 1529, 15166, 1408, 1312, 1294, 1130, 754 cm$^{-1}$; Anal. for C$_{36}$H$_{44}$N$_2$O$_6$S Calcd. C, 68.70; H, 7.17; N, 4.33: Found. C, 68.64; H, 7.03; N, 4.31.

Reference Example 151

In DMF (120 ml) was dissolved 2-bromophenol (12 g), and to the solution were added potassium carbonate (14.4 g) and sodium iodide (10.4 g). To the mixture was added 2-bromoethylpropylether (10.4 ml), and the mixture was stirred at 90° C. for 16 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=12/1) to give 1-bromo-2-(2-propoxyethoxy)benzene (14.4 g).

$^1$H-NMR (200 MHz, CDCl$_3$) δ 0.94 (3H, t, J=7.4 Hz), 1.56–1.73 (2H, m), 3.55 (2H, t, J=6.6 Hz), 3.82–3.87 (2H, m), 4.15–4.21 (2H, m), 6.79–6.96 (2H, m), 7.20–7.29 (1H, m), 7.53 (1H, dd, J=7.6,1.6 Hz).

Reference Example 152

To a solution of magnesium (1.39 g) in THF (14 ml) was added 1,2-dibromoethane (catalytic amount) and at room temperature a solution of 1-bromo-2-(2-propoxyethoxy)benzene (14.1 g) in THF (113 ml) was gradually added dropwise to the mixture. The mixture was stirred at 60° C. for 1 hour and cooled to −78° C. To the mixture was added dropwise a solution of trimethyl borate (8.5 g) in THF (8.5 ml), and the mixture was gradually warmed to room temperature and stirred at room temperature for 12 hours. To the mixture was added 2N hydrochloric acid (56 ml), and the mixture was stirred for 15 minutes. The reaction mixture was added to water, and the mixture was extracted with ethyl acetate, washed with saturated brine and dried with magnesium sulfate. Under reduced pressure, the solvent was evaporated, and the residue was washed with hexane/isopropylether to give 2-(2-propoxyethoxy)phenyl borate (12.2 g).

$^1$H-NMR (200 MHz, DMSO-d$_6$) δ 0.89 (3H, t, J=7.2 Hz), 1.50–1.62 (2H, m), 3.43 (2H, t, J=6.6 Hz), 3.71–3.76 (2H, m), 4.15–4.20 (2H, m), 6.92–7.04 (2H, m), 7.35–7.44 (1H, m), 7.63–7.70 (3H, m).

Working Example 117 (Production of Compound 114)

To 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) was added toluene/ethanol/water (20/1/1, 13.9 ml) and then were added 2-(propoxyethoxy)phenyl borate (155 mg) and potassium carbonate (176 mg), and the mixture was stirred at room temperature for 30 minutes. To the mixture was added tetrakistriphenylphosphinepalladium (27 mg), and the mixture was refluxed for 12 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give N-[4-[[N-methyl-N-(tetrahydropyran-4-yl)amino]methyl]phenyl]-7-[2-(2-propoxyethoxy)phenyl]-1,1-dioxo-2,3-dihydro-1-benzothiepine-4-carboxamide (Compound 114) (230 mg).

m.p. 164–166° C.; $^1$H-NMR (200 MHz, CDCl$_3$) δ 0.85 (3H, t, J=7.4 Hz), 1.50–1.82 (6H, m), 2.20 (3H, s), 2.64 (1H, m), 3.19 (2H, t, J=6.2 Hz), 3.32–3.42 (2H, m), 3.40 (2H, t, J=6.6 Hz), 3.57 (2H, s), 3.69–3.78 (4H, m), 4.00–4.19 (2H, m), 4.16 (2H, t, J=6.6 Hz), 7.02 (1H, d, J=8.4 Hz), 7.09 (1H, d, J=8.2 Hz), 7.29–7.34 (6H, m), 7.(53 (2H, d, J=8.4 Hz), 7.74–7.80 (2H, m), 8.18 (1H, d, J=8.2 Hz); IR(KBr) 2938, 2847, 1667, 1599, 1516, 1408, 1312, 1294, 1130, 754 cm$^{-1}$; Anal. for C$_{35}$H$_{42}$N$_2$O$_6$S Calcd. C, 67.94; H, 6.84; N, 4.53: Found. C, 67.90; H, 6.89; N, 4.46.

Reference Example 153

In DMF (120 ml) was dissolved 3-bromophenol (12 g). To the mixture was added potassium carbonate (12.5 g) and then was added 2-bromoethylethyl ether (9.1 ml), and the mixture was stirred at 70° C. for 16 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=12/1) to give 1-bromo-3-(2-ethoxyethoxy)benzene (12.1 g).

$^1$H-NMR (200 MHz, CDCl$_3$) δ 1.24 (3H, t, J=6.8 Hz), 3.60 (2H, q, J=6.8 Hz), 3.75–3.80 (2H, m), 4.07–4.12 (2H, m), 6.83–6.89 (1H, m), 7.05–7.14 (2H, m).

Reference Example 154

To a solution of magnesium (1.25 g) in THF (12.5 ml) was added 1,2-dibromoethane (catalytic amount), and at room temperature a solution of 1-bromo-3-(2-ethoxyethoxy)benzene (12 g) in THF (96 ml) was gradually added dropwise to the mixture. The mixture was stirred at 60° C. for 1 hour and cooled to −78° C. To the mixture was added dropwise a solution of trimethyl borate (7.6 g) in THF (7.6 ml), and the mixture was gradually warmed to room temperature and stirred at room temperature for 12 hours. To the mixture was added 2N hydrochloric acid (48 ml), and the mixture was stirred for 15 minutes. The reaction mixture was added to water, and the mixture was extracted with ethyl acetate, washed with saturated brine and dried with magnesium sulfate. Under reduced pressure, the solvent was evaporated, and the residue was washed with hexane/isopropylether to give 3-(2-ethoxyethoxy)phenyl borate (7.4 g).

$^1$H-NMR (200 MHz, DMSO-d$_6$) δ 1.24 (3H, t, J=6.8 Hz), 3.51 (2H, t, J=6.8 Hz), 3.67–3.72 (2H, m), 4.04–4.10 (2H, m), 6.92–6.98 (1H, m), 7.19–7.28 (1H, m), 7.33–7.37 (2H, m), 8.00 (2H, br).

Working Example 118 (Production of Compound 115)

To 7-bromo-N-[4-[[N-methyl-N-(tetrahydropyran- 4-yl)amino]methyl]phenyl]-1,1-dioxo-2,3-dihydro-1-benzothiepine-4-carboxamide (300 mg) was added toluene/ethanol/water (20/1/1, 13.9 ml) and then were added 3-(2-ethoxyethoxy)phenyl borate (145 mg) and potassium carbonate (176 mg), and the mixture was stirred at room temperature for 30 minutes. To the mixture was added tetrakistriphenylphosphinepalladium (27 mg), and the mixture was refluxed for 10 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[3-(2-ethoxyethoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 115) (152 mg).

m.p. 180–182° C.; $^1$H-NMR (200 MHz, CDCl$_3$) δ 1.26 (3H, t, J=7.0 Hz), 1.58–1.82 (4H, m), 2.21 (3H, s), 2.65 (1H, m), 3.17 (2H, t, J=6.6 Hz), 3.31–3.44 (2H, m), 3.57 (2H, s), 3.61 (2H, q, J=7.0 Hz), 3.71–3.75 (2H, m), 3.83 (2H, t, J=4.8 Hz), 3.98–4.10 (2H, m), 4.20 (2H, t, J=4.8 Hz), 6.97–7.03 (1H, m), 7.14–7.19 (2H, m), 7.30–7.44 (5H, m), 7.55 (2H, d, J=8.4 Hz), 7.64–7.71 (2H, m), 7.95 (1H, s), 8.21 (1H, d, J=8.4 Hz); IR(KBr) 2945, 2845, 1667, 1595. 1526, 1408, 1312, 1221, 1130 cm$^{-1}$.

Working Example 119 (Production of Compound 116)

To 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) was added toluene/ethanol/water (20/1/1, 13.9 ml) and then were added 3-chlorophenyl borate (108 mg) and potassium carbonate (176 mg), and the mixture was stirred at room temperature for 30 minutes. To the mixture was added tetrakistriphenylphosphinepalladium (27 mg), and the mixture was refluxed for 10 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-(3-chlorophenyl)-N-[4-[[N-methyl-N-(tetrahydropyran-4-yl)amino]methyl]phenyl]-1,1-dioxo-2,3-dihydro-1-benzothiepine-4-carboxamide (Compound 116) (64 mg).

m.p. 221–224° C.; $^1$H-NMR (200 MHz, CDCl$_3$) δ 1.58–1.81 (4H, m), 2.21 (3H, s), 2.65 (1H, m), 3.15–3.22 (2H, m), 3.30–3.45 (2H, m), 3.57 (2H, s), 3.69–3.77 (2H, m), 4.00–4.10 (2H, m), 7.30–7.71 (1H, m), 7.82 (1H, s), 8.25 (1H, d, J=8.0 Hz); IR(KBr) 2951, 2845, 1653, 1595, 1410, 1315, 1294, 1221, 1130 cm$^{-1}$.

Reference Example 155

In DMF (96 ml) was dissolved 3-bromophenol (12 g). To the mixture was added potassium carbonate (12.5 g) and then 2-bromoethylethylether (6.7 ml), and the mixture was stirred at room temperature for 16 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=12/1) to give 1-bromo-3-ethoxybenzene (11.6 g).

$^1$H-NMR (200 MHz, CDCl$_3$) δ 1.40 (3H, t, J=7.0 Hz), 4.00 (2H, q, J=7.0 Hz), 6.78–6.84 (1H, m), 7.02–7.16 (3H, m).

Reference Example 156

In THF (115 ml) was dissolved 1-bromo-3-ethoxybenzene (11.5 g). To the mixture was added dropwise at −78° C. 1.6M n-butyllithium/hexane (39.3 ml), and the mixture was stirred for 1 hour. To the mixture was added dropwise a solution of trimethyl borate (11.9 g) in THF (11.9 ml), and the mixture was stirred for 30 minutes and warmed to room temperature. To the mixture was added 2N hydrochloric acid (46 ml), and the mixture was stirred for 15 minutes. The reaction mixture was extracted with ethyl acetate, washed with saturated brine and dried with magnesium sulfate. Under reduced pressure, the solvent was evaporated, and the residue was washed with hexane/isopropylether to give 3-ethoxyphenyl borate (7.1 g).

$^1$H-NMR (200 MHz, DMSO-d$_6$) δ 1.33 (3H, t, J=7.0 Hz), 4.01 (2H, q, J=7.0 Hz), 6.90–6.96 (1H, m), 7.18–7.47 (3H, m), 7.74 (2H, br).

Working Example 120 (Production of Compound 117)

To 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) was added toluene/ethanol/water (20/1/1, 13.9 ml) and then were added 3-ethoxyphenyl borate (115 mg) and potassium carbonate (176 mg), and the mixture was stirred at room temperature for 30 minutes. To the mixture was added tetrakistriphenylphosphinepalladium (27 mg), and the mixture was refluxed for 10 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-(3-ethoxyphenyl)-N-[4-[[N-methyl-N-(tetrahydropyran-4-yl)amino]methyl]phenyl]-1,1-dioxo-2,3-dihydro-1-benzothiepine-4-carboxamide (Compound 117) (180 mg).

m.p. 192–195° C.; $^1$H-NMR (200 MHz, CDCl$_3$) δ 1.45 (3H, t, J=7.0 Hz), 1.66–1.79 (4H, m), 2.21 (3H, s), 2.64 (1H, m), 3.18 (2H, t, J=6.6 Hz), 3.30–3.44 (2H, m), 3.57 (2H, s), 3.69–3.76 (2H, m), 3.99–4.10 (2H, m), 4.11 (2H, q, J=7.0 Hz), 6.94–7.00 (1H, m), 7.10–7.19 (1H, m), 7.30–7.44 (4H, m), 7.54 (2H, d, J=8.4 Hz), 7.65–7.73 (2H, m), 7.83 (1H, s), 8.22 (1H, d, J=8.4 Hz). IR(KBr) 2945, 1669, 1597, 1526, 1408, 1312, 1223, 1130 cm$^{-1}$.

Reference Example 157

In DMF (120 ml) was dissolved 2-bromophenol (12 g). To the mixture was added potassium carbonate (12.5 g) and then was added 2-bromoethylethyl ether (9.1 ml), and the mixture was stirred at 70° C. for 4 hours. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=12/1) to give 1-bromo-2-(2-ethoxyethoxy)benzene (14.8 g).

$^1$H-NMR (200 MHz, CDCl$_3$) δ 1.24 (3H, t, J=7.0 Hz), 3.66 (2H, q, J=7.0 Hz), 3.82–3.88 (2H, m), 4.15–4.20 (2H, m), 6.79–6.95 (1H, m), 7.20–7.29 (1H, m), 7.53 (1H, dd, J=7.8,1.4 Hz).

Reference Example 158

To a solution of magnesium (1.46 g) in THF (14.6 ml) was added 1,2-dibromoethane (catalytic amount), and at room temperature a solution of 1-bromo-2-(2-ethoxyethoxy)benzene (14 g) in THF (112 ml) was gradually added dropwise to the mixture. The mixture was stirred at 60° C. for 1 hour and cooled to −78° C. To the mixture was added dropwise a solution of trimethyl borate (8.9 g) in THF (8.9 ml), and the mixture was gradually warmed to room temperature. To the mixture was added 2N hydrochloric acid (56 ml), and the mixture was stirred for 15 minutes. The reaction mixture was added to water, and the mixture was extracted with ethyl acetate, washed with saturated brine and dried with magnesium sulfate. Under reduced pressure, the solvent was evaporated, and the residue was washed with hexane/isopropylether to give 2-(2-ethoxyethoxy)phenyl borate (6.3 g).

$^1$H-NMR (200 MHz, DMSO-d$_6$) δ 1.15 (3H, t, J=7.0 Hz), 3.53 (2H, q, J=7.0 Hz), 3.70–3.76 (2H, m), 4.14–4.20 (2H, m), 6.93–7.04 (2H, m), 7.35–7.44 (1H, m), 7.62–7.70 (3H, m).

Working Example 121 (Production of Compound 118)

To 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) was added toluene/ethanol/water (20/1/1, 13.9 ml) and then were added 2-(2-ethoxyethoxy)phenyl borate (145 mg) and potassium carbonate (176 mg), and the mixture was stirred at room temperature for 30 minutes. To the mixture was added tetrakistriphenylphosphinepalladium (27 mg), and the mixture was refluxed for 10 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-[2-(2-ethoxyethoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 118) (245 mg).

$^1$H-NMR (200 MHz, CDCl$_3$) δ 1.16 (3H, t, J=7.0 Hz), 1.63–1.78 (4H, m), 2.20 (3H, s), 2.64 (1H, m), 3.18 (2H, t, J=6.6 Hz), 3.30–3.43 (2H, m), 3.51 (2H, q, J=7.0 Hz), 3.56 (2H, s), 3.68–3.75 (2H, m), 3.98–4.07 (2H, m), 4.13–4.19 (2H, m), 6.99–7.11 (2H, m), 7.28–7.42 (5H, m), 7.52 (2H, d, J=8.4 Hz), 7.74–7.79 (2H, m), 7.86 (1H, s), 8.17 (1H, d, J=8.8 Hz); IR(KBr) 3347, 2944, 2845, 1642, 1597, 1510, 1410, 1290, 1132, 747 cm$^{-1}$;

Reference Example 159

In DMF (120 ml) was dissolved 2-bromophenol (12 g). To the mixture was added potassium carbonate (12.5 g) and then was added iodoethane (6.7 ml), and the mixture was stirred at room temperature for 1 hour. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=12/1) to give 1-bromo-2-ethoxybenzene (12.2 g).

$^1$H-NMR (200 MHz, CDCl$_3$) δ 1.47 (3H, t, J=7.0 Hz), 4.10 (2H, q, J=7.0 Hz), 6.76–6.90 (2H, m), 7.19–7.29 (1H, m), 7.50–7.56 (1H, m).

Reference Example 160

In THF (120 ml) was dissolved 1-bromo-2-ethoxybenzene (12.0 g). To the mixture was added dropwise at −78° C. 1.6M n-butyllithium/hexane (41.1 ml), and the mixture was stirred for 1 hour. To the mixture was added dropwise a solution of trimethylborate (12.4 g) in THF (12.4 ml), and the mixture was stirred for 30 minutes and warmed to room temperature. To the mixture was added 2N hydrochloric acid (48 ml), and the mixture was stirred for 15 minutes. The reaction mixture was extracted with ethyl acetate, washed with saturated brine and dried with magnesium sulfate. Under reduced pressure, the solvent was evaporated, and the residue was washed with hexane/isopropylether to give 2-ethoxyphenyl borate (7.1 g).

$^1$H-NMR (200 MHz, DMSO-d$_6$) δ 1.37 (3H, t, J=7.0 Hz), 4.09 (2H, q, J=7.0 Hz), 6.89–6.99 (1H, m), 7.33–7.42 (1H, dd, J=7.2, 1.6 Hz), 7.66 (2H, s).

Working Example 122 (Production of Compound 119)

To 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) was added toluene/ethanol/water (20/1/1, 13.9 ml) and then were added 2-ethoxyphenyl borate (115 mg) and potassium carbonate (176 mg), and the mixture was stirred at room temperature for 30 minutes. To the mixture was added tetrakistriphenylphosphinepalladium (27 mg), and the mixture was refluxed for 14 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=3/1) and recrystallized from ethanol to give 7-(2-ethoxyphenyl)-N-[4-[[N-methyl-N-(tetrahydropyran-4-yl)amino]methyl]phenyl]-1,1-dioxo-2,3-dihydro-1-benzothiepine-4-carboxamide (Compound 119) (145 mg).

m.p. 171–173° C.; $^1$H-NMR (200 MHz, CDCl$_3$) δ 1.36 (3H, t, J=7.0 Hz), 1.63–1.77 (4H, m), 2.20 (3H, s), 2.64 (1H, m), 3.18 (2H, t, J=6.6 Hz), 3.30–3.44 (2H, m), 3.57 (2H, s), 3.68–3.76 (2H, m), 4.00–4.10 (2H, m), 4.08 (2H, q, J=7.0 Hz), 6.98–7.09 (2H, m), 7.30–7.52 (5H, m), 7.54 (2H, d, J=8.4 Hz), 7.66 (1H, s), 7.72 (1H, dd, J=8.0, 1.4 Hz), 7.88 (1H, s), 8.18 (1H, d, J=8.0 Hz); IR(KBr) 3270, 2944, 1645, 1599, 1514, 1410, 1319, 1292, 1130, 748 cm$^{-1}$.

Reference Example 161

In THF (150 ml) was dissolved 1-bromo-3-trifluoromethylbenzene (15.0 g). To the mixture was added dropwise at −78° C. 1.6M n-butyllithium/hexane (45.8 ml), and the mixture was stirred for 1 hour. To the mixture was added dropwise a solution of trimethyl borate (13.9 g) in THF (13.9 ml), and the mixture was stirred for 30 minutes and warmed to room temperature. To the mixture was added 2N hydrochloric acid (60 ml), and the mixture was stirred for 15 minutes. The reaction mixture was extracted with ethyl acetate, washed with saturated brine and dried with magnesium sulfate. Under reduced pressure, the solvent was evaporated, and the residue was washed with hexane/isopropylether to give 3-trifluoromethylphenyl borate (5.7 g).

$^1$H-NMR (200 MHz, DMSO-d$_6$) δ 7.53–7.80 (3H, m), 8.06–8.21 (1H, m), 8.13 (2H, s).

Working Example 123 (Production of Compound 120)

To 7-bromo-N-[4-[[N-methyl-N-(tetrahydropyran-4-yl)amino]methyl]phenyl]-1,1-dioxo-2,3-dihydro-1- benzothiepine-4-carboxamide (300 mg) was added toluene/ethanol/water (20/1/1, 13.9 ml) and then were added 3-trifluoromethylphenyl borate (131 mg) and potassium carbonate (176 mg), and the mixture was stirred at room temperature for 30 minutes. To the mixture was added tetrakistriphenylphosphinepalladium (27 mg), and the mixture was refluxed for 10 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=4/1) and recrystallized from ethanol to give N-[4-[[N-methyl-N-(tetrahydropyran-4-yl)amino]methyl]phenyl]-7-(3-trifluoromethylphenyl)-1,1-dioxo-2,3-dihydro-1-benzothiepine-4-carboxamide (Compound 120) (148 mg).

m.p. 236–238° C.; $^1$H-NMR (200 MHz, CDCl$_3$) δ 1.62–1.81 (4H, m), 2.20 (3H, s), 2.65 (1H, m), 3.19 (2H, t, J=6.6 Hz), 3.31–3.43 (2H, m), 3.57 (2H, s), 3.70–3.78 (2H, m), 3.98–4.10 (2H, m), 7.30–7.38 (3H, m), 7.52–7.87 (9H, m), 8.27 (1H, d, J=8.0 Hz); IR(KBr) 2942, 1648, 1599, 1530, 1412, 1318, 1294, 1130, 801 cm$^{-1}$; Anal. for C$_{31}$H$_{31}$F$_3$N$_2$O$_4$S Calcd. C, 63.68; H, 5.34; N, 4.79: Found. C, 63.51; H, 5.42; N, 4.70.

Reference Example 162

In DMF (120 ml) was dissolved 4-bromo-3-methylphenol (12 g). To the mixture were added potassium carbonate (11.5 g) and sodium iodide (9.6 g) and then added dropwise 2-chloroethylpropylether (9.7 ml), and the mixture was stirred at 90° C. for 10 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=12/1) to give 4-bromo-3-methyl-1-(2-propoxyethoxy)benzene (11.0 g). $^1$H-NMR (200 MHz, CDCl$_3$) δ 0.93 (3H, t, J=7.2 Hz), 1.54–1.71 (2H, m), 2.25 (3H, s), 3.48 (2H, t, J=6.6 Hz), 3.73–3.79 (2H, m), 4.05–4.10 (2H, m), 6.63 (1H, dd, J=8.8, 2.8 Hz), 6.82 (1H, d, J=2.8 Hz), 7.38 (1H, d, J=8.8 Hz).

Reference Example 163

To a solution of magnesium (0.98 g) in THF (9.8 ml) was added 1,2-dibromoethane (3 drops). While refluxing the mixture, a solution of 4-bromo-3-methyl-1-(2-propoxyethoxy)benzene (10.5 g) in THF (84 ml) was gradually added dropwise to the mixture. The mixture was stirred for 15 minutes and cooled to –78° C. To the mixture was added dropwise a solution of trimethyl borate (6.0 g) in THF (6.0 ml), and the mixture was gradually warmed to room temperature and stirred at room temperature for 6 hours. To the mixture was added 2N hydrochloric acid (42 ml), and the mixture was stirred for 15 minutes, extracted with ethyl acetate, washed with saturated brine and dried with magnesium sulfate. Under reduced pressure, the solvent was evaporated, and the residue was washed with hexane/isopropylether to give 2,3-dimethyl-4-(2-propoxyethoxy)phenyl borate (3.8 g).

$^1$H-NMR (200 MHz, DMSO-d$_6$) δ 0.88 (3H, t, J=7.2 Hz), 1.42–1.61 (2H, m), 2.63 (3H, s), 3.41 (2H, t, J=6.6 Hz), 3.66–3.72 (2H, m), 4.03–4.10 (2H, m), 6.65–6.74 (2H, m), 7.82 (1H, d, J=9.2 Hz).

Working Example 124 (Production of Compound 121)

To 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) was added toluene/ethanol/water (20/1/1, 13.9 ml) and then were added 2-methyl-4-(2-propoxyethoxy)phenyl borate (165 mg) and potassium carbonate (176 mg), and the mixture was stirred at room temperature for 30 minutes. To the mixture was added tetrakistriphenylphosphinepalladium (27 mg), and the mixture was refluxed for 14 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=4/1) and recrystallized from ethanol to give 7-[2-methyl-4-(2-propoxyethoxy)phenyl]-N[4-[[N-methyl-N-(tetrahydropyran-4-yl)amino]methyl]phenyl]-1,1-dioxo-2,3-dihydro-1-benzothiepine-4-carboxamide (Compound 121) (184 mg).

m.p. 149–151° C.; $^1$H-NMR (200 MHz, CDCl$_3$) δ 60.94 (3H, t, J=7.4 Hz), 1.56–1.82 (6H, m), 2.20 (3H, s), 2.64 (1H, m), 3.18 (2H, t, J=6.4 Hz), 3.30–3.43 (2H, m), 3.51 (2H, t, J=6.4 Hz), 3.56 (2H, s), 3.68–3.75 (2H, m), 3.78–3.83 (2H, m), 3.99–4.18 (2H, m), 6.79–6.87 (2H, m), 7.11 (1H, d, J=8.2 Hz), 7.28–7.55 (7H, m), 7.91 (1H, s), 8.18 (1H, d, J=8.2 Hz); IR(KBr) 3374, 2953, 1659, 1609, 1505, 1406, 1290, 1242, 1127 cm$^{-1}$; Anal. for C$_{36}$H$_{44}$N$_2$O$_6$S Calcd. C, 68.33; H, 7.01; N, 4.43: Found. C, 68.18; H, 6.93; N, 4.53.

Reference Example 164

In DMF (82 ml) was dissolved 4-bromo-2,3-dimethylphenol (8.2 g). To the mixture were added potassium carbonate (7.3 g) and sodium iodide (6.1 g) and then was added dropwise 2-chloroethylpropylether (6.2 ml), and the mixture was stirred at 90 for 10 hours and cooled to room temperature. The reaction mixture was added to water, and the mixture was extracted with ethyl acetate, washed with saturated brine and dried with magnesium sulfate. Under reduced pressure, the solvent was evaporated, and the residue was purified with silica gel column chromatography (hexane/ethyl acetate=12/1) to give 4-bromo-2,3-dimethyl-1-(2-propoxyethoxy)benzene (7.5 g).

$^1$H-NMR (200 MHz, CDCl$_3$) δ 0.94 (3H, t, J=7.4 Hz), 1.55–1.70 (2H, m), 2.20 (3H, s), 2.36 (3H, s), 3.50 (2H, t, J=6.6 Hz), 3.75–3.81 (2H, m), 4.03–4.10 (2H, m), 6.60 (1H, d, J=8.8 Hz), 7.21 (1H, d, J=8.4 Hz).

Reference Example 165

To a solution of magnesium (0.62 g) in THF (9.3 ml) was added 1,2-dibromoethane (3 drops). While refluxing the mixture, a solution of 4-bromo-2,3-dimethyl-1-(2-propoxyethoxy)benzene (7.0 g) in THF (56 ml) was gradually added dropwise to the mixture, and the mixture was stirred for 15 minutes and cooled to –78° C. To the mixture was added dropwise a solution of trimethyl borate (3.8 g) in THF (3.8 ml), and the mixture was gradually warmed to room temperature and stirred at room temperature for 6 hours. To the mixture was added 2N hydrochloric acid (28 ml), and the mixture was stirred for 15 minutes, extracted with ethyl acetate, washed with saturated brine and dried with magnesium sulfate. Under reduced pressure, the solvent was evaporated, and the residue was washed with hexane/isopropylether to give 2,3-dimethyl-4-(2-propoxyethoxy)phenyl borate (3.8 g).

$^1$H-NMR (200 MHz, DMSO-d$_6$) δ 0.89 (3H, t, J=7.2 Hz), 1.46–1.61 (2H, m), 2.08 (3H, s), 2.31 (3H, s), 3.44 (2H, t, 6.6 Hz), 3.68–3.74 (2H, m), 4.02–4.07 (2H, m), 6.72 (1H, d, J=8.4 Hz), 7.22 (1H, d, J=8.2 Hz), 7.75 (2H, br).

Working Example 125 (Production of Compound 122)

To 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) was added toluene/ethanol/water (20/1/1, 13.9 ml) and then were added 3-trifluoromethylphenyl borate (174 mg) and potassium carbonate (176 mg), and the mixture was stirred at room temperature for 30 minutes. To the mixture was added tetrakistriphenylphosphinepalladium (27 mg), and the mixture was refluxed for 14 hours and cooled to room temperature. The mixture was added to water, and the mixture was extracted with ethyl acetate, washed with saturated brine and dried with magnesium sulfate. Under reduced pressure, the solvent was evaporated, and the residue was purified with silica gel column chromatography (ethyl acetate/ethanol=4/1) and recrystallized from ethanol to give 7-[2,3-dimethyl-4-(2-propoxyethoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 122) (211 mg).

m.p. 158–159° C.; $^1$H-NMR (200 MHz, CDCl$_3$) δ 0.95 (3H, t, J=7.4 Hz), 1.55–1.83 (6H, m), 2.16 (3H, s), 2.20 (3H, s), 2.24 (3H, s), 2.64 (1H, m), 3.19 (2H, t, J=6.4 Hz), 3.30–3.43 (2H, m), 3.53 (2H, t, J=6.6 Hz), 3.57 (2H, s), 3.69–3.76 (2H, m), 3.84 (2H, t, J=4.8 Hz), 3.97–4.09 (2H, m), 4.16 (2H, t. J=4.8 Hz), 6.80 (1H, d, J=8.4 Hz), 7.00 (1H, d. J=8.4 Hz), 7.28–7.38 (5H, m), 7.43 (1H, dd, J=8.0, 1.4 Hz), 7.53 (1H, d, J=8.4 Hz), 7.87 (1H, s), 8.18 (1H, d, J=8.0 Hz); IR(KBr) 3331, 2942,1651,1593, 1518,1408, 1289, 1130, 1096, 820 cm$^{-1}$; Anal. for C$_{37}$H$_{46}$N$_2$O$_6$S Calcd. C, 68.70; H, 7.17; N, 4.33: Found. C, 68.70; H, 7.19; N, 4.09.

Reference Example 166

A mixture of triphenylphosphine (33 g) and 2-bromoethylethyl ether (25 g) was stirred at 140° C. for 1 hour and cooled to precipitate crystals (51.5 g), which were collected by filtration and washed with acetone and diethylether. The obtained crystals (27 g) and p-bromobenzaldehyde (8 g) were suspended in DMSO (25 ml) and THF (500 ml). To the suspension was added under ice-cooling potassium t-butoxide (7.3 g), and the mixture was stirred under nitrogen atmosphere at room temperature for 1 hour, poured into ice-water, concentrated and extracted with ethyl acetate. The organic layer was washed with and saturated brine and dried with anhydrous magnesium sulfate. The solvent was evaporated, and the residue was purified with silica gel column chromatography (hexane/diethylether) to give colorless oil (5.6 g), which was dissolved in ethyl acetate (150 ml). The mixture was subjected to reduction with 5% palladium carbon (0.6 g) at room temperature for 4 hours. The catalyst was filtered off, and the solvent of the filtrate was evaporated. The residue was distilled under reduced pressure to give 1-bromo-4-(3-ethoxypropyl)benzene (3.3 g) as colorless oil.

b.p. 104–111° C./3 mmHg. $^1$H-NMR(δ ppm, CDCl$_3$) 1.21 (3H, t, J=6.9 Hz), 1.79–1.93 (2H, m), 2.65 (2H, t, J=7.7 Hz), 3.37–3.52 (4H, m), 7.07 (2H, d, J=8.4 Hz), 7.39 (2H, d, J=8.4 Hz).

Reference Example 167

In THF (5 ml) was suspended magnesium (0.37 g), and to the suspension was added under nitrogen atmosphere dibromoethane (catalytic amount) and then was added dropwise a solution of 1-bromo-4-(3-ethoxypropyl)benzene (3.4 g) in THF (30 ml). The mixture was stirred at 50° C. for 1.5 hours and cooled with dry ice/acetone. To the mixture was added dropwise trimethyl borate (3.1 ml), and the mixture was stirred at room temperature overnight. To the mixture was added 1N hydrochloric acid, and the mixture was stirred at room temperature for 30 minutes, concentrated and extracted with ethyl acetate. The organic layer was washed with water and saturated brine, and dried with anhydrous magnesium sulfate. The solvent was evaporated, and the residue was purified with silica gel column chromatography (ethyl acetate/methanol/triethylamine) to give 4-(3-ethoxypropyl)phenyl borate (1.2 g) as pale yellow oil.

$^1$H-NMR (δ ppm, CDCl$_3$) 1.23 (3H, t, J=7.0 Hz), 1.90–2.00 (2H, m), 2.79 (2H, t, J=7.7 Hz), 3.42–3.55 (4H, m), 7.34 (2H, d, J=7.6 Hz), 8.16 (2H, d, J=7.6 Hz).

Reference Example 168

A solution of 4-bromo-2,6-dimethylphenol (20 g) in DMF (10 ml) was added dropwise to a suspension of 60% sodium hydride (4.4 g) in DMF (50 ml) under ice-cooling, and the mixture was stirred under nitrogen atmosphere at room temperature for 2 hours. To the mixture were added bromoethylethyl ether (12.3 ml) and sodium iodide (16.4 g), and the mixture was stirred at 75° C. overnight. The mixture was poured into water, and the mixture was extracted with ethyl acetate. The organic layer was washed with water and saturated brine and dried with anhydrous magnesium sulfate. The solvent was evaporated, and the residue was distilled under reduced pressure to give 5-bromo-2-(2-ethoxyethoxy)-1,3-dimethylbenzene (24.1 g) as colorless oil.

$^1$H-NMR (δ ppm, CDCl$_3$) 1.25 (3H, t, J=7.0 Hz), 2.26 (6H, s), 3.60 (2H, q, J=7.0 Hz), 3.72–3.77 (2H, m), 3.88–3.93 (2H, m), 7.13 (2H, s).

Reference Example 169

In THF (100 ml) was suspended magnesium (2.36 g). To the suspension was added under nitrogen atmosphere dibromoethane (catalytic amount) and then was added dropwise a solution of 5-bromo-2-(2-ethoxyethoxy)-1,3-dimethylbenzene (24.1 g) in THF (100 ml). The mixture was stirred at 55° C. for 2.5 hours and cooled with dryice/acetone. To the mixture was added dropwise trimethyl borate (19.8 ml), and the mixture was stirred at room temperature was stirred overnight. To the mixture was added 1N hydrochloric acid, and the mixture was stirred at room temperature for 30 minutes, concentrated and extracted with ethyl acetate. The organic layer was washed with water and saturated brine, and dried with anhydrous magnesium sulfate. The solvent was evaporated to give 4-(2-ethoxyethoxy)-3,5-dimethylphenyl borate (8.4 g) as colorless crystals.

$^1$H-NMR (δ ppm, DMSO-d$_6$) 1.16 (3H, t, J=7.2 Hz), 2.21 (3H, s), 2.26 (3H, s), 3.46 (2H, q, J=7.2 Hz), 3.65–3.69 (2H, m), 3.85–3.90 (2H, m), 7.48 (2H, s).

Reference Example 170

A suspension of 4-bromo-2-ethoxyphenol (8 g), 1-bromopropane (4 ml), sodium iodide (5.5 g) and potassium carbonate (10.2 g) in DMF (10 ml) was stirred under nitrogen atmosphere at 75° C. overnight. The solvent was evaporated, and to the residue was added water. The mixture was extracted with ethyl acetate. The organic layer was washed with water and saturated brine and dried with anhydrous magnesium sulfate. The solvent was evaporated, and the residue was distilled under reduced pressure to give 1-bromo-3-ethoxy-4-propoxybenzene (8.5 g) as pale yellow oil.

b.p. 109–113° C./2 mmHg. $^1$H-NMR (δ ppm, CDCl$_3$) 1.03 (3H, t, J=7.5 Hz), 1.44 (3H, t, J=7.0 Hz), 1.77–1.89 (2H, m), 3.90–4.11 (4H, m), 6.74 (1H, d, J=9.2 Hz), 6.96–7.02 (2H, m).

Reference Example 171

In THF (5 ml) was suspended magnesium (0.88 g). To the suspension was added under nitrogen atmosphere dibromoethane (catalytic amount), and then was added dropwise a solution of 1-bromo-3-ethoxy-4-propoxybenzene (8.5 g) in THF (30 ml). The mixture was stirred at 50° C. for 1 hour and cooled with dry ice/acetone. To the mixture was added dropwise trimethyl borate (7.4 ml), and the mixture was stirred at room temperature was stirred overnight. To the mixture was added 1N hydrochloric acid, and the mixture was stirred at room temperature for 30 minutes, concentrated and extracted with ethyl acetate. The organic layer was washed with water and saturated brine, and dried with anhydrous magnesium sulfate. The solvent was evaporated to give 3-ethoxy-4-propoxyphenyl borate (4.7 g) as colorless crystals.

$^1$H-NMR (δ ppm, DMSO-d$_6$) 0.98 (3H, t, J=7.5 Hz), 1.32 (3H, t, J=6.9 Hz), 1.67–1.78 (2H, m), 3.89–4.06 (4H, m), 6.90 (1H, d, J=8.4 Hz), 7.32–7.37 (2H, m), 7.82 (2H, s).

Reference Example 172

A suspension of 4-bromo-2-ethoxyphenol (8 g), bromoethylethyl ether (5 ml), sodium iodide (5.5 g) and potassium carbonate (10.2 g) in DMF (10 ml) was stirred under nitrogen atmosphere at 90° C. overnight. The solvent was evaporated, and to the residue was added water. The mixture was extracted with ethyl acetate. The organic layer was washed with water and saturated brine, and dried with anhydrous magnesium sulfate. The solvent was evaporated, and the residue was distilled under reduced pressure to give 1-bromo-3-ethoxy-4-(2-ethoxyethoxy)benzene (8.1 g) as yellow oil.

b.p. 131–134° C./2 mmHg. $^1$H-NMR (δ ppm, CDCl$_3$) 1.23 (3H, t, J=7.2 Hz), 1.44 (3H, t, J=7.0 Hz), 3.61 (2H, q, J=7.0 Hz), 3.79 (2H, t, J=5.2 Hz), 4.00–4.16 (4H, m), 6.80 (1H, d, J=8.8 Hz), 6.96–7.02 (2H, m).

Reference Example 173

In THF (5 ml) was suspended magnesium (0.79 g). To the suspension was added under nitrogen atmosphere dibromoethane (catalytic amount) and then was added dropwise a solution of 1-bromo-3-ethoxy-4-(2-ethoxyethoxy)benzene (8.1 g) in THF (30 ml). The mixture was stirred at 50° C. for 1 hour and cooled with dry ice/acetone. To the mixture was added dropwise trimethyl borate (6.6 ml), and the mixture was stirred at room temperature was stirred overnight. To the mixture was added 1N hydrochloric acid, and the mixture was stirred at room temperature for 30 minutes, concentrated and extracted with ethyl acetate. The organic layer was washed with water and saturated brine, and dried with anhydrous magnesium sulfate. The solvent was evaporated to give 3-ethoxy-4-(2-ethoxyethoxy)phenyl borate (2.1 g) as pale red crystals.

$^1$H-NMR (δ ppm, DMSO-d$_6$) 1.13 (3H, t, J=6.9 Hz), 1.32 (3H, t, J=6.9 Hz), 3.52 (2H, q, J=6.9 Hz), 3.67–3.72 (2H, m), 3.97–4.10 (4H, m), 6.92 (1H, d, J=7.8 Hz), 7.32–7.39 (2H, m), 7.84 (2H, s).

Reference Example 174

A suspension of 4-bromocathechol (9.7 g), chloroethylethyl ether (13.3 ml), sodium iodide (15.4 g) and potassium carbonate (21.3 g) in DMF (10 ml) was stirred under nitrogen atmosphere at 85° C. overnight. The solvent was evaporated, and to the residue was added water. The mixture was extracted with ethyl acetate. The organic layer was washed with water and saturated brine, and dried with anhydrous magnesium sulfate. The solvent was evaporated, and the residue was distilled under reduced pressure to give 1-bromo-3,4-bis(2-ethoxyethoxy)benzene (12.7 g) as orange oil.

b.p. 154–161° C./1.5 mmHg. $^1$H-NMR (δ ppm, CDCl$_3$) 1.23 (6H, t, J=7.2 Hz), 3.60 (4H, q, J=7.2 Hz), 3.76–3.82 (4H, m), 4.10–4.16 (4H, m), 6.79 (1H, d, J=8.0 Hz), 7.02 (1H, dd, J=2.2, 8.0 Hz), 7.04 (1H, s).

Reference Example 175

In THF (10 ml) was suspended magnesium (1.0 g). To the suspension was added under nitrogen atmosphere dibromoethane (catalytic amount) and then was added dropwise a solution of 1-bromo-3,4-bis(2-ethoxyethoxy)benzene (12.7 g) in THF (80 ml). The mixture was stirred at 50° C. for 1 hour and cooled with dry ice/acetone. To the mixture was added dropwise trimethyl borate (8.5 ml), and the mixture was stirred at room temperature was stirred overnight. To the mixture was added 1N hydrochloric acid, and the mixture was stirred at room temperature for 30 minutes, concentrated and extracted with ethyl acetate. The organic layer was washed with water and saturated brine, and dried with anhydrous magnesium sulfate. The solvent was evaporated, and the residue was purified with silica gel column chromatography (ethyl acetate/methanol/triethylamine) to give 3,4-bis(2-ethoxyethoxy)phenyl borate (1.65 g) as colorless crystals.

$^1$H-NMR (δ ppm, DMSO-d$_6$) 1.07–1.17 (6H, m), 3.44–3.58 (4H, m), 3.67–3.71 (4H, m), 4.01–4.11 (4H, m), 6.93 (1H, d, J=8.0 Hz), 7.34–7.41 (2H, m), 7.85 (2H, s).

Working Example 126 (Production of Compound 123)

A mixture of 7-bromo-N-[4-[[N-methyl-N-(tetrahydro-2H-pyran-4-yl)amino]methyl]phenyl]-1,1-dioxo-2,3-dihydro-1-benzothiepine-4-carboxamide (0.3 g), 4-(3-ethoxypropyl)phenyl borate (0.18 g), 1M potassium carbonate solution (1.3 ml), ethanol (1.3 ml) and toluene (25 ml) was stirred under argon atmosphere at room temperature for 30 minutes. To the mixture was added tetrakistriphenylphosphinepalladium (0.03 g), and the mixture was refluxed under argon atmosphere for 6 hours and extracted with ethyl acetate. The organic layer was washed with water and saturated brine, and dried with anhydrous magnesium sulfate. The solvent was evaporated, and the residue was purified with silica gel column chromatography (ethyl acetate/methanol/triethylamine) to give crude crystals, which were recrystallized from ethanol to give 7-[4-(3-ethoxypropyl)phenyl]-N-[4-[[N-methyl-N-(tetrahydro-2H-pyran-4-yl)amino]methyl]phenyl]-1,1-dioxo-2,3-dihydro-1-benzothiepine-4-carboxamide (Compound 123) (0.25 g) as colorless crystals.

mp 217–219° C.; $^1$H-NMR (δ ppm, CDCl$_3$) 1.23 (3H, t, J=7.0 Hz), 1.60–1.86 (4H, m), 1.87–2.01 (2H, m), 2.21 (3H, s), 2.59–2.73 (1H, m), 2.77 (2H, t, J=7.9 Hz), 3.18 (2H, t, J=6.7 Hz), 3.33–3.55 (6H, m), 3.57 (2H, s), 3.72 (2H, t, J=6.7 Hz), 4.01–4.07 (2H, m), 7.31–7.35 (4H, m), 7.51–7.56

(4H, m), 7.66 (1H, s), 7.70 (1H, d, J=8.2 Hz), 7.80 (1H, s), 8.21 (1H, d, J=8.2 Hz). IR(KBr) v: 2946, 2853, 1657, 1597, 1518 cm$^{-1}$. Anal. calcd. for $C_{35}H_{42}N_2O_5S$: C, 69.74; H, 7.02; N, 4.65. Found C, 69.47; H, 7.26; N, 4.61.

Working Example 127 (Production of Compound 124)

A mixture of 7-bromo-N-[4-[[N-methyl-N-(tetrahydro-2H-pyran-4-yl)amino]methyl]phenyl]-1,1-dioxo-2,3-dihydro-1-benzothiepine-4-carboxamide (0.3 g), 4-(2-ethoxyethoxy)-3,5-dimethylphenyl borate (0.16 g), 1M potassium carbonate solution (1.3 ml), ethanol (1.3 ml) and toluene (25 ml) was stirred under argon atmosphere at room temperature for 30 minutes. To the mixture was added tetrakistriphenylphosphinepalladium (0.03 g), and the mixture was refluxed under argon atmosphere for 6 hours and extracted with ethyl acetate. The organic layer was washed with water and saturated brine, and dried with anhydrous magnesium sulfate. The solvent was evaporated to precipitate crude crystals, which were collected by filtration, washed with ethyl acetate/hexane, recrystallized from ethanol to give 7-[4-(2-ethoxyethoxy)-3,5-dimethylphenyl]-N-[4-[[N-methyl-N-(tetrahydro-2H-pyran-4-yl)amino]methyl]phenyl]-1,1-dioxo-2,3-dihydro-1-benzothiepine-4-carboxamide (Compound 124) (0.32 g) as colorless crystal.

mp 211–212° C. $^1$H-NMR (δ ppm, CDCl$_3$) 1.27 (3H, t, J=7.0 Hz), 1.59–1.77 (4H, m), 2.21 (3H, s), 2.37 (6H, s), 2.58–2.70 (1H, m), 3.17 (2H, t, J=6.6 Hz), 3.37 (2H, dt, J=3.0, 11.0Hz), 3.57 (2H, s), 3.61–3.82 (6H, m), 3.97–4.06 (4H, m), 7.25–7.35 (4H, m), 7.54 (2H, d, J=8.4 Hz), 7.63 (1H, s), 7.66 (1H, dd, J=1.8, 9.8 Hz), 7.79 (1H, s), 8.19 (1H, d, J=8.0 Hz). IR(KBr) v: 2928, 2841, 1669, 1597, 1520 cm$^{-1}$. Anal. calcd. for $C_{36}H_{44}N_2O_6S$: C, 68.33; H, 7.01; N, 4.43. Found C, 68.23; H, 6.95; N, 4.38.

Working Example 128 (Production of Compound 125)

A mixture of 7-bromo-N-[4-[[N-methyl-N-(tetrahydro-2H-pyran-4-yl)amino]methyl]phenyl]-1,1-dioxo-2,3-dihydro-1-benzothiepine-4-carboxamide (0.3 g), 3-ethoxy-4-propoxyphenyl borate (0.16 g), 1M potassium carbonate solution (1.3 ml), ethanol (1.3 ml) and toluene (25 ml) was stirred under argon atmosphere at room temperature for 30 minutes. To the mixture was added tetrakistriphenylphosphinepalladium (0.03 g), and the mixture was refluxed under argon atmosphere for 6 hours and extracted with ethyl acetate. The organic layer was washed with water and saturated brine, and dried with anhydrous magnesium sulfate. The solvent was evaporated, and the residue was purified with silica gel column chromatography (ethyl acetate/methanol/triethylamine) to give crude crystals, which were recrystallized from ethanol to give 7-(3-ethoxy-4-propoxyphenyl)-N-[4-[[N-methyl-N-(tetrahydro-2H-pyran-4-yl)amino]methyl]phenyl]-1,1-dioxo-2,3-dihydro-1-benzothiepine-4-carboxamide (Compound 125) (0.16 g) as colorless crystals.

mp 203–205° C.; $^1$H-NMR (δ ppm, CDCl$_3$) 1.07 (3H, t, J=7.5 Hz), 1.48 (3H, t, J=6.7 Hz), 1.64–1.94 (6H, m), 2.21 (3H, s), 2.60–2.71 (1H, m), 3.17 (2H, t, J=6.7 Hz), 3.37 (2H, dt, J=2.4, 10.9 Hz), 3.58 (2H, s), 3.71 (2H, t, J=6.7 Hz), 3.74–4.22 (6H, m), 6.97 (1H, d, J=8.0 Hz), 7.11–7.18 (2H, m), 7.31–7.35 (3H, m), 7.52–7.64 (4H, m), 7.94 (1H, s), 8.16 (1H, d, J=8.0 Hz). IR(KBr) v: 2940, 2845, 1669, 1595, 1516 cm$^{-1}$. Anal. calcd. for $C_{35}H_{42}N_2O_6S \cdot 0.2\ H_2$: C, 67.54; H, 6.87; N, 4.50. Found C, 67.44; H, 6.67; N, 4.50.

Working Example 129 (Production of Compound 126)

A mixture of 7-bromo-N-[4-[[N-methyl-N-(tetrahydro-2H-pyran-4-yl)amino]methyl]phenyl]-1,1-dioxo-2,3-dihydro-1-benzothiepine-4-carboxamide (0.3 g), 3-ethoxy-4-(2-ethoxyethoxy)phenyl borate (0.18 g), 1M potassium carbonate solution (1.3 ml), ethanol (1.3 ml) and toluene (25 ml) was stirred under argon atmosphere at room temperature for 30 minutes. To the mixture was added tetrakistriphenylphosphinepalladium (0.03 g), and the mixture was refluxed under argon atmosphere for 6 hours and extracted with ethyl acetate. The organic layer was washed with water and saturated brine, and dried with anhydrous magnesium sulfate. The solvent was evaporated, and the residue was purified with silica gel column chromatography (ethyl acetate/methanol/triethylamine) to give crude crystals, which were recrystallized from ethanol to give 7-[3-ethoxy-4-(2-ethoxyethoxy)phenyl]-N-[4-[[N-methyl-N-(tetrahydro-2H-pyran-4-yl)amino]methyl]phenyl]-1,1-dioxo-2,3-dihydro-1-benzothiepine-4-carboxamide (Compound 126) (0.26 g) as colorless crystals.

mp 164–168° C.; $^1$H-NMR (δ ppm, CDCl$_3$) 1.24 (3H, t, J=7.0 Hz), 1.47 (3H, t, J=7.0 Hz), 1.61–1.75 (4H, m), 2.21 (3H, s), 2.59–2.75 (1H, m), 3.17 (2H, t, J=6.9 Hz), 3.38 (2H, dt, J=3.6, 11.2 Hz), 3.57 (2H, s), 3.61–3.74 (4H, m), 3.85 (2H, t, J=4.9 Hz), 4.01–4.23 (6H, m), 6.98–7.14 (3H, m), 7.30–7.35 (3H, m), 7.53–7.65 (4H, m), 7.88 (1H, s), 8.17 (1H, d, J=8.0 Hz). IR(KBr) v: 2946, 2843, 1661, 1599, 1518 cm$^{-1}$. Anal. calcd. for $C_{36}H_{44}N_2O_7S$: C, 66.64; H, 6.84; N, 4.32. Found C, 66.44; H, 6.99; N, 4.19.

Working Example 130 (Production of Compound 127)

A mixture of 7-bromo-N-[4-[[N-methyl-N-(tetrahydro-2H-pyran-4-yl)amino]methyl]phenyl]-1,1-dioxo-2,3-dihydro-1-benzothiepine-4-carboxamide (0.3 g), 3,4-bis(2-ethoxyethoxy)phenylborate (0.23 g), 1M potassium carbonate solution (1.3 ml), ethanol (1.3 ml) and toluene (25 ml) was stirred under argon atmosphere at room temperature for 30 minutes. To the mixture was added tetrakistriphenylphosphinepalladium (0.03 g), and the mixture was refluxed under argon atmosphere for 6 hours and extracted with ethyl acetate. The organic layer was washed with water and saturated brine, and dried with anhydrous magnesium sulfate. The solvent was evaporated, and the residue was purified with silica gel column chromatography (ethyl acetate/methanol/triethylamine) to give crude crystals, which were recrystallized from ethanol to give 7-[3,4-bis(2-ethoxyethoxy)phenyl]-N-[4-[[N-methyl-N-(tetrahydro-2H-pyran-4-yl)amino]methyl]phenyl]-1,1-dioxo-2,3-dihydro-1-benzothiepine-4-carboxamide (Compound 127) (0.3 g) as colorless crystals.

mp 150–151° C.; $^1$H-NMR (δ ppm, CDCl$_3$) 1.22 (3H, t, J=7.0 Hz), 1.23 (3H, t, J=6.9 Hz), 1.64–1.75 (4H, m), 2.21 (3H, s), 2.59–2.70 (1H, m), 3.18 (2H, t, J=6.4 Hz), 3.38 (2H, dt, J=2.6, 11.1 Hz), 3.55–3.73 (8H, m), 3.79–3.84 (4H, m), 4.01–4.08 (2H, m), 4.19–4.27 (4H, m), 6.99 (1H, d, J=8.0 Hz), 7.11–7.19 (2H, m), 7.30–7.34 (3H, m), 7.55–7.63 (4H, m), 7.99 (1H, s), 8.16 (1H, d, J=8.0 Hz). IR(KBr) v: 2975, 2960, 2880, 1665, 1597, 1516 cm$^{-1}$. Anal. calcd. for $C_{38}H_{48}N_2O_8S$: C, 65.87; H, 6.98; N. 4.04. Found C, 65.65; H, 6.90; N, 4.16.

Reference Example 176

To a solution of p-bromophenol (10.0 g), 3-methoxy-3-methylbutanol (8.2 g) and triphenylphosphone (18.2 g) in tetrahydrofuran (60 ml) was added dropwise under nitrogen atmosphere at 0° C. diethylazodicarbonate (40% toluene solution, 12.1 g) for 15 minutes, and the mixture was allowed to warm to room temperature, stirred for 16 hours and concentrated under reduced pressure. To the residue was added diethylether, and insoluble materials were filtered off. The filtrate was washed with 1N sodium hydroxide solution and saturated brine, and dried with magnesium sulfate. Under reduced pressure, the solvent was evaporated, and the residue was purified with silica gel column chromatography (ethyl acetate/hexane 1:5) to give yellow oil of 4-bromo-(3-methoxy-3-methyl)butoxybenzene (15.4 g).

$^1$H-NMR (200 MHz, CDCl$_3$) δ 1.23 (6H, s), 1.98 (2H, t, J=7.4 Hz), 3.21 (3H, s), 4.02 (2H, t, J=6.0 Hz), 6.78 (2H, dd, J=8.0, 2.2 Hz), 7.36 (2H, dd, J=9.2, 2.2 Hz).

Reference Example 177

To a mixture of magnesium (1.39 g), 1,2-dibromoethane (0.15 ml) and anhydrous tetrahydrofuran (50 ml) was added dropwise under argon atmosphere a solution of 4-bromo-(3-methoxy-3-methyl)butoxybenzene (15.0 g) in anhydrous tetrahydrofuran (100 ml) for 1 hour, and the mixture was stirred at 60° C. for 1 hour. To the mixture was added dropwise at −78° C. a solution of trimethyl borate (11.5 g) in anhydrous tetrahydrofuran (20 ml), and the mixture was stirred at room temperature for 2 hours. To the mixture was added at 0° C. 3N hydrochloric acid, and the mixture was stirred for 30 minutes and extracted with ethyl acetate (twice). The organic layer was washed with saturated brine (twice) and dried with magnesium sulfate. Under reduced pressure, the solvent was evaporated to give solid, which was washed with hexane (20 ml) and dried in vacuo to give colorless solid of 4-(3-methoxy-3-methyl)butoxyphenyl borate (5.7 g). The filtrate obtained by washing with hexane was purified with silica gel column chromatography to give 4-(3-methoxy-3-methyl)butoxyphenyl borate (0.8 g).

$^1$H-NMR (200 MHz, DMSO-d$_6$) δ 1.17 (6H, s), 1.91 (2H, t, J=7.0 Hz), 3.12 (3H, s), 4.04 (2H, t, J=7.4 Hz), 6.88 (2H, d, J=8.4 Hz), 7.72 (2H, d, J=8.4 Hz), 7.83 (2H, s).

Reference Example 178

To a solution of o-cresol (6.0 g) in dichloromethane (120 ml) and methanol (80 ml) was added little by little the solid of tetrabutylammonium tribromide (27.0 g), and the mixture was stirred for 1 hour and concentrated under reduced pressure. To the residue was added water, and the mixture was extracted with ether (4 times). The organic layer was washed with saturated brine (twice) and dried with magnesium sulfate. Under reduced pressure, the solvent was evaporated to give solid, which was dried in vacuo to give colorless solid of 4-bromo-2-methylphenol (9.3 g).

$^1$H-NMR (200 MHz, CDCl$_3$) δ 2.22 (3H, s), 4.96 (1H, s), 6.65 (1H, d, J=8.4 Hz), 7.15 (1H, dd, J=8.4, 1.8 Hz), 7.24 (1H, d, J=1.8 Hz).

Reference Example 179

To a solution of 4-bromo-2-methylphenol (9.3 g) in DMF (50 ml) was added potassium carbonate (9.62 g) and then was added dropwise 2.-bromoethyl ethyl ether (7.99 g), and the mixture was stirred at 70° C. for 3 days. To the mixture was added dropwise 2-bromoethyl ethyl ether (1.52 g), and the mixture was stirred at 70° C. for 4.5 hours and cooled. To the mixture was added water, and the mixture was extracted with ether. The organic layer was washed with 1N sodium hydroxide solution and saturated brine, and dried with magnesium sulfate. Under reduced pressure, the solvent was evaporated, and the residue was distilled under reduced pressure (3 mmHg, 170° C.) to give colorless oil of 4-bromo-2-methyl-(2-ethoxyethoxy)benzene (10.6 g).

$^1$H-NMR (200 MHz, CDCl$_3$) δ 1.24 (3H, t, J=6.0 Hz), 2.21 (3H, s), 3.61 (2H, q, J=6.2 Hz), 3.79 (2H, t, J=3.4 Hz), 4.09 (2H, t, J=4.6 Hz), 6.69 (1H, d, J=9.0 Hz), 7.20–7.26 (2H, m).

Reference Example 180

To a mixture of magnesium (966 mg), 1,2-dibromoethane (0.1 ml) and anhydrous tetrahydrofuran (35 ml) was added dropwise under argon atmosphere a solution of 4-bromo-2-methyl-(2-ethoxyethoxy)benzene (10.0 g) in anhydrous tetrahydrofuran (70 ml) for 1 hour, and the mixture was stirred at 70 for 1 hour and 20 minutes. To the mixture was added dropwise at 0° C. a solution of trimethyl borate (8.0 g) in anhydrous tetrahydrofuran (15 ml), and the mixture was stirred at room temperature for 16 hours. To the mixture was added at 0° C. 1N hydrochloric acid (200 ml), and the mixture was stirred for 30 minutes and extracted with ethyl acetate (twice). The organic layer was washed with saturated brine (twice) and dried with magnesium sulfate. Under reduced pressure, the solvent was evaporated to give solid, which was washed with hexane (40 ml) and dried in vacuo to give colorless solid of 4-(2-ethoxyethoxy)-3-methylphenyl borate (3.5 g).

$^1$H-NMR (200 MHz, DMSO-d$_6$) δ 1.13 (3H, t, J=7.0 Hz), 2.14 (3H, s), 3.51 (2H, q, J=7.2 Hz), 3.71 (2H, t, J=4.4 Hz), 4.09 (2H, t, J=4.6 Hz), 6.87 (1H, d, J=8.0 Hz), 7.50–7.61 (2H, m), 7.75 (2H, s).

Reference Example 181

To a solution of 3-chloro-2,2-dimethylpropanol (5.0 g) and 2,3-dihydropyran (4.12 g) in ethyl acetate (20 ml) was added camphor sulfonic acid (57 mg), and the mixture was stirred for 19 hours. To the mixture was added water, and the mixture was extracted with ethyl acetate. The organic layer was washed with O.1N sodium hydroxide solution and saturated brine, and dried with magnesium sulfate. The solvent was evaporated under reduced pressure and distilled under reduced pressure (2 mmHg, 108° C.) to give colorless oil of 2-(3-chloro-2,2-dimethylpropoxy)tetrahydropyran (6.07 g).

$^1$H-NMR (200 MHz, CDCl$_3$) δ 1.01 (6H, d, J=4.8 Hz), 1.43–1.90 (6H, m), 3.15 (1H, d, J=9.2 Hz), 3.42–3.59 (4H, m), 3.80–3.91 (1H, m), 4.60 (1H, t, J=2.8 Hz).

Reference Example 182

Sodium hydride (60% oil, 1.34 g) was washed with hexane (thrice), to which was added DMF (50 ml). To the mixture was added dropwise a solution of p-bromophenol (4.82 g) in DMF (50 ml) at 0° C., and the mixture was stirred at room temperature for 30 minutes. To the mixture was added dropwise at 0° C. a solution of 2-(3-chloro-2,2-dimethylpropoxy)tetrahydropyran (4.8 g) in DMF (30 ml) and then was added sodium iodide (4.9 g), and the mixture was stirred at 165° C. for 3 days and cooled. To the mixture was added water, and the mixture was extracted with ethyl acetate (twice). The organic layer was washed with 1N sodium hydroxide solution and saturated brine, and dried with magnesium sulfate. Under reduced pressure, the solvent was evaporated, and the residue was purified with silica gel column chromatography (ethyl acetate:hexane=1:10 to give colorless oil of 4-bromo-[2,2-dimethyl-3-(2-tetrahydropyranoxy)propoxy]benzene (7.37 g).

$^1$H-NMR (200 MHz, CDCl$_3$) δ 1.03 (6H, d, J=2.6 Hz), 1.45–1.79 (6H, m), 3.20 (1H, d, J=9.4 Hz), 3.43–3.52 (1H, m). 3.62 (1H, d, J=9.2 Hz), 3.66–3.82 (3H, m), 4.55 (1H, t, J=3.0 Hz), 6.79 (2H, dd, J=8.8, 2.2 Hz), 7.35 (2H, dd, J=9.2, 2.2 Hz).

Reference Example 183

To a solution of 4-bromo-[2,2-dimethyl-3-(2-tetrahydropyranoxy)propoxy]benzene (7.37 g) in methanol (80 ml) was added p-toluenesulfonic acid (205 mg), and the mixture was stirred at room temperature for 15.5 hours. To the mixture was added water, and the mixture was extracted with ethyl acetate. The organic layer was washed with saturated brine and dried with magnesium sulfate. Under reduced pressure. The solvent was evaporated, and the residue was purified with silica gel column chromatography (ethyl acetate:hexane=1:5 to give colorless crystals of 4-bromo-(2,2-dimethyl-3-hydroxy)propoxybenzene (4.80 g).

$^1$H-NMR (200 MHz, CDCl$_3$) δ 1.02 (6H, s), 1.74 (1H, t, J=4.8 Hz), 3.54 (2H, d, J=5.8 Hz), 3.73 (2H, s), 6.79 (2H, dd, J=8.8, 2.2 Hz), 7.37 (2H, dd, J=9.2, 2.2 Hz). Anal. for C$_{11}$H$_{15}$O2BrCalcd. C, 50.98; H,5.83: Found. C, 50.93; H, 6.01.

Reference Example 184

Sodium hydride (60% oil, 1.28 g) was washed with hexane (thrice), to which was added DMF (40 ml). To the mixture was added dropwise at 0° C. a solution of 4-bromo-(2,2-dimethyl-3-hydroxy)butoxybenzene (4.5 g) in DMF (50 ml) under nitrogen atmosphere, and the mixture was stirred at room temperature for 30 minutes. To the mixture was added dropwise at 0° C. a solution of iodoethane (7.82 g) in DMF (80 ml), and the mixture was stirred at room temperature for 16 hours. To the mixture was added water, and the mixture was extracted with hexane. The organic layer was washed with 1N sodium hydroxide solution and saturated brine, and dried with magnesium sulfate. Under reduced pressure, the solvent was evaporated, and the residue was purified with silica gel column chromatography (ethyl acetate:hexane=1:5 to give colorless oil of 4-bromo-(2,2-dimethyl-3-ethoxy)propoxybenzene (7.37 g).

$^1$H-NMR (200 MHz, CDCl$_3$) δ 1.00 (6H, s), 1.14 (3H, t, J=7.0 Hz), 3.25 (2H, s), 3.44 (2H, q, J=7.4 Hz), 3.69 (2H, s), 6.79 (2H, dd, J=9.0, 2.2 Hz), 7.35 (2H, dd, J=9.2, 2.2 Hz).

Reference Example 185

To a mixture of magnesium (262 mg), 1,2-dibromoethane (0.05 ml) and anhydrous tetrahydrofuran (25 ml) was added dropwise under nitrogen atmosphere a solution of 4-bromo-(2,2-dimethyl-3-ethoxy)propoxybenzene (3.0 g) in anhydrous tetrahydrofuran (25 ml) for 30 minutes, and the mixture was stirred at 70° C. for 3 hours and cooled to −78° C. To the mixture was added dropwise at −78° C. a solution of trimethyl borate (2.17 g) in anhydrous tetrahydrofuran (10 ml), and the mixture was stirred at room temperature for 19 hours. To the mixture was added at 0° C. 1N hydrochloric acid (50 ml), and the mixture was stirred for 30 minutes and extracted with ethyl acetate (three times). The organic layer was washed with saturated brine and dried with magnesium sulfate. Under reduced pressure, the solvent was evaporated, and the residue was purified with silica gel column chromatography (ethyl acetate:hexane=1:1 to give colorless solid of 4-(2,2-dimethyl-3-ethoxy)propoxyphenyl borate (505 mg).

$^1$H-NMR (200 MHz, DMSO-d$_6$) δ 0.96 (6H, s), 1.07 (3H, t, J=7.0 Hz), 3.23 (2H, s), 3.40 (2H, q, J=7.0 Hz), 3.71 (2H, s), 6.88 (2H, t, J=7.5 Hz), 7.69 (2H, t, J=7.6 Hz), 7.80 (2H, s).

Reference Example 186

To a solution of 4-bromo-3-chlorophenol (10.0 g), 3-ethoxypropanol (6.0 g) and triphenylphosphine (15.2 g) in tetrahydrofuran (50 ml) was added dropwise under nitrogen atmosphere at 0° C. diethylazodicarbonate (40% toluene solution, 25.2 g) for 15 minutes, and the mixture was stirred at room temperature for 2 hours and concentrated under reduced pressure. To the residue was added diethylether, and insoluble materials were filtered off. The filtrate was washed with saturated brine and dried with magnesium sulfate. Under reduced pressure, the solvent was evaporated, and the residue was purified with silica gel column chromatography (ethyl acetate/hexane 1:5) and distilled under reduced pressure (1.5 mmHg, 190° C.) to give colorless oil of 4-bromo-3-chloro-(3-ethoxypropoxy)benzene (11.2 g).

$^1$H-NMR (200 MHz, CDCl$_3$) δ 1.19 (3H, t, J=7.0 Hz), 2.08 (2H, m), 3.50 (2H, q, J=7.4 Hz), 3.62 (2H, t, J=6.2 Hz), 4.11 (2H, t, J=3.6 Hz), 6.82 (1H, d, J=8.8 Hz), 7.31 (1H, dd, J=8.4, 2.2 Hz), 7.49 (1H, d, J=2.2 Hz).

Reference Example 187

To a mixture of magnesium (853 mg), 1,2-dibromoethane (0.2 ml) and anhydrous tetrahydrofuran (35 ml) was added dropwise under nitrogen atmosphere a solution of 4-bromo-3-chloro-(3-ethoxypropoxy)benzene (10.0 g) in anhydrous tetrahydrofuran (70 ml) for 50 minutes, and the mixture was stirred at 65° C. for 2.5 hours and cooled to −78° C. To the mixture was added dropwise at −78° C. a solution of trimethyl borate (7.08 g) in anhydrous tetrahydrofuran (15 ml), and the mixture was stirred at room temperature for 19 hours. To the mixture was added at 0° C. 1N hydrochloric acid (50 ml), and the mixture was stirred for 30 minutes and extracted with ethyl acetate (three times). The organic layer was washed with saturated brine (twice) and dried with magnesium sulfate. Under reduced pressure, the solvent was evaporated, and the solid washed with hexane (35 ml) to give colorless solid of 3-chloro-4-(3-ethoxypropoxy)phenyl borate (5.65 g).

$^1$H-NMR (200 MHz, DMSO-d$_6$) δ 1.10 (3H, t, J=7.0 Hz), 1.97 (2H, m), 3.43 (2H, q, J=7.0 Hz), 3.53 (2H, t, J=6.2 Hz), 4.12 (2H, t, J=6.2 Hz), 7.10 (1H, d, J=8.4 Hz), 7.71 (1H, dd, J=8.0, 1.6 Hz), 7.79 (1H, d, J=1.4 Hz), 8.03 (2H, s).

Working Example 131 (Production of Compound 128)

In toluene (10 ml), ethanol (1 ml) and water (1 ml) were suspended 4-(3-methoxy-3-methyl)butoxyphenyl borate (119 mg), 7-bromo-N-[4-[[N-methyl-N-(tetrahydropyran-4-yl)amino]methyl]phenyl]-1,1-dioxo-2,3-dihydro-1-benzothiepine-4-carboxamide (200 mg) and potassium carbonate (138 mg), and the suspension was stirred under argon atmosphere for 30 minutes. To the mixture was added tetrakistriphenylphosphinepalladium (31 mg), and the mixture was stirred under argon atmosphere at 100° C. for 8 hours and cooled. To the mixture was added saturated brine, and the mixture was extracted with ethyl acetate (twice). The organic layer was dried with magnesium sulfate. Under reduced pressure, the solvent was evaporated, and the residue was purified with silica gel column chromatography (ethyl acetate:methanol=3:1) and recrystallized from ethanol (19 ml) to give colorless crystals of 7-[4-(3-methoxy-3-methyl)butoxyphenyl]-N-[4-[[N-methyl-N-(tetrahydropyran-4-yl)amino]methyl]phenyl]-1,1-dioxo-2,3-dihydro-1-benzothiepine-4-carboxamide (Compound 128) (136 mg).

m.p. 204.5–205.5° C.; $^1$H-NMR (200 MHz, CDCl$_3$) δ 1.26 (6H, s), 1.75 (4H, br), 2.04 (2H, t, J=6.8 Hz), 2.21 (3H, s), 3.17 (2H, t, J=7.2 Hz), 3.24 (3H, s), 3.37 (2H, dt, J=11.0, 2.2 Hz), 3.58 (2H, s), 3.73 (2H, t, J=7.4 Hz), 4.02–4.17 (4H, m), 7.01 (2H, d, J=8.8 Hz), 7.31–7.35 (3H, m), 7.52–7.57 (4H, m), 7.63–7.70 (2H, m), 8.20 (1H, d, J=8.4 Hz). Anal. for $C_{36}H_{27}N_2O_4S$ Calcd. C, 68.33; H, 7.01; N, 4.43: Found. C, 68.03; H, 6.78; N, 4.33.

Working Example 132 (Production of Compound 129)

In toluene (10 ml), ethanol (1 ml) and water (1 ml) were suspended 4-(2-ethoxyethoxy)-3-methylphenyl borate (119 mg), 7-bromo-N-[4-[[N-methyl-N-(tetrahydropyran-4-yl)amino]methyl]phenyl]-1,1-dioxo-2,3-dihydro-1-benzothiepine-4-carboxamide (212 mg) and potassium carbonate (147 mg), and the suspension was stirred under argon atmosphere for 30 minutes. To the mixture was added tetrakistriphenylphosphinepalladium (33 mg), and the mixture was stirred under argon atmosphere at 100° C. for 8 hours and cooled. To the mixture was added saturated brine, and the mixture was extracted with ethyl acetate (twice). The organic layer was dried with magnesium sulfate. Under reduced pressure, the solvent was evaporated, and the residue was purified with silica gel column chromatography (ethyl acetate:methanol=7:1) and recrystallized from ethanol (22.5 ml) to give colorless crystals of 7-[4-(2-ethoxyethoxy)-3-methyl-phenyl]-N-[4-[[N-methyl-N-(tetrahydropyran-4-yl)amino]methyl]phenyl]-1,1-dioxo-2,3-dihydro-1-benzothiepine-4-carboxamide (Compound 129) (131 mg).

m.p. 212–213° C.; $^1$H-NMR (200 MHz, CDCl$_3$) δ 1.26 (3H, t, J=6.4 Hz), 1.75 (4H, br), 2.21 (3H, s), 2.31 (3H, s), 2.65 (1H, br), 3.16 (2H, t, J=7.0 Hz), 3.38 (2H, dt, J=9.0, 3.0 Hz), 3.57–3.75 (6H, m), 3.85 (2H, t, J=4.4 Hz), 4.04 (2H, d, J=11.2 Hz), 4.19 (2H, t, J=5.2 Hz), 6.92 (2H, d, J=9.2 Hz), 7.26–7.39 (4H, m), 7.54 (2H, d, J=8.8 Hz), 7.62–7.68 (2H, m), 7.87 (1H, s), 8.18 (1H, d, J=8.2 Hz). Anal. for $C_{35}H_{42}N_2O_6S.0.1$ $H_2O$ Calcd. C, 67.94; H, 6.84; N, 4.53: Found. C, 67.45; H, 6.63; N, 4.53.

Working Example 133 (Production of Compound 130)

A mixture of 4-(3-ethoxy-2,2-dimethyl)propoxyphenyl borate (189 mg), 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) and potassium carbonate (208 mg) was suspended in toluene (15 ml), ethanol (1.5 ml) and water (1.5 ml), and the suspension was stirred under argon atmosphere for 30 minutes. To the mixture was added tetrakistriphenylphosphinepalladium (47 mg), and the mixture was stirred under argon atmosphere at 100° C. for 8 hours and cooled. To the mixture was added saturated brine, and the mixture was extracted with ethyl acetate (twice). The organic layer was dried with magnesium sulfate. Under reduced pressure, the solvent was evaporated, and the residue was purified with silica gel column chromatography (ethyl acetate:methanol=8:1) and recrystallized from ethanol (22.5 ml) to give colorless crystals of 7-[4-(3-ethoxy-2,2-dimethylpropoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 130) (175 mg).

m.p. 209–210° C.; $^1$H-NMR (200 MHz, CDCl$_3$) δ 1.04 (6H, s), 1.16 (3H, t, J=7.2 Hz), 1.76 (4H, br), 2.21 (3H, s), 3.17 (2H, t, J=6.2 Hz), 3.20 (2H, s), 3.38–3.51 (4H, m), 3.58 (2H, s), 3.69–3.79 (4H, m), 4.04 (2H, d, J=11.4 Hz), 7.03 (2H, d, J=8.8 Hz), 7.31–7.35 (3H, m), 7.52–7.70 (6H, m), 7.85 (1H, s), 8.20 (1H, d, J=8.0 Hz). Anal. for $C_{37}H_{46}N_2O_6S$ Calcd. C, 68.70; H, 7.17; N, 4.33: Found. C, 68.83; H, 7.25; N, 4.36.

Working Example 134 (Production of Compound 131)

In toluene (15 ml), ethanol (1.5 ml) and water (1.5 ml) were suspended 3-chloro-4-(3-ethoxypropoxy)phenyl borate (194 mg), 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) and potassium carbonate (208 mg). Under argon atmosphere, the suspension was stirred for 30 minutes, and to the mixture was added tetrakistriphenylphosphinepalladium (47 mg). Under argon atmosphere, the mixture was heated at 100° C. for 8 hours and cooled. To the mixture was added saturated brine, and the mixture was extracted with ethyl acetate. The organic layer was dried with magnesium sulfate. Under reduced pressure, the solvent was evaporated, and the residue was purified with silica gel column chromatography (ethyl acetate:ethano=18:1) and recrystallized from ethanol (23 ml) to give colorless crystals of 7-[3-chloro-4-(3-ethoxypropoxy)phenyl]-N-[4-[[N-methyl-N-(tetrahydropyran-4-yl)amino]methyl]phenyl]-1,1-dioxo-2,3-dihydro-1-benzothiepine-4-carboxamide (Compound 131) (229 mg).

m.p. 182–183° C.; $^1$H-NMR (200 MHz, CDCl$_3$) δ 1.21 (3H, t, J=6.8 Hz), 1.75 (4H, m), 2.14 (2H, m), 2.21 (3H, s), 2.65 (1H, m), 3.17 (2H, t, J=7.0 Hz), 3.31–3.76 (1OH, m), 4.04 (2H, d, J=11.4 Hz), 4.21 (2H, t, J=6.6 Hz), 7.05 (1H, d, J=8.4 Hz), 7.31–7.35 (3H, m), 7.43–7.68 (6H, m), 7.88 (1H, s), 8.21 (1H, d, J=8.0 Hz).

Reference Example 188

In DMF (98 ml) was dissolved 4-bromo-3-chlorophenol (9.8 g), and to the solution were added at room temperature potassium carbonate (9.8 g), sodium iodide (7.8 g) and 2-chloroethylpropylether (7.8 ml). The mixture was stirred at 90° C. for 16 hours, cooled to room temperature, poured into water, and the mixture was extracted with ethyl acetate, washed with saturated brine and dried with magnesium sulfate. Under reduced pressure, the solvent was removed, and the residue was purified with silica gel column chromatography (hexane/ethyl acetate=8/1) to give 1-bromo-2-chloro-4-(2-propoxyethoxy)benzene (8.8 g).

$^1$H-NMR (200 MHz, CDCl$_3$) δ 0.93(3H, t, J=7.4 Hz), 1.55–1.70(2H, m), 3.48(2H, t, J=6.6 Hz), 3.76(2H, t, J=4.4 Hz), 4.08(2H, t, J=4.4 Hz), 6.72(1H, dd, J=8.8, 3.0 Hz), 7.04(1H, d, J=3.0 Hz), 7.46(1H, d, J=9.2 Hz).

Reference Example 189

In THF (70 ml) was dissolved 1-bromo-2-chloro-4-(2-propoxyethoxy)benzene (7.0 g), and to the solution was added dropwise at –78° C. 1.6M n-butyllithium/hexane(17.3 ml). The mixture was stirred for 1 hour, and to the mixture was added dropwise trimethoxyborane (7.8 g). The mixture was stirred for 30 minutes and warmed to room temperature. To the mixture was added 2N hydrochloric acid (28 ml), and the mixture was stirred for 15 minutes. The reaction solution was extracted with ethyl acetate, washed with saturated brine and dried with magnesium sulfate. Under reduced pressure, the solvent was removed, and the residue was purified with silica gel column chromatography (hexane/ethyl acetate=2/1) to give 2-chloro-4-(2-propoxyethoxy)phenyl borate (1.70 g).

$^1$H-NMR (200 MHz, DMSO-d$_6$) δ 0.86(3H, t, J=7.2 Hz), 1.43–1.58(2H, m), 3.40(2H, t, 6.6 Hz), 3.65–3.71(2H, m), 4.08–4.15(2H, m), 6.84–6.95(1H, m), 7.38(1H, d, J=8.0 Hz), 7.84(1H, d, J=8.4 Hz), 8.08(2H, br).

Working Example 135 (Production of Compound 132)

To 7-bromo-N-[4-[[N-methyl-N-(tetrahydropyran-4-yl)amino]methyl]phenyl]-1,1-dioxo-2,3-dihydro-1-benzothiepine-4-carboxamide (0.40 g) was added toluene/ethanol/water (10/1/1, 19.2 ml). To the mixture were added 2-chloro-4-(2-propoxyethoxy)phenyl borate (0.24 g) and potassium carbonate (0.24 g), and the mixture was stirred at room temperature for 30 minutes. To the mixture was added tetrakistriphenylphosphinepalladium (45 mg), and the mixture was refluxed for 14 hours and cooled to room temperature. The reaction solution was poured into water, and the mixture was extracted with ethyl acetate, washed with saturated brine and dried with magnesium sulfate. Under reduced pressure, the solvent was removed, and the residue was purified with silica gel column chromatography (ethyl acetate/ethanol=4/1) and recrystallized from ethanol to give 7-[2-chloro-4-(2-propoxyethyl)phenyl]-N-[4-[[N-methyl-N-(tetrahydropyran-4-yl)amino]methyl]phenyl]-1,1-dioxo-2,3-dihydro-1-benzothiepine-4-carboxamide (Compound 132) (206 mg).

m.p. 150–152° C.; $^1$H-NMR (200 MHz, CDCl$_3$) δ 0.94 (3H,t, J=7.4 Hz), 1.55–1.82(6H, m), 2.20(3H, s), 2.64(1H, m), 3.15–3.22(2H, m), 3.30–3.44(2H, m), 3.51(2H, t, J=6.6 Hz), 3.56(2H, s), 3.72(2H, t, J=6.6 Hz), 3.75–3.84(2H, m), 3.98–4.08(2H, m), 4.17(2H, t, J=4.8 Hz), 6.94(1H, dd, J=8.8, 2.6 Hz), 7.08(1H, d, J=2.4 Hz), 7.21–7.33(4H, m), 7.50–7.60(4H, m), 7.83(1H, s), 8.20(1H, d, J=8.0 Hz). IR(KBr) 3349, 2959, 1651, 1603, 1516, 1408, 1289, 1128, 1060, 822 cm$^{-1}$; Elemental Analysis for $C_{35}H_{41}FN_2O_6S$; Calcd. C, 64.35; H, 6.33; N, 4.29: Found. C, 64.17; H, 6.24; N, 4.22.

Reference Example 190

In DMF (90 ml) was dissolved 4-bromo-3-fluorophenol (9.0 g), and to the solution were added at room temperature potassium carbonate (9.8 g), sodium iodide (7.8 g) and 2-chloroethylpropylether(7.7 ml). The mixture was stirred at 90° C. for 16 hours and cooled to room temperature. The reaction solution was poured into water, and the mixture was extracted with ethyl acetate, washed with saturated brine and dried with magnesium sulfate. Under reduced pressure, the solvent was removed, and the residue was purified with silica gel column chromatography (hexane/ethyl acetate=8/1) to give 1-bromo-2-fluoro-4-(2-propoxyethoxy)benzene (8.8 g).

$^1$H-NMR (200 MHz, CDCl$_3$) δ 0.93(3H, t, J=7.4 Hz), 1.54–1.73(2H, m), 3.48(2H, t, J=6.6 Hz), 3.74–3.81(2H, m), 4.06–4.13(2H, m), 6.69–6.76(1H, m), 7.37(1H, d, J=8.0 Hz), 7.69(1H, d, J=7.2 Hz).

Reference Example 191

In THF (96 ml) was dissolved 1-bromo-2-fluoro-4-(2-propoxyethoxy)benzene (8.0 g), and to the solution was added dropwise at −78° C. 1.6M n-butyllithium/hexane(19.8 ml). The mixture was stirred for 1 hour, and to the mixture was added dropwise trimethoxyborane (9.0 g). The mixture was stirred for 30 minutes and warmed to room temperature. To the mixture was added 2N hydrochloric acid (32 ml), and the mixture was stirred for 15 minutes. The reaction solution was extracted with ethyl acetate, washed with saturated brine and dried with magnesium sulfate. Under reduced pressure, the solvent was removed, and the residue was purified with silica gel column chromatography (hexane/ethyl acetate=2/1) to give 2-fluoro-4-(2-propoxyethoxy)phenyl borate (1.17 g).

$^1$H-NMR (200 MHz, DMSO-d$_6$) δ 0.87(3H, t, J=7.2 Hz), 1.46–1.60(2H, m), 3.37–3.45(2H, m), 3.66–3.72(2H, m), 4.08–4.13(2H, m),6.70–6.77(2H, m), 7.50(1H,d,J=8.0 Hz), 7.89(2H, br).

Working Example 136 (Production of Compound 133)

To 7-bromo-N-[4-[[N-methyl-N-(tetrahydropyran-4-yl)amino]methyl]phenyl]-1,1-dioxo-2,3-dihydro-1-benzothiepine-4-carboxamide (0.35 g) was added toluene/ethanol/water (10/1/1, 16.3 ml). To the mixture were added 2-fluoro-4-(2-propoxyethoxy)phenyl borate (0.20 g) and potassium carbonate (0.20 g), and the mixture was stirred at room temperature for 30 minutes. To the mixture was added tetrakistriphenylphosphinepalladium (31 mg), and the mixture was refluxed for 14 hours and cooled to room temperature. The reaction solution was poured into water, and the mixture was extracted with ethyl acetate, washed with saturated brine and dried with magnesium sulfate. Under reduced pressure, the solvent was removed, and the residue was purified with silica gel column chromatography (ethyl acetate/ethanol=4/1) and recrystallized from ethanol to give 7-[2-fluoro-4-(2-propoxyethyl)phenyl]-N-[4-[[N-methyl-N-(tetrahydropyran-4-yl)amino]methyl]phenyl]-1,1-dioxo-2,3-dihydro-1-benzothiepine-4-carboxamide (Compound 133) (105 mg).

m.p. 172–174° C.; $^1$H-NMR (200 MHz, CDCl$_3$) δ 0.94 (3H, t, J=7.4 Hz), 1.58–1.76 (6H, m), 2.21 (3H, s), 2.65(1H, m), 3.17(2H, t, J=6.6 Hz), 3.32–3.44 (2H, m), 3.51 (2H, t, J=6.6 Hz), 3.57 (2H, s), 3.72 (2H, t, J=6.2 Hz), 3.79–3.84 (2H, m), 3.98–4.08 (2H, m), 4.17 (2H, t, J=4.4 Hz), 6.75–6.87(2H, m), 7.30–7.40(4H, m), 7.51–7.67(4H, m), 7.85(1H, s), 8.20(1H, d, J=8.6 Hz); IR(KBr) 3345, 2940, 1651, 1620, 1520, 1410, 1316, 1288, 1127, 816 cm$^{-1}$; Elemental Analysis for $C_{35}H_{41}ClN_2O_6S \cdot 0.3\ H_2O$; Calcd. C, 65.46; H, 6.53; N, 4.36: Found. C, 65.44; H, 6.38; N, 4.31.

Working Example 137 (Production of Compound 134)

In THF (30 ml) was dissolved N-[4-[[N-methyl-N-(tetrahydropyran-4-yl)amino]methyl]phenyl]-7-[4-(2-propoxyethoxy)phenyl)]-1,1-dioxo-2,3-dihydro-1-benzothiepine-4-carboxamide (1.0 g). To the solution was added L-tartaric acid (0.36 mg), and the mixture was stirred at room temperature for 12 hours. Under reduced pressure, the solvent was removed, and the residue was recrystallized from ethanol to give N-[4-[[N-methyl-N-(tetrahydropyran-4-yl)amino]methyl]phenyl]-7-[4-( 2-propoxyethoxy)phenyl)]-1,1-dioxo-2,3-dihydro-1-benzothiepine-4-carboxamide L-tartarate (Compound 134) (1.7 g).

m.p. 116–119° C.; $^1$H-NMR (200 MHz, DMSO-d$_6$) δ 0.88(3H, t, J=7.2 Hz), 1.42–1.81 (6H, m), 2.22 (3H, s), 2.79 (1H, m), 3.22–3.30 (2H, m), 3.39–3.46(2H, m), 3.69–3.82 (6H, m), 3.70(2H, s), 3.89–3.97(2H, m), 4.17(2H, s), 4.14–4.19(2H, m), 7.10(2H, d, J=8.8 Hz), 7.33(2H, d, J=8.4 Hz), 7.55(1H, s), 7.69–7.89(5H, m), 8.05–8.09(2H, m), 10.22(1H, s); IR(KBr) 3247, 2965, 1663, 1607, 1518, 1416, 1292, 1252, 1128, 826 cm$^{-1}$; Elemental Analysis for $C_{39}H_{48}N_2O_6S \cdot 0.2\ H_2O$; Calcd. C, 60.64; H, 6.32; N, 3.63: Found. C, 60.59; H, 6.12; N, 3.64.

Reference Example 192

In THF (94 ml) was dissolved 5-bromo-2-methyl-1,3-benzoxazole (9.4 g), and to the solution was added dropwise at −78° C. 1.6M n-butyllithium/hexane (30.5 ml). The mixture was stirred for 1 hour, and to the mixture was added dropwise a solution of trimethoxyborane (9.2 ml) in THF (9.2 ml). The mixture was stirred for 30 minutes and warmed to room temperature. To the mixture was added water (37.6 ml), and the mixture was stirred for 15 minutes. The reaction solution was extracted with ethyl acetate, washed with saturated brine and dried with magnesium sulfate. Under reduced pressure, the solvent was removed, and the residue was washed with hexane/isopropylether to give 2-methyl-1,3-benzoxazol-5-yl borate (5.5 g).

$^1$H-NMR (200 MHz, DMSO-d$_6$) δ 2.17(3H, s), 6.88–6.93 (1H, m), 7.14–7.40(1H, m), 7.48–7.56(1H, m), 10.24(2H, br).

Working Example 138 (Production of Compound 135)

To 7-bromo-N-[4-[[N-methyl-N-(tetrahydropyran-4-yl)amino]methyl]phenyl]-1,1-dioxo-2,3-dihydro-1-benzothiepine-4-carboxamide (0.35 g) was added toluene/ethanol/water (10/1/1,16.3 ml) and then were added 2-methyl-1,3-benzoxazol-5-yl borate (0.14 g) and potassium carbonate (0.23 g), and the mixture was stirred at room temperature for 30 minutes. To the mixture was added tetrakistriphenylphosphinepalladium (31 mg), and the mixture was refluxed for 14 hours, cooled to room temperature, poured into water. The mixture was extracted with ethyl acetate, washed with saturated brine and dried with magnesium sulfate. Under reduced pressure, the solvent was removed, and the residue was purified with silica gel column chromatography (ethyl acetate/ethanol=4/1) and recrystallized from ethanol to give 7-(2-methyl-1,3-benzoxazol-5-yl)-N-[4-([N-methyl-N-(tetrahydropyran-4-yl)amino]methyl]phenyl]-1,1-dioxo-2,3-dihydro-1-benzothiepine-4-carboxamide (Compound 135) (110 mg).

m.p. 236–240° C.; $^1$H-NMR (200 MHz, DMSO-d$_6$) δ 1.42–1.76(4H, m), 2.10(3H, s), 2.50(3H, s),3.06(2H, t, J=6.6 Hz), 3.20–3.32(2H, m), 3.52(2H, s), 3.75–3.83(2H, m), 3.85–3.94(2H, m), 7.27(2H, d, J=8.2 Hz), 7.38(1H, s), 7.65(2H, d, J=8.4 Hz), 7.79–7.85(1H, d, J=8.4 Hz), 10.15 (1H, s); IR(KBr) 3256, 2953, 2836, 1655, 1634, 1534, 1412, 1319, 1130, 885, 822 cm$^{-1}$.

Reference Example 193

In THF (57 ml) was dissolved 5-bromo-2-(hydroxymethyl)-1-benzofuran (5.7 g), and to the solution was added at 0° C. 60% sodium hydride (1.4 g). The mixture was stirred at room temperature for 1 hour, and to the mixture was added at 0° C. 1-bromopropane (3.1 ml). The mixture was stirred at 65° C. for 16 hours and cooled to room temperature. The reaction solution was poured into water, and the mixture was extracted with ethyl acetate, washed with saturated brine and dried with magnesium sulfate. Under reduced pressure, the solvent was removed, and the residue was purified with silica gel column chromatography (hexane/ethyl acetate=8/1) to give 5-bromo-2-(propoxymethyl)-1-benzofuran (5.0 g).

$^1$H-NMR (200MHZ, CDCl$_3$) δ 0.94(3H, t, J=7.2 Hz), 1.56–1.72(2H, m), 3.50(2H, t, J=6.6 Hz), 4.59(2H, s), 6.63 (1H, S), 7.35–7.36(2H, m), 7.66–7.68(1H, m).

Reference Example 194

In THF (48 ml) was dissolved 5-bromo-2-(propoxymethyl)-1-benzofuran (4.8 g), and to the solution was added dropwise at –50° C. 1.6M n-butyllithium/hexane (12.3 ml). The mixture was stirred for 1 hour, and to the mixture was added dropwise trimethoxyborane (5.6 g). The mixture was stirred for 30 minutes, warmed to room temperature and stirred for 12 hours. To the mixture was added 2N hydrochloric acid (19.2 ml), and the mixture was stirred for 15 minutes. The reaction solution was extracted with ethyl acetate, washed with saturated brine and dried with magnesium sulfate. Under reduced pressure, the solvent was removed, and the residue was purified with silica gel column chromatography (hexane/ethyl acetate=2/1) to give 2-(propoxymethyl)-1-benzofuran-5-yl borate (0.22 g).

$^1$H-NMR (200 MHz, DMSO-d$_6$) δ 0.84(3H, t, J=7.0 Hz), 1.40–1.55(2H, m), 3.30–3.36(2H, m), 3.31(2H, s), 4.37–4.41(1H, m), 6.80(1H, s), 7.47(1H, d, J=8.2 Hz), 7.72(1H, d, J=8.4 Hz), 7.95(2H, br).

Working Example 139 (Production of Compound 136)

To 7-bromo-N-[4-[[N-methyl-N-(tetrahydropyran-4-yl)amino]methyl]phenyl]-1,1-dioxo-2,3-dihydro-1-benzothiepine-4-carboxamide (0.41 g) was added toluene/ethanol/water (10/1/1,19.2 ml) and then were added 2-(propoxymethyl)-1-benzofuran-5-yl borate (0.22 g) and potassium carbonate (0.24 g), and the mixture was stirred at room temperature for 30 minutes. To the mixture was added tetrakistriphenylphosphinepalladium (45 mg), and the mixture was refluxed for 14 hours, cooled to room temperature and poured into water. The mixture was extracted with ethyl acetate, washed with saturated brine and dried with magnesium sulfate. Under reduced pressure, the solvent was removed, and the residue was purified with silica gel column chromatography (ethyl acetate/ethanol=4/1) and recrystallized from ethanol to give N-[4-[[N-methyl-N-(tetrahydropyran-4-yl)amino]methyl]phenyl]-7-[2-(propoxymethyl)-1-benzofuran-5-yl]-1,1-dioxo-2,3-dihydro-1-benzothiepine-4-carboxamide (Compound 136) (184 mg).

m.p. 204–206° C.; $^1$H-NMR (200 MHz, DMSO-d$_6$) δ 0.92(3H, t, J=7.2 Hz), 1.30–1.43(2H, m), 1.55–1.77(4H, m), 2.20(3H, s), 2.64(1H, m), 3.17(2H, t, J=6.2 Hz), 3.30–3.54 (4H, m), 3.57(2H, s), 3.98–4.09(2H, m), 4.39(1H,t, J=6.6 Hz), 6.68(1H, s), 7.29–7.37(3H, m), 7.43–7.59(4H, m), 7.66–7.74(3H, m), 8.02(1H, s), 8.21(1H, d, J=8.0 Hz); IR(KBr) 3254, 2948, 1655, 1599, 1530, 1410, 1316, 1128, 806 cm$^{-1}$.

Reference Example 195

To a solution of 4-bromo-2-methylphenol (14.2 g) in DMF (75 ml) was added potassium carbonate (14.7 g), and to the mixture was added dropwise bromopropane (9.33 g). The mixture was stirred at 70° C. for 3 hours and cooled, and to the mixture was added water. The mixture was extracted with hexane, and the organic layer was washed with 1N sodium hydroxide solution and saturated brine, and dried with magnesium sulfate. Under reduced pressure, the solvent was evaporated to give colorless oil of 4-bromo-2-methyl-propoxybenzene (10.6 g).

$^1$H-NMR (200 MHz, CDCl$_3$) δ 1.04 (t, 3H, J=7.4 Hz), 1.73–1.90 (m, 2H), 2.19 (s, 3H), 3.89 (t, 2H, J=6.2 Hz), 6.66 (dd, 1H, J=7.4, 1.8 Hz), 7.19–7.24 (m, 2H).

Reference Example 196

To a mixture of magnesium (1.09 g), 1,2-dibromoethane (0.2 ml) and anhydrous tetrahydrofuran (35 ml) was added dropwise, under argon atmosphere, a solution of 4-bromo-2-methylphenol (10.0 g) in anhydrous tetrahydrofuran (70 ml) for 1 hour, and the mixture was stirred at 65° C. for 1 hour and 45 minutes. To the mixture was added dropwise at −78° C. a solution of trimethyl borate (9.07 g) in anhydrous tetrahydrofuran (15 ml), and the mixture was and stirred for 16 hours while gradually warming to room temperature. To the mixture was added at 0° C. 1N hydrochloric acid (200 ml), and the mixture was stirred at 30 minutes and extracted with ethyl acetate (twice). The organic layer was washed with saturated brine (twice) and dried with magnesium sulfate. Under reduced pressure, the solvent was evaporated, and the resulting solid was washed with hexane (35 ml) and dried in vacuo to give colorless solid of 3-methyl-4-propoxyphenyl borate (1.32 g).

$^1$H-NMR (200 MHz, DMSO-d$_6$) δ 1.00 (t, 3H, J=7.4 Hz), 1.66–1.83 (m, 2H), 2.14 (s, 3H), 3.94 (t, 2H, J=6.6 Hz), 6.85 (d, 1H, J=8.0 Hz), 7.52–7.61 (m, 2H), 7.75 (s, 2H).

Reference Example 197

To a suspension of 4-propoxyphenol (10.0 g) and potassium carbonate (10.0 g) in DMF (50 ml) was added bromoacetaldehydedimethylacetal (12.2 g), and the mixture was refluxed for 14 hours and cooled. To the mixture was added water, and the mixture was extracted with ethyl acetate (twice). The organic layer was washed with 1N sodium hydroxide solution (twice) and then washed with saturated brine, and dried with magnesium sulfate. Under reduced pressure, the solvent was evaporated, and the residue was purified with silica gel column chromatography to give yellow oil of 4-(2,2-dimethoxy)ethoxypropoxybenzene (12.2 g).

$^1$H-NMR (200 MHz, CDCl$_3$) δ 1.02 (t, 3H, J=7.4 Hz), 1.69–1.83 (m, 2H), 3.45 (s, 6H), 3.86 (t, 2H, J=6.6 Hz), 3.96 (d, 2H, J=5.6 Hz), 4.70 (t, 1H, J=5.2 Hz), 6.78–6.89 (m, 4H).

Reference Example 198

To a suspension of polyphosphoric acid (5.2 g) in toluene (120 ml) was added 4-(2,2-dimethoxy)ethoxypropoxybenzene (5.0 g), and the mixture was stirred at 100° C. overnight and cooled. To the mixture was added water, and the mixture was separated. The organic layer was washed with 1N sodium hydroxide solution and saturated brine, and dried with magnesium sulfate. Under reduced pressure, the solvent was evaporated, and the residue was purified with silica gel column chromatography to give brown oil of 5-propoxybenzofuran (1.7 g).

$^1$H-NMR (200 MHz, CDCl$_3$) δ 1.05 (t, 3H, J=7.4 Hz), 1.74–1.92 (m, 2H), 3.95 (t, 2H, J=6.6 Hz), 6.69 (dd, 1H, J=2.2, 0.8 Hz), 6.90 (dd, 1H, J=9.2, 2.6 Hz), 7.05 (d, 1H, J=2.6 Hz), 7.37 (d, 1H, J=9.4 Hz), 7.58 (d, 1H, J=2.2 Hz).

Reference Example 199

To a solution of 5-propoxybenzofuran (1.50 g) in anhydrous tetrahydrofuran (15 ml) was added dropwise at 0° C., under argon atmosphere, a solution of n-butyllithium in hexane (1.6M, 6.4 ml) in anhydrous tetrahydrofuran (15 ml), and the mixture was stirred for 2 hours. To the mixture was added at −78° C. a solution of trimethyl borate (2.65 g) in anhydrous tetrahydrofuran (15 ml), and the mixture was stirred overnight while gradually warming to room temperature. At 0° C., to the reaction solution was added 1N hydrochloric acid, and the mixture was stirred for 30 minutes and extracted with ethyl acetate. The organic layer was washed with saturated brine and dried with magnesium sulfate. Under reduced pressure, the solvent was evaporated, and the residue was purified with silica gel column chromatography to give red solid of 5-propoxybenzofuran-2-yl borate (0.62 g).

$^1$H-NMR (200 MHz, DMSO-d$_6$) δ 1.06 (t, 3H, J=7.4 Hz), 1.75–1.92 (m, 2H), 3.95 (t, 2H, J=6.6 Hz), 5.27 (br, 2H), 6.98 (dd, 1H, J=9.2, 3.0 Hz), 7.07 (d, 1H, J=2.6 Hz), 7.30 (d, 1H, J=0.8 Hz), 7.39 (d, 1H, J=8.8 Hz).

Reference Example 200

To a suspension of 4-methoxyphenol (26.7 g) and potassium carbonate (32.8 g) in DMF (150 ml) was added bromoacetaldehydedimethylacetal (40.1 g), and the mixture was refluxed for 2.5 hours and cooled. To the mixture was added water, and the mixture was extracted with ethyl acetate (twice). The organic layer was washed with 1N sodium hydroxide solution (twice) and then washed with saturated brine, and dried with magnesium sulfate. Under reduced pressure, the solvent was evaporated to give dark brown oil of 4-methoxy-(2,2-dimethoxy)ethoxybenzene (40.4 g).

$^1$H-NMR (200 MHz, CDCl$_3$) δ 3.45 (s, 6H), 3.77 (s, 3H), 3.96 (d, 2H, J=5.2 Hz), 4.70 (t, 1H, J=5.2 Hz), 6.79–6.90 (m, 4H).

Reference Example 201

To a suspension of polyphosphoric acid (38.3 g) in toluene (400 ml) was added 4-methoxy-(2,2-dimethoxy)ethoxybenzene (38.0 g), and the mixture was stirred at 100° C. overnight and cooled. To the mixture was added water, and the mixture was separated. The organic layer was washed with 1N sodium hydroxide solution and then washed with saturated brine, and dried with magnesium sulfate. Under reduced pressure, the solvent was evaporated, and the residue was purified with silica gel column chromatography to give brown oil of 5-methoxybenzofuran (6.5 g).

$^1$H-NMR (200 MHz, CDCl$_3$) δ 3.85 (s, 3H), 6.71–7.00 (m, 2H), 7.06 (d, 1H, J=2.2 Hz), 7.39 (d, 1H, J=9.8 Hz), 7.59 (d, 1H, J=2.2 Hz).

Reference Example 202

To a solution of 5-methoxybenzofuran (3.6 g) in collidine (20 ml) was added lithium iodide (6.5 g), and the mixture was refluxed, under argon atmosphere, overnight, cooled, made acidic (pH=4) with hydrochloric acid and extracted with ethyl acetate (three times). The organic layer was washed with 1N hydrochloric acid (twice) and then washed with water and saturated brine, and dried with magnesium sulfate. Under reduced pressure, the solvent was evaporated, and the residue was purified with silica gel column chromatography to give yellow oil of 5-hydroxybenzofuran (1.6 g).

$^1$H-NMR (200 MHz, CDCl$_3$) δ 6.61 (dd, 1H, J=2.2, 0.6 Hz), 6.82 (dd, 1H, J=8.8, 2.6 Hz), 7.01 (d, 1H, J=2.6 Hz), 7.34 (d, 1H, J=8.8 Hz), 7.58 (d, 1H, J=2.2 Hz).

Reference Example 203

To a solution of 5-hydroxybenzofuran (1.90 g) in DMF (30 ml) were added potassium carbonate (5.09 g) and sodium iodide (5.52 g) and then was added 2-chloroethylpropylether (3.47 g), and the mixture was stirred, under nitrogen atmosphere, at 95° C. for 3 days and cooled. To the mixture was added water, and the mixture was extracted with ethyl acetate (twice). The organic layer washed with 1N sodium hydroxide solution, water and saturated brine, and dried with magnesium sulfate. Under reduced pressure, the solvent was evaporated, and the residue was purified with silica gel column chromatography to give yellow oil of 5-propoxyethoxybenzofuran (1.22 g).

¹H-NMR (200 MHz, CDCl₃) δ 0.94 (t, 3H, J=7.8 Hz), 1.56–1.74 (m, 2H), 3.51 (t, 2H, J=6.4 Hz), 3.81(t, 2H, J=5.2 Hz), 4.16 (t, 2H, J=4.6 Hz), 6.70 (dd, 1H, J=2.2, 1.2 Hz), 6.94 (dd, 1H, J=9.0, 2.6 Hz), 7.09 (d, 1H, J=2.2 Hz), 7.38 (d, 1H, J=8.8 Hz), 7.59 (d, 1H, J=2.2 Hz).

Reference Example 204

To a solution of 5-propoxyethoxybenzofuran (1.20 g) in anhydrous tetrahydrofuran (10 ml) was added dropwise at 0° C., under argon atmosphere, a solution of n-butyllithium in hexane (1.6M, 4.5 ml), and the mixture was stirred for 1 hour.

To the mixture was added dropwise at −78° C. a solution of trimethyl borate (1.54 g) in anhydrous tetrahydrofuran (15 ml), and the mixture was stirred overnight while gradually warming to room temperature. At 0° C., to the reaction solution was added 1N hydrochloric acid, and the mixture was stirred for 30 minutes and extracted with ethyl acetate. The organic layer was washed with water and saturated brine, and dried with magnesium sulfate. Under reduced pressure, the solvent was evaporated, the resulting solid was washed with hexane to give pale red solid of 5-propoxyethoxybenzofuran-2-yl borate (0.82 g).

¹H-NMR (200 MHz, DMSO-d₆) δ 0.88 (t, 3H, J=7.4 Hz), 1.45–1.59 (m, 2H), 3.44 (t, 2H, J=6.6 Hz), 3.71 (t, 2H, J=4.4 Hz), 4.11 (t, 2H, J=4.4 Hz), 6.94 (dd, 1H, J=9.2, 2.6 Hz), 7.19 (d, 1H, J=2.4 Hz), 7.38 (s, 1H), 7.45 (d, 1H, J=9.2 Hz), 8.51 (s, 2H).

Reference Example 205

To a suspension of 2-hydroxy-4-methoxybenzaldehyde (20.0 g) and potassium carbonate (20.0 g) in 2-butanone (80 ml) was added diethyl bromomalonate (39.3 g), and the mixture was refluxed under nitrogen atmosphere for 7 hours and cooled. To the mixture was added water, and the mixture was made acidic with 1N hydrochloric acid and extracted with ethyl acetate. The organic layer was washed with saturated brine and dried with magnesium sulfate. Under reduced pressure, the solvent was evaporated, and the resulting dark brown oil was suspended in a solution of potassium hydroxide (20.0 g) in ethanol (200 ml). The suspension was refluxed for 1 hour and cooled, and to the mixture was added water. The mixture was made acidic with 1N hydrochloric acid and extracted with ethylacetate(twice). The organic layer was washed with water and saturated brine, and dried with magnesium sulfate. Under reduced pressure, the solvent was evaporated, and the resulting solid was washed with hexane to give yellow solid of 6-methoxybenzofuran-2-carboxylic acid (11.8 g).

¹H-NMR (200 MHz, CDCl₃) δ 3.89 (s, 3H), 6.91–7.00 (m, 1H), 7.07 (br, 1H), 7.47–7.62 (m, 2H).

Reference Example 206

A suspension of 6-methoxybenzofuran-2-carboxylic acid (22.2 g) and copper powder (3.7 g) in quinoline (200 ml) was refluxed under nitrogen atmosphere for 2 hours and cooled, and to the suspension was added 2N hydrochloric acid. The mixture was extracted with ethyl acetate, and the organic layer was washed with 2N hydrochloric acid (6 times) and then washed with water and saturated brine, and dried with magnesium sulfate. Under reduced pressure, the solvent was evaporated to give dark brown oil of 6-methoxybenzofuran (17.1 g).

¹H-NMR (200 MHz, CDCl₃) δ 3.86 (s, 3H), 6.69 (dd, 1H, J=2.2, 1.2 Hz), 6.88 (dd, 1H, J=8.4, 2.2 Hz), 7.04 (br, 1H), 7.45 (d, 1H, J=6.6 Hz), 7.53 (d, 1H, J=1.4 Hz).

Reference Example 207

To a solution of 6-methoxybenzofuran (16.9 g) in collidine (200 ml) was added lithium iodide (30.5 g), and the mixture was refluxed under argon atmosphere for 1 day and cooled. To the mixture was added 1N hydrochloric acid, and the mixture was extracted with ethyl acetate. The organic layer was washed with 2N hydrochloric acid (5 times) and then washed with water and saturated brine, and dried with magnesium sulfate. Under reduced pressure, the solvent was evaporated, and the residue was purified with silica gel column chromatography to give dark brown oil of 6-hydroxybenzofuran (2.9 g).

¹H-NMR (200 MHz, CDCl₃) δ 8 5.04 (s, 1H), 6.69 (dd, 1H, J=2.6, 1.0 Hz), 6.79 (dd, 1H, J=8.4, 2.2 Hz), 7.00 (d, 1H, J=2.0 Hz), 7.42 (d, 1H, J=8.4 Hz), 7.52 (d, 1H, J=2.2 Hz).

Reference Example 208

To a solution of 6-hydroxybenzofuran (1.30 g) in DMF (15 ml) was added potassium carbonate (1.88 g) and then was added dropwise bromopropane (1.44 g) under nitrogen atmosphere, and the mixture was refluxed overnight. To the mixture was added water, and the mixture was extracted with ethyl acetate (twice). The organic layer was washed with water (three times) and then washed with saturated brine, and dried with magnesium sulfate. Under reduced pressure, the solvent was evaporated to give yellow oil of 7-propoxybenzofuran (0.93 g).

¹H-NMR (200 MHz, CDCl₃) δ 1.06 (t, 3H, J=7.4 Hz), 1.75–1.93 (m, 2H), 3.96 (t, 2H, J=6.6 Hz), 6.69 (d, 1H, J=2.2 Hz), 6.88 (dd, 1H, J=8.4, 2.0 Hz), 7.03 (d, 1H, J=2.2 Hz), 7.44 (d, 1H, J=8.8 Hz), 7.52 (d, 1H, J=2.2 Hz).

Reference Example 209

To a solution of 6-propoxybenzofuran (0.83 g) in anhydrous tetrahydrofuran (12 ml) was added dropwise at 0° C., under argon atmosphere, a solution of n-butyllithium in hexane (1.6M, 4.7 ml), and the mixture was stirred for 1 hour. To the mixture was added dropwise at −78° C. a solution of trimethyl borate (1.47 g) in anhydrous tetrahydrofuran (15 ml), and the mixture was stirred overnight while gradually warming to room temperature. At 0° C., to the reaction solution was added 1N hydrochloric acid, and the mixture was stirred for 30 minutes and extracted with ethyl acetate (twice). The organic layer was washed with water and saturated brine, and dried with magnesium sulfate. Under reduced pressure, the solvent was evaporated, and the resulting solid was washed with hexane to give pale red solid of 6-propoxybenzofuran-2-yl borate (0.56 g).

¹H-NMR (200 MHz, DMSO-d₆) δ 1.00 (t, 3H, J=7.8 Hz), 1.71–1.81 (m, 2H), 3.97 (t, 2H, J=6.6 Hz), 6.85 (dt, 1H, J=8.4, 2.2 Hz), 7.10 (s, 1H), 7.37 (s, 1H), 7.53 (d, 1H, J=8.4 Hz), 8.41 (s, 2H).

Reference Example 210

To a solution of 6-hydroxybenzofuran (1.38 g) in DMF (40 ml) were added potassium carbonate (3.70 g) and sodium iodide (4.01 g) and then was added 2-chloroethylpropylether (2.52 g), and the mixture was stirred, under nitrogen atmosphere, at 95° C. for 3 days and cooled. To the mixture was added water, and the mixture was extracted with ethyl acetate (twice). The organic layer was washed with 1N sodium hydroxide solution (4 times), water (three times) and saturated brine, and dried with magnesium sulfate. Under reduced pressure, the solvent was evaporated to give yellow oil of 6-propoxyethylbenzofuran (1.50 g).

¹H-NMR (200 MHz, CDCl₃) δ 0.94 (t, 3H, J=7.4 Hz), 1.56–1.74 (m, 2H). 3.51 (t, 2H, J=6.6 Hz), 3.81 (t, 2H, J=4.4 Hz), 4.17 (t, 2H, J=4.4 Hz), 6.69 (d, 1H, J=2.2 Hz), 6.91 (dd, 1H, J=8.6, 2.2 Hz), 7.06 (d, 1H, J=2.2 Hz), 7.44 (d, 1H, J=8.6 Hz), 7.53 (d, 1H, J=2.2 Hz).

Reference Example 211

To a solution of 6-propoxyethoxybenzofuran (1.34 g) in anhydrous tetrahydrofuran (15 ml) was added dropwise at 0° C., under argon atmosphere, a solution of n-butyllithium in hexane (1.6M, 5.7 ml), and the mixture was stirred for 1 hour. To the mixture was added dropwise at −78° C. a solution of trimethyl borate (1.90 g) in anhydrous tetrahydrofuran (15 ml), and the mixture was stirred overnight while gradually warming to room temperature. At 0° C., to the reaction solution was added 1N hydrochloric acid, and the mixture was stirred for 30 minutes and extracted with ethyl acetate (twice). The organic layer was washed with water and saturated brine, and dried with magnesium sulfate. Under reduced pressure, the solvent was evaporated, and the residue was purified with silica gel column chromatography to give brown solid of 6-propoxyethoxybenzofuran-2-yl borate (0.27 g).

¹H-NMR (200 MHz, DMSO-d₆) δ 0.88 (t, 3H, J=7.0 Hz), 1.45–1.59 (m, 2H), 3.43 (t, 2H, J=6.6 Hz), 3.70 (t, 2H, J=4.6 Hz), 4.17 (t, 2H, J=5.2 Hz), 6.82 (d, 1H, J=2.2 Hz), 6.98 (d, 1H, J=8.8 Hz), 7.55 (d, 1H, J=8.2 Hz), 7.83 (d, 1H, J=2.2 Hz), 8.04 (s, 2H).

Reference Example 212

To a suspension of o-vanillin (25.0 g) and potassium carbonate (28.4 g) in 2-butanone (10 ml) was added diethyl bromomalonate (49.1 g), and the mixture was refluxed under nitrogen atmosphere for 7 hours and cooled. To the mixture was added 1N hydrochloric acid, and the mixture was extracted with ethyl acetate. The organic layer was washed with saturated brine and dried with magnesium sulfate. Under reduced pressure, the solvent was evaporated, and the resulting red oil was suspended in a solution of potassium hydroxide (17.5 g) in ethanol (175 ml). The suspension was refluxed for 2 hours and cooled, and to the mixture was added water. The mixture was made acidic with 1N hydrochloric acid and extracted with ethyl acetate (twice). The organic layer was washed with water and saturated brine, and dried with magnesium sulfate. Under reduced pressure, the solvent was evaporated to give yellow solid of 7-methoxybenzofuran-2-carboxylic acid (11.8 g).

¹H-NMR (200 MHz, DMSO-d₆) δ 3.96 (s, 3H), 7.09 (dd, 1H, J=7.4, 1.4 Hz), 7.26 (t, 1H, J=7.8 Hz), 7.33 (dd, 1H, J=6.2, 1.8 Hz), 7.64 (s, 1H).

Reference Example 213

A suspension of 7-methoxybenzofuran-2-carboxylicacid (11.04 g) and copper powder (1.83 g) in quinoline (200 ml) was refluxed under nitrogen atmosphere for 2 hours and cooled, and to the suspension was added 2N hydrochloric acid. The mixture was extracted with ethyl acetate, and the organic layer was washed with 2N hydrochloric acid (8 times), water and saturated brine, and dried with magnesium sulfate. Under reduced pressure, the solvent was evaporated, and the residue was purified with silica gel column chromatography to give dark brown oil of 7-methoxybenzofuran (8.19 g).

¹H-NMR (200 MHz, CDCl₃) δ 4.02 (s, 3H), 6.77 (d, 1H, J=1.8 Hz), 6.81 (dd, 1H, J=6.8, 2.2 Hz), 7.16 (t, 1H, J=7.8 Hz), 7.21 (d, 1H, J=5.6 Hz), 7.63 (d, 1H, J=2.2 Hz).

Reference Example 214

To a solution of 7-methoxybenzofuran (8.0 g) in collidine (80 ml) was added lithium iodide (14.5 g), and the mixture was refluxed under argon atmosphere for 1 day and cooled. To the mixture was added 1N hydrochloric acid, and the mixture was extracted with ethyl acetate (twice). The organic layer was washed with 1N hydrochloric acid (twice), water and saturated brine, and dried with magnesium sulfate. Under reduced pressure, the solvent was evaporated, and the residue was purified with silica gel column chromatography to give dark brown oil of 7-hydroxybenzofuran (7.0 g).

¹H-NMR (200 MHz, CDCl₃) δ 5.45 (br, 1H), 6.78 (d, 1H, J=2.2 Hz), 6.84 (dd, 1H, J=7.0, 1.4 Hz), 7.09 (d, 1H, J=7.4 Hz), 7.17 (dd, IH, J=7.8, 1.8 Hz), 7.61 (d, 1H, J=2.2 Hz).

Reference Example 215

To a solution of 7-hydroxybenzofuran (2.60 g) in DMF (30 ml) was added potassium carbonate (3.75 g) and then was added dropwise bromopropane (2.87 g) under nitrogen atmosphere, and the mixture was stirred overnight. To the mixture was added water, and the mixture was extracted with ethyl acetate. The organic layer was washed with water (three times) and saturated brine, and dried with magnesium sulfate. Under reduced pressure, the solvent was evaporated to give brown oil of 7-propoxybenzofuran (2.73 g).

¹H-NMR (200 MHz, CDCl₃) δ 1.09 (t, 3H, J=7.6 Hz), 1.84–2.01 (m, 2H), 4.15 (t, 2H, J=7.0 Hz), 6.76 (d, 1H, J=2.2 Hz), 6.80 (dd, 1H, J=7.0, 1.8 Hz), 7.09–7.21 (m, 2H), 7.62 (d, 1H, J=2.2 Hz).

Reference Example 216

To a solution of 7-propoxybenzofuran (2.4 g) in anhydrous tetrahydrofuran (20 ml) was added dropwise at 0° C., under argon atmosphere, a solution of n-butyllithium in hexane (1.6M, 15.4 ml), and the mixture was stirred for 1 hour. To the mixture was added dropwise at −78° C. a solution of trimethyl borate (5.0 g) in anhydrous tetrahydrofuran (30 ml), and the mixture was stirred overnight while gradually warming to room temperature. At 0° C., to the reaction solution was added 1N hydrochloric acid, and the mixture was stirred for 30 minutes and extracted with ethyl acetate. The organic layer was washed with water and saturated brine, and dried with magnesium sulfate. Under reduced pressure, the solvent was evaporated, and the residue was washed with hexane to give pale red solid of 7-propoxybenzofuran-2-yl borate (1.5 g).

¹H-NMR (200 MHz, CDCl₃) δ 1.10 (t, 3H, J=7.4 Hz), 1.85–2.02 (m, 2H), 4.15 (t, 2H, J=6.6 Hz), 5.23 (br, 2H), 6.85 (dd, 1H, J=7.8, 1.6 Hz), 7.15 (t, 1H, J=7.8 Hz), 7.22 (dd, 1H, J=8.0, 1.2 Hz), 7.37(s, 1H).

Reference Example 217

To a solution of 7-hydroxybenzofuran (2.609) in DMF (70 ml) were added potassium carbonate (6.97 g) and sodium iodide (7.55 g) and then was added 2-chloroethylpropylether (4.76 g), and the mixture was stirred, under nitrogen atmosphere, at 95° C. for 3 days and cooled. To the mixture was added water, and the mixture was extracted with ethyl acetate. The organic layer was washed with water (three times) and saturated brine, and dried with magnesium sulfate. Under reduced pressure, the solvent was evaporated, and the residue was purified with silica gel column chromatography to give brown oil of 7-propoxyethoxybenzofuran (3.76 g).

¹H-NMR (200 MHz, CDCl₃) δ 0.93 (t, 3H, J=7.6 Hz), 1.55–1.73 (m, 2H), 3.53 (t, 2H, J=6.6 Hz), 3.88 (t, 2H, J=4.8

Hz), 4.37 (t, 2H, J=5.2 Hz), 6.76 (d, 1H, J=2.0 Hz), 6.84 (dd, 1H, J=7.4, 1.4 Hz), 7.13 (t, 1H, J=6.6 Hz), 7.21 (dd, 1H, J=7.6, 1.6 Hz), 7.62 (d, 1H, J=2.2 Hz).

Reference Example 218

To a solution of 7-propoxyethoxybenzofuran (3.4 g) in anhydrous tetrahydrofuran (30 ml) was added dropwise at 0° C., under argon atmosphere, a solution of n-butyllithium in hexane (1.6M, 14.5 ml), and the mixture was stirred for 30 minutes. To the mixture was added dropwise at −78° C. a solution of trimethyl borate (4.8 g) in anhydrous tetrahydrofuran (30 ml), and the mixture was stirred overnight while gradually warming to room temperature. At 0° C., to the reaction solution was added 1N hydrochloric acid, and the mixture was stirred for 30 minutes and extracted with ethyl acetate (twice). The organic layer was washed with water and saturated brine, and dried with magnesium sulfate. Under reduced pressure, the solvent was evaporated, and the residue was purified with silica gel column chromatography to give brown oil of 7-propoxyethoxybenzofuran-2-yl borate (0.8 g).

$^1$H-NMR (200 MHz, DMSO-d$_6$) δ 0.87 (t, 3H, J=7.4 Hz), 1.45–1.62 (m, 2H), 3.44 (t, 2H, J=6.6 Hz), 3.78 (t, 2H, J=4.4 Hz), 4.29 (t, 2H, J=4.8 Hz), 6.93 (d, 1H, J=6.6 Hz), 7.11 (t, 1H, J=7.6 Hz), 7.23 (d, 1H, J=7.6 Hz), 7.43 (s, 1H), 8.53 (s, 2H).

Working Example 140 (Production of Compound 137)

In toluene (23 ml), ethanol (2.3 ml) and water (2.3 ml) were suspended 3-methyl-4-propoxyphenyl borate (219 mg), 7-bromo-N-[4-[[N-methyl-N-(tetrahydropyran-4-yl)amino]methyl]phenyl]-1,1-dioxo-2,3-dihydro-1-benzothiepine-4-carboxamide (450 mg) and potassium carbonate (312 mg), and the suspension was stirred under argon atmosphere for 30 minutes. To the mixture was added tetrakistriphenylphosphinepalladium (70 mg), and the mixture was stirred, under argon atmosphere, at 100° C. for 8 hours and cooled. To the mixture was added water, and the mixture was extracted with ethyl acetate (twice). The organic layer was washed with saturated brine and dried with magnesium sulfate. Under reduced pressure, the solvent was evaporated, and the residue was purified with silica gel column chromatography and recrystallized from ethanol (125 ml) to give colorless crystals of 7-(3-methyl-4-propoxyphenyl)-N-[4-[[N-methyl-N-(tetrahydropyran-4-yl)amino]methyl]phenyl]-1,1-dioxo-2,3-dihydro-1-benzothiepine-4-carboxamide (Compound 137) (242 mg).

m.p. 230.5–231.5° C.;

$^1$H-NMR (200 MHz, CDCl$_3$) δ 1.08 (t, 3H, J=7.4 Hz), 1.70–1.92 (m, 6H), 2.21 (s, 3H), 2.30 (s, 3H), 2.64 (br, 1H), 3.16 (t, 2H, J=7.2 Hz), 3.38 (dt, 2H, J=8.6, 1.8 Hz), 3.58 (s, 2H), 3.73 (t, 2H, J=7.2 Hz), 3.96–4.07 (m, 4H), 6.91 (d, 1H, J=9.2 Hz), 7.30–7.39 (m, 5H), 7.55 (d, 2H, J=8.0 Hz), 7.63 (s, 1H), 7.67 (d, 1H, J=8.0 Hz), 7.93 (s, 1H), 8.18 (d, 1H, J=8.0 Hz). Elemental Analysis for C$_{34}$H$_{40}$N$_2$O$_5$S; Calcd. C, 69.36; H, 6.85; N, 4.76: Found. C, 69.13; H, 6.78; N, 4.64.

Working Example 141 (Production of Compound 138)

In toluene (15 ml), ethanol (1.5 ml) and water (1.5 ml) were suspended benzofuran-2-yl borate (122 mg), 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) and potassium carbonate (208 mg), and the suspension was stirred under argon atmosphere for 30 minutes. To the mixture was added tetrakistriphenylphosphinepalladium (47 mg), and the mixture was stirred, under argon atmosphere, at 100° C. for 8 hours and cooled. To the mixture was added water, and the mixture was extracted with ethyl acetate. The organic layer was washed with saturated brine and dried with magnesium sulfate. Under reduced pressure, the solvent was evaporated, and the residue was purified with silica gel column chromatography and recrystallized from ethanol (120 ml) to give colorless crystals of 7-(benzofuran-2-yl)-N-[4-[[N-methyl-N-(tetrahydropyran-4-yl)amino]methyl]phenyl]-1,1-dioxo-2,3-dihydro-1-benzothiepine-4-carboxamide (Compound 138) (188 mg).

m.p. 234.0–235.0° C.; $^1$H-NMR (200 MHz, CDCl$_3$) δ 1.75 (br, 4H), 2.22 (s, 3H), 2.66 (br, 1H), 3.18 (t, 2H, J=6.6 Hz), 3.39 (t, 2H, J=8.6 Hz), 3.59 (s, 2H), 3.74 (t, 2H, J=5.8 Hz), 4.47 (d, 2H, J=8.8 Hz), 7.21 (s, 1H), 7.28–7.41 (m, 5H), 7.54–7.66 (m, 4H), 7.92–7.96 (m, 3H), 8.23 (d, 1H, J=8.8 Hz).

Working Example 142 (Production of Compound 139)

In toluene (15 ml), ethanol (1.5 ml) and water (1.5 ml) were suspended 5-propoxy-benzofuran-2-yl borate (165 mg), 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) and potassium carbonate (208 mg), and the suspension was stirred under argon atmosphere for 30 minutes. To the mixture was added tetrakistriphenylphosphinepalladium (47 mg), and the mixture was stirred, under argon atmosphere, at 100° C. for 8 hours and cooled. To the mixture was added water, and the mixture was extracted with ethyl acetate. The organic layer was washed with saturated brine and dried with magnesium sulfate. Under reduced pressure, the solvent was evaporated, and the residue was purified with silica gel column chromatography and recrystallized from ethanol (750 ml) to give colorless crystals of N-[4-[[N-methyl-N-(tetrahydropyran-4-yl)amino]methyl]phenyl]-1,1-dioxo-7-(5-propoxybenzofuran-2-yl)-2,3-dihydro-1-benzothiepine-4-carboxamide (Compound 139) (115 mg).

m.p. 241.0–242.0° C.; $^1$H-NMR (200 MHz, CDCl$_3$) δ 1.07 (t, 3H, J=7.2 Hz), 1.67–1.90 (m, 6H), 2.21 (s, 3H), 2.67 (br, 1H), 3.18 (t, 2H, J=7.4 Hz), 3.38 (dd, 2H, J=10.6, 2.6 Hz), 3.58 (s, 2H), 3.73 (t, 2H, J=7.0 Hz), 3.97 (t, 2H, J=7.0 Hz), 4.04 (d, 2H, J=12.8 Hz), 6.98 (dd, 1H, J=8.6, 2.6 Hz), 7.06–7.13 (m, 2H), 7.32–7.60 (m, 3H), 7.42 (d, 1H, J=8.6 Hz), 7.56 (d, 2H, J=8.8 Hz), 7.89–7.94 (m, 3H), 8.22 (d, 1H, J=8.4 Hz). Elemental Analysis for C$_{35}$H$_{38}$N$_2$O$_6$S; Calcd. C, 68.38; H, 6.23; N, 4.56: Found. C, 68.02; H, 6.26; N, 4.56.

Working Example 143 (Production of Compound 140)

In toluene (15 ml), ethanol (1.5 ml) and water (1.5 ml) were suspended 5-propoxyethoxy-benzofuran-2-yl borate (198 mg), 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) and potassium carbonate (208 mg), and the suspension was stirred under argon atmosphere for 30 minutes. To the mixture was added tetrakistriphenylphosphinepalladium (47 mg), and the mixture was stirred, under argon atmosphere, at 100° C. for 8 hours and cooled. To the mixture was added water, and the mixture was extracted with ethyl acetate. The organic layer was washed with saturated brine and dried with magnesium sulfate. Under reduced pressure, the solvent was evaporated, and the residue was purified with silica gel column chromatography and recrystallized from ethanol to give colorless crystals of N-[4-[[N-methyl-N-(tetrahydropyran-4-yl)amino]methyl]phenyl]-1,1-dioxo-7-(5-propoxyethoxybenzofuran-2-yl)-2,3-dihydro-1-benzothiepine-4-carboxamide (Compound 140) (200 mg).

m.p. 227.0–228.0° C.; $^1$H-NMR (200 MHz, CDCl$_3$) δ 0.95 (t, 3H, J=7.2 Hz), 1.58–1.80 (m, 6H), 2.22 (s, 3H), 2.65 (br, 1H), 3.18 (t, 2H, J=6.8 Hz), 3.39 (dd, 2H, J=10.6, 2.6 Hz), 3.52 (t, 2H, J=6.6 Hz), 3.58 (s, 2H), 3.73 (t, 2H, J=6.8 Hz), 3.82 (t, 2H, J=5.6 Hz), 4.04 (d, 2H, J=10.8 Hz), 4.18 (t, 2H, J=4.8 Hz), 7.01 (dd, 1H, J=9.2, 2.6 Hz), 7.11 (d, 2H, J=7.4 Hz), 7.32–7.36 (m, 3H), 7.42 (d, 1H, J=9.2 Hz), 7.56 (d, 2H, J=8.4 Hz), 7.90–7.94 (m, 3H), 8.22 (d, 1H, J=8.4 Hz). Elemental Analysis for C$_{37}$H$_{42}$N$_2$O$_7$S; Calcd. C, 67.45; H, 6.43; N, 4.25: Found. C, 67.14; H, 6.35; N, 4.25.

Working Example 144 (Production of Compound 141)

In toluene (15 ml), ethanol (1.5 ml) and water (1.5 ml) were suspended 6-propoxy-benzofuran-2-yl borate (165 mg), 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) and potassium carbonate (208 mg), and the suspension was stirred under argon atmosphere for 30 minutes. To the mixture was added tetrakistriphenylphosphinepalladium (47 mg), and the mixture was stirred, under argon atmosphere, at 100° C. for 10 hours and cooled. To the mixture was added water, and the mixture was extracted with ethyl acetate. The organic layer was washed with saturated brine and dried with magnesium sulfate. Under reduced pressure, the solvent was evaporated, and the residue was purified with silica gel column chromatography and recrystallized from ethanol (40 ml) to give colorless crystals of N-[4-[[N-methyl-N-(tetrahydropyran-4-yl)amino]methyl]phenyl]-1,1-dioxo-7-(6-propoxybenzofuran-2-yl)-2,3-dihydro-1-benzothiepine-4-carboxamide (Compound 141) (192 mg).

m.p. 215.0–216.0° C.; $^1$H-NMR (200 MHz, CDCl$_3$) δ 1.08 (t, 3H, J=7.8 Hz), 1.72–1.77 (m, 4H), 1.81–1.92 (m, 2H), 2.21 (s, 3H), 2.65 (br, 1H), 3.16 (t, 2H, J=6.2 Hz), 3.38 (dt, 2H, J=10.8, 2.4 Hz), 3.58 (s, 2H), 3.73 (t, 2H, J=7.2 Hz), 3.96–4.07 (m, 4H), 6.92 (dd, 1H, J=8.8, 2.2 Hz), 7.04 (s, 1H), 7.11 (s, 1H), 7.31–7.35 (m, 3H), 7.48 (d, 1H, J=8.4 Hz), 7.58 (d, 2H, J=8.6 Hz), 7.83–7.86 (m, 2H), 8.18 (d, 1H, J=8.8 Hz), 8.25 (s, 1H), Elemental Analysis for C$_{35}$H$_{38}$N$_2$O$_6$S; Calcd. C, 68.38; H, 6.23; N, 4.56: Found. C, 68.17; H, 6.38; N, 4.50.

Working Example 145 (Production of Compound 142)

In toluene (15 ml), ethanol (1.5 ml) and water (1.5 ml) were suspended 6-propoxyethoxy-benzofuran-2-yl borate (250 mg), 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) and potassium carbonate (262 mg), and the suspension was stirred under argon atmosphere for 30 minutes. To the mixture was added tetrakistriphenylphosphinepalladium (47 mg), and the mixture was stirred, under argon atmosphere, at 100° C. for 1 day and cooled. To the mixture was added water, and the mixture was extracted with ethyl acetate. The organic layer was washed with saturated brine and dried with magnesium sulfate. Under reduced pressure, the solvent was evaporated, and the residue was purified with silica gel column chromatography to give yellow amorphous of N-[4-[[N-methyl-N-(tetrahydropyran-4-yl)amino]methyl]phenyl]-1,1-dioxo-7-(6-propoxyethoxybenzofuran-2-yl)-2,3-dihydro-1-benzothiepine-4-carboxamide (Compound 142) (200 mg).

$^1$H-NMR (200 MHz, CDCl$_3$) δ 0.86 (t, 3H, J=7.2 Hz), 1.51–1.80 (m, 6H), 2.21 (s, 3H), 2.65 (br, 1H), 3.20 (t, 2H, J=6.6 Hz), 3.31–3.44 (m, 4H), 3.58 (s, 2H), 3.68–3.78 (m, 4H), 4.03 (d, 2H, J=11.4 Hz), 4.19 (t, 2H, J=4.8 Hz), 6.77 (d, 1H, J=2.2 Hz), 7.04 (d, 1H, J=8.4 Hz), 7.30–7.34 (m, 3H), 7.52–7.57 (m, 4H), 7.92–7.98 (m, 3H), 8.24 (d, 1H, J=8.0 Hz). Elemental Analysis for C$_{37}$H$_{42}$N$_2$O$_7$S.0.4 H$_2$O; Calcd. C, 66.72; H, 6.35; N, 4.21: Found. C, 66.42; H, 6.49; N, 4.01.

Working Example 146 (Production of Compound 143)

In toluene (15 ml), ethanol (1.5 ml) and water (1.5 ml) were suspended 7-propoxy-benzofuran-2-yl borate (165 mg), 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) and potassium carbonate (208 mg), and the suspension was stirred under argon atmosphere for 30 minutes. To the mixture was added tetrakistriphenylphosphinepalladium (47 mg), and the mixture was stirred, under argon atmosphere, at 100° C. for 8 hours and cooled. To the mixture was added water, and the mixture was extracted with ethyl acetate. The organic layer was washed with saturated brine and dried with magnesium sulfate. Under reduced pressure, the solvent was evaporated, and the residue was purified with silica gel column chromatography and recrystallized from ethanol to give colorless crystals of N-[4-[[N-methyl-N-(tetrahydropyran-4-yl)amino]methyl]phenyl]-1,1-dioxo-7-(7-propoxybenzofuran-2-yl)-2,3-dihydro-1-benzothiepine-4-carboxamide (Compound 143) (213 mg).

m.p. 246.5–247.5° C.; $^1$H-NMR (200 MHz, CDCl$_3$) δ 1.12 (t, 3H, J=7.4 Hz), 1.76 (br, 4H), 1.90–2.01 (m, 2H), 2.21 (s, 3H), 2.65 (br, 1H), 3.17 (t, 2H, J=7.8 Hz), 3.38 (dt, 2H, J=11.8, 3.4 Hz), 3.58 (s, 2H), 3.74 (t, 2H, J=7.2 Hz), 4.05 (d, 2H, J=11.0 Hz), 4.19 (t, 2H, J=6.6 Hz), 6.87 (dd, 1H, J=6.6, 2.6 Hz), 7.14–7.24 (m, 3H), 7.32–7.55 (m, 3H), 7.57 (d, 2H, J=8.4 Hz), 7.94–7.99 (m, 3H), 8.22 (d, 1H, J=8.8 Hz). Elemental Analysis for C$_{35}$H$_{38}$N$_2$O$_6$S; Calcd. C, 68.38; H, 6.23; N, 4.56: Found. C, 68.18; H, 6.18; N, 4.60.

Working Example 147 (Production of Compound 144)

In toluene (15 ml), ethanol (1.5 ml) and water (1.5 ml) were suspended 7-propoxyethoxy-benzofuran-2-yl borate (229 mg), 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) and potassium carbonate (240 mg), and the suspension was stirred under argon atmosphere for 30 minutes. To the mixture was added tetrakistriphenylphosphinepalladium (47 mg), and the mixture was stirred, under argon atmosphere, at 100° C. for 8 hours and cooled. To the mixture was added water, and the mixture was extracted with ethyl acetate. The organic layer was washed with saturated brine and dried with magnesium sulfate. Under reduced pressure, the solvent was evaporated, and the residue was purified with silica gel column chromatography and recrystallized from ethanol (40 ml) to give N-[4-[[N-methyl-N-(tetrahydropyran-4-yl)amino]methyl]phenyl]-1,1-dioxo-7-(7-propoxyethoxybenzofuran-2-yl)-2,3-dihydro-1-benzothiepine-4-carboxamide (Compound 144) (154 mg).

m.p. 178.5–179.5° C.; $^1$H-NMR (200 MHz, CDCl$_3$) δ 0.94 (t, 3H, J=7.8 Hz), 1.56–1.80 (m, 6H), 2.21 (s, 3H), 2.65 (br, 1H), 3.17 (t, 2H, J=6.2 Hz), 3.38 (dt, 2H, J=10. 6, 3.0 Hz), 3.54 (t, 2H, J=7.0 Hz), 3.57 (s, 2H), 3.73 (t, 2H, J=7.0 Hz), 3.91 (t, 2H, J=4.6 Hz), 4.03 (d, 2H, J=7.6 Hz), 4.41 (t, 2H, J=5.2 Hz), 6.91 (dt, 1H, J=7.2, 1.8 Hz), 7.13–7.21 (m, 3H), 7.33 (d, 2H, J=8.8 Hz), 7.38 (s, 1H), 7.58 (d, 2H, J=8.4 Hz), 7.91–7.95 (m, 2H), 8.09 (s, 1H), 8.21 (d, 1H, J=8.8 Hz). Elemental Analysis for C$_{37}$H$_{42}$N$_2$O$_7$S; Calcd. C, 67.45; H, 6.43; N, 4.25: Found. C, 67.26; H, 6.31; N, 4.25.

Working Example 148 (Production of Compound 145)

In toluene (15 ml), ethanol (1.5 ml) and water (1.5 ml) were suspended benzothiophen-2-yl borate (134 mg), 7-bromo-N-[4-[[N-methyl-N-(tetrahydropyran-4-yl)amino]methyl]phenyl]-1,1-dioxo-2,3-dihydro-1-benzothiepine-4-carboxamide (300 mg) and potassium carbonate (208 mg), and the suspension was stirred under argon atmosphere for 30 minutes. To the mixture was added tetrakistriphenylphosphinepalladium (47 mg), and the mixture was stirred, under argon atmosphere, at 100° C. for 1 day and cooled. To the mixture was added water, and the mixture was extracted with ethyl acetate (twice). The organic layer was washed with saturated brine and dried with magnesium sulfate. Under reduced pressure, the solvent was evaporated, and the residue was purified with silica gel column chromatography and recrystallized from ethanol to give colorless crystals of 7-(benzothiophen-2-yl)-N-[4-[[N-methyl-N-(tetrahydropyran-4-yl)amino]methyl]phenyl]-1,1-dioxo-2,3-dihydro-1-benzothiepine-4-carboxamide (Compound 145) (27 mg).

m.p. 270.0–271.0° C.; $^1$H-NMR (200 MHz, CDCl$_3$) δ 1.75 (br, 4H), 2.21 (s, 3H), 2.65 (br, 1H), 3.18 (t, 2H, J=6.6 Hz), 3.38 (dt, 2H, J=11.8, 3.0 Hz), 3.58(s, 2H), 3.74 (t, 2H, J=7.41 Hz), 4.05 (d, 2H, J=13.4 Hz), 7.32–7.42 (m, 5H), 7.56 (d, 2H, J=8.2 Hz), 7.69 (s, 1H), 7.76–7.90 (m, 4H), 7.98 (s, 1H), 8.21 (d, 1H, J=8.4 Hz). Elemental Analysis for C$_{32}$H$_{32}$N$_2$O$_4$S$_2$.0.1 H$_2$O; Calcd. C, 66.90; H, 5.65; N, 4.88: Found. C, 66.67; H, 5.60; N, 4.91.

Working Example 149 (Production of Compound 146)

To a suspension of N-[4-[N-methyl-N-(tetrahydropyran-4-yl)aminomethyl]phenyl]-7-[4-(2-propoxyethoxy)phenyl]-1,1-dioxo-2,3-dihydro-1-benzothiepine-4-carboxamide (0.80 g) in ethanol (50 ml) was added at room temperature methanesulfonic acid (84 μl), and the mixture was stirred for 1 hour and concentrated under reduced pressure. The residue was crystallized from 2-propanol to give colorless crystals of N-[4-[N-methyl-N-(tetrahydropyran-4-yl)aminomethyl]phenyl]-7-[4-(2-propoxyethoxy)phenyl]-1,1-dioxo-2,3-dihydro-1-benzothiepine-4-carboxamide methanesulfonate (Compound 146) (0.78 g).

m.p. 178–181° C.; $^1$H-NMR (200 MHz, CDCl$_3$) δ 0.95 (3H,t, J=7.5 Hz), 1.56–2.15 (6H, m), 2.59 (3H, s), 2.77 (3H, s), 3.09 (2H, t, J=6.8 Hz), 3.21–3.55 (5H, m), 3.74–3.84 (4H, m), 3.88–4.09 (3H, m), 4.13–4.32 (3H, m), 7.03 (2H, d, J=8.6 Hz), 7.44 (2H, d, J=8.8 Hz), 7.59–7.67 (3H, m), 7.80–7.92 (4H, m), 8.14 (1H, d, J=8.4 Hz), 9.43 (1H, s), 10.46 (1H, m). IR (KBr) 3273, 1644, 1607, 1520, 1416, 1318, 1292, 1250, 1246, 1194, 1165 cm$^{-1}$; Elemental Analysis for C$_{36}$H$_{46}$N$_2$O$_7$S$_2$.0.25 H$_2$O; Calcd. C, 60.11; H, 6.52; N, 3.89: Found. C, 59.93; H, 6.48; N, 3.85.

Working Example 150 (Production of Compound 147)

To a solution of N-[4-[N-methyl-N-(tetrahydropyran-4-yl)aminomethyl]phenyl]-7-[4-(2-propoxyethoxy)phenyl]-1,1-dioxo-2,3-dihydro-1-benzothiepine-4-carboxamide (1.10 g) in THF (40 ml) was added at room temperature benzenesulfonic acid (313 mg), and the mixture was stirred for 1 hour and concentrated under reduced pressure. To the residue was added 2-propanol, and the mixture was concentrated under reduced pressure. The residue was crystallized from 2-propanol to give crude crystals, which were recrystallized from 2-propanol to give colorless crystals of N-[4-[N-methyl-N-(tetrahydropyran-4-yl)aminomethyl]phenyl]-7-[4-(2-propoxyethoxy)phenyl]-1,1-dioxo-2,3-dihydro-1-benzothiepine-4-carboxamide benzenesulfonate (Compound 147) (1.19 g).

m.p. 187–189° C.; $^1$H-NMR (200 MHz, DMSO-d$_6$) δ 0.87 (3H, t, J=7.5 Hz), 1.44–1.63 (2H, m), 1.65–1.90 (2H, m), 1.95–2.08 (2H, m), 2.62 (3H, s), 3.02–3.15 (2H, m), 3.25–3.60 (5H, m), 3.69–3.86 (4H, m), 3.94–4.22 (5H, m), 4.47 (1H, d, J=12.0 Hz), 7.10 (2H, d, J=8.81 Hz), 7.29–7.34 (3H, m), 7.49–7.62 (5H, m), 7.74–7.91 (5H, m), 8.05–8.09 (2H, m), 10.39 (1H, s). IR (KBr) 3239, 1665, 1642, 1605, 1518, 1318, 1292, 1167, 1121, 1017 cm$^{-1}$; Elemental Analysis for C$_{41}$H$_{48}$N$_2$O$_9$S; Calcd. C, 63.38; H, 6.23; N, 3.61: Found. C, 63.14; H, 6.20; N, 3.72.

Working Example 151 (Production of Compound 148)

To a solution of N-[4-[N-methyl-N-(tetrahydropyran-4-yl)aminomethyl]phenyl]-7-[4-(2-propoxyethoxy)phenyl]-1,1-dioxo-2,3-dihydro-1-benzothiepine-4-carboxamide (1.10 g) in acetone (150 ml) was added at room temperature 47% sulfuric acid (0.27 ml), and the mixture was stirred for 0.5 hours and concentrated under reduced pressure. To the residue was added 2-propanol, and the mixture was concentrated. To the residue was added 2-propanol, and the resulting solid was collected by filtration and dissolved in 2-propanol under heating. The solution was cooled, and the resulting powder was collected by filtration to give colorless amorphous of N-[4-[N-methyl-N-(tetrahydropyran-4-yl)aminomethyl]phenyl]-7-[4-(2-propoxyethoxy)phenyl]-1,1-dioxo-2,3-dihydro-1-benzothiepine-4-carboxamide sulfate (Compound 148) (1.21 g).

$^1$H-NMR (200 MHz, DMSO-d$_6$) δ 0.88 (3H, t, J=7.5 Hz), 1.44–1.62 (2H, m), 1.64–2.11 (4H, m), 2.62 (3H, br s), 3.02–3.15 (2H, m), 3.24–3.57 (5H, m), 3.67–3.87 (4H, m), 3.95–4.23 (5H, m), 4.38–4.58 (1H, m), 7.10 (2H, d, J=9.2 Hz), 7.49–7.56 (3H, m), 7.74–7.91 (5H, m), 8.05–8.09 (2H, m), 10.38 (1H, s). IR (KBr) 3274, 1663, 1606, 1518, 1414, 1292, 1252, 1127 cm$^{-1}$; Elemental Analysis for C$_{35}$H$_{44}$N$_2$O$_{10}$S$_2$.0.5 H$_2$O; Calcd. C, 57.91; H, 6.25; N, 3.86: Found. C, 57.95; H, 6.22; N, 4.01.

Working Example 152 (Production of Compound 149)

To a solution of 7-(4-butoxyphenyl)-N-[4-[N-methyl-N-(tetrahydropyran-4-yl)aminomethyl]phenyl]-1,1-dioxo-2,3-dihydro-1-benzothiepine-4-carboxamide (300 mg) in DMF (7 ml) was added at room temperature methyl iodide (63 μl), and the mixture was stirred for 18 hours and concentrated under reduced pressure. To the residue was added ethyl acetate, and the resulting crystals were collected by filtration and recrystallized from ethanol to give pale yellow of crystals N-[4-[[7-(4-butoxyphenyl)-1,1-dioxo-2,3-dihydro-1-benzothiepine-4-carbonyl]amino]benzyl]-N,N-dimethyltetrahydro-2H-pyran-4-aminium iodide (Compound 149) (290 mg).

m.p. 186–190° C.; $^1$H-NMR (200 MHz, DMSO-d$_6$) δ 0.95 (3H, t, J=7.3 Hz), 1.36–1.55 (2H, m), 1.66–2.00 (4H, m), 2.09–2.55 (2H, m), 2.88 (6H, s), 3.01–3.16 (2H, m), 3.23–3.66 (3H, m), 3.77–3.84 (2H, m), 4.00–4.15 (4H, m), 4.47 (2H, s), 7.09 (2H, d, J=8.8 Hz), 7.55–7.59 (3H, m), 7.76 (2H, d, J=8.8 Hz), 7.86–7.91 (3H, m), 8.06–8.10 (2H, m), 10.44 (1H, s). IR (KBr) 3220, 1669, 1607, 1593, 1518, 1474, 1410, 1314, 1285, 1246, 1128 cm$^{-1}$; Elemental Analysis for $C_{35}H_{43}N_2O_5SI.0.5$ $H_2O$; Calcd. C, 56.83; H, 6.00; N, 3.79: Found. C, 56.58; H, 6.13; N, 3.63.

Reference Example 219

With using CHIRALCEL OD (hexane/ethano=18:2), (4-aminophenyl)-(2-pyridyl)methanol (0.93 g) was separated to give (+)-(4-aminophenyl)-(2-pyridyl)methanol (0.41 g, 99.6%ee) and (−)-(4-aminophenyl)-(2-pyridyl)methanol (0.43 g, 99.4%ee). (+)-(4-aminophenyl)-(2-pyridyl)methanol[α]$_D$=+43.4° (−)-(4-aminophenyl)-(2-pyridyl)methanol[α]$_D$=−43.6°.

Working Example 153 (Production of Compound 150)

To a solution of 7-[4-(2-butoxyethoxy)phenyl]-1,1-dioxo-2,3-dihydro-1-benzothiepine-4-carboxylic acid (300 mg) in THF (10 ml) were added at room temperature thionyl chloride (0.1 ml) and DMF (1 drop), and the mixture was stirred 1 hour. Under reduced pressure, the solvent was evaporated, and the residue was dissolved in THF (20 ml). At 0° C., the solution was added dropwise to a solution of (+)-(4-aminophenyl)-(2-pyridyl)methanol (150 mg) and triethylamine (0.58 ml) in THF (5 ml), and the mixture was stirred at room temperature for 40 hours. To the mixture was added water, and the mixture was extracted with ethyl acetate. The organic layer was washed with saturated brine, dried with magnesium sulfate and concentrated under reduced pressure, and the residue was purified with column chromatography (ethyl acetate) to give colorless crystals of 7-[4-(2-butoxyethoxy)phenyl]-N-[4-[hydroxy(2-pyridyl)methyl]phenyl]-1,1-dioxo-2,3-dihydro-1-benzothiepine-4-carboxamide (Compound 150) (273 mg).

m.p. 173–174° C.; $^1$H-NMR (200 MHz, CDCl$_3$) δ 0.93 (3H, t, J=7.1 Hz), 1.30–1.46 (2H, m), 1.52–1.66 (2H, m), 3.11–3.18 (2H, m), 3.55 (2H, t, J=6.6 Hz), 3.68–3.75 (2H, m), 3.79–3.84 (2H, m), 4.16–4.20 (2H, m), 5.32 (1H, d, J=4.4 Hz), 5.75 (1H, d, J=4.4 Hz), 7.04 (2H, d, J=8.8 Hz), 7.12–7.28 (2H, m), 7.34 (1H, s), 7.39 (2H, d, J=8.6 Hz), 7.52–7.69 (7H, m), 7.96 (1H, s), 8.19 (1H, d, J=8.4 Hz), 8.56–8.59 (1H, m). IR (KBr) 3403, 3339, 1649, 1609, 1595, 1518, 1314, 1289, 1252, 1128 cm$^{-1}$; Elemental Analysis for $C_{35}H_{36}N_2O_6S$; Calcd. C, 68.61; H, 5.92; N, 4.57: Found. C, 68.60; H, 5.98; N, 4.53.

Working Example 154 (Production of Compound 151)

To a solution of 7-[4-(2-butoxyethoxy)phenyl]-N-[4-[hydroxy(2-pyridyl)methyl]phenyl]-1,1-dioxo-2,3-dihydro-1-benzothiepine-4-carboxamide (Compound 150) (230 mg) in dichloromethane (10 ml) was added at 0° C. 3-chloroperbenzoic acid (70%, 0.12 g), and the mixture was stirred at room temperature for 24 hours. To the reaction mixture was added sodium thiosulfate solution, and the mixture was stirred for a few minutes and extracted with ethyl acetate. The organic layer was washed with sodium bicarbonate solution and saturated brine, dried with magnesium sulfate and concentrated under reduced pressure, and the residue was purified with column chromatography (ethanol/ethyl acetate=1:9→1:4) to give colorless crystals of 7-[4-(2-butoxyethoxy)phenyl]-N-[4-[hydroxy(1-oxidopyridin-2-yl)methyl]phenyl]-1,1-dioxo-2,3-dihydro-1-benzothiepine-4-carboxamide (Compound 151) (187 mg).

m.p. 125–128° C.; $^1$H-NMR (200 MHz, CDCl$_3$) δ 0.93 (3H, t, J=7.3 Hz), 1.30–1.46 (2H, m), 1.54–1.68 (2H, m), 3.14–3.20 (2H, m), 3.56 (2H, t, J=6.6 Hz), 3.68–3.75 (2H, m), 3.79–3.84 (2H, m), 4.16–4.21 (2H, m), 6.07 (1H, d, J=4.6 Hz), 6.38 (1H, d, J=4.6 Hz), 6.94–7.01 (1H, m), 7.04 (2H, d, J=9.2 Hz), 7.24–7.28 (1H, m), 7.37 (1H, s), 7.44–7.56 (5H, m), 7.62–7.69 (4H, m), 8.06 (1H, s), 8.18 (1H, d, J=8.0 Hz), 8.24–8.28 (1H, m). IR (KBr) 3351, 3118, 1665, 1605, 1518, 1310, 1291, 1252, 1167, 1130 cm$^{-1}$; Elemental Analysis for $C_{35}H_{36}N_2O_7S.1.0$ $H_2O$; Calcd. C, 65.00; H, 5.92; N. 4.33: Found. C, 65.02; H, 5.90; N, 4.16.

Working Example 155 (Production of Compound 152)

To a solution of 7-[4-(2-butoxyethoxy)phenyl]-1,1-dioxo-2,3-dihydro-1-benzothiepine-4-carboxylic acid (300 mg) in THF (10 ml) were added at room temperature thionyl chloride (0.1 ml) and DMF (1 drop), and the mixture was stirred for 1 hour. Under reduced pressure, the solvent was evaporated, and the residue was dissolved in THF (20 ml). At 0° C., the solution was added dropwise a solution of (−)-(4-aminophenyl)-(2-pyridyl)methanol (150 mg) and triethylamine (0.58 ml) in THF (3 ml), and the mixture was stirred at room temperature for 64 hours. To the mixture was added water, and the mixture was extracted with ethyl acetate. The organic layer was washed with saturated brine, dried with magnesium sulfate and concentrated under reduced pressure, and the resulting crystals were collected by filtration and washed with ethyl acetate to give colorless crystals of 7-[4-(2-butoxyethoxy)phenyl]-N-[4-[hydroxy(2-pyridyl)methyl]phenyl]-1,1-dioxo-2,3-dihydro-1-benzothiepine-4-carboxamide (Compound 152) (201 mg).

m.p. 171–173° C.; $^1$H-NMR (200 MHz, CDCl$_3$) δ 0.93 (3H, t, J=7.1 Hz), 1.30–1.46 (2H, m), 1.52–1.72 (2H, m), 3.11–3.17 (2H, m), 3.56 (2H, t, J=6.8 Hz), 3.68–3.75 (2H, m), 3.79–3.84 (2H, m), 4.16–4.20 (2H, m), 5.34 (1H, br s), 5.75 (1H, br s), 7.03 (2H, d, J=8.8 Hz), 7.12–7.28 (2H, m), 7.33 (1H, s), 7.38 (2H, d, J=8.4 Hz), 7.52–7.69 (7H, m), 8.02 (1H, s), 8.18 (1H, d, J=8.2 Hz), 8.56–8.58 (1H, m). IR (KBr) 3448, 3339, 1649, 1609, 1595, 1518, 1312, 1289, 1252, 1128 cm$^{-1}$; Elemental Analysis for $C_{35}H_{36}N_2O_6S.0.25$ $H_2O$; Calcd. C, 68.11; H. 5.96; N, 4.54: Found. C, 68.09; H, 5.84; N, 4.50.

Working Example 156 (Production of Compound 153)

To a solution of 7-[4-(2-butoxyethoxy)phenyl]-N-[4-[hydroxy(2-pyridyl)methyl]phenyl]-1,1-dioxo-2,3-dihydro-1-benzothiepine-4-carboxamide (Compound 152) (157 mg) in dichloromethane (10 ml) was added at 0° C. 3-chloroperbenzoic acid (70%, 98 mg), and the mixture was stirred at room temperature for 2 days. To the reaction mixture was added sodium thiosulfate solution, and the mixture was stirred for a few minutes and extracted with ethyl acetate. The organic layer was washed with sodium bicarbonate solution and saturated brine, dried with magnesium sulfate and concentrated under reduced pressure, and the residue was purified with column chromatography (ethanol/ethyl acetate=1:9→1:4) to give pale yellow crystals of 7-[4-(2-butoxyethoxy)phenyl]-N-[4-[hydroxy(1-oxidopyridin-2-yl)methyl]phenyl]-1,1-dioxo-2,3-dihydro-1-benzothiepine-4-carboxamide (Compound 153) (67 mg).

m.p. 104–107° C.; $^1$H-NMR (200 MHz, CDCl$_3$) δ 0.93 (3H, t, J=7.1 Hz), 1.30–1.46 (2H, m), 1.54–1.68 (2H, m), 3.14–3.20 (2H, m), 3.56 (2H, t, J=6.6 Hz), 3.68–3.75 (2H, m), 3.79–3.84 (2H, m), 4.16–4.21 (2H, m), 6.06 (1H, s), 6.94–7.01 (1H, m), 7.04 (2H, d, J=8.8 Hz), 7.24–7.28 (1H, m), 7.37 (1H, s), 7.44–7.56 (5H, m), 7.62–7.69 (4H, m), 8.13 (1H, s), 8.18 (1H, d, J=8.0 Hz), 8.24–8.28 (1H, m). IR (KBr) 3368, 3210, 1663, 1607, 1518, 1310, 1292, 1252, 1128 cm$^{-1}$; Elemental Analysis for $C_{35}H_{36}N_2O_7S \cdot 1.0$ $H_2O$; Calcd. C, 65.00 H, 5.92; N, 4.33: Found. C, 65.06; H, 5.81; N, 4.28.

Working Example 157 (Production of Compound 154)

To a solution of 7-[4-(2-butoxyethoxy)phenyl]-1,1-dioxo-2,3-dihydro-1-benzothiepine-4-carboxylic acid (200 mg) in THF (10 ml) were added at room temperature thionyl chloride (0.067 ml) and DMF (1 drop), and the mixture was stirred for 1 hour. Under reduced pressure, the solvent was evaporated, and the residue was dissolved in THF (15 ml). The solution was added dropwise at 0° C. to a solution of 1-(4-aminobenzyl)-phosphorinane-1-oxide (154 mg) and triethylamine (0.33 ml) in THF/DMF (5/5 ml), and the mixture was stirred at room temperature for 20 hours. To the mixture was added water, and the mixture was extracted with ethyl acetate. The organic layer was washed with saturated brine, dried with magnesium sulfate and concentrated under reduced pressure, and the residue was purified with column chromatography (ethanol/ethyl acetate= 1:3→1:2) and recrystallized from ethanol/2-propanol to give colorless crystals of 7-[4-(2-butoxyethoxy)phenyl]-N-(4-pentamethylenephosphorylmethylphenyl)-1,1-dioxo-2,3-dihydro-1-benzothiepine-4-carboxamide (Compound 154) (114 mg).

m.p. 222–224° C.; $^1$H-NMR (200 MHz, CDCl$_3$) δ 0.93 (3H, t, J=7.2 Hz), 1.34–1.76 (12H, m), 1.82–2.11 (2H, m), 3.13 (2H, d, J=13.2 Hz), 3.17–3.23 (2H, m), 3.58 (2H, t, J=6.6 Hz), 3.67–3.74 (2H, m), 3.80–3.84 (2H, m), 4.16–4.21 (2H, m), 7.04 (2H, d, J=8.4 Hz), 7.21–7.26 (2H, m), 7.46 (1H, s), 7.53–7.69 (6H, m), 8.20 (1H, d, J=8.0 Hz), 8.76–8.90 (1H, m). IR (KBr) 3185, 1661, 1597, 1516, 1252, 1159, 1130 cm$^{-1}$; Elemental Analysis for $C_{35}H_{42}NO_6SP$ Calcd. C, 66.12; H, 6.66; N, 2.20: Found. C, 65.81; H, 6.58; N, 2.38.

Reference Example 220

In acetone (100 ml) were suspended 4-bromo-1,2-dihydroxybenzene (9.0 g), 1-bromopropane (9.1 ml), potassium carbonate (19.7 g) and sodium iodide (15.0 g), and the mixture was refluxed overnight. The solvent was evaporated, and to the residue was added water. The mixture was extracted with ethyl acetate, and the organic layer was washed with water and saturated brine, and dried with anhydrous magnesium sulfate. The solvent was evaporated, and the residue was purified with distillation under reduced pressure to give 4-bromo-1,2-dipropoxybenzene (11.2 g) as colorless oil.

bp$_{0.8}$=114–118° C.; $^1$H NMR (CDCl$_3$) δ 1.03 (3H, t, J=7.3 Hz), 1.04 (3H, t, J=7.4 Hz), 1.73–1.93 (4H, m), 3.92 (2H, t, J=6.8 Hz), 3.93 (2H, t, J=6.6 Hz), 6.74 (1H, d, J=9.0 Hz), 6.96–7.01 (2H, m). IR (neat) v 2965, 2938, 2878, 1586, 1503, 1470 cm$^{-1}$.

Reference Example 221

In THF (5 ml) was suspended magnesium (1.1 g), and to the suspension was added under nitrogen atmosphere dibromoethane (catalytic amount) and then was added dropwise a solution of 4-bromo-1,2-dipropoxybenzene (11.2 g) in THF (30 ml). The mixture was stirred at 50 for hour and cooled with dry ice/acetone, and to the mixture was added dropwise trimethoxyborane (9.2 ml). The mixture was stirred at room temperature overnight, and to the mixture was added 1N hydrochloric acid. The mixture was stirred at room temperature for 30 minutes, concentrated and extracted with ethyl acetate. The organic layer was washed with water and saturated brine, and dried with anhydrous magnesium sulfate, and the solvent was evaporated to give 3,4-dipropoxyphenyl borate (7.1 g) as colorless crystals.

$^1$H NMR (CDCl$_3$) δ 0.95–1.04 (6H, m), 1.63–1.77 (4H, m), 3.87–3.95 (4H, m), 6.90 (1H, d, J=8.0 Hz), 7.32–7.39 (2H, m), 7.82 (1H, s).

Working Example 158 (Production of Compound 155)

A mixture of 7-bromo-N-(4-((N-methyl-N-(tetrahydro-2H-pyran-4-yl)amino)methyl)phenyl)-1,1-dioxo-2,3-dihydro-1-benzothiepine-4-carboxamide (0.3 g), 3,4-dipropoxyphenyl borate (0.17 g), 1M potassium carbonate solution (1.3 ml), ethanol (1.3 ml) and toluene (25 ml) was stirred under argon atmosphere at room temperature for 30 minutes. To the mixture was added tetrakis (triphenylphosphine)palladium (0.03 g), and the mixture was refluxed under argon atmosphere for 6 hours and extracted with ethyl acetate. The organic layer washed with water and saturated brine and dried with anhydrous magnesium sulfate, and the solvent was evaporated. The residue was purified with silica gel column chromatography (ethyl acetate/methanol/triethylamine) to give crude crystals, which were recrystallized from ethanol to give 7-(3,4-dipropoxyphenyl)-N-(4-((N-methyl-N-(tetrahydro-2H-pyran-4-yl)amino)methyl)phenyl)-1,1-dioxo-2,3-dihydro-1-benzothiepine-4-carboxamide (Compound 155) (0.27 g) as colorless crystals.

mp 206–208° C.; $^1$H NMR (CDCl$_3$) δ 1.07 (6H, t, J=7.5 Hz), 1.63–1.97 (8H, m), 2.21 (3H, s), 2.59–2.67 (1H, m), 3.17 (2H, t, J=6.7 Hz), 3.38 (2H, dt, J=3.2, 22.0 Hz), 3.58 (2H, s), 3.71 (2H, t, J=6.7 Hz), 3.99–4.08 (6H, m), 6.97 (1H, d, J=8.2 Hz), 7.11–7.17 (2H, m), 7.31–7.35 (3H, m), 7.53–7.66 (4H, m), 7.85 (1H, s), 8.18 (1H, d, J=8.2 Hz). IR (KBr) v 3330, 2963, 1667, 1597, 1520 cm$^{-1}$. Anal. calcd. for $C_{36}H_{44}N_2O_6S$: C, 68.33; H, 7.01; N, 4.43. Found C, 68.25; H, 7.06; N, 4.32.

Working Example 159 (Production of Compound 156)

In DMF (8 ml) were dissolved 7-(4-(2-butoxyethoxy)phenyl)-1,1-dioxo-2,3-dihydro-1-benzothiepine-4-carboxylic acid (0.4 g), 2-(4-aminobenzyl)-1,3,2-dioxaphosphorinane-2-oxide (0.22 g) and 1-hydroxybenzotriazole (0.13 g), and to the solution were added 1-ethyl-3-(3-dimethylaminopropyl)carbodiimide hydrochloride (0.36 g) and triethylamine (0.4 ml). Under nitrogen atmosphere, the mixture was stirred at room temperature overnight, poured into water and extracted with ethyl acetate, and the organic layer was washed with water and saturated brine, and dried with anhydrous magnesium sulfate. The solvent was evaporated to give crude crystals, which were recrystallized from ethanol to give 2-(4-(7-(4-(2-butoxyethoxy)phenyl)-1,1-dioxo-2,3-dihydro-1-benzothiepine-4-carbonylamino) benzyl)-1,3,2-dioxaphosphorinane-2-oxide (Compound 156) (0.40 g) as colorless crystals.

mp 222–223° C.; $^1$H NMR (CDCl$_3$) δ 0.93 (3H, t, J=7.3 Hz), 1.21–1.48 (2H, m), 1.55–1.69 (2H, m), 1.70–1.90 (2H, m), 3.12–3.18 (2H, m), 3.24 (2H, d, J=21.2 Hz), 3.56 (2H, t, J=6.6 Hz), 3.69–3.75 (2H, m), 3.82 (2H, t, J=5.0 Hz), 4.02–4.21 (4H, m), 4.33–4.47 (2H, m), 7.04 (2H, d, J=8.8 Hz), 7.23–7.28 (1H, m), 7.43 (1H, s), 7.52–7.68 (6H, m), 8.18 (1H, d, J=8.6 Hz), 8.44 (1H, br). IR (KBr) ν 2957, 2922, 1657, 1607, 1597, 1537, 1518 cm$^{-1}$. Anal. calcd. for C$_{33}$H$_{38}$NO$_8$PS: C, 61.96; H, 5.99; N, 2.19. Found C, 61.63; H, 6.25; N. 2.07.

Working Example 160 (Production of Compound 157)

To a solution of 7-(4-propoxyphenyl)-1,1-dioxo-2,3-dihydro-1-benzothiepine-4-carboxylic acid (205 mg) in THF (10 ml) were added at room temperature thionyl chloride (0.08 ml) and DMF (1 drop), and the mixture was stirred for 1 hour. Under reduced pressure, the solvent was evaporated, and the residue was dissolved in THF (15 ml). The solution was added dropwise at 0° C. to a solution of (+)-(4-aminophenyl)-(2-pyridyl)methanol (121 mg) and triethylamine (0.46 ml) in THF (5 ml), and the mixture was stirred at room temperature for 40 hours. To the mixture was added water, and the mixture was extracted with ethyl acetate. The organic layer was washed with saturated brine, dried with sodium sulfate and concentrated under reduced pressure, and the residue was purified with column chromatography (ethyl acetate) to give colorless crystals of N-[4-[hydroxy(2-pyridyl)methyl]phenyl]-7-(4-propoxyphenyl)-1,1-dioxo-2,3-dihydro-1-benzothiepine-4-carboxamide (Compound 157) (220 mg).

m.p. 208–210° C.; $^1$H-NMR (200 MHz, CDCl$_3$) δ 1.06 (3H,t, J=7.5 Hz), 1.75–1.92 (2H, m), 3.11–3.18 (2H, m), 3.68–3.75 (2H, m), 3.98 (2H, t, J=6.6 Hz), 5.33 (1H, d, J=4.0 Hz), 5.75 (1H, d, J=4.0 Hz), 7.00 (2H, d, J=8.8 Hz), 7.12–7.28 (2H, m), 7.34 (1H, s), 7.39 (2H, d, J=8.6 Hz), 7.52–7.69 (7H, m), 7.89 (1H, s), 8.19 (1H, d, J=8.0 Hz), 8.54–8.60 (1H, m).

Working Example 161 (Production of Compound 158)

To a solution of N-[4-[hydroxy(2-pyridyl)methyl]phenyl]-7-(4-propoxyphenyl)-1,1-dioxo-2,3-dihydro-1-benzothiepine-4-carboxamide (Compound 157) (180 mg) in dichloromethane (10 ml) was added at 0° C. 3-chloroperbenzoic acid (70%, 96 mg), and the mixture was stirred at room temperature for 18 hours. To the reaction mixture was added a solution of sodium thiosulfate, and the mixture was stirred for a few minutes and extracted with ethyl acetate. The organic layer was washed with a solution of sodium bicarbonate and saturated brine, dried with magnesium sulfate and concentrated under reduced pressure, and the residue was purified with column chromatography (ethanol/ethyl acetate=1:9→1:4) and crystallized from ethanol/diisopropylether to give colorless crystals of N-[4-[hydroxy(1-oxidepyridin-2-yl)methyl]phenyl]-7-(4-propoxyphenyl)-1,1-dioxo-2,3-dihydro-1-benzothiepine-4-carboxamide (Compound 158) (99 mg).

m.p. 184–186° C.; $^1$H-NMR (200 MHz, CDCl$_3$) δ 1.07 (3H, t, J=7.6 Hz), 1.76–1.94 (2H, m), 3.14–3.20 (2H, m), 3.69–3.76 (2H, m), 3.99 (2H, t, J=6.6 Hz), 6.07 (1H, d, J=4.4 Hz), 6.40 (1H, d, J=4.4 Hz), 6.94–7.03 (3H, m), 7.24–7.29 (2H, m), 7.38 (1H, s), 7.47 (2H, d, J=8.8 Hz), 7.54 (2H, d, J=9.2 Hz), 7.63–7.70 (4H, m), 8.04 (1H, s), 8.19 (1H, d, J=8.0 Hz), 8.25–8.28 (1H, m).

Working Example 162 (Production of Compound 159)

To a solution of 7-(4-butoxyphenyl)-1,1-dioxo-2,3-dihydro-1-benzothiepine-4-carboxylic acid (240 mg) in THF (10 ml) were added at room temperature thionyl chloride (0.09 ml) and DMF (1 drop), and the mixture was stirred for 1 hour. Under reduced pressure, the solvent was evaporated, and the residue was dissolved in THF (20 ml). The solution was added dropwise at 0° C. to a solution of (+)-(4-aminophenyl)-(2-pyridyl)methanol (137 mg) and triethylamine (0.5 ml) in THF (5 ml), and the mixture was stirred at room temperature for 20 hours. To the mixture was added water, and the mixture was extracted with ethyl acetate. The organic layer was washed with saturated brine, dried with sodium sulfate and concentrated under reduced pressure, and the residue was purified with column chromatography (ethyl acetate) to give colorless crystals of 7-(4-butoxyphenyl)-N-[4-[hydroxy(2-pyridyl)methyl]phenyl]-1,1-dioxo-2,3-dihydro-1-benzothiepine-4-carboxamide (Compound 159) (253 mg).

m.p. 142–145° C.; $^1$H-NMR (200 MHz, CDCl$_3$) δ 1.00 (3H, t, J=7.1 Hz), 1.42–1.64 (2H, m), 1.71–1.89 (2H, m), 3.15 (2H, t, J=6.8 Hz), 3.72 (2H, t, J=6.8 Hz), 4.02 (2H, t, J=6.5 Hz), 5.34 (iH, d, J=3.7 Hz), 5.75 (1H, d, J=3.7 Hz), 7.00 (2H, d, J=8.8 Hz), 7.12–7.29 (2H, m), 7.34 (1H, s), 7.39 (2H, d, J=8.8 Hz), 7.52–7.69 (7H, m), 7.94 (1H, s), 8.18 (1H, d, J=8.0 Hz), 8.55–8.61 (1H, m).

Working Example 163 (Production of Compound 160)

To a solution of 7-(4-butoxyphenyl)-N-[4-[hydroxy(2-pyridyl)methyl]phenyl]-1,1-dioxo-2,3-dihydro-1-benzothiepine-4-carboxamide (Compound 160) (200 mg) in dichloromethane (10 ml) was added at 0° C. 3-chloroperbenzoic acid (70%, 104 mg), and the mixture was stirred at room temperature for 20 hours. To the reaction mixture was added a solution of sodium thiosulfate, and the mixture was stirred for a few minutes and extracted with ethyl acetate. The organic layer was washed with a solution of sodium bicarbonate and saturated brine, dried with magnesium sulfate and concentrated under reduced pressure, and the residue was purified with column chromatography (ethanol/ethyl acetate=1:9→1:4) and crystallized from ethanol/diisopropylether to give pale yellow crystals of 7-(4-butoxyphenyl)-N-[4-[hydroxy(1-oxidepyridin-2-yl)methyl]phenyl]-1,1-dioxo-2,3-dihydro-1-benzothiepine-4-carboxamide (Compound 163) (125 mg).

m.p. 133–136° C.; $^1$H-NMR (200 MHz, CDCl$_3$) δ 1.00 (3H,t,J=7.3 Hz), 1.42–1.65 (2H, m), 1.72–1.86 (2H, m), 3.13–3.20 (2H, m), 3.69–3.75 (2H, m), 4.03 (2H, t, J=6.4 Hz), 6.07 (1H, d, J=4.4 Hz), 6.39 (1H, d, J=4.4 Hz), 6.93–7.05 (3H, m), 7.24–7.29 (2H, m), 7.38 (1H, s), 7.46 (2H, d, J=8.4 Hz), 7.54 (2H, d, J=8.8 Hz), 7.62–7.69 (4H, m), 8.09 (1H, s), 8.18 (1H, d, J=8.0 Hz), 8.24–8.28 (1H, m).

Industrial Applicability

The compound of the formula (I) of the present invention has potent CCR5 antagonistic activity and can be advantageously used for the treatment or prevention of infectious disease of various HIV in human (e.g. AIDS).

What is claimed is:

1. A compound of the formula:

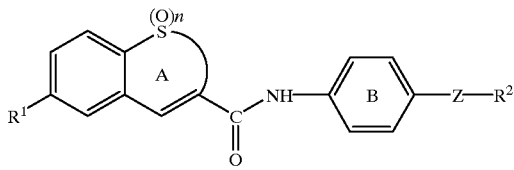

wherein $R^1$ is an optionally substituted 5- to 6-membered ring; the ring A is an optionally substituted 6- to 7-membered ring; the ring B is an optionally substituted benzene ring; n is an integer of 1 or 2; Z is a chemical bond or a divalent group; $R^2$ is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, (3) a group binding through a sulfur atom or (4) a group of the formula:

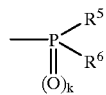

wherein k is 0 or 1, and when k is 0, a phosphorus atom may form a phosphonium; and $R^5$ and $R^6$ are independently an optionally substituted hydrocarbon group, an optionally substituted hydroxy group or an optionally substituted amino group, and $R^5$ and $R^6$ may bind to each other to form a cyclic group together with the adjacent phosphorus atom, or a salt thereof.

2. A pro-drug of the compound or a salt thereof as claimed in claim 1.

3. A compound according to claim 1, wherein $R^1$ is benzene, furan, thiophene, pyridine, cyclopentane, cyclohexane, pyrrolidine, piperidine, piperazine, morpholine, thiomorpholine or tetrahydropyran, each of which may be substituted.

4. A compound according to claim 1, wherein $R^1$ is an optionally substituted benzene.

5. A compound according to claim 1, wherein the ring A is a group of the formula:

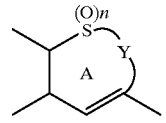

wherein Y is —$(CH_2)_m$— (m is an integer of 1 or 2), —CH=CH— or —N=CH—, which may have a substituent at any possible position.

6. A compound according to claim 5, wherein Y is —$(CH_2)_m$— (m is an integer of 1 or 2).

7. A compound according to claim 5, wherein Y is —$(CH_2)_2$—.

8. A compound according to claim 1, wherein the ring B is a benzene which may be substituted with a substituent selected from the class consisting of a halogen atom, a $C_{1-4}$ alkyl group optionally substituted with a halogen atom and a $C_{1-4}$ alkoxy group optionally substituted with a halogen atom.

9. A compound according to claim 1, wherein n is 2.

10. A compound according to claim 1, wherein Z is an optionally substituted $C_{1-3}$ alkylene.

11. A compound according to claim 1, wherein Z is a divalent group of the formula: —Z'—$(CH_2)n'$— (Z' is —CH(OH)—, —C(O)— or —$CH_2$—, and n' is an integer of 0–2) in which an optional methylene group may be substituted.

12. A compound according to claim 1, wherein Z is methylene.

13. A compound according to claim 1, wherein $R^2$ is (1) an optionally substituted amino group, (2) an optionally substituted nitrogen-containing heterocyclic ring group which may contain a sulfur atom or an oxygen atom as ring constituting atoms, (3) a group binding through a sulfur atom or (4) a group of the formula:

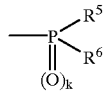

wherein k is 0 or 1; and $R^5$ and $R^6$ are independently an optionally substituted hydrocarbon group or an optionally substituted amino group, and $R^5$ and $R^6$ may bind to each other to form a cyclic group together with the adjacent phosphorus atom.

14. A compound according to claim 1, wherein R is (1) an optionally substituted amino group, (2) an optionally substituted nitrogen-containing heterocyclic ring group which may contain a sulfur atom or an oxygen atom as ring constituting atoms or (3) a group of the formula:

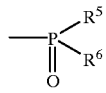

wherein $R^5$ and $R^6$ are independently an optionally substituted hydrocarbon group, and $R^5$ and $R^6$ may bind to each other to form a cyclic group together with the adjacent phosphorus atom.

15. A compound according to claim 1, wherein $R^2$ is a group of the formula: —NRR'
wherein R and R' are independently an optionally substituted aliphatic hydrocarbon group or an optionally substituted non-aromatic heterocyclic ring group.

16. A compound according to claim 15, wherein R is an optionally substituted acyclic hydrocarbon group and R' is an optionally substituted alicyclic hydrocarbon group or an optionally substituted non-aromatic heterocyclic ring group.

17. A compound according to claim 15, wherein R is an optionally substituted $C_{1-6}$ alkyl group and R' is an optionally substituted $C_{3-8}$ cycloalkyl group or an optionally substituted saturated heterocyclic ring group.

18. A compound according to claim 17, wherein R' is an optionally substituted cyclohexyl, an optionally substituted tetrahydropyranyl, an optionally substituted tetrahydrothiopyranyl or an optionally substituted piperidyl.

19. A compound selected from the class consisting of N-[4-[N-methyl-N-(tetrahydropyran-4-yl)aminomethyl] phenyl]-7-(4-propoxyphenyl)-1,1-dioxo-2,3-dihydro-1-benzothiepine-4-carboxamide, 7-(4-butoxyphenyl)-N-[4-[N-methyl-N-(tetrahydropyran-4-yl)aminomethyl]phenyl]-1,1-dioxo-2,3-dihydro-1-benzothiepine-4-carboxamide, 7-[4-[N-methyl-N-(2-propoxyethyl)amino]phenyl]-N-[4-[[N-methyl-N-(tetrahydropyran-4-yl)amino]methyl] phenyl]-1,1-dioxo-2,3-dihydro-1-benzothiepine-4-carboxamide, 7-[4-(2-ethoxyethoxy)phenyl]-N-[4-[[N-methyl-N-(tetrahydropyran-4-yl)amino]methyl]phenyl]-1, 1-dioxo-2,3-dihydro-1-benzothiepine-4-carboxamide, N-[4-[[N-methyl-N-(tetrahydropyran-4-yl)amino]methyl] phenyl]-7-[4-(2-propoxyethoxy)phenyl]-1,1-dioxo-2,3-dihydro-1-benzothiepine-4-carboxamide, 7-[4-(2-butoxyethoxy)phenyl]-N-[4-[[N-methyl-N-(tetrahydropyran-4-yl)amino]methyl]phenyl]-1,1-dioxo-2, 3-dihydro-1-benzothiepine-4-carboxamide, 7-[4-(2-ethoxyethoxy)-3,5-dimethylphenyl]-N-[4-[[N-methyl-N-(tetrahydro-2H-pyran-4-yl)amino]methyl]phenyl]-1,1-dioxo-2,3-dihydro-1-benzothiepine-4-carboxamide, 7-[2-chloro-4-(2-propoxyethyl)phenyl]-N-[4-[[N-methyl-N-(tetrahydropyran-4-yl)amino]methyl]phenyl]-1,1-dioxo-2, 3-dihydro-1-benzothiepine-4-carboxamide, 7-(3-methyl-4-propoxyphenyl)-N-[4-[[N-methyl-N-(tetrahydropyran-4-yl) amino]methyl]phenyl]-1,1-dioxo-2,3-dihydro-1-benzothiepine-4-carboxamide and 7-(3,4-dipropoxyphenyl)-N-(4-((N-methyl-N-(tetrahydro-2H-pyran-4-yl)amino)methyl)phenyl)-1,1-dioxo-2,3-dihydro-1-benzothiepine-4-carboxamide; or a salt thereof.

20. A method for producing a compound of the formula:

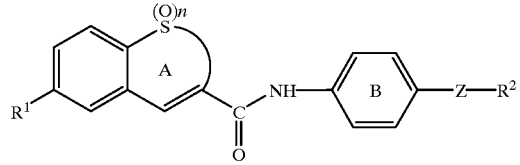

wherein each symbol is as defined in claim 1, or a salt thereof, which comprises subjecting a compound of the formula:

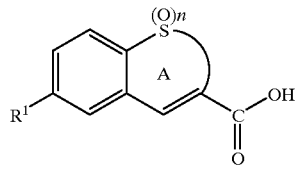

wherein each symbol is as defined in claim 1, a salt or a reactive derivative thereof to condensation reaction with a compound of the formula:

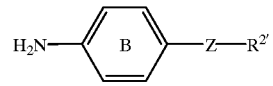

wherein B and Z is as defined in claim 1 and $R^{2'}$ is (1) an optionally substituted amino group in which a nitrogen atom may form a quaternary ammonium; (2) an optionally substituted nitrogen-containing heterocyclic ring group which may contain a sulfur atom or an oxygen atom as ring constituting atoms and wherein a nitrogen atom may form a quaternary ammonium; (3) a group binding through a sulfur atom; or (4) a group of the formula:

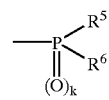

wherein k is 0 or 1, and when k is 0, a phosphorus atom may form a phosphonium; and $R^5$ and $R^6$ are independently an optionally substituted hydrocarbon group, an optionally substituted hydroxy group or an optionally substituted amino group, and $R^5$ and $R^6$ may bind to each other to form a cyclic group together with the adjacent phosphorus atom; each of which may be protected, or a salt thereof, and, if desired, subjecting the obtained product to deprotection, oxidation, reduction and/or ammoniumation.

21. A compound of the formula:

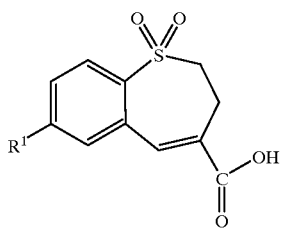

wherein $R^1$ is an optionally substituted 5- to 6-membered ring, or a salt thereof.

22. A pharmaceutical composition which comprises the compound as claimed in claim 1 or a salt thereof.

23. A composition according to claim 22, which is for antagonizing CCR.

24. A composition according to claim 22, which is for antagonizing CCR5.

25. A composition according to claim 22, which is for the treatment or prevention of infectious disease of HIV.

26. A composition according to claim 22, which is for the treatment or prevention of AIDS.

27. A composition according to claim 22, which is for the prevention of the progression of AIDS.

28. A composition according to claim 25, which is used in combination with a protease inhibitor and/or a reverse transcriptase inhibitor.

29. A composition according to claim 28, wherein the reverse transcriptase inhibitor is zidovudine, didanosine, zalcitabine, lamivudine, stavudine, nevirapine, delavirdine, efavirenz or abacavir.

30. A composition according to claim 28, wherein the protease inhibitor is saquinavir, ritonavir, indinavir, amprepavir or nelfinavir.

31. A method of using the compound as claimed in claim 1 or a salt thereof in combination with a protease inhibitor and/or a reverse transcriptase inhibitor for the treatment or prevention of infectious disease of HIV.

32. A method for antagonizing CCR which comprises administering to a mammal in need thereof an effective amount of the compound as claimed in claim 1 or a salt thereof.

33. A method of using the compound as claimed in claim 1 or a salt thereof, for the manufacture of a medicament for antagonizing CCR.

* * * * *